(12) United States Patent
Takeuchi et al.

(10) Patent No.: US 9,242,977 B2
(45) Date of Patent: Jan. 26, 2016

(54) TRK-INHIBITING COMPOUND

(71) Applicant: ONO PHARMACEUTICAL CO., LTD., Osaka-shi, Osaka (JP)

(72) Inventors: Jun Takeuchi, Osaka (JP); Masahiro Ikura, Osaka (JP); Masato Higashino, Osaka (JP); Maki Iwahashi, Osaka (JP); Kazuya Hashimura, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/397,070

(22) PCT Filed: Apr. 25, 2013

(86) PCT No.: PCT/JP2013/062158
§ 371 (c)(1),
(2) Date: Oct. 24, 2014

(87) PCT Pub. No.: WO2013/161919
PCT Pub. Date: Oct. 31, 2013

(65) Prior Publication Data
US 2015/0111865 A1    Apr. 23, 2015

(30) Foreign Application Priority Data

Apr. 26, 2012 (JP) .................................. 2012-101211

(51) Int. Cl.
| | |
|---|---|
| C07D 417/12 | (2006.01) |
| A61K 31/513 | (2006.01) |
| C07D 417/14 | (2006.01) |
| A61K 31/4439 | (2006.01) |
| A61K 31/444 | (2006.01) |
| A61K 31/5377 | (2006.01) |
| A61K 31/55 | (2006.01) |
| A61K 45/06 | (2006.01) |

(52) U.S. Cl.
CPC ............ *C07D 417/14* (2013.01); *A61K 31/444* (2013.01); *A61K 31/4439* (2013.01); *A61K 31/513* (2013.01); *A61K 31/5377* (2013.01); *A61K 31/55* (2013.01); *A61K 45/06* (2013.01); *C07D 417/12* (2013.01)

(58) Field of Classification Search
CPC ............... C07D 417/12; C07D 417/14; A61K 31/4439; A61K 31/444; A61K 31/513
USPC ........................................... 544/316; 514/274
See application file for complete search history.

(56) References Cited

U.S. PATENT DOCUMENTS

| | | |
|---|---|---|
| 2002/0025976 A1 | 2/2002 | Chu et al. |
| 2003/0207870 A1 | 11/2003 | Dumas et al. |
| 2006/0167247 A1 | 7/2006 | Michelotti et al. |
| 2007/0078121 A1 | 4/2007 | Flynn et al. |
| 2008/0227783 A1 | 9/2008 | Wan et al. |
| 2008/0227828 A1 | 9/2008 | Dumas et al. |
| 2008/0261961 A1 | 10/2008 | Flynn et al. |
| 2009/0105250 A1 | 4/2009 | Sim et al. |
| 2009/0124633 A1 | 5/2009 | Jonczyk et al. |
| 2011/0015195 A1 | 1/2011 | Dumas et al. |
| 2011/0129440 A1 | 6/2011 | Tadikonda et al. |
| 2011/0195110 A1 | 8/2011 | Smith et al. |
| 2012/0202818 A1 | 8/2012 | Tao et al. |
| 2012/0289552 A1 | 11/2012 | Dumas et al. |

FOREIGN PATENT DOCUMENTS

| | | |
|---|---|---|
| EP | 2206707 A1 | 7/2010 |
| JP | 2003-501420 A | 1/2003 |
| JP | 2008-523071 A | 7/2008 |
| JP | 2008-525498 A | 7/2008 |
| JP | 2008-528585 A | 7/2008 |
| JP | 2009-503073 A | 1/2009 |
| JP | 2009-518298 A | 5/2009 |
| JP | 2009-533362 A | 9/2009 |
| JP | 2011-502160 A | 1/2011 |

(Continued)

OTHER PUBLICATIONS

Bundgaard, Design of Prodrugs, p. 1, 1985.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. I: Principles and Practice, pp. 975-977, 1995.*

(Continued)

*Primary Examiner* — Deepak Rao
(74) *Attorney, Agent, or Firm* — Sughrue Mion, PLLC

(57) ABSTRACT

An object of the present invention is to provide a drug containing a compound having Trk-inhibiting activity as an active ingredient in prophylaxis and/or therapy of diseases such as pain, pruritus, lower urinary tract dysfunction, asthma, allergic rhinitis, inflammatory bowel disease or Chagas disease. A compound represented by the general formula (I):

(wherein all symbols represent the same meanings as described in the specification), a salt thereof, an N-oxide thereof, a solvate thereof or a prodrug thereof is useful as a drug component having Trk-inhibiting activity in prophylaxis and/or therapy of diseases such as pain, pruritus, lower urinary tract dysfunction, asthma, allergic rhinitis, inflammatory bowel disease or Chagas disease.

15 Claims, No Drawings

(56) References Cited

FOREIGN PATENT DOCUMENTS

| WO | 03/068228 A1 | 8/2003 |
|---|---|---|
| WO | 2008/131227 A1 | 10/2008 |
| WO | 2008/131276 A1 | 10/2008 |
| WO | 2010/144522 A1 | 12/2010 |

OTHER PUBLICATIONS

Silverman, Prodrugs and Drug Delivery Systems, The Organic Chemistry of Drug Design and Drug Action, pp. 352-399, 1992.*

Search Report dated Jul. 2, 2013 issued by the International Searching Authority in counterpart International Patent Application No. PCT/JP2013/062158.

Ghilardi et al.; "Administration of a tropomyosin receptor kinase inhibitor attenuates sarcoma-induced nerve sprouting, neuroma formation and bone cancer pain"; Molecular Pain; BioMed Central; vol. 6; No. 87; Dec. 2010; 12 pages; http://www.molecularpain.com/content/6/1/87.

Wild et al.; "Antibodies to Nerve Growth Factor Reverse Established Tactile Allodynia in Rodent Models of Neuropathic Pain without Tolerance"; Pharmacology and Experimental Therapeutics; vol. 322; No. 1; 2007; pp. 282-287.

Katz et al.; "Efficacy and safety of tanezumab in the treatment of chronic low back pain"; PAIN; vol. 152; 2011; pp. 2248-2258; DOI: 10.1016/j.pain.2011.05.003.

di Mola et al.; "Nerve growth factor and Trk high affinity receptor (TrkA) gene expression in inflammatory bowel disease"; Gut; vol. 46; 2000; pp. 670-678.

Shelton et al.; "Nerve growth factor mediates hyperalgesia and cachexia in auto-immune arthritis"; PAIN; vol. 116; 2005; pp. 8-16; DOI: 10.1016/j.pain.2005.03.039.

Zhu et al.; "Nerve Growth Factor Modulates TRPV1 Expression and Function and Mediates Pain in Chronic Pancreatitis"; Gastroenterology; vol. 141; Jul. 2011; pp. 370-377; DOI: 10.1053/j.gastro.2011.03.046.

Botchkarev et al.; "Neurotrophins in Skin Biology and Pathology"; Journal of Investigative Dermatology; The Society for Investigative Dermatology; vol. 126; 2006; pp. 1719-1727; DOI: 10.1038/sj.jid.5700270.

Hefti et al.; "Novel class of pain drugs based on antagonism of NGF";Trends in Pharmacological Sciences; vol. 27; No. 2; Feb. 2006; pp. 85-91; 10.1016/j.tips.2005.12.001.

Evans et al.; "Proof of Concept Trial of Tanezumab for the Treatment of Symptoms Associated With Interstitial Cystitis"; The Journal of Urology; American Urological Association Education and Research, Inc.; vol. 185; May 2011; pp. 1716-1721; DOI: 10.1016/j.juro.2010.12.088.

Ghilardi et al.; "Sustained blockade of neurotrophin receptors TrkA, TrkB and TrkC reduces non-malignant skeletal pain but not the maintenance of sensory and sympathetic nerve fibers"; Bone; ScienceDirect; vol. 48; 2011; pp. 389-398; DOI: 10.1016/j.bone.2010.09.019.

Lane et al.; "Tanezumab for the Treatment of Pain from Osteoarthritis of the Knee"; The New England Journal of Medicine; vol. 363; No. 16; Oct. 14, 2010; pp. 1521-1531.

Scuri et al.; "The Role of Neurotrophins in Inflammation and Allergy"; Inflammation & Allergy—Drug Targets; vol. 9; No. 3; 2010; pp. 173-180.

Raap et al.; "The role of neurotrophins in the pathophysiology of allergic rhinitis"; Upper Airway Disease; 2010; pp. 8-13; DOI: 10.1097/ACI.0b013e328334f5de.

Huang et al.; "Trk Receptors: Roles in Neuronal Signal Trandsduction"; Annu. Rev. Biochem.; vol. 72; 2003; pp. 609-642; DOI: 10.1146/annurev.biochem.72.121801.161629.

Wang et al.; "Trk kinase inhibitors as new treatments for cancer and pain"; Expert Opinion Ther. Patents; Informa healthcare; vol. 19; No. 3; 2009; pp. 305-319.

Communication issued on Aug. 14, 2015 by the European Patent Application in related Application No. 13782584.0.

* cited by examiner

TRK-INHIBITING COMPOUND

TECHNICAL FIELD

The present invention relates to a Trk-inhibiting compound or a salt thereof and a medicament containing the same as an active ingredient. More specifically, the present invention relates to a Trk-inhibiting compound represented by the general formula (I):

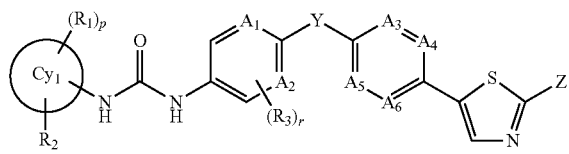

(I)

wherein all symbols represent the same meanings as described hereinbelow, and a salt thereof, an N-oxide thereof, a solvate thereof or a prodrug thereof (hereinafter collectively referred to as "the present compound") and a medicament containing the same as an active ingredient.

BACKGROUND ART

The tropomyosin receptor kinase (hereinafter abbreviated as "Trk") family is classified as receptor tyrosine kinases and comprises TrkA which is a high-affinity receptor of nerve growth factor (hereinafter abbreviated as NGF), TrkB which is a high-affinity receptor of brain-derived neutrophic factor (BDNF) and neurotrophin (hereinafter abbreviated as NT)-4/5 and TrkC which is a high-affinity receptor of NT-3. All Trk receptors are highly expressed in nerve tissues and are involved in differentiation and maintenance of functions of nerve cells (see Non-Patent Document 1). Meanwhile it has been known that activation of TrkA in peripheral nerves by NGF initiates hyperalgesia (see Non-Patent Document 2) and based on clinical and non-clinical test results using anti-NGF antibodies and non-clinical test results using low-molecular weight Trk inhibitors, involvement of TrkA has been reported in nociceptive pain of osteoarthritis, chronic low back pain, rheumatoid arthritis, bone fracture, interstitial cystitis and chronic pancreatitis, neuropathic pain as well as cancer pain combining both types of pain described above (see Non-Patent Document 3 to 10). Moreover, Trk receptors are expressed on cancer cells such as neuroblastoma, prostate cancer and pancreatic cancer, inflammatory cells such as mast cells and eosinophils, immunocompetent cells such as T cells and B cells and keratinocytes and are reported to be potentially involved in proliferation, migration and metastasis of cancer cells, inflammatory diseases such as ulcerative colitis and Crohn's disease, allergic diseases such as asthma, rhinitis and atopic dermatitis and other diseases such as psoriasis (see Non-Patent Document 11 to 15). Therefore compounds having Trk-inhibiting activity may be applied to therapy of nociceptive pain, neuropathic pain and pain combining both types of pain, cancer, inflammatory diseases, allergic diseases and psoriasis.

Accordingly it is expected that development of Trk-inhibiting agents may provide novel types of prophylactic and/or therapeutic agents for pain and the like.

Meanwhile Patent Document 1 discloses a method for treating or preventing a disease in a human or other mammal regulated by tyrosine kinase, comprising administering, to a human or other mammal in need thereof, a compound of the following formula (Ia), a salt thereof, an isomer thereof or a prodrug of the compound.

The general formula (Ia) is as follows:

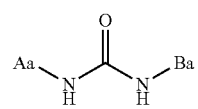

(Ia)

wherein Aa is selected from the group consisting of the following (i) to (iii) and the like;
(i) phenyl, optionally substituted with 1 to 3 substituents independently selected from the group consisting of $Ra^1$, $ORa^1$, a halogen and the like;
(ii) naphthyl, optionally substituted with 1 to 3 substituents independently selected from the group consisting of $Ra^1$, $ORa^1$, a halogen and the like;
(iii) a 5- to 6-membered monocyclic heteroaryl group, optionally substituted with 1 to 3 substituents independently selected from the group consisting of $Ra^1$, $ORa^1$, a halogen and the like and having 1 to 3 heteroatoms independently selected from the group consisting of O, N and S;

Ba is selected from the group consisting of the following (i) to (iii) and the like;
(i) phenyl, optionally substituted with 1 to 3 substituents independently selected from the group consisting of —La-Ma, a $C_1$-$C_5$ linear or branched alkyl, a halogen and the like;
(ii) naphthyl, optionally substituted with 1 to 3 substituents independently selected from the group consisting of —La-Ma, a $C_1$-$C_5$ linear or branched alkyl, a halogen and the like;
(iii) a 5- to 6-membered monocyclic heteroaryl group, optionally substituted with 1 to 3 substituents independently selected from the group consisting of —La-Ma, a $C_1$-$C_5$ linear or branched alkyl, a halogen and the like and having 1 to 3 heteroatoms independently selected from the group consisting of O, N and S;

La is selected from the group consisting of —$(CH_2)_{ma}$—O—$(CH_2)_{la}$—, —$(CH_2)_{ma}$—C(O)—$(CH_2)_{la}$— and the like, wherein the variables ma and la are integers independently selected from 0 to 4;

Ma is selected from the group consisting of the following (i) to (iii) and the like;
(i) phenyl, optionally substituted with 1 to 3 substituents independently selected from the group consisting of $Ra^1$, $ORa^1$, a halogen and the like;
(ii) naphthyl, optionally substituted with 1 to 3 substituents independently selected from the group consisting of $Ra^1$, $ORa^1$, a halogen and the like;
(iii) a 5- to 6-membered monocyclic heteroaryl group, optionally substituted with 1 to 3 substituents independently selected from the group consisting of $Ra^1$, $ORa^1$, a halogen and the like and having 1 to 3 heteroatoms independently selected from the group consisting of O, N and S;

wherein $Ra^1$ is independently selected from the group consisting of (a) a hydrogen, (b) a $C_1$-$C_6$ alkyl, (c) phenyl, (d) a 5- to 6-membered monocyclic heteroaryl or a 8- to 10-membered bicyclic heteroaryl both having 1 to 4 heteroatoms selected from the group consisting of O, N and S, (e) a $C_1$-$C_3$ alkyl-phenyl and (f) an alkyl-heteroaryl having 1 to 4 heteroatoms selected from the group consisting of O, N and S; $Ra^1$ is, when it is not a hydrogen, optionally substituted with 1 to 3 substituents independently selected from the group consisting of a $C_1$-$C_5$ linear, branched or cyclic alkyl, a $C_1$-$C_3$ alkoxy, hydroxy, amino, a $C_1$-$C_3$ alkylamino, a $C_2$-$C_6$ dialkylamino, a halogen, cyano and nitro (the definitions of the groups are partially abstracted).

Patent Document 1 discloses that the compound therein inhibits KDR and thereby is used for a method of treatment of diseases mediated by VEGF induced signal transduction pathways in a human or other mammal, particularly retinopathy or retinopathy of prematurity. However, it is not disclosed or suggested that the compound disclosed therein has Trk-inhibiting activity and Patent Document 1 does not specifically disclose the present compound.

Patent Document 2 discloses that a compound represented by the general formula (Ib):

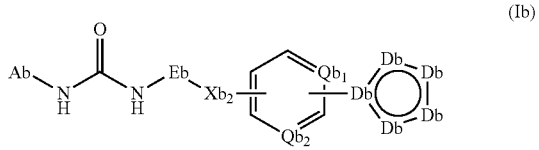

(Ib)

wherein:

$Qb_1$ and $Qb_2$ are individually and independently selected from the group consisting of N and CH, and at least one of $Qb_1$ and $Qb_2$ is N;

each Db is individually selected from the group consisting of C, CH, C—$Rb_{20}$, N—$Zb_3$, N, O and S, such that the resultant ring is taken from the group consisting of pyrazolyl, triazolyl, isoxazolyl, isothiazolyl, oxazolyl and thiadiazolyl;

Eb is selected from the group consisting of phenyl, pyridyl and pyrimidinyl;

$Xb_2$ is selected from the group consisting of —O—, —$S(CH_2)_{nb}$—, —$N(Rb_3)(CH_2)_{nb}$— and —$(CH_2)_{pb}$—;

when only one of $Qb_1$ and $Qb_2$ is N, the ring Ab is selected from the group consisting of cyclopentyl, cyclohexyl, $Gb_1$, $Gb_2$, $Gb_3$ and $Gb_4$ optionally substituted with the substituent $Zb_2$, $Rb_2$ and the like;

$Gb_1$ is a heteroaryl selected from the group consisting of pyrrolyl, furyl, thienyl, oxazolyl, thiazolyl, pyrazolyl and the like;

$Gb_4$ is selected from the group consisting of phenyl, naphthyl, pyrazinyl, pyridazinyl, triazinyl, pyridinyl and pyrimidinyl;

$Zb_2$ is selected from the group consisting of aryl, a C1-C6 alkyl, a C3-C8 cycloalkyl, a branched C3-C7 alkyl and the like;

$Rb_2$ is selected from the group consisting of a substituted aryl, substituted $Gb_1$, substituted $Gb_4$, a halogen and the like (the definitions of the groups are partially abstracted), a stereoisomer, regioisomer and tautomer of the compound have Abl-inhibiting activity, c-Met-inhibiting activity, b-Raf-inhibiting activity and c-Kit-inhibiting activity. However, it is not disclosed or suggested that the compounds have Trk-inhibiting activity. In addition, Patent Document 2 does not disclose the present compound.

Patent Document 3 discloses that a compound represented by the general formula (Ic):

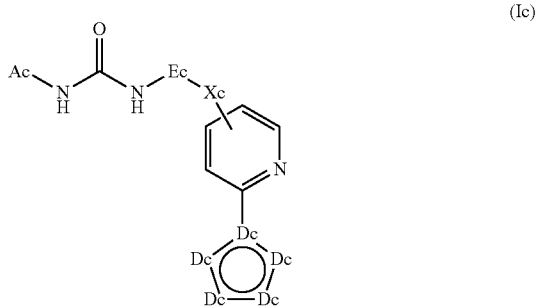

(Ic)

wherein:

each Dc is individually selected from the group consisting of C, CH, C—$Rc_{20}$, N—$Zc_3$ and N, such that the resultant ring is pyrazole;

Ec is selected from the group consisting of phenyl, pyridyl and pyrimidinyl;

Xc is selected from the group consisting of —O—, —$S(CH_2)_{nc}$—, —$N(Rc_3)(CH_2)_{nc}$— and —$(CH_2)_{pc}$—;

Ac is a ring system selected from the group consisting of phenyl, naphthyl, cyclopentyl, cyclohexyl, $Gc_1$, $Gc_2$ and $Gc_3$, optionally substituted with the substituent $Zc_2$, $Rc_2$ and the like;

$Gc_1$ is a heteroaryl selected from the group consisting of pyrrolyl, furyl, thienyl, oxazolyl, thiazolyl, pyrazolyl and the like;

$Gc_2$ is a fused bicyclic heteroaryl selected from the group consisting of indolyl, indolinyl, isoindolyl and the like;

$Gc_3$ is a heterocyclyl selected from the group consisting of oxetanyl, tetrahydrofuranyl, pyrrolidinyl and the like;

$Zc_2$ is selected from the group consisting of an aryl, a C1-C6 alkyl, a C3-C8 cycloalkyl, a branched C3-C7 alkyl and the like;

$Rc_2$ is selected from the group consisting of a C1-C6 alkyl, a branched C3-C8 alkyl, a halogen and the like (the definitions of the groups are partially abstracted), a stereoisomer, regioisomer and tautomer of the compound have Abl-inhibiting activity, c-Met-inhibiting activity and c-Kit-inhibiting activity. However, it is not disclosed or suggested that the compounds have Trk-inhibiting activity. In addition, Patent Document 3 does not disclose the present compound.

Patent Document 1: WO 2003/068228
Patent Document 2: WO 2008/131276
Patent Document 3: WO 2008/131227
Non-Patent Document 1: Annual Review of Biochemistry, vol. 72, pp. 609-642, 2003
Non-Patent Document 2: Trends in Pharmacological Sciences, vol. 27, pp. 85-91, 2006
Non-Patent Document 3: New England Journal of Medicine, vol. 363, pp. 1521-1531, 2010
Non-Patent Document 4: Pain, vol. 152, pp. 2248-2258, 2011
Non-Patent Document 5: Journal of Urology, vol. 185, pp. 1716-1721, 2011
Non-Patent Document 6: Pain, vol. 116, pp. 8-16, 2005
Non-Patent Document 7: Bone, vol. 48, pp. 389-398, 2010
Non-Patent Document 8: Molecular Pain, vol. 6, p. 87, 2010
Non-Patent Document 9: Journal Pharmacological Experimental Therapeutics, vol. 322, pp. 282-287, 2007
Non-Patent Document 10: Gastroenterology, vol. 141, pp. 370-377, 2011
Non-Patent Document 11: Expert Opinion Therapeutic Patents, vol. 19, pp. 305-315, 2009
Non-Patent Document 12: Gut, vol. 46, pp. 670-679, 2000
Non-Patent Document 13: Current Opinion in Allergy and Clinical Immunology, vol. 10, pp. 8-13, 2010
Non-Patent Document 14: Inflammation and Allergy Drug Targets, vol. 9, pp. 173-180, 2010
Non-Patent Document 15: Journal of Investigative Dermatology, vol. 126, pp. 1719-1727, 2006

DISCLOSURE OF INVENTION

An object of the present invention is to create a compound having selective Trk-inhibiting activity and find a compound useful as a prophylactic and/or therapeutic agent for various diseases typically including pain.

The present inventors have carried out exhaustive studies in order to find compounds which have selective Trk-inhibiting activity and can be safe prophylactic and/or therapeutic agents for various diseases typically including pain, and as a result have found that the compounds represented by the following general formula (I) have Trk-inhibiting action, have excellent kinase selectivity and can persistently suppress NGF vascular hyper permeability in an in vivo test, thereby completing the present invention.

Thus the present invention relates to the followings:

[1] A compound represented by the general formula (I):

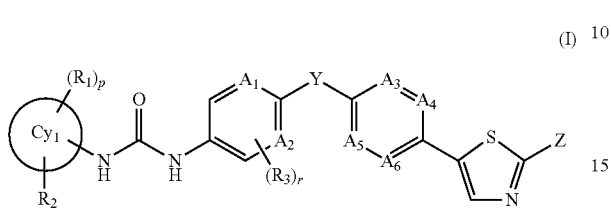

wherein:

a ring $Cy_1$ represents a C3-10 monocyclic carbocycle or bicyclic carbocycle or a 4- to 10-membered monocyclic heterocycle or bicyclic heterocycle;

$R_1$ represents:
(1) a halogen;
(2) a C1-6 alkyl group optionally substituted with a halogen or an oxo group;
(3) a C3-6 cycloalkyl group optionally substituted with a halogen or a C1-3 alkyl group;
(4) a C1-6 alkyl group having an oxygen atom substituting for a carbon atom and optionally substituted with a halogen or an oxo group; or
(5) a C3-6 cycloalkyl group having an oxygen atom substituting for a carbon atom and optionally substituted with a halogen or a C1-3 alkyl group;

$R_2$ represents:
(1) a C1-6 alkyl group, a C2-6 alkenyl group or a C2-6 alkynyl group optionally substituted with a substituent selected from the group consisting of:
 (i) a halogen;
 (ii) a hydroxy group;
 (iii) —NH(C1-3 alkyl);
 (iv) —N(C1-3 alkyl)$_2$;
 (v) an amino group;
 (vi) a cyano group;
 (vii) a nitro group;
 (viii) a C1-4 alkylsulfonyl group,
 (ix) a sulfonamide group;
 (x) a C1-4 alkylsulfonamide group;
 (xi) an oxo group;
 (xii) a carboxyl group;
 (xiii) —C(O)(O—C1-4 alkyl);
 (xiv) a phosphonooxy group;
 (xv) —OP(O) (O—C1-4 alkyl)$_2$;
 (xvi) a carbamoyl group;
 (xvii) a C1-4 alkylamide group; and
 (xviii) a C1-4 alkylcarbamate group;
(2) a hydrogen atom;
(3) a hydroxy group;
(4) a carboxyl group;
(5) —C(O) (O—C1-4 alkyl);
(6) a phosphonooxy group;
(7) —OP(O)(O—C1-4 alkyl)$_2$;
(8) an amino group;
(9) a cyano group;
(10) a nitro group;
(11) a C1-4 alkylsulfonyl group;
(12) a sulfonamide group;
(13) a C1-4 alkylsulfonamide group;
(14) an oxo group;
(15) a carbamoyl group;
(16) a C1-4 alkylamide group;
(17) a C1-4 alkylcarbamate group; or
(18)

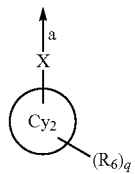

wherein an arrow a represents binding to the ring $Cy_1$;

X represents a bond, an oxygen atom, C=O or NH;

a ring $Cy_2$ represents a C3-10 monocyclic carbocycle or bicyclic carbocycle or a 4- to 10-membered monocyclic heterocycle or bicyclic heterocycle;

$R_6$ represents:
(1) a C1-6 alkyl group, a C2-6 alkenyl group, a C2-6 alkynyl group or a C3-6 cycloalkyl group optionally substituted with a substituent selected from the group consisting of:
 (i) a halogen;
 (ii) a hydroxy group;
 (iii) an oxo group;
 (iv) —NH(C1-3 alkyl);
 (v) —N(C1-3 alkyl)$_2$;
 (vi) a C1-6 alkoxy group;
 (vii) an amino group;
 (viii) a cyano group;
 (ix) a nitro group;
 (x) a C1-4 alkylsulfonyl group;
 (xi) a sulfonamide group;
 (xii) a C1-4 alkylsulfonamide group;
 (xiii) a carboxyl group;
 (xiv) —C(O)(O—C1-4 alkyl);
 (xv) a phosphonooxy group;
 (xvi) —OP(O)(O—C1-4 alkyl)$_2$;
 (xvii) a carbamoyl group;
 (xviii) a C1-4 alkylamide group; and
 (xix) a C1-4 alkylcarbamate group;
(2) a halogen;
(3) a C1-4 alkoxy group;
(4) a phosphonooxy group;
(5) —OP(O) (O—C1-4 alkyl)$_2$;
(6) a sulfonamide group;
(7) an oxo group;
(8) —NH(C1-3 alkyl);
(9) —N(C1-3 alkyl)$_2$;
(10) a carboxyl group;
(11) —C(O)(O—C1-4 alkyl);
(12) a carbamoyl group;
(13) a C1-4 alkylamide group;
(14) a hydroxy group;
(15) an amino group;
(16) a cyano group;
(17) a nitro group;
(18) a C1-4 alkylsulfonyl group;
(19) a C1-4 alkylsulfonamide group; or
(20) a C1-4 alkylcarbamate group;

$A_1$ and $A_2$ respectively and independently represent =CR$_3$—, =CH— or =N—;

$A_3$, $A_4$, $A_5$ and $A_6$ respectively and independently represent =CR$_4$— or =N—;

R<sub>3</sub> represents:

(1) a halogen; or (2) a C1-3 alkyl group or C1-3 alkoxy group optionally substituted with a halogen;

R<sub>4</sub> represents (1) a halogen;

(2) a C1-3 alkyl group or C1-3 alkoxy group optionally substituted with a halogen; or (3) a hydrogen atom;

Y represents an oxygen atom, an optionally oxidized sulfur atom, a methylene group or C=O;

Z represents:

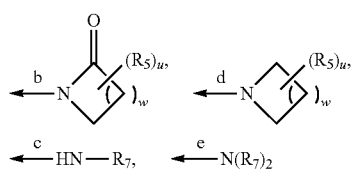

or a group:

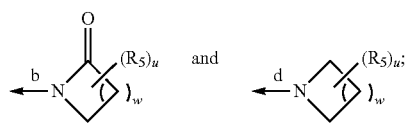

having an oxygen atom substituting for a carbon atom forming the ring;

R<sub>5</sub> represents a halogen, a hydroxy group or a C1-4 alkyl group optionally substituted with a hydroxy group;

R<sub>7</sub> respectively and independently represents:

(1) a C1-6 alkyl group, a C3-6 cycloalkyl group, a C1-6 alkyl group having an oxygen atom substituting for a carbon atom, or a C3-6 cycloalkyl group having an oxygen atom substituting for a carbon atom, all of which may be optionally substituted with:

(i) a halogen;

(ii) a C3-6 cycloalkyl group;

(iii) a hydroxy group;

(iv) an oxo group; and (v) a 4- to 6-membered monocyclic heterocycle; or (2) a hydrogen atom;

arrows b, c, d and e represent binding to the thiazole ring;

p represents an integer of 0 to 5;

q represents an integer of 0 to 7;

r represents an integer of 0 to 2;

w represents an integer of 1 to 5; and u represents an integer of 0 to 2;

provided that when p, q, r and u respectively represent an integer of 2 or more, R<sub>1</sub>, R<sub>3</sub>, R<sub>5</sub> and R<sub>6</sub> groups may be respectively and independently the same or different;

a salt thereof, an N-oxide thereof, a solvate thereof or a prodrug thereof;

[2] the compound according to the above [1], wherein the general formula (I) is:

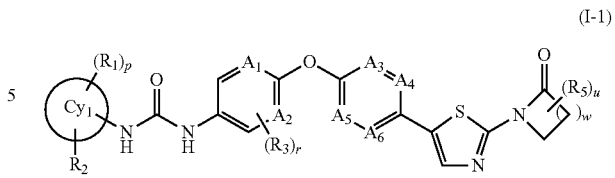

wherein all symbols represent the same meanings as those described in the above [1];

[3] the compound according to the above [2], wherein the general formula (I-1) is:

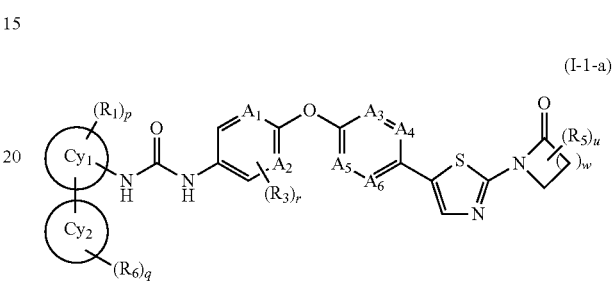

wherein all symbols represent the same meanings as those described in the above [1];

[4] the compound according to the above [2] or [3], wherein the ring Cy<sub>1</sub> is a benzene ring or a 5- to 6-membered monocyclic aromatic heterocycle;

[5] the compound according to any one of the above [1] to [4], wherein one of A<sub>1</sub> and A<sub>2</sub> is =N— and the other is =CH— or both are =N— and A<sub>3</sub>, A<sub>4</sub>, A<sub>5</sub> and A<sub>6</sub> are =CH—;

[6] the compound according to the above [1], wherein the general formula (I) is:

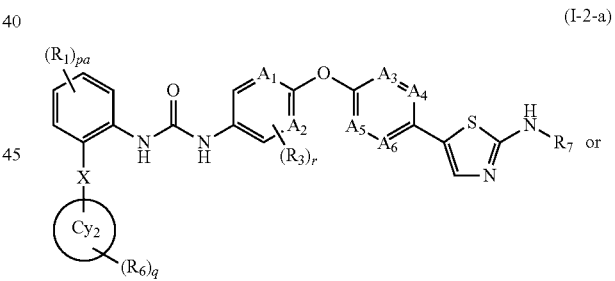

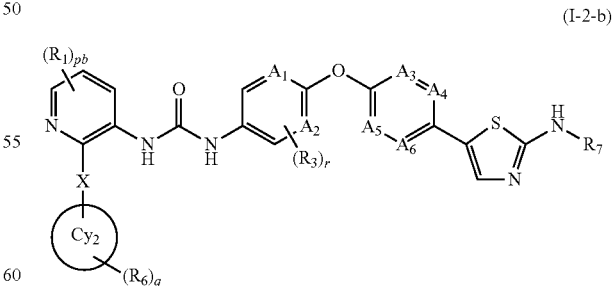

wherein pa represents an integer of 0 to 4; pb represents an integer of 0 to 3; and other symbols represent the same meanings as those described in the above [1], provided that when pa and pb respectively represent an integer of 2 or more, R<sub>1</sub> groups may be the same or different;

[7] the compound according to the above [6], wherein one of A$_1$ and A$_2$ is =N— and the other is =CH— or both are =N— and A$_3$, A$_4$, A$_5$ and A$_6$ are =CH—;

[8] the compound according to the above [1], wherein the general formula (I) is:

(I-3-a)

(I-3-b)

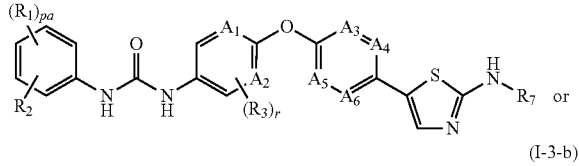

wherein all symbols represent the same meanings as those described in the above [1] and [6];

[9] the compound according to the above [8], wherein one of A$_1$ and A$_2$ is =N— and the other is =CH— or both are =N— and A$_3$, A$_4$, A$_5$ and A$_6$ are =CH—;

[10] a pharmaceutical composition comprising the compound represented by the general formula (I) described in the above [1], a salt thereof, an N-oxide thereof, a solvate thereof or a prodrug thereof as an active ingredient;

[11] the pharmaceutical composition according to the above [10], which is a Trk inhibitor;

[12] the pharmaceutical composition according to the above [10], which is a prophylactic and/or therapeutic agent for pain, pruritus, lower urinary tract dysfunction, asthma, allergic rhinitis, inflammatory bowel disease or Chagas disease;

[13] the pharmaceutical composition according to the above [12], wherein the pain is pain of osteoarthritis, cancer pain, chronic low back pain, low back pain of osteoporosis, pain of bone fracture, pain of rheumatoid arthritis, neuropathic pain, postherpetic pain, pain of diabetic neuropathy, fibromyalgia, pain of pancreatitis, pain of interstitial cystitis, pain of endometriosis, pain of irritable bowel syndrome, migraine or pain of pulpitis;

[14] a medicament which is a combination of the compound represented by the general formula (I) described in the above [1], a salt thereof, an N-oxide thereof, a solvate thereof or a prodrug thereof and at least one selected from acetaminophen, a nonsteroid antiinflammatory drug, an opioid, an antidepressant, an antiepileptic agent, an N-methyl-D-aspartate antagonist, a muscle relaxant, an antiarrhythmic agent, a steroid and a bisphosphonate;

[15] a method for prophylaxis and/or therapy of pain, pruritus, lower urinary tract dysfunction, asthma, allergic rhinitis, inflammatory bowel disease or Chagas disease, comprising administering, to a patient, an effective amount of the compound represented by the general formula (I) described in the above [1], a salt thereof, an N-oxide thereof, a solvate thereof or a prodrug thereof;

[16] the compound represented by the general formula (I) described in the above [1], a salt thereof, an N-oxide thereof, a solvate thereof or a prodrug thereof for prophylaxis and/or therapy of pain, pruritus, lower urinary tract dysfunction, asthma, allergic rhinitis, inflammatory bowel disease or Chagas disease;

[17] a method for inhibiting Trk, comprising administering, to a patient, an effective amount of the compound represented by the general formula (I) described in the above [1], a salt thereof, an N-oxide thereof, a solvate thereof or a prodrug thereof; and

[18] use of the compound represented by the general formula (I) described in the above [1], a salt thereof, an N-oxide thereof, a solvate thereof or a prodrug thereof for manufacturing a prophylactic and/or therapeutic agent for pain, pruritus, lower urinary tract dysfunction, asthma, allergic rhinitis, inflammatory bowel disease or Chagas disease.

The present compound has Trk-inhibiting activity. The present compound further has excellent kinase selectivity. In addition, the present compound persistently suppresses NGF vascular hyper permeability in an in vivo test, and thus can be a safe prophylactic and/or therapeutic agent for diseases to which Trk is involved, for example pain, pruritus, lower urinary tract dysfunction, asthma, allergic rhinitis, inflammatory bowel disease or Chagas disease.

BEST MODE FOR CARRYING OUT THE INVENTION

The present invention is hereinafter specifically described.

In the present invention, "a C3-10 monocyclic carbocycle or bicyclic carbocycle" for the ring Cy$_1$ may include, for example, cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene rings, and the like.

In the present invention, "a 4- to 10-membered monocyclic heterocycle or bicyclic heterocycle" for the ring Cy$_1$ may include, for example, oxetane, azetidine, pyrrole, imidazole, triazole, tetrazole, pyrazole, pyridine, piperidine, piperazine, pyrazine, pyrimidine, pyridazine, azepine, diazepine, furan, pyran, oxepin, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolidine, purine, phthalazine, pteridine, naphthyridine, quinoxaline, quinazoline, cinnoline, benzoxazole, benzothiazole, benzimidazole, benzodioxole, benzoxathiole, chromene, benzofurazan, benzothiadiazole, benzotriazole, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dioxaindane, benzodioxane, thiochromane, dihydrobenzodioxine, dihydrobenzoxathiine, chromane rings, and the like.

In the present invention, "a C1-6 alkyl group" in "a C1-6 alkyl group optionally substituted with a halogen or an oxo group" for $R_1$ may include methyl, ethyl, n-propyl, isopropyl, n-butyl, sec-butyl, tert-butyl, isobutyl, pentyl, 1-methylbutyl, 2-methylbutyl, 3-methylbutyl, 1,1-dimethylpropyl, 1,2-dimethylpropyl, 2,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 1-methyl-1-ethylpropyl, 2-methyl-2-ethylpropyl, 1-ethylbutyl, 2-ethylbutyl, 1,1-dimethylpentyl groups, and the like.

In the present invention, "a C3-6 cycloalkyl group" in "a C3-6 cycloalkyl group optionally substituted with a halogen or a C1-3 alkyl group" for $R_1$ may include cyclopropyl, cyclobutyl, cyclopentyl and cyclohexyl groups.

In the present invention, "a C1-3 alkyl group" in "a C3-6 cycloalkyl group optionally substituted with a halogen or a C1-3 alkyl group" for $R_1$ may include methyl, ethyl, n-propyl and isopropyl groups.

In the present invention, "a C1-6 alkyl group having an oxygen atom substituting for a carbon atom" in "a C1-6 alkyl group having an oxygen atom substituting for a carbon atom and optionally substituted with a halogen or an oxo group" for $R_1$ is a C1-6 alkyl group having an oxygen atom (—O—) that substitutes one methylene group (—CH$_2$—) in the alkyl group and may include, for example, a hydroxy group, methoxy, hydroxymethyl, ethoxy, methoxymethyl, 2-hydroxyethyl, 1-hydroxyethyl, 2-hydroxypropyl, isopropoxy, 1-methyl-2-hydroxyethyl, 1-methoxyethyl, 1-hydroxypropyl, 1-hydroxy-1-methylethyl, 1-hydroxy-1-methylpropyl, 2-hydroxy-1-methylpropyl and 2-hydroxy, 2-methylpropyl groups, and the like.

In the present invention, "a C3-6 cycloalkyl group having an oxygen atom substituting for a carbon atom and optionally substituted with a halogen or a C1-3 alkyl group" for $R_1$ represents a C3-6 cycloalkyl group having an oxygen atom substituting for a carbon atom, the cycloalkyl group optionally being substituted with a halogen, a C1-3 alkyl group or a C1-3 alkyl group having an oxygen atom substituting for a carbon atom.

In this context, "a C3-6 cycloalkyl group having an oxygen atom substituting for a carbon atom" is a C3-6 cycloalkyl group having an oxygen atom (—O—) that substitutes one methylene group (—CH$_2$—) in the cycloalkyl group and may include, for example, oxylanyl, 1-oxetanyl, 2-oxetanyl, 1-tetrahydrofuranyl, 2-tetrahydrofuranyl, 1-tetrahydro-2H-pyranyl, 2-tetrahydro-2H-pyranyl, 3-tetrahydro-2H-pyranyl groups, and the like.

Further in this context, "a C1-3 alkyl group" may include methyl, ethyl, n-propyl and isopropyl groups.

Further in this context, "a C1-3 alkyl group having an oxygen atom substituting for a carbon atom" is a C1-3 alkyl group having an oxygen atom (—O—) that substitutes one methylene group (—CH$_2$—) in the alkyl group and may include, for example, a hydroxy group, methoxy, hydroxymethyl, ethoxy, methoxymethyl, 2-hydroxyethyl, 1-hydroxyethyl groups, and the like.

In the present invention, "a C1-6 alkyl group" in "a C1-6 alkyl group optionally substituted with a substituent selected from the group consisting of: (i) a halogen; (ii) a hydroxy group; (iii) —NH(C1-3 alkyl); (iv) —N(C1-3 alkyl)$_2$; (v) an amino group; (vi) a cyano group; (vii) a nitro group; (viii) a C1-4 alkylsulfonyl group, (ix) a sulfonamide group; (x) a C1-4 alkylsulfonamide group; (xi) an oxo group; (xii) a carboxyl group; (xiii) —C(O)(O—C1-4 alkyl); (xiv) a phosphonooxy group; (xv) —OP(O) (O—C1-4 alkyl)$_2$; (xvi) a carbamoyl group; (xvii) a C1-4 alkylamide group; and (xviii) a C1-4 alkylcarbamate group" for $R_2$ may include methyl, ethyl, n-propyl, isopropyl, n-butyl, sec-butyl, tert-butyl, isobutyl, pentyl, 1-methylbutyl, 2-methylbutyl, 3-methylbutyl, 1,1-dimethylpropyl, 1,2-dimethylpropyl, 2,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 1-methyl-1-ethylpropyl, 2-methyl-2-ethylpropyl, 1-ethylbutyl, 2-ethylbutyl, 1,1-dimethylpentyl groups, and the like.

In the present invention, "a C2-6 alkenyl group" in "a C2-6 alkenyl group optionally substituted with a substituent selected from the group consisting of: (i) a halogen; (ii) a hydroxy group; (iii) —NH(C1-3 alkyl); (iv) —N(C1-3 alkyl)$_2$; (v) an amino group; (vi) a cyano group; (vii) a nitro group; (viii) a C1-4 alkylsulfonyl group, (ix) a sulfonamide group; (x) a C1-4 alkylsulfonamide group; (xi) an oxo group; (xii) a carboxyl group; (xiii) —C(O)(O—C1-4 alkyl); (xiv) a phosphonooxy group; (xv) —OP(O) (O—C1-4 alkyl)$_2$; (xvi) a carbamoyl group; (xvii) a C1-4 alkylamide group; and (xviii) a C1-4 alkylcarbamate group" for $R_2$ may include vinyl, 1-propenyl, 2-propenyl, 1-butenyl, 2-butenyl, 3-butenyl, 1-pentenyl, 2-pentenyl, 3-pentenyl, 4-pentenyl, 3-methyl-1-butenyl, 3-methyl-2-butenyl, 3-methyl-3-butenyl, 1-hexenyl, 2-hexenyl, 3-hexenyl, 4-hexenyl, 5-hexenyl groups, and the like.

In the present invention, "a C2-6 alkynyl group" in "a C2-6 alkynyl group optionally substituted with a substituent selected from the group consisting of: (i) a halogen; (ii) a hydroxy group; (iii) —NH(C1-3 alkyl); (iv) —N(C1-3 alkyl)$_2$; (v) an amino group; (vi) a cyano group; (vii) a nitro group; (viii) a C1-4 alkylsulfonyl group, (ix) a sulfonamide group; (x) a C1-4 alkylsulfonamide group; (xi) an oxo group; (xii) a carboxyl group; (xiii) —C(O)(O—C1-4 alkyl); (xiv) a phosphonooxy group; (xv) —OP(O) (O—C1-4 alkyl)$_2$; (xvi) a carbamoyl group; (xvii) a C1-4 alkylamide group; and (xviii) a C1-4 alkylcarbamate group" for $R_2$ may include ethynyl, 1-propynyl, 2-propynyl, 1-butynyl, 2-butynyl, 3-butynyl, 1-pentynyl, 2-pentynyl, 3-pentynyl, 4-pentynyl, 3-methyl-1-butynyl, 1-hexynyl, 2-hexynyl, 3-hexynyl, 4-hexynyl, 5-hexynyl groups, and the like.

In the present invention, "a C1-3 alkyl" in "(iii) —NH(C1-3 alkyl) and (iv) —N(C1-3 alkyl)$_2$" which are substituents of "(1) a C1-6 alkyl group, a C2-6 alkenyl group or a C2-6 alkynyl group" for $R_2$ may include methyl, ethyl, n-propyl and isopropyl groups. In case of —N(C1-3 alkyl)$_2$, the respective "C1-3 alkyl" groups may be the same or different.

In the present invention, "a C1-4 alkylsulfonyl group" in "(11) a C1-4 alkylsulfonyl group" for $R_2$ and in "(viii) a C1-4 alkylsulfonyl group" which is a substituent of "(1) a C1-6 alkyl group, a C2-6 alkenyl group or a C2-6 alkynyl group" for $R_2$ may include a methylsulfonyl group, an ethylsulfonyl group, a n-propylsulfonyl group, an isopropylsulfonyl group, a n-butylsulfonyl group, a sec-butylsulfonyl group, a tert-butylsulfonyl group and an isobutylsulfonyl group.

In the present invention, "a sulfonamide group" in "(12) a sulfonamide group" for $R_2$ and in "(ix) a sulfonamide group" which is a substituent of "(1) a C1-6 alkyl group, a C2-6 alkenyl group or a C2-6 alkynyl group" for $R_2$ is a —SO$_2$NH$_2$ group.

In the present invention, "a C1-4 alkylsulfonamide group" in "(13) a C1-4 alkylsulfonamide group" for $R_2$ and in "(x) a C1-4 alkylsulfonamide group" which is a substituent of "(1) a C1-6 alkyl group, a C2-6 alkenyl group or a C2-6 alkynyl group" for $R_2$ represents —SO$_2$NH(C1-4 alkyl), —SO$_2$N(C1-4 alkyl)$_2$, —NHSO$_2$(C1-4 alkyl), —N(C1-4 alkyl)SO$_2$(C1-4 alkyl) and —N(SO$_2$(C1-4 alkyl))$_2$, and "C1-4 alkyl" in "a C1-4 alkylsulfonamide group" may include methyl, ethyl, n-propyl, isopropyl, n-butyl, sec-butyl, tert-butyl and isobutyl groups.

In cases of —SO$_2$N(C1-4 alkyl)$_2$, —N(C1-4 alkyl)SO$_2$(C1-4 alkyl) and —N(SO$_2$(C1-4 alkyl))$_2$, the respective "C1-4 alkyl" groups may be the same or different.

In the present invention, "—C(O) (O—C1-4 alkyl)" in "(5) —C(O) (O—C1-4 alkyl)" for $R_2$ and in "(xiii) —C(O)(O—C1-4 alkyl)" which is a substituent of "(1) a C1-6 alkyl group, a C2-6 alkenyl group or a C2-6 alkynyl group" for $R_2$ represents a carboxylic ester group and may specifically include, for example, methyl ester, ethyl ester, n-propyl ester, isopropyl ester, n-butyl ester, sec-butyl ester, tert-butyl ester and isobutyl ester groups.

In the present invention, "a phosphonooxy group" in "(6) a phosphonooxy group" for $R_2$ and in "(xiv) a phosphonooxy group" which is a substituent of "(1) a C1-6 alkyl group, a C2-6 alkenyl group or a C2-6 alkynyl group" for $R_2$ is a —OP(O)(OH)$_2$ group.

In the present invention, "—OP(O) (O—C1-4 alkyl)$_2$" in "(7) —OP(O) (O—C1-4 alkyl)$_2$" for $R_2$ and in "(xv) —OP(O) (O—C1-4 alkyl)$_2$" which is a substituent of "(1) a C1-6 alkyl group, a C2-6 alkenyl group or a C2-6 alkynyl group" for $R_2$ represents a phosphonic ester group, and "C1-4 alkyl" in "—OP(O)(O—C1-4 alkyl)$_2$" may include methyl, ethyl, n-propyl, isopropyl, n-butyl, sec-butyl, tert-butyl and isobutyl groups with the respective "C1-4 alkyl" groups being the same or different.

In the present invention, "a carbamoyl group" in "(15) a carbamoyl group" for $R_2$ and in "(xvi) a carbamoyl group" which is a substituent of "(1) a C1-6 alkyl group, a C2-6 alkenyl group or a C2-6 alkynyl group" for $R_2$ is a —C(O)NH$_2$ group.

In the present invention, "a C1-4 alkylamide group" in "(16) a C1-4 alkylamide group" for $R_2$ and in "(xvii) a C1-4 alkylamide group" which is a substituent of "(1) a C1-6 alkyl group, a C2-6 alkenyl group or a C2-6 alkynyl group" for $R_2$ represents —C(O)NH(C1-4 alkyl), —C(O)N(C1-4 alkyl)$_2$, —NHC(O)(C1-4 alkyl), —N(C1-4 alkyl)C(O)(C1-4 alkyl) and —N(C(O)(C1-4 alkyl))$_2$, and "C1-4 alkyl" in "a C1-4 alkylamide group" may include methyl, ethyl, n-propyl, isopropyl, n-butyl, sec-butyl, tert-butyl and isobutyl groups. In cases of —C(O)N(C1-4 alkyl)$_2$, —N(C1-4 alkyl)C(O)(C1-4 alkyl) and —N(C(O) (C1-4 alkyl))$_2$, the respective "C1-4 alkyl" groups may be the same or different.

In the present invention, "a C1-4 alkylcarbamate group" in "(17) a C1-4 alkylcarbamate group" for $R_2$ and in "(xviii) a C1-4 alkylcarbamate group" which is a substituent of "(1) a C1-6 alkyl group, a C2-6 alkenyl group or a C2-6 alkynyl group" for $R_2$ represents —NHC(O)O(C1-4 alkyl), —N(C1-4 alkyl)C(O)O(C1-4 alkyl) and —N(C(O)O(C1-4 alkyl))$_2$, and "C1-4 alkyl" in "a C1-4 alkylcarbamate group" may include methyl, ethyl, n-propyl, isopropyl, n-butyl, sec-butyl, tert-butyl and isobutyl groups. In cases of —N(C1-4 alkyl)C(O)O(C1-4 alkyl) and —N(C(O)O(C1-4 alkyl))$_2$, the respective "C1-4 alkyl" groups may be the same or different.

In the present invention, "a C3-10 monocyclic carbocycle or bicyclic carbocycle" for the ring $Cy_2$ may include, for example, cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene and perhydronaphthalene rings.

In the present invention, "a 4- to 10-membered monocyclic heterocycle or bicyclic heterocycle" for the ring $Cy_2$ may include, for example, oxetane, azetidine, pyrrole, imidazole, triazole, tetrazole, pyrazole, pyridine, piperidine, piperazine, pyrazine, pyrimidine, pyridazine, azepine, diazepine, furan, pyran, oxepin, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolidine, purine, phthalazine, pteridine, naphthyridine, quinoxaline, quinazoline, cinnoline, benzoxazole, benzothiazole, benzimidazole, benzodioxole, benzoxathiole, chromene, benzofurazan, benzothiadiazole, benzotriazole, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dioxaindane, benzodioxane, thiochromane, dihydrobenzodioxine, dihydrobenzoxathiine, pyridine, chromane rings, and the like.

In the present invention, "a C1-6 alkyl group" in "a C1-6 alkyl group optionally substituted with a substituent selected from the group consisting of: (i) a halogen; (ii) a hydroxy group; (iii) an oxo group; (iv) —NH(C1-3 alkyl); (v) —N(C1-3 alkyl)$_2$; (vi) a C1-6 alkoxy group; (vii) an amino group; (viii) a cyano group; (ix) a nitro group; (x) a C1-4 alkylsulfonyl group; (xi) a sulfonamide group; (xii) a C1-4 alkylsulfonamide group; (xiii) a carboxyl group; (xiv) —C(O)(O—C1-4 alkyl); (xv) a phosphonooxy group; (xvi) —OP(O)(O—C1-4 alkyl)$_2$; (xvii) a carbamoyl group; (xviii) a C1-4 alkylamide group; and (xix) a C1-4 alkylcarbamate group" for $R_6$ has the same meaning as "a C1-6 alkyl group" in "a C1-6 alkyl group optionally substituted with a halogen or an oxo group" for $R_1$ as described above.

In the present invention, "a C2-6 alkenyl group" in "a C2-6 alkenyl group optionally substituted with a substituent selected from the group consisting of: (i) a halogen; (ii) a hydroxy group; (iii) an oxo group; (iv) —NH(C1-3 alkyl); (v) —N(C1-3 alkyl)$_2$; (vi) a C1-6 alkoxy group; (vii) an amino group; (viii) a cyano group; (ix) a nitro group; (x) a C1-4 alkylsulfonyl group; (xi) a sulfonamide group; (xii) a C1-4 alkylsulfonamide group; (xiii) a carboxyl group; (xiv) —C(O)(O—C1-4 alkyl); (xv) a phosphonooxy group; (xvi) —OP(O)(O—C1-4 alkyl)$_2$; (xvii) a carbamoyl group; (xviii) a C1-4 alkylamide group; and (xix) a C1-4 alkylcarbamate group" for $R_6$ has the same meaning as "a C2-6 alkenyl group" for $R_2$ as described above.

In the present invention, "a C2-6 alkynyl group" in "a C2-6 alkynyl group optionally substituted with a substituent selected from the group consisting of: (i) a halogen; (ii) a hydroxy group; (iii) an oxo group; (iv) —NH(C1-3 alkyl); (v) —N(C1-3 alkyl)$_2$; (vi) a C1-6 alkoxy group; (vii) an amino group; (viii) a cyano group; (ix) a nitro group; (x) a C1-4 alkylsulfonyl group; (xi) a sulfonamide group; (xii) a C1-4 alkylsulfonamide group; (xiii) a carboxyl group; (xiv) —C(O)(O—C1-4 alkyl); (xv) a phosphonooxy group; (xvi) —OP(O)(O—C1-4 alkyl)$_2$; (xvii) a carbamoyl group; (xviii) a C1-4 alkylamide group; and (xix) a C1-4 alkylcarbamate group" for $R_e$ has the same meaning as "a C2-6 alkynyl group" for $R_2$ as described above.

In the present invention, "a C3-6 cycloalkyl group" in "a C3-6 cycloalkyl group optionally substituted with a substituent selected from the group consisting of: (i) a halogen; (ii) a hydroxy group; (iii) an oxo group; (iv) —NH(C1-3 alkyl); (v) —N(C1-3 alkyl)$_2$; (vi) a C1-6 alkoxy group; (vii) an amino group; (viii) a cyano group; (ix) a nitro group; (x) a C1-4 alkylsulfonyl group; (xi) a sulfonamide group; (xii) a C1-4 alkylsulfonamide group; (xiii) a carboxyl group; (xiv) —C(O)(O—C1-4 alkyl); (xv) a phosphonooxy group; (xvi) —OP(O)(O—C1-4 alkyl)$_2$; (xvii) a carbamoyl group; (xviii) a C1-4 alkylamide group; and (xix) a C1-4 alkylcarbamate group" for $R_6$ has the same meaning as "a C3-6 cycloalkyl group" in "a C3-6 cycloalkyl group optionally substituted with a halogen or a C1-3 alkyl group" for $R_1$ as described above.

In the present invention, "C1-3 alkyl" in "(iv) —NH(C1-3 alkyl) and (v) —N(C1-3 alkyl)$_2$" which are substituents of "(1) a C1-6 alkyl group, a C2-6 alkenyl group, a C2-6 alkynyl group or a C3-6 cycloalkyl group" for $R_6$ and in "—NH(C1-3 alkyl) and —N(C1-3 alkyl)$_2$" in "(8) —NH(C1-3 alkyl) and (9) —N(C1-3 alkyl)$_2$" for $R_6$ may include methyl, ethyl, n-propyl and isopropyl groups. In case of —N(C1-3 alkyl)$_2$, the respective "C1-3 alkyl" groups may be the same or different.

In the present invention, "a C1-6 alkoxy group" in "(vi) a C1-6 alkoxy group" which is a substituent of "(1) a C1-6 alkyl group, a C2-6 alkenyl group, a C2-6 alkynyl group or a C3-6 cycloalkyl group" for $R_6$ may include, for example, methoxy, ethoxy, propoxy, isopropoxy, butoxy, 1-methylpropoxy, tert-butoxy, isobutoxy, pentyloxy, 1-methylbutoxy, 2-methylbutoxy, 3-methylbutoxy, 1,1-dimethylpropoxy, 1,2-dimethylpropoxy, 2,2-dimethylpropoxy, hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 1-methyl-1-ethylpropoxy, 1-methyl-2-ethylpropoxy, 1,2-dimethylbutoxy, 2,2-dimethylbutoxy, 1-ethyl-2-methylpropoxy, 2-ethyl-2-methylpropoxy and 1-ethylbutoxy groups.

In the present invention, "a C1-4 alkylsulfonyl group" in "(18) a C1-4 alkylsulfonyl group" for $R_6$ and in "(x) a C1-4 alkylsulfonyl group" which is a substituent of "(1) a C1-6 alkyl group, a C2-6 alkenyl group, a C2-6 alkynyl group or a C3-6 cycloalkyl group" for $R_6$ has the same meaning as "a C1-4 alkylsulfonyl group" in "(11) a C1-4 alkylsulfonyl group" for $R_2$ as described above.

In the present invention, "a C1-4 alkylsulfonamide group" in "(19) a C1-4 alkylsulfonamide group" for $R_6$ and "(xii) a C1-4 alkylsulfonamide group" which is a substituent of "(1) a C1-6 alkyl group, a C2-6 alkenyl group, a C2-6 alkynyl group or a C3-6 cycloalkyl group" for $R_6$ has the same meaning as "a C1-4 alkylsulfonamide group" in "(13) a C1-4 alkylsulfonamide group" for $R_2$ as described above.

In the present invention, "—C(O) (O—C1-4 alkyl)" in "(11) —C(O) (O—C1-4 alkyl)" for $R_6$ and in "(xiv) —C(O) (O—C1-4 alkyl)" which is a substituent of "(1) a C1-6 alkyl group, a C2-6 alkenyl group, a C2-6 alkynyl group or a C3-6 cycloalkyl group" for $R_6$ has the same meaning as "—C(O) (O—C1-4 alkyl)" in "(5) —C(O) (O—C1-4 alkyl)" for $R_2$ as described above.

In the present invention, "a carbamoyl group" in "(12) a carbamoyl group" for $R_6$ and in "(xvii) a carbamoyl group" which is a substituent of "(1) a C1-6 alkyl group, a C2-6 alkenyl group, a C2-6 alkynyl group or a C3-6 cycloalkyl group" for $R_6$ is a —C(O)NH$_2$ group.

In the present invention, "a C1-4 alkylamide group" in "(13) a C1-4 alkylamide group" for $R_6$ and in "(xviii) a C1-4 alkylamide group" which is a substituent of "(1) a C1-6 alkyl group, a C2-6 alkenyl group, a C2-6 alkynyl group or a C3-6 cycloalkyl group" for $R_6$ has the same meaning as "a C1-4 alkylamide group" in "(16) a C1-4 alkylamide group" for $R_2$ described above.

In the present invention, "a C1-4 alkylcarbamate group" in "(20) a C1-4 alkylcarbamate group" for $R_6$ and in "(xix) a C1-4 alkylcarbamate group" which is a substituent of "(1) a C1-6 alkyl group, a C2-6 alkenyl group, a C2-6 alkynyl group or a C3-6 cycloalkyl group" for $R_6$ has the same meaning as "a C1-4 alkylcarbamate group" in "(17) a C1-4 alkylcarbamate group" for $R_2$ as described above.

In the present invention, "a C1-4 alkoxy group" in "(3) a C1-4 alkoxy group" for $R_6$ may include, for example, methoxy, ethoxy, propoxy, isopropoxy, butoxy, 1-methylpropoxy, tert-butoxy, isobutoxy and the like.

In the present invention, "a phosphonooxy group" in "(4) a phosphonooxy group" for $R_6$ and in "(xv) a phosphonooxy group" which is a substituent of "(1) a C1-6 alkyl group, a C2-6 alkenyl group, a C2-6 alkynyl group or a C3-6 cycloalkyl group" for $R_6$ is a —OP(O)(OH)$_2$ group.

In the present invention, "—OP(O) (O—C1-4 alkyl)$_2$" in "(5) —OP(O) (O—C1-4 alkyl)$_2$" for $R_6$ and in "(xvi) —OP(O) (O—C1-4 alkyl)$_2$" which is a substituent of "(1) a C1-6 alkyl group, a C2-6 alkenyl group, a C2-6 alkynyl group or a C3-6 cycloalkyl group" for $R_6$ represents a phosphonic ester group, and "C1-4 alkyl" in "—OP(O) (O—C1-4 alkyl)$_2$" may include methyl, ethyl, n-propyl, isopropyl, n-butyl, sec-butyl, tert-butyl and isobutyl groups with the respective "C1-4 alkyl" being the same or different.

In the present invention, "a sulfonamide group" in "(6) a sulfonamide group" for $R_6$ and in "(xi) a sulfonamide group" which is a substituent of "(1) a C1-6 alkyl group, a C2-6 alkenyl group, a C2-6 alkynyl group or a C3-6 cycloalkyl group" for $R_6$ is a —SO$_2$NH$_2$ group.

In the present invention, "a C1-3 alkyl group" in "a C1-3 alkyl group optionally substituted with a halogen" for $R_3$ has the same meaning as "a C1-3 alkyl group" in "a C3-6 cycloalkyl group optionally substituted with a halogen or a C1-3 alkyl group" for $R_1$ as described above.

In the present invention, "a C1-3 alkoxy group" in "a C1-3 alkoxy group optionally substituted with a halogen" for $R_3$ may include methoxy, ethoxy, propoxy and isopropoxy groups.

In the present invention, "a C1-3 alkyl group" in "a C1-3 alkyl group optionally substituted with a halogen" for $R_4$ has the same meaning as "a C1-3 alkyl group" in "a C3-6 cycloalkyl group optionally substituted with a halogen or a C1-3 alkyl group" for $R_1$ as described above.

In the present invention, "a C1-3 alkoxy group" in "a C1-3 alkoxy group optionally substituted with a halogen" for $R_4$ has the same meaning as "a C1-3 alkoxy group" in "a C1-3 alkoxy group optionally substituted with a halogen" for $R_3$ as described above.

In the present invention, "an optionally oxidized sulfur atom" for Y represents "a sulfur atom" and "an oxidized sulfur atom" and "an oxidized sulfur atom" represents a sulfoxide group (—SO—) and a sulfonyl group (—SO$_2$—).

In the present invention, "a group:

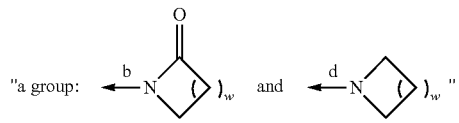

having an oxygen atom substituting for a carbon atom forming the ring" for Z is a group having an oxygen atom (—O—) which substitutes one methylene group (—CH$_2$—) forming the ring and may include, for example:

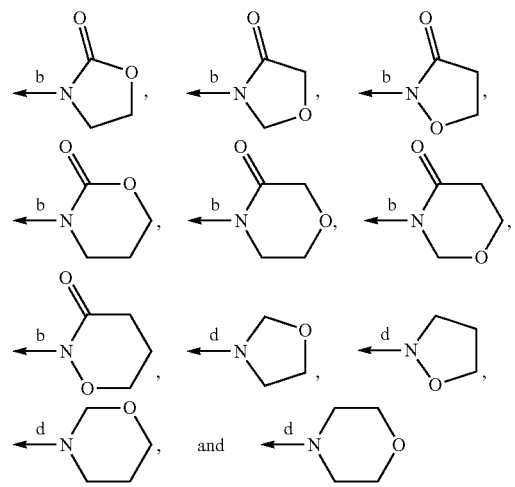

rings.

In the present invention, "a C1-4 alkyl group" in "a C1-4 alkyl group optionally substituted with a hydroxy group" for $R_5$ may include methyl, ethyl, n-propyl, isopropyl, n-butyl, sec-butyl, tert-butyl and isobutyl groups.

In the present invention, "a C1-6 alkyl group" in "(1) a C1-6 alkyl group, a C3-6 cycloalkyl group, a C1-6 alkyl group having an oxygen atom substituting for a carbon atom or a C3-6 cycloalkyl group having an oxygen atom substituting for a carbon atom" for $R_7$ has the same meaning as "a C1-6 alkyl group" in "a C1-6 alkyl group optionally substituted with a halogen or an oxo group" for $R_1$ as described above.

In the present invention, "a C1-6 alkyl group having an oxygen atom substituting for a carbon atom" in "(1) a C1-6 alkyl group, a C3-6 cycloalkyl group, a C1-6 alkyl group having an oxygen atom substituting for a carbon atom or a C3-6 cycloalkyl group having an oxygen atom substituting for a carbon atom" for $R_7$ is a C1-6 alkyl group having an oxygen atom (—O—) which substitutes one methylene group (—CH$_2$—) in the alkyl group and may include, for example, a hydroxy group, methoxy, hydroxymethyl, ethoxy, methoxymethyl, 2-hydroxyethyl, 1-hydroxyethyl, 2-hydroxypropyl, isopropoxy, 1-methyl-2-hydroxyethyl, 1-methoxyethyl, 1-hydroxypropyl, 1-hydroxy-1-methylethyl, butoxy, propoxymethyl, 2-ethoxyethyl, 3-methoxypropyl, 1-ethoxyethyl, 1-methoxypropan-2-yl, sec-butoxy, 2-methoxypropyl, isobutoxy, isopropoxymethyl, 1-hydroxy-1-methylpropyl, 2-hydroxy-1-methylpropyl and 2-hydroxy 2-methylpropyl groups.

In the present invention, "a C3-6 cycloalkyl group" in "(1) a C1-6 alkyl group, a C3-6 cycloalkyl group, a C1-6 alkyl group having an oxygen atom substituting for a carbon atom or a C3-6 cycloalkyl group having an oxygen atom substituting for a carbon atom" for $R_7$ and in "(ii) a C3-6 cycloalkyl group" which is a substituent of "(1) a C1-6 alkyl group, a C3-6 cycloalkyl group, a C1-6 alkyl group having an oxygen atom substituting for a carbon atom or a C3-6 cycloalkyl group having an oxygen atom substituting for a carbon atom" for $R_7$ has the same meaning as "a C3-6 cycloalkyl group" in "a C3-6 cycloalkyl group optionally substituted with a halogen or a C1-3 alkyl group" for $R_1$ as described above.

In the present invention, "a C3-6 cycloalkyl group having an oxygen atom substituting for a carbon atom" in "(1) a C1-6 alkyl group, a C3-6 cycloalkyl group, a C1-6 alkyl group having an oxygen atom substituting for a carbon atom or a C3-6 cycloalkyl group having an oxygen atom substituting for a carbon atom" for $R_7$ is, for example, a C3-6 cycloalkyl group having an oxygen atom (—O—) which substitutes one methylene group (—CH$_2$—) in the cycloalkyl group, and may include oxiranyl, 1-oxetanyl, 2-oxetanyl, 1-tetrahydrofuranyl, 2-tetrahydrofuranyl, 1-tetrahydro-2H-pyranyl, 2-tetrahydro-2H-pyranyl, 3-tetrahydro-2H-pyranyl groups, and the like.

In the present invention, "a 4- to 6-membered monocyclic heterocycle" in "(v) a 4- to 6-membered monocyclic heterocycle" which is a substituent of "(1) a C1-6 alkyl group, a C3-6 cycloalkyl group, a C1-6 alkyl group having an oxygen atom substituting for a carbon atom or a C3-6 cycloalkyl group having an oxygen atom substituting for a carbon atom" for $R_7$ may include oxetane, thietane, azetidine, pyrrole, imidazole, triazole, tetrazole, pyrazole, pyridine, piperidine, piperazine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, cycloxabutane, oxathiane rings, and the like.

In the present invention, "a halogen" may include fluorine, chlorine, bromine and iodine.

In the present invention, "a 5- to 6-membered monocyclic aromatic heterocycle" for the ring $Cy_1$ may include, for example, furan, thiophene, pyrrole, isoxazole, oxazole, isothiazole, thiazole, pyrazole, imidazole, 1,2,3-triazole, 1,2,4-triazole, tetrazole, pyridine, pyridazine, pyrimidine, pyrazine, 1,2,4-triazine, 1,2,3-triazine rings, and the like.

In the present invention, the phrase "optionally substituted" indicates unsubstitution or substitution with any number of substituents. The number of substituents is preferably 1 to 10, more preferably 1 to 8 and still more preferably 1 to 6.

In the present invention, the ring $Cy_1$ is preferably benzene, naphthalene, cyclohexane, piperidine and a 5- to 10-membered monocyclic aromatic heterocycle or bicyclic aromatic heterocycle, more preferably benzene, cyclohexane, piperidine and a 5- to 6-membered monocyclic aromatic heterocycle, still more preferably benzene and a 5- to 6-membered monocyclic aromatic heterocycle, yet more preferably benzene, furan, thiophene, pyrrole, isoxazole, oxazole, isothiazole, thiazole, pyrazole, imidazole, pyridine, pyridazine, pyrimidine or pyrazine, particularly preferably benzene, pyridine or pyrazole and the most preferably benzene or pyridine.

In the present invention, $R_1$ is preferably (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl, or (9) an oxetanyl group substituted with a methyl group, more preferably a halogen, a methyl, trifluoromethyl, tert-butyl, 1,1-difluoroethyl, isopropyl, cyclopropyl, oxetanyl or difluoromethyl group, still more preferably a halogen, methyl or trifluoromethyl and particularly preferably trifluoromethyl.

In the present invention, $R_2$ is preferably isopropyl, sec-butyl, tert-butyl, isobutyl, a hydrogen atom, a hydroxy group, a carboxyl group, 1-hydroxy-1-methylethyl, 2-hydroxypropyl, 3-hydroxy-3-methyl-1-butynyl, methylsulfonyl (—SO$_2$CH$_3$), methylsulfonamide (—SO$_2$NHCH$_3$) or dimethylsulfonamide (—SO$_2$N(CH$_3$)$_2$) group, or:

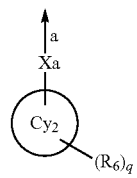

wherein, Xa represents a bond or an oxygen atom and other symbols represent the same meanings as those described in the above [1]; more preferably an isopropyl, methylsulfonyl, methylsulfonamide or dimethylsulfonamide group, or:

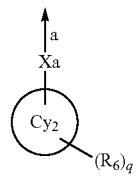

wherein, Xa represents a bond or an oxygen atom and other symbols represent the same meanings as those described in the above [1]; and still more preferably:

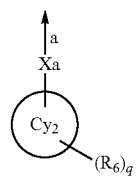

wherein, Xa represents a bond or an oxygen atom and other symbols represent the same meanings as those described in the above [1].

In the present invention, X is preferably a bond or an oxygen atom and more preferably a bond.

In the present invention, Xa is preferably a bond.

In the present invention, the ring $Cy_2$ is preferably a C3-10 monocyclic carbocycle or a 5- to 10-membered monocyclic heterocycle or bicyclic heterocycle, more preferably cyclopropane, benzene, cyclohexane, indane, tetrahydronaphthalene, pyran, furan, thiophene, pyrrole, isoxazole, oxazole, isothiazole, thiazole, pyrazole, imidazole, triazole, pyridine, pyridone, pyridazine, pyrimidine, pyrazine, tetrahydropyran, tetrahydrothiopyran, piperidine, morpholine, thiomorpholine, tetrahydropyridine, benzodioxane, piperazine, perhydroindene, dihydrobenzofuran, dihydrobenzothiophene, indoline, benzodioxole, benzoxathiole, dihydrobenzoxazole, dihydrobenzothiazole, chromane, thiochromane, tetrahydroquinoline, dihydrobenzodioxine, dihydrobenzoxathiine, dihydrobenzoxazine, indole, benzofuran, benzothiophene, indazole or tetrahydronaphthalene, still more preferably benzene, cyclohexane, pyrazole, imidazole, triazole or pyridine, particularly preferably benzene, pyridine, pyrazole, imidazole or triazole and the most preferably benzene or pyridine.

In the present invention, $R_e$ is preferably a halogen, a hydroxy group, a C1-4 alkyl, a C1-4 alkyl substituted with a halogen, a C1-4 alkyl substituted with a hydroxy group, a C3-6 cycloalkyl, a C1-4 alkoxy, carboxyl, —CO$_2$(C1-4 alkyl), an acetylamide group (—NHCOCH$_3$), a phosphonooxy group and/or a sulfonamide group, more preferably a fluorine, a chlorine, methyl, trifluoromethyl, ethyl, n-propyl, isopropyl, cyclopropyl, cyclobutyl, cyclopentyl, cyclohexyl, methoxy, ethoxy, n-propoxy, isopropoxy, n-butoxy, sec-butoxy, tert-butoxy, isobutoxy, 1-hydroxypropyl, 1-hydroxyethyl, hydroxymethyl, carboxyl, methoxycarbonyl, ethoxycarbonyl or an acetylamide group, a phosphonooxy group or a sulfonamide group, still more preferably a fluorine, a chlorine, methyl, trifluoromethyl, ethyl, n-propyl, isopropyl, methoxy, ethoxy, n-propoxy, n-butoxy, hydroxymethyl, methoxycarbonyl or an acetylamide group, a phosphonooxy group or a sulfonamide group, particularly preferably a fluorine, a chlorine, methyl, trifluoromethyl, ethyl, methoxy or hydroxymethyl and the most preferably a fluorine, a chlorine, methyl or trifluoromethyl.

In the present invention, $R_3$ is preferably fluorine, chlorine, methyl, trifluoromethyl or a methoxy group and still more preferably a fluorine.

In the present invention, $R_4$ is preferably a hydrogen, a fluorine, a chlorine, methyl, trifluoromethyl or a methoxy group, more preferably a hydrogen, a fluorine, a chlorine or a methoxy group and still more preferably a hydrogen or a fluorine.

In the present invention, Y is preferably an oxygen atom.
In the present invention, Z is preferably:

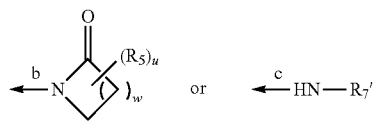

more preferably:

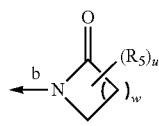

wherein all symbols represent the same meanings as those described in the above [1].

In the present invention, $R_5$ is preferably a hydroxy group or a hydroxymethyl group.

In the present invention, $R_7$ is preferably a C1-6 alkyl, more preferably ethyl, n-propyl, isopropyl or a tert-butyl group and still more preferably an n-propyl group.

In the present invention, p is preferably an integer of 0 to 2.
In the present invention, q is preferably an integer of 0 to 2.
In the present invention, r is preferably an integer of 0 to 2.
In the present invention, w is preferably an integer of 2 to 4.
In the present invention, u is preferably an integer of 0 to 1.
In the present invention, pa is preferably an integer of 0 to 2.

In the present invention, pb is preferably an integer of 0 to 2.

In the present invention, pc as described hereinbelow is preferably an integer of 0 to 1.

In the present invention, ra as described hereinbelow is preferably an integer of 0 to 1.

In the present invention, t as described hereinbelow is preferably an integer of 0 to 2.

In the present invention, the general formula (I) is preferably those having the combinations of preferable definitions for the ring $Cy_1$, $R_1$, $R_2$, X, the ring $Cy_2$, $R_6$, $R_3$, $R_4$, Y, Z, $R_5$, $R_7$, p, q, r, w, u, pa, pb, pc, ra and t, and more preferably a compound represented by:

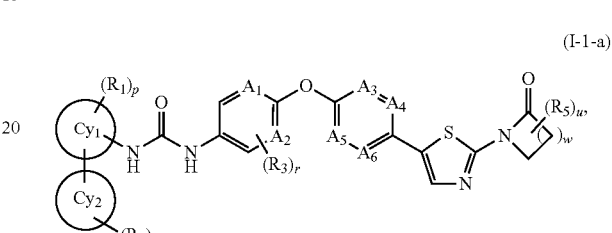

(I-1-a)

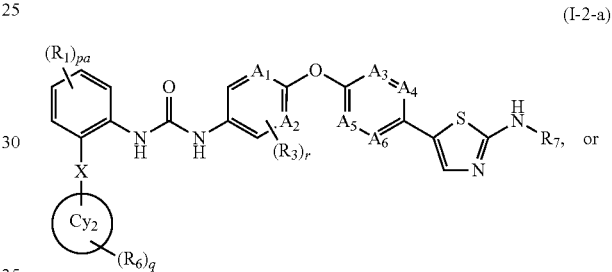

(I-2-a)

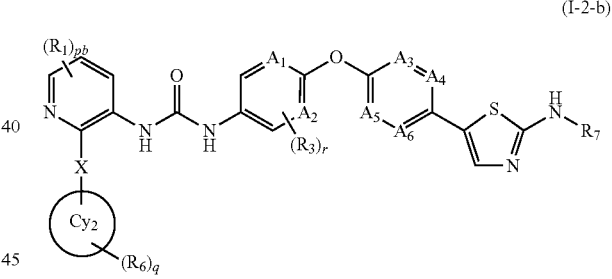

(I-2-b)

wherein all symbols represent the same meanings as those described in the above [1] and [6]; a salt thereof, an N-oxide thereof, a solvate thereof or a prodrug thereof.

Among the compounds represented by the general formula (I), the compound represented by the general formula (I-1-a) is still more preferably a compound represented by the following general formula (I-1-a-1) or general formula (I-1-a-2):

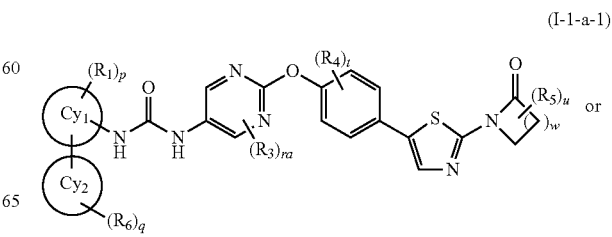

(I-1-a-1)

(I-1-a-2)

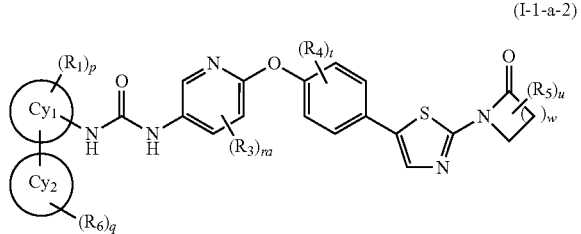

(I-1-a-2-ii)

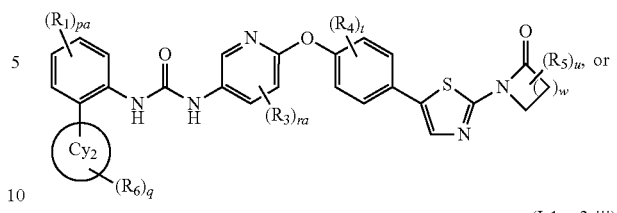

wherein ra represents an integer of 0 to 3; t represents an integer of 0 to 4; and other symbols represent the same meanings as those described in the above [1]; a salt thereof, an N-oxide thereof, a solvate thereof or a prodrug thereof.

Among the compounds represented by the general formula (I), the compound represented by the general formula (I-1-a-1) or the compound represented by the general formula (I-1-a-2) is particularly preferably a compound represented by the following general formula (I-1-a-1-i), general formula (I-1-a-1-ii), general formula (I-1-a-1-iii), general formula (I-1-a-2-i), general formula (I-1-a-2-ii) or general formula (I-1-a-2-iii):

(I-1-a-1-i)

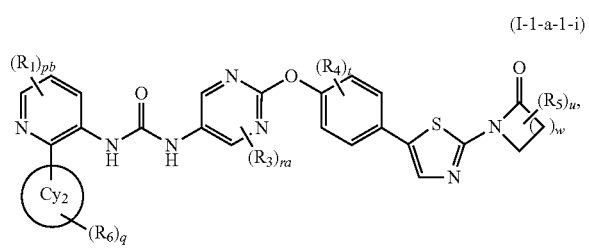

(I-1-a-1-ii)

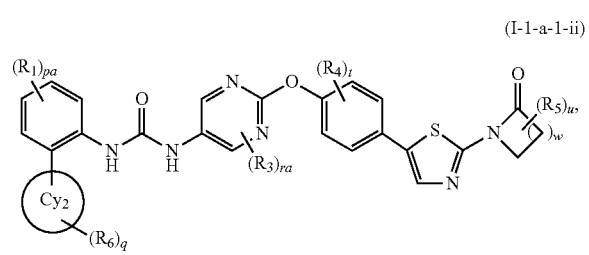

(I-1-a-1-iii)

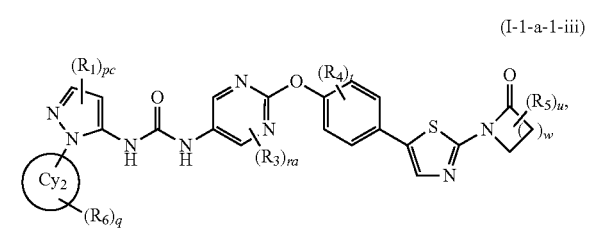

(I-1-a-2-i)

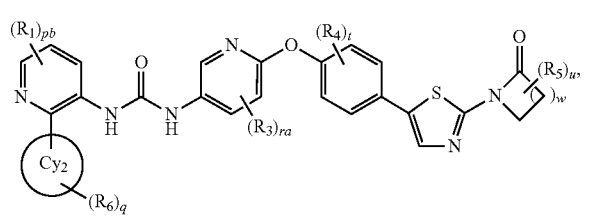

wherein ra represents an integer of 0 to 3; t represents an integer of 0 to 4; pc represents an integer of 0 to 2; and other symbols represent the same meanings as those described in the above [1] and [6]; a salt thereof, an N-oxide thereof, a solvate thereof or a prodrug thereof.

Among the compounds represented by the general formula (I), the compound represented by the general formula (I-1-a-1-i), the compound represented by the general formula (I-1-a-1-ii), the compound represented by the general formula (I-1-a-1-iii), the compound represented by the general formula (I-1-a-2-i), the compound represented by the general formula (I-1-a-2-ii) or the compound represented by the general formula (I-1-a-2-iii) is particularly preferably a compound having the general formula wherein the ring $Cy_2$ is a C3-10 monocyclic carbocycle or a 5- to 10-membered monocyclic heterocycle or bicyclic heterocycle; $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_3$ is a fluorine, a chlorine, methyl, trifluoromethyl or a methoxy group; $R_4$ is a fluorine, a chlorine, methyl, trifluoromethyl or a methoxy group; $R_5$ is a hydroxy group or a hydroxymethyl group; $R_6$ is (1) a halogen, (2) a hydroxy group, (3) a C1-4 alkyl, (4) a C1-4 alkyl substituted with a halogen, (5) a C1-4 alkyl substituted with a hydroxy group, (6) a C3-6 cycloalkyl, (7) a C1-4 alkoxy, (8) carboxyl, (9) —$CO_2$(C1-4 alkyl), (10) an acetylamide group, (11) a phosphonooxy group or (12) a sulfonamide group; pa is an integer of 0 to 2; pb is an integer of 0 to 2; pc is an integer of 0 to 1; q is an integer of 0 to 2; ra is an integer of 0 to 1; t is an integer of 0 to 2; u is an integer of 0 to 1; and w is an integer of 2 to 4; a salt thereof, an N-oxide thereof, a solvate thereof or a prodrug thereof, more preferably a compound having the general formula wherein the ring $Cy_2$ is cyclopropane, benzene, cyclohexane, indane, tetrahydronaphthalene, pyran, furan, thiophene, pyrrole, isoxazole, oxazole, isothiazole, thiazole, pyrazole, imidazole, triazole, pyridine, pyridone, pyridazine, pyrimidine, pyrazine, tetrahydropyran, tetrahydrothiopyran, piperidine, morpholine, thiomorpholine, tetrahydropyridine, benzodioxane, piperazine, perhydroindene, dihydrobenzofuran, dihydrobenzothiophene, indoline, benzodioxole, benzoxathiole, dihydrobenzoxazole, dihydrobenzothiazole, chromane, thiochromane, tetrahydroquinoline, dihydrobenzodioxine, dihydrobenzoxathiine, dihydrobenzoxazine, indole, benzofuran, benzothiophene, indazole or tetrahydronaphthalene; $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_3$ is a fluorine, a chlorine, methyl, trifluoromethyl or a methoxy group; $R_4$ is a fluorine, a chlorine, methyl, trifluoromethyl or a methoxy group; $R_5$ is a hydroxy group or a hydroxymethyl group; $R_6$ is (1) a halogen, (2) a hydroxy group, (3) a C1-4 alkyl, (4) a C1-4 alkyl substituted with a halogen, (5) a C1-4 alkyl substituted with a hydroxy group, (6) a C3-6 cycloalkyl, (7) a C1-4 alkoxy, (8) carboxyl, (9) —$CO_2$(C1-4 alkyl), (10) an acetylamide group, (11) a phosphonooxy group or (12) a sulfonamide group; pa is an integer of 0 to 2; pb is an integer of 0 to 2; pc is an integer of 0 to 1; q is an integer of 0 to 2; ra is an integer of 0 to 1; t is an integer of 0 to 2; u is an integer of 0 to 1; and w is an integer of 2 to 4; a salt thereof, an N-oxide thereof, a solvate thereof or a prodrug thereof, still more preferably a compound having the general formula wherein the ring $Cy_2$ is benzene, pyridine, pyrazole, imidazole or triazole; $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_3$ is a fluorine, a chlorine, methyl, trifluoromethyl or a methoxy group; $R_4$ is a fluorine, a chlorine, methyl, trifluoromethyl or a methoxy group; $R_5$ is a hydroxy group or a hydroxymethyl group; $R_6$ is (1) a halogen, (2) a hydroxy group, (3) a C1-4 alkyl, (4) a C1-4 alkyl substituted with a halogen, (5) a C1-4 alkyl substituted with a hydroxy group, (6) a C3-6 cycloalkyl, (7) a C1-4 alkoxy, (8) carboxyl, (9) —$CO_2$(C1-4 alkyl), (10) an acetylamide group, (11) a phosphonooxy group or (12) a sulfonamide group; pa is an integer of 0 to 2; pb is an integer of 0 to 2; pc is an integer of 0 to 1; q is an integer of 0 to 2; ra is an integer of 0 to 1; t is an integer of 0 to 2; u is an integer of 0 to 1 and w is an integer of 2 to 4; a salt thereof, an N-oxide thereof, a solvate thereof or a prodrug thereof.

Among the compounds represented by the general formula (I), the compound represented by the general formula (I-1-a-1) or the compound represented by the general formula (I-1-a-2) is the most preferably:

(1) 1-[5,6'-bis(trifluoromethyl)-2,3'-bipyridin-3-yl]-3-(2-{4-[2-(2-oxo-1-piperidinyl)-1,3-thiazol-5-yl]phenoxy}-5-pyrimidinyl)urea, (2) 1-[5,6'-bis(trifluoromethyl)-2,3'-bipyridin-3-yl]-3-(2-{4-[2-(2-oxo-1-pyrrolidinyl)-1,3-thiazol-5-yl]phenoxy}-5-pyrimidinyl)urea, (3) 1-[2-(3,4-dimethylphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea, (4) 1-[2-(3,4-dimethylphenyl)-5-(trifluoromethyl)-3-pyridinyl]-3-(2-{4-[2-(2-oxo-1-piperidinyl)-1,3-thiazol-5-yl]phenoxy}-5-pyrimidinyl)urea, (5) 1-(2-{4-[2-(2-oxo-1-piperidinyl)-1,3-thiazol-5-yl]phenoxy}-5-pyrimidinyl)-3-[2-phenyl-5-(trifluoromethyl)-3-pyridinyl]urea, (6) 1-[2-(2-methylphenyl)-5-(trifluoromethyl)-3-pyridinyl]-3-(2-{4-[2-(2-oxo-1-piperidinyl)-1,3-thiazol-5-yl]phenoxy}-5-pyrimidinyl)urea, (7) 1-(2-{4-[2-(2-oxo-1-pyrrolidinyl)-1,3-thiazol-5-yl]phenoxy})-5-pyrimidinyl)-3-[2-phenyl-5-(trifluoromethyl)-3-pyridinyl]urea, (8) 1-[2-(2-methylphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea, (9) 1-[2-(4-methylphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,

(10) 1-[2-(3-methylphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,

(11) 1-[2-(3,4-dimethylphenyl)-5-(trifluoromethyl)-3-pyridinyl]-3-(2-{4-[2-(2-oxo-1-azepanyl)-1,3-thiazol-5-yl]phenoxy}-5-pyrimidinyl)urea,

(12) 1-[2-(1-methyl-1H-pyrazol-4-yl)-5-(trifluoromethyl)-3-pyridinyl]-3-(2-{4-[2-(2-oxo-1-piperidinyl)-1,3-thiazol-5-yl]phenoxy}-5-pyrimidinyl)urea,

(13) 1-[1-(3,4-dimethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(14) 1-[1-(3,4-dimethylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(15) 1-[1-(2,3-dihydro-1H-inden-5-yl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(16) 1-[1-(2,3-dihydro-1H-inden-5-yl)-3-(2-methyl-2-propanyl)-1H-pyrazol-5-yl]-3-(2-{2-fluoro-4-[2-(2-oxo-1-pyrrolidinyl)-1,3-thiazol-5-yl]phenoxy}-5-pyrimidinyl)urea,

(17) 1-[1-(2,3-dihydro-1H-inden-5-yl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(18) 1-[1-(2,3-dihydro-1H-inden-5-yl)-3-(2-methyl-2-propanyl)-1H-pyrazol-5-yl]-3-(2-{3-fluoro-4-[2-(2-oxo-1-pyrrolidinyl)-1,3-thiazol-5-yl]phenoxy})-5-pyrimidinyl)urea,

(19) 1-(2-{2-chloro-4-[2-(2-oxo-1-pyrrolidinyl)-1,3-thiazol-5-yl]phenoxy}-5-pyrimidinyl)-3-[1-(2,3-dihydro-1H-inden-5-yl)-3-(2-methyl-2-propanyl)-1H-pyrazol-5-yl]urea,

(20) 1-[1-(2,3-dihydro-1H-inden-5-yl)-3-(2-methyl-2-propanyl)-1H-pyrazol-5-yl]-3-(2-{4-[2-(2-oxo-1-azepanyl)-1,3-thiazol-5-yl]phenoxy}-5-pyrimidinyl)urea,

(21) 1-{1-[3-(hydroxymethyl)-4-methylphenyl]-3-(2-methyl-2-propanyl)-1H-pyrazol-5-yl}-3-(2-{4-[2-(2-oxo-1-pyrrolidinyl)-1,3-thiazol-5-yl]phenoxy})-5-pyrimidinyl)urea,

(22) 1-{1-[4-(hydroxymethyl)-3-methylphenyl]-3-(2-methyl-2-propanyl)-1H-pyrazol-5-yl}-3-(2-{4-[2-(2-oxo-1-pyrrolidinyl)-1,3-thiazol-5-yl]phenoxy})-5-pyrimidinyl)urea,

(23) 1-{3-(2-methyl-2-propanyl)-1-[4-methyl-3-(trifluoromethyl)phenyl]-1H-pyrazol-5-yl}-3-(2-{4-[2-(2-oxo-1-pyrrolidinyl)-1,3-thiazol-5-yl]phenoxy}-5-pyrimidinyl)urea,

(24) 1-[3-(2-methyl-2-propanyl)-1-[3,4,5-trimethylphenyl]-1H-pyrazol-5-yl]-3-(2-{4-[2-(2-oxo-1-piperidinyl)-1,3-thiazol-5-yl]phenoxy})-5-pyrimidinyl)urea,

(25) 1-[3-(2-methyl-2-propanyl)-1-[3,4,5-trimethylphenyl]-1H-pyrazol-5-yl]-3-(2-{4-[2-(2-oxo-1-pyrrolidinyl)-1,3-thiazol-5-yl]phenoxy}-5-pyrimidinyl)urea,

(26) 1-[1-(4-fluorophenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(27) 1-[1-(4-methoxy-3,5-dimethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy})-5-pyrimidinyl)urea,

(28) 1-{3-(2-methyl-2-propanyl)-1-[4-(trifluoromethyl)phenyl]-1H-pyrazol-5-yl}-3-(2-{4-[2-(2-oxo-1-pyrrolidinyl)-1,3-thiazol-5-yl]phenoxy}-5-pyrimidinyl)urea,

(29) 1-[3-(2-methyl-2-propanyl)-1-phenyl-1H-pyrazol-5-yl]-3-(2-{4-[2-(2-oxo-1-pyrrolidinyl)-1,3-thiazol-5-yl]phenoxy}-5-pyrimidinyl)urea,

(30) 1-[1-(4-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(31) 1-[1-mesityl-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(32) 1-[1-(2-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(33) 1-[1-(2,3-dihydro-1-benzofuran-5-yl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(34) 1-[1-(2,3-dimethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(35) 1-[l-(4-methoxyphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(36) 1-[1-(4-fluoro-2-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(37) 1-[1-(2-fluorophenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(38) 1-[1-(2-fluoro-3-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(39) 1-[1-(3-fluorophenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(40) 1-[1-(2-methylphenyl)-3-(2-methyl-2-propanyl)-H-pyrazol-5-yl]-3-(2-{4-[2-(2-oxo-1-piperidinyl)-1,3-thiazol-5-yl]phenoxy}-5-pyrimidinyl)urea,

(41) methyl 3-[3-(2-methyl-2-propanyl)-5-{[(2-{4-[2-(2-oxo-1-pyrrolidinyl)-1,3-thiazol-5-yl]phenoxy}-5-pyrimidinyl)carbamoyl]amino}-1H-pyrazol-1-yl]benzoate,

(42) N-{4-[3-(2-methyl-2-propanyl)-5-{[(2-{4-[2-(2-oxo-1-pyrrolidinyl)-1,3-thiazol-5-yl]phenoxy}-5-pyrimidinyl)carbamoyl]amino}-1H-pyrazol-1-yl]phenyl}acetamide,

(43) 1-[1-(1,3-benzodioxol-5-yl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(44) 1-[3-(2-methyl-2-propanyl)-1-phenyl-1H-pyrazol-5-yl]-3-(2-{4-[2-(2-oxo-1-piperidinyl)-1,3-thiazol-5-yl]phenoxy}-5-pyrimidinyl)urea,

(45) 1-[1-(2,3-dimethoxyphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(46) 1-[1-(2-fluoro-4-methoxyphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(47) 1-{1-[2-fluoro-4-(trifluoromethyl)phenyl]-3-(2-methyl-2-propanyl)-1H-pyrazol-5-yl}-3-(2-{4-[2-(2-oxo-1-piperidinyl)-1,3-thiazol-5-yl]phenoxy}-5-pyrimidinyl)urea,

(48) 1-[1-(2-chloro-4-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(49) 1-[1-(2,5-dimethylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(50) 1-[1-(2-fluorophenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(51) 1-[1-(2-fluoro-4-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(52) 1-[1-(4-fluorophenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(53) 1-[1-(3-butoxyphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(54) 1-[3-(2-methyl-2-propanyl)-1-(4-propylphenyl)-1H-pyrazol-5-yl]-3-(2-{4-[2-(2-oxo-1-piperidinyl)-1,3-thiazol-5-yl]phenoxy}-5-pyrimidinyl)urea,

(55) 1-[1-(3-chloro-4-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(56) 1-{3-(2-methyl-2-propanyl)-1-[4-(trifluoromethyl)phenyl]-1H-pyrazol-5-yl}-3-(2-{4-[2-(2-oxo-1-piperidinyl)-1,3-thiazol-5-yl]phenoxy}-5-pyrimidinyl)urea,

(57) 1-[1-(4-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(58) 1-[1-(3-methoxy-4-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(59) 1-[1-(3-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(60) 1-[1-(3,4-dihydro-2H-chromen-6-yl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(61) 1-{1-[4-(3-hydroxypropyl)phenyl]-3-(2-methyl-2-propanyl)-1H-pyrazol-5-yl}-3-(2-{4-[2-(2-oxo-1-piperidinyl)-1,3-thiazol-5-yl]phenoxy}-5-pyrimidinyl)urea,

(62) 1-[1-(3-methoxyphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(63) 1-[1-(2,3-dihydro-1,4-benzodioxin-6-yl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(64) 1-[1-(2,5-dimethylphenyl)-3-(2-methyl-2-propanyl)-pyrazol-5-yl]-3-(2-{4-[2-(2-oxo-1-pyrrolidinyl)-1,3-thiazol-5-yl]phenoxy}-5-pyrimidinyl)urea,

(65) 1-{1-[3-(2-hydroxyethyl)phenyl]-3-(2-methyl-2-propanyl)-1H-pyrazol-5-yl}-3-(2-{4-[2-(2-oxo-1-piperidinyl)-1,3-thiazol-5-yl]phenoxy}-5-pyrimidinyl)urea,

(66) 1-[1-(3,5-dimethyl-4-propoxyphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(67) 1-[1-(3-isopropylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(68) 1-[1-(2,3-dihydro-1-benzofuran-5-yl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(69) 1-[1-(2-chloro-6-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(70) 1-[1-(3-fluoro-2-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(71) 1-[1-(5-fluoro-2-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(72) 1-[1-(2-ethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(73) 1-[1-(2-methylphenyl)-3-(2-methyl-2-propanyl)-1H-pyrazol-5-yl]-3-(2-{4-[2-(2-oxo-1-azepanyl)-1,3-thiazol-5-yl]phenoxy}-5-pyrimidinyl)urea,

(74) 1-[1-(2-chlorophenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(75) 1-{3-(2-methyl-2-propanyl)-1-[3-(trifluoromethyl)phenyl]-1H-pyrazol-5-yl}-3-(2-{4-[2-(2-oxo-1-piperidinyl)-1,3-thiazol-5-yl]phenoxy}-5-pyrimidinyl)urea,

(76) 1-[1-(3-ethylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea,

(77) 1-[1-(2-chloro-4-fluorophenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(78) 1-[1-(4-chloro-2-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(79) 1-[1-(3-methoxy-2,4-dimethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(80) 1-[1-(2-methoxyphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(81) 1-[1-(2-fluoro-5-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(82) 1-[1-(2-chloro-5-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(83) 1-[1-(2-fluoro-4-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(84) 1-[1-(3-fluoro-2,4-dimethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(85) 1-[1-(2-chloro-4-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(86) 4-[3-(2-methyl-2-propanyl)-5-{[(2-{4-[2-(2-oxo-1-pyrrolidinyl)-1,3-thiazol-5-yl]phenoxy}-5-pyrimidinyl)carbamoyl]amino]-1H-pyrazol-1-yl]benzenesulfonamide,

(87) 1-[1-(2-methylphenyl)-3-(2-methyl-2-propanyl)-1H-pyrazol-5-yl]-3-(6-{4-[2-(2-oxo-1-pyrrolidinyl)-1,3-thiazol-5-yl]phenoxy}-3-pyridinyl)urea,

(88) 1-(5-methyl-6-{4-[2-(2-oxo-1-pyrrolidinyl)-1,3-thiazol-5-yl]phenoxy}-3-pyridinyl)-3-[1-(2-methylphenyl)-3-(2-methyl-2-propanyl)-1H-pyrazol-5-yl]urea,

(89) 1-[1-(1-methyl-1H-indol-5-yl)-3-(2-methyl-2-propanyl) pyrazol-5-yl]-3-(2-{4-[2-(2-oxo-1-pyrrolidinyl)-1,3-thiazol-5-yl]phenoxy}-5-pyrimidinyl)urea,

(90) 1-[1-(1-methyl-1H-indazol-5-yl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea,

(91) 1-[1-(2-methylphenyl)-3-(trifluoromethyl)-1H-pyrazol-5-yl]-3-(2-{4-[2-(2-oxo-1-pyrrolidinyl)-1,3-thiazol-5-yl]phenoxy}-5-pyrimidinyl)urea,

(92) 1-[1-(3,4-dimethylphenyl)-3-(trifluoromethyl)-1H-pyrazol-5-yl]-3-(2-{4-[2-(2-oxo-1-pyrrolidinyl)-1,3-thiazol-5-yl]phenoxy}-5-pyrimidinyl)urea,

(93) 1-[3-(1,1-difluoroethyl)-1-(2-methylphenyl)-1H-pyrazol-5-yl]-3-(2-{4-[2-(2-oxo-1-pyrrolidinyl)-1,3-thiazol-5-yl]phenoxy}-5-pyrimidinyl)urea,

(94) 1-[1-(4-fluorophenyl)-3-(trifluoromethyl)-1H-pyrazol-5-yl]-3-(2-{4-[2-(2-oxo-1-pyrrolidinyl)-1,3-thiazol-5-yl]phenoxy}-5-pyrimidinyl)urea,

(95) 1-[1-(2-methylphenyl)-3-(trifluoromethyl)-1H-pyrazol-5-yl]-3-(2-{4-[2-(2-oxo-1-piperidinyl)-1,3-thiazol-5-yl]phenoxy}-5-pyrimidinyl)urea,

(96) 1-[3-(1,1-difluoroethyl)-1-(2-methylphenyl)-1H-pyrazol-5-yl]-3-(2-{4-[2-(2-oxo-1-piperidinyl)-1,3-thiazol-5-yl]phenoxy}-5-pyrimidinyl)urea,

(97) 1-(3-cyclopropyl-1-phenyl-1H-pyrazol-5-yl)-3-(2-{4-[2-(2-oxo-1-pyrrolidinyl)-1,3-thiazol-5-yl]phenoxy}-5-pyrimidinyl)urea,

(98) 1-(3-isopropyl-1-phenyl-1H-pyrazol-5-yl)-3-(2-{4-[2-(2-oxo-1-pyrrolidinyl)-1,3-thiazol-5-yl]phenoxy}-5-pyrimidinyl)urea,

(99) 1-[1-(6-methoxy-3-pyridinyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea, (100) 1-[3-(2-methyl-2-propanyl)-1-(6-methyl-3-pyridinyl)-1H-pyrazol-5-yl]-3-(2-{4-[2-(2-oxo-1-pyrrolidinyl)-1,3-thiazol-5-yl]phenoxy}-5-pyrimidinyl)urea, (101) 1-[3-(2-methyl-2-propanyl)-1-(3-pyridinyl)-1H-pyrazol-5-yl]-3-(2-{4-[2-(2-oxo-1-pyrrolidinyl)-1,3-thiazol-5-yl]phenoxy}-5-pyrimidinyl)urea, (102) 1-[1-(6-isopropoxy-3-pyridinyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea, (103) 1-[3-(2-methyl-2-propanyl)-1-(6-methyl-3-pyridinyl)-1H-pyrazol-5-yl]-3-(2-{4-[2-(2-oxo-1-piperidinyl)-1,3-thiazol-5-yl]phenoxy}-5-pyrimidinyl)urea, (104) 1-[3-(2-methyl-2-propanyl)-1-(3-pyridinyl)-1H-pyrazol-5-yl]-3-(2-{4-[2-(2-oxo-1-piperidinyl)-1,3-thiazol-5-yl]phenoxy}-5-pyrimidinyl)urea, (105) 1-(2-{4-[2-(2-oxo-1-pyrrolidinyl)-1,3-thiazol-5-yl]phenoxy}-5-pyrimidinyl)-3-[2-(4-pyridinyl)-5-(trifluoromethyl)phenyl]urea, (106) 1-[2-(4-morpholinyl)-5-(trifluoromethyl)phenyl]-3-(2-{4-[2-(2-oxo-1-piperidinyl)-1,3-thiazol-5-yl]phenoxy}-5-pyrimidinyl)urea, (107) 1-[2-(4-methyl-1-piperazinyl)-5-(trifluoromethyl)phenyl]-3-(2-{4-[2-(2-oxo-1-piperidinyl)-1,3-thiazol-5-yl]phenoxy}-5-pyrimidinyl)urea, (108) 1-[3-(2-methyl-2-propanyl)-1-(1,2,3,4-tetrahydro-2-naphthalenyl)-1H-pyrazol-5-yl]-3-(2-{4-[2-(2-oxo-1-pyrrolidinyl)-1,3-thiazol-5-yl]phenoxy}-5-pyrimidinyl)urea, (109) 1-[3-(2-methyl-2-propanyl)-1-(tetrahydro-2H-pyran-4-yl) 1H-pyrazol-5-yl]-3-(2-{4-[2-(2-oxo-1-pyrrolidinyl)-1,3-thiazol-5-yl]phenoxy}-5-pyrimidinyl)urea, (110) 1-[1-cyclohexyl-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea, (111) 1-[2-cyclohexyl-5-(trifluoromethyl)-3-pyridinyl]-3-(2-{4-[2-(2-oxo-1-pyrrolidinyl)-1,3-thiazol-5-yl]phenoxy}-5-pyrimidinyl)urea, (112) 1-[2-(3,4-dimethylphenyl)-5-methyl-3-pyridinyl]-3-(2-{4-[2-(2-oxo-1-pyrrolidinyl)-1,3-thiazol-5-yl]phenoxy}-5-pyrimidinyl)urea, (113) 1-[2-(3,4-dimethylphenyl)-3-pyridinyl]-3-(2-{4-[2-(2-oxo-1-pyrrolidinyl)-1,3-thiazol-5-yl]phenoxy}-5-pyrimidinyl)urea, (114) 1-(3-isopropyl-1-phenyl-1H-pyrazol-5-yl)-3-(2-{4-[2-(2-oxo-1-pyrrolidinyl)-1,3-thiazol-5-yl]phenoxy}-5-pyrimidinyl)urea, (115) 1-(2-{4-[2-(2-oxo-1-pyrrolidinyl)-1,3-thiazol-5-yl]phenoxy})-5-pyrimidinyl)-3-[2-(3-pyridinyl)-5-(trifluoromethyl)phenyl]urea, (116) 1-(6-{4-[2-(2-oxo-1-pyrrolidinyl)-1,3-thiazol-5-yl]phenoxy}-3-pyridinyl)-3-[2-(4-pyridinyl)-5-(trifluoromethyl)phenyl]urea, (117) 1-[6'-methyl-5-(trifluoromethyl)-2,3'-bipyridin-3-yl]-3-(6-{4-[2-(2-oxo-1-pyrrolidinyl)-1,3-thiazol-5-yl]phenoxy}-3-pyridinyl)urea, (118) 1-(6-{4-[2-(2-oxo-1-pyrrolidinyl)-1,3-thiazol-5-yl]phenoxy}-3-pyridinyl)-3-[2-(3-pyridinyl)-5-(trifluoromethyl)phenyl]urea,
(119) 1-(6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea,
(120) 1-(6-{4-[2-(2-oxo-1-pyrrolidinyl)-1,3-thiazol-5-yl]phenoxy}-3-pyridinyl)-3-[5-(trifluoromethyl)-2,4'-bipyridin-3-yl]urea,
(121) 1-[2-(4-methylphenyl)-5-(trifluoromethyl)-3-pyridinyl]-3-(6-{4-[2-(2-oxo-1-pyrrolidinyl)-1,3-thiazol-5-yl]phenoxy}-3-pyridinyl)urea,
(122) 1-[2-(6-methyl-3-pyridinyl)-5-(trifluoromethyl)phenyl]-3-(6-{4-[2-(2-oxo-1-pyrrolidinyl)-1,3-thiazol-5-yl]phenoxy}-3-pyridinyl)urea,
(123) 1-[1-oxido-2-phenyl-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,
(124) 1-(6-{4-[2-(2-oxo-1-pyrrolidinyl)-1,3-thiazol-5-yl]phenoxy}-3-pyridinyl)-3-{5-(trifluoromethyl)-2-[6-(trifluoromethyl)-3-pyridinyl]phenyl}urea,
(125) 1-[2-(6-methyl-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea,
(126) 1-(6-{4-[2-(2-oxo-1-pyrrolidinyl)-1,3-thiazol-5-yl]phenoxy}-3-pyridinyl)-3-[5-(trifluoromethyl)-2,3'-bipyridin-3-yl]urea,
(127) 1-[2-(6-methoxy-3-pyridinyl)-5-(trifluoromethyl)phenyl]-3-(6-{4-[2-(2-oxo-1-pyrrolidinyl)-1,3-thiazol-5-yl]phenoxy}-3-pyridinyl)urea,
(128) 1-[2-(3-hydroxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,
(129) 1-(2-{4-[2-(2-oxo-1-pyrrolidinyl)-1,3-thiazol-5-yl]phenoxy}-5-pyrimidinyl)-3-[5-(trifluoromethyl)-2,3'-bipyridin-3-yl]urea,
(130) 1-[2-(1-oxido-4-pyridinyl)-5-(trifluoromethyl)phenyl]-3-(6-{4-[2-(2-oxo-1-pyrrolidinyl)-1,3-thiazol-5-yl]phenoxy}-3-pyridinyl)urea,
(131) 1-(6-{4-[2-(2-oxo-1-pyrrolidinyl)-1,3-thiazol-5-yl]phenoxy}-3-pyridinyl)-3-[4-(trifluoromethyl)-2-biphenylyl]urea,
(132) 1-[2-(4-hydroxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,
(133) 1-[2-(1-oxido-4-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea,
(134) 1-[2-(1-oxido-3-pyridinyl)-5-(trifluoromethyl)phenyl]-3-(6-{4-[2-(2-oxo-1-pyrrolidinyl)-1,3-thiazol-5-yl]phenoxy}-3-pyridinyl)urea,
(135) 1-[2-(1-oxido-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea,
(136) 1-[2-(2-methoxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,
(137) 1-[2-(3-methoxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,
(138) 1-[2-(2-hydroxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,
(139) 1-(1-oxido-6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea,
(140) 1-[2-(4-methoxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,
(141) 1-[2-cyclohexyl-5-(trifluoromethyl)-3-pyridinyl]-3-(2-{4-[2-(2-oxo-1-piperidinyl)-1,3-thiazol-5-yl]phenoxy}-5-pyrimidinyl)urea,
(142) 1-[3-(2-methyl-2-propanyl)-1-phenyl-1H-pyrazol-5-yl]-3-(6-{4-[2-(2-oxo-1-piperidinyl)-1,3-thiazol-5-yl]phenoxy}-3-pyridinyl)urea,
(143) 1-(6-{4-[2-(2-oxo-1-piperidinyl)-1,3-thiazol-5-yl]phenoxy}-3-pyridinyl)-3-[2-phenyl-5-(trifluoromethyl)-3-pyridinyl]urea,
(144) 1-(6-{4-[2-(2-oxo-1-piperidinyl)-1,3-thiazol-5-yl]phenoxy}-3-pyridinyl)-3-[2-(4-pyridinyl)-5-(trifluoromethyl)phenyl]urea,
(145) 1-(6-{4-[2-(2-oxo-1-piperidinyl)-1,3-thiazol-5-yl]phenoxy}-3-pyridinyl)-3-[2-(3-pyridinyl)-5-(trifluoromethyl)phenyl]urea,
(146) 1-(2-{4-[2-(2-oxo-1-piperidinyl)-1,3-thiazol-5-yl]phenoxy}-5-pyrimidinyl)-3-[5-(trifluoromethyl)-2,4'-bipyridin-3-yl]urea,
(147) 1-(2-{4-[2-(2-oxo-1-piperidinyl)-1,3-thiazol-5-yl]phenoxy}-5-pyrimidinyl)-3-[2-(3-pyridinyl)-5-(trifluoromethyl)phenyl]urea,
(148) 1-(2-{4-[2-(2-oxo-1-piperidinyl)-1,3-thiazol-5-yl]phenoxy}-5-pyrimidinyl)-3-[5-(trifluoromethyl)-2,3'-bipyridin-3-yl]urea,
(149) 1-(2-{4-[2-(2-oxo-1-piperidinyl)-1,3-thiazol-5-yl]phenoxy}-5-pyrimidinyl)-3-[2-(4-pyridinyl)-5-(trifluoromethyl)phenyl]urea,
(150) 1-[2-(6-methyl-3-pyridinyl)-5-(trifluoromethyl)phenyl]-3-(2-{4-[2-(2-oxo-1-piperidinyl)-1,3-thiazol-5-yl]phenoxy}-5-pyrimidinyl)urea,
(151) 3-[3-{[(2{4-[2-(2-oxo-1-pyrrolidinyl)-1,3-thiazole-5-pyrimidinyl)carbamoyl]amino]-5-(trifluoromethyl)-2-pyridinyl]phenyl dihydrogen phosphate,
(152) 1-[6-({6-[2-(2-oxo-1-pyrrolidinyl)-1,3-thiazol-5-yl]-3-pyridinyl}oxy)-3-pyridinyl]-3-[2-phenyl-5-(trifluoromethyl)-3-pyridinyl]urea,
(153) 1-[2-(4-{2-[(4S)-4-hydroxy-2-oxo-1-pyrrolidinyl]-1,3-thiazol-5-yl}phenoxy)-5-pyrimidinyl]-3-[2-phenyl-5-(trifluoromethyl)-3-pyridinyl]urea,
(154) 1-(2-{2-fluoro-4-[2-(2-oxo-1-pyrrolidinyl)-1,3-thiazol-5-yl]phenoxy}-5-pyrimidinyl)-3-[2-phenyl-5-(trifluoromethyl)-3-pyridinyl]urea,
(155) 1-(2-{2-fluoro-4-[2-(2-oxo-1-pyrrolidinyl)-1,3-thiazol-5-yl]phenoxy}-5-pyrimidinyl)-3-[2-(3-pyridinyl)-5-(trifluoromethyl)phenyl]urea,
(156) 1-[2-(1-oxido-3-pyridinyl)-5-(trifluoromethyl)-3-pyridinyl]-3-(6-{4-[2-(2-oxo-1-pyrrolidinyl)-1,3-thiazol-5-yl]phenoxy}-3-pyridinyl)urea,
(157) 1-[2-(1-oxido-3-pyridinyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,
(158) 1-(6-{2-fluoro-4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea,
(159) 1-(6-{2-fluoro-4-[2-(2-oxo-1-pyrrolidinyl)-1,3-thiazol-5-yl]phenoxy}-3-pyridinyl)-3-[2-(3-pyridinyl)-5-(trifluoromethyl)phenyl]urea,
(160) 1-[2-(2-methyl-4-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea,
(161) 1-(2-{4-[2-(2-oxo-1-pyrrolidinyl)-1,3-thiazol-5-yl]phenoxy}-5-pyrimidinyl)-3-[2-(4-piperidinyl)-5-(trifluoromethyl)phenyl]urea, (162) 1-(2-{4-[2-(2-oxo-1-pyrrolidinyl)-1,3-thiazol-5-yl]phenoxy}-5-pyrimidinyl)-3-[2-(1,2,3,6-tetrahydro-4-pyridinyl)-5-(trifluoromethyl)phenyl]urea, (163) 1-(4-methyl-6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea, (164) 1-(4-methyl-6-{4-[2-(2-oxo-1-pyrrolidinyl)-1,3-thiazol-5-yl]phenoxy}-3-pyridinyl)-3-[2-(3-pyridinyl)-5-(trifluoromethyl)phenyl]urea, (165) 1-[2-(1-methyl-4-piperidinyl)-5-(trifluoromethyl)phenyl]-3-(2-{4-[2-(2-oxo-1-pyrrolidinyl)-1,3-thiazol-5-yl]phenoxy}-5-pyrimidinyl)urea, (166) 1-(2-{4-[2-(2-oxo-1-pyrrolidinyl)-1,3-thiazol-5-yl]phenoxy}-5-pyrimidinyl)-3-[2-(1H-pyrazol-3-yl)-5-(trifluoromethyl)phenyl]urea, (167) 1-(2-methyl-6-{4-[2-(2-oxo-1-pyrrolidinyl)-1,3-thiazol-5-yl]phenoxy}-3-pyridinyl)-3-[2-(3-pyridinyl)-5-(trifluoromethyl)phenyl]urea, (168) 1-(2-methyl-6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea, (169) 1-[2-(1H-imidazol-1-yl)-5-(trifluoromethyl)phenyl]-3-(2-{4-[2-(2-oxo-1-pyrrolidinyl)-1,3-thiazol-5-yl]phenoxy}-5-pyrimidinyl)urea, (170) 1-(2-{4-[2-(2-methyl-5-oxo-1-pyrrolidinyl)-1,3-thiazol-5-yl]phenoxy}-5-pyrimidinyl)-3-[2-phenyl-5-(trifluoromethyl)-3-pyridinyl]urea, (171) 1-(2-{4-[2-(2-methyl-5-oxo-1-pyrrolidinyl)-1,3-thiazol-5-yl]phenoxy}-5-pyrimidinyl)-3-[2-(3-pyridinyl)-5-(trifluoromethyl)phenyl]urea, (172) 1-[5-(2-methyl-2-propanyl)-2-(3-pyridinyl)phenyl]-3-(2-{4-[2-(2-oxo-1-pyrrolidinyl)-1,3-thiazol-5-yl]phenoxy}-5-pyrimidinyl)urea, (173) 1-(5-methyl-6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea, (174) 1-(5-methyl-6-{4-[2-(2-oxo-1-pyrrolidinyl)-1,3-thiazol-5-yl]phenoxy}-3-pyridinyl)-3-[2-(3-pyridinyl)-5-(trifluoromethyl)phenyl]urea, (175) 1-[2-(1-methyl-6-oxo-1,6-dihydro-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea, (176) 1-[2-(6-oxo-1,6-dihydro-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea, (177) 1-[5-(3-oxetanyl)-2-phenyl-3-pyridinyl]-3-(2-{4-[2-(2-oxo-1-pyrrolidinyl)-1,3-thiazol-5-yl]phenoxy}-5-pyrimidinyl)urea, (178) 1-(2-{4-[2-(2-oxo-1-azetidinyl)-1,3-thiazol-5-yl]phenoxy}-5-pyrimidinyl)-3-[2-(3-pyridinyl)-5-(trifluoromethyl)phenyl]urea, (179) 1-[5-(3-oxetanyl)-2-(3-pyridinyl)phenyl]-3-(2-{4-[2-(2-oxo-1-pyrrolidinyl)-1,3-thiazol-5-yl]phenoxy}-5-pyrimidinyl)urea, (180) 1-(2-{3-methyl-4-[2-(2-oxo-1-pyrrolidinyl)-1,3-thiazol-5-yl]phenoxy}-5-pyrimidinyl)-3-[2-(3-pyridinyl)-5-(trifluoromethyl)phenyl]urea, (181) 1-[2-(4-{2-[4-(hydroxymethyl)-2-oxo-1-pyrrolidinyl]-1,3-thiazol-5-yl}phenoxy)-5-pyrimidinyl]-3-[2-(3-pyridinyl)(trifluoromethyl)phenyl]urea, (182) 1-[2-({6-[2-(2-oxo-1-pyrrolidinyl)-1,3-thiazol-5-yl]-3-pyridinyl}oxy)-5-pyrimidinyl]-3-[2-(3-pyridinyl)-5-(trifluoromethyl)phenyl]urea, (183) 1-[2-(3-oxetanyl)-5-(trifluoromethyl)phenyl]-3-(2-{4-[2-(2-oxo-1-pyrrolidinyl)-1,3-thiazol-5-yl]phenoxy}-5-pyrimidinyl)urea, (184) 1-(2-{4-[2-(2-oxo-1-pyrrolidinyl)-1,3-thiazol-5-yl]phenoxy}-5-pyrimidinyl)-3-[2-(1H-pyrazol-1-yl)-5-(trifluoromethyl)phenyl]urea, (185) 1-[5-fluoro-2-(1H-imidazol-1-yl)phenyl]-3-(2-{4-[2-(2-oxo-1-pyrrolidinyl)-1,3-thiazol-5-yl]phenoxy}-5-pyrimidinyl)urea, (186) 1-[2-(4-methyl-1H-imidazol-1-yl)-5-(trifluoromethyl)phenyl]-3-(2-{4-[2-(2-oxo-1-pyrrolidinyl)-1,3-thiazol-5-yl]phenoxy}-5-pyrimidinyl)urea, (187) 1-(2-{4-[2-(2-oxo-1-pyrrolidinyl)-1,3-thiazol-5-yl]phenoxy}-5-pyrimidinyl)-3-[2-(1H-1,2,3-triazol-1-yl)-5-(trifluoromethyl)phenyl]urea, (188) 1-[2-(4-{2-[3-(2-hydroxy-2-propanyl)-2-oxo-1-pyrrolidinyl]-1,3-thiazol-5-yl}phenoxy)-5-pyrimidinyl]-3-[2-(3-pyridinyl)-5-(trifluoromethyl)phenyl]urea, (189) 1-[2-(2-methyl-1H-imidazol-1-yl)-5-(trifluoromethyl)phenyl]-3-(2-{4-[2-(2-oxo-1-pyrrolidinyl)-1,3-thiazol-5-yl]phenoxy}-5-pyrimidinyl)urea, (190) 1-[2-(1H-imidazol-1-yl)-5-(trifluoromethyl)phenyl]-3-[2-({6-[2-(2-oxo-1-pyrrolidinyl)-1,3-thiazol-5-yl]-3-pyridinyl}oxy)-5-pyrimidinyl]urea, (191) 1-(2-{4-[2-(2-oxo-1-pyrrolidinyl)-1,3-thiazol-5-yl]phenoxy}-5-pyrimidinyl)-3-[2-(4H-1,2,4-triazol-4-yl)-5-(trifluoromethyl)phenyl]urea, (192) 1-[6'-methyl-5-(trifluoromethyl)-2,3'-bipyridin-3-yl]-3-(2-{4-[2-(2-oxo-1-pyrrolidinyl)-1,3-thiazol-5-yl]phenoxy}-5-pyrimidinyl)urea, (193) 1-[2-(4-{2-[3-(2-hydroxy-2-propanyl)-2-oxo-1-pyrrolidinyl]-1,3-thiazol-5-yl}phenoxy)-5-pyrimidinyl]-3-[2-phenyl-5-(trifluoromethyl)-3-pyridinyl]urea, (194) 1-[5-fluoro-2-(3-pyridinyl)phenyl]-3-(2-{4-[2-(2-oxo-1-pyrrolidinyl)-1,3-thiazol-5-yl]phenoxy}-5-pyrimidinyl)urea, (195) 1-(5-methoxy-6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea, (196) 1-[2-(2-methyl-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea, (197) 1-[2-(4-methyl-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea, (198) 1-(5-fluoro-2,3'-bipyridin-3-yl)-3-(2-{4-[2-(2-oxo-1-pyrrolidinyl)-1,3-thiazol-5-yl]phenoxy}-5-pyrimidinyl)urea, (199) 1-[2-(5-methyl-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea, (200) 1-[5-fluoro-2-(4-pyridinyl)phenyl]-3-(2-{4-[2-(2-oxo-1-pyrrolidinyl)-1,3-thiazol-5-yl]phenoxy}-5-pyrimidinyl)urea, (201) 1-[2-(1-methyl-1H-imidazol-4-yl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea, (202) 1-(2-{4-[2-(2-oxo-1-pyrrolidinyl)-1,3-thiazol-5-yl]phenoxy}-5-pyrimidinyl)-3-[5-(trifluoromethyl)-2,2'-bipyridin-3-yl]urea, (203) 1-[5-fluoro-2-(2-pyridinyl)phenyl]-3-(2-{4-[2-(2-oxo-1-pyrrolidinyl)-1,3-thiazol-5-yl]phenoxy}-5-pyrimidinyl)urea, or (204) 1-[2-cyclopropyl-5-(trifluoromethyl)-3-pyridinyl]-3-(2-{4-[2-(2-oxo-1-pyrrolidinyl)-1,3-thiazol-5-yl]phenoxy}-5-pyrimidinyl)urea, a salt thereof, an N-oxide thereof, a solvate thereof or a prodrug thereof.

Among the compounds represented by the general formula (I), the compound represented by the general formula (I-2-a) is still more preferably a compound represented by the following general formula (I-2-a-1) or general formula (I-2-a-2):

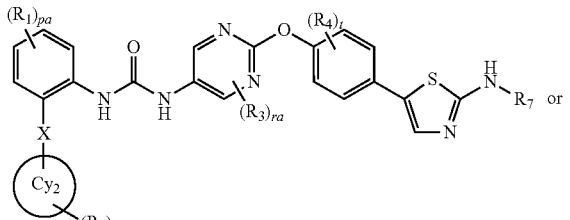

(I-2-a-1)

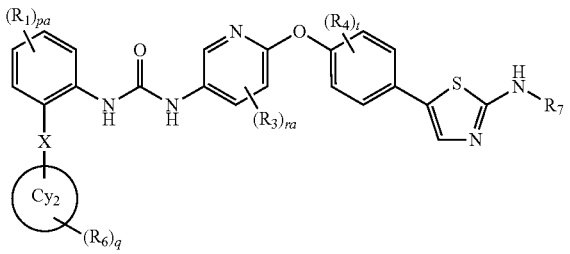

(I-2-a-2)

wherein ra represents an integer of 0 to 3; t represents an integer of 0 to 4; and other symbols represent the same meanings as those described in the above [1] and [6]; a salt thereof, an N-oxide thereof, a solvate thereof or a prodrug thereof.

Among the compounds represented by the general formula (I), the compound represented by the general formula (I-2-b) is still more preferably a compound represented by the following general formula (I-2-b-1) or general formula (I-2-b-2):

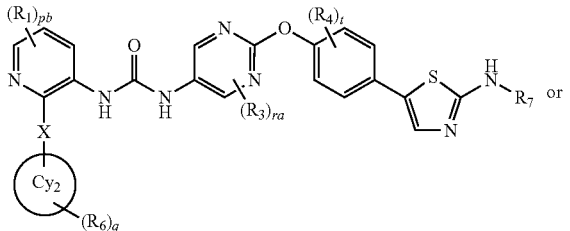

(I-2-b-1)

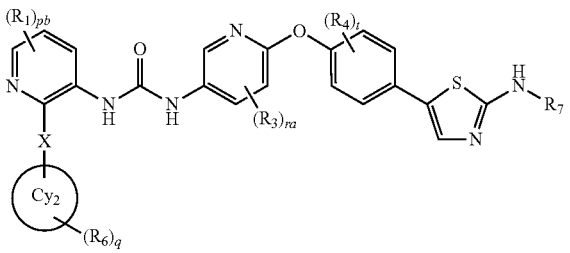

(I-2-b-2)

wherein ra represents an integer of 0 to 3; t represents an integer of 0 to 4; and other symbols represent the same meanings as those described in the above [1] and [6]; a salt thereof, an N-oxide thereof, a solvate thereof or a prodrug thereof.

Among the compounds represented by the general formula (I), the compound represented by the general formula (I-2-a-1), the compound represented by the general formula (I-2-a-2), the compound represented by the general formula (I-2-b-1) or the compound represented by the general formula (I-2-b-2) is preferably a compound having the general formula wherein the ring $Cy_2$ is a C3-10 monocyclic carbocycle or a 5- to 10-membered monocyclic heterocycle or bicyclic heterocycle; $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_3$ is a fluorine, a chlorine, methyl, trifluoromethyl or a methoxy group; $R_4$ is a fluorine, a chlorine, methyl, trifluoromethyl or a methoxy group; $R_6$ is (1) a halogen, (2) a hydroxy group, (3) a C1-4 alkyl, (4) a C1-4 alkyl substituted with a halogen, (5) a C1-4 alkyl substituted with a hydroxy group, (6) a C3-6 cycloalkyl, (7) a C1-4 alkoxy, (8) carboxyl, (9) —$CO_2$(C1-4 alkyl), (10) an acetylamide group, (11) a phosphonooxy group or (12) a sulfonamide group; $R_7$ is a C1-6 alkyl; X is a bond or an oxygen atom; pa is an integer of 0 to 2; pb is an integer of 0 to 2; q is an integer of 0 to 2; ra is an integer of 0 to 1; and t is an integer of 0 to 2; a salt thereof, an N-oxide thereof, a solvate thereof or a prodrug thereof, more preferably a compound having the general formula wherein the ring $Cy_2$ is cyclopropane, benzene, cyclohexane, indane, tetrahydronaphthalene, pyran, furan, thiophene, pyrrole, isoxazole, oxazole, isothiazole, thiazole, pyrazole, imidazole, triazole, pyridine, pyridone, pyridazine, pyrimidine, pyrazine, tetrahydropyran, tetrahydrothiopyran, piperidine, morpholine, thiomorpholine, tetrahydropyridine, benzodioxane, piperazine, perhydroindene, dihydrobenzofuran, dihydrobenzothiophene, indoline, benzodioxole, benzoxathiole, dihydrobenzoxazole, dihydrobenzothiazole, chromane, thiochromane, tetrahydroquinoline, dihydrobenzodioxine, dihydrobenzoxathiine, dihydrobenzoxazine, indole, benzofuran, benzothiophene, indazole or tetrahydronaphthalene; $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_3$ is a fluorine, a chlorine, methyl, trifluoromethyl or a methoxy group; $R_4$ is a fluorine, a chlorine, methyl, trifluoromethyl or a methoxy group; $R_6$ is (1) a halogen, (2) a hydroxy group, (3) a C1-4 alkyl, (4) a C1-4 alkyl substituted with a halogen, (5) a C1-4 alkyl substituted with a hydroxy group, (6) a C3-6 cycloalkyl, (7) a C1-4 alkoxy, (8) carboxyl, (9) —$CO_2$(C1-4 alkyl), (10) an acetylamide group, (11) a phosphonooxy group or (12) a sulfonamide group; $R_7$ is a C1-6 alkyl; X is a bond or an oxygen atom; pa is an integer of 0 to 2; pb is an integer of 0 to 2; q is an integer of 0 to 2; ra is an integer of 0 to 1; and t is an integer of 0 to 2; a salt thereof, an N-oxide thereof, a solvate thereof or a prodrug thereof, and still more preferably a compound having the general formula wherein the ring $Cy_2$ is benzene, pyridine, pyrazole, imidazole or triazole; $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_3$ is a fluorine, a chlorine, methyl, trifluoromethyl or a methoxy group; $R_4$ is a fluorine, a chlorine, methyl, trifluoromethyl or a methoxy group; $R_6$ is (1) a halogen, (2) a hydroxy group, (3) a C1-4 alkyl, (4) a C1-4 alkyl substituted with a halogen, (5) a C1-4 alkyl substituted with a hydroxy group, (6) a C3-6 cycloalkyl, (7) a C1-4 alkoxy, (8) carboxyl, (9) —$CO_2$(C1-4 alkyl), (10)

an acetylamide group, (11) a phosphonooxy group or (12) a sulfonamide group; $R_7$ is a C1-6 alkyl; X is a bond or an oxygen atom; pa is an integer of 0 to 2; pb is an integer of 0 to 2; q is an integer of 0 to 2; ra is an integer of 0 to 1; and t is an integer of 0 to 2; a salt thereof, an N-oxide thereof, a solvate thereof or a prodrug thereof.

Among the compounds represented by the general formula (I), the compound represented by the general formula (I-2-a) or the compound represented by the general formula (I-2-b) is the most preferably:

(1) 1-[5,6'-bis(trifluoromethyl)-2,3'-bipyridin-3-yl]-3-(2-{4-[2-(ethylamino)-1,3-thiazol-5-yl]phenoxy}-5-pyrimidinyl)urea, (2) 1-[2-(3,4-dimethylphenyl)-5-(trifluoromethyl)-3-pyridinyl]-3-(2-{4-[2-(ethylamino)-1,3-thiazol-5-yl]phenoxy}-5-pyrimidinyl)urea, (3) 1-[2-(3,4-dimethylphenyl)-5-(trifluoromethyl)-3-pyridinyl]-3-(2-{4-[2-(isopropylamino)-1,3-thiazol-5-yl]phenoxy}-5-pyrimidinyl)urea, (4) 1-(2-{4-[2-(ethylamino)-1,3-thiazol-5-yl]phenoxy}-5-pyrimidinyl)-3-[2-(4-methylphenyl)-5-(trifluoromethyl)-3-pyridinyl]urea, (5) 1-(2-{4-[2-(ethylamino)-1,3-thiazol-5-yl]phenoxy}-5-pyrimidinyl)-3-[2-phenyl-5-(trifluoromethyl)-3-pyridinyl]urea, (6) 1-(2-{4-[2-(ethylamino)-1,3-thiazol-5-yl]phenoxy}-5-pyrimidinyl)-3-[2-(3-methylphenyl)-5-(trifluoromethyl)-3-pyridinyl]urea, (7) 1-[2-(3,4-dimethylphenyl)-5-(trifluoromethyl)-3-pyridinyl]-3-[2-(4-{2-[(2-methyl-2-propanyl)amino]-1,3-thiazol-5-yl}phenoxy)-5-pyrimidinyl]urea, (8) 1-[2-(3,4-dimethylphenyl)-5-(trifluoromethyl)-3-pyridinyl]-3-(6-{4-[2-(ethylamino)-1,3-thiazol-5-yl]phenoxy}-3-pyridinyl)urea, (9) 1-(6-{4-[2-(ethylamino)-1,3-thiazol-5-yl]phenoxy}-3-pyridinyl)-3-[2-phenyl-5-(trifluoromethyl)-3-pyridinyl]urea,

(10) 1-(2-{4-[2-(ethylamino)-1,3-thiazol-5-yl]phenoxy}-5-pyrimidinyl)-3-{2-[3-(hydroxymethyl)phenyl]-5-(trifluoromethyl)-3-pyridinyl}urea,

(11) 1-(2-{4-[2-(ethylamino)-1,3-thiazol-5-yl]phenoxy}-5-pyrimidinyl)-3-[5-(trifluoromethyl)-2,3'-bipyridin-3-yl]urea,

(12) 1-[2-(3,4-dimethylphenyl)-5-(trifluoromethyl)-3-pyridinyl]-3-[2-(4-{2-[(2-ethoxyethyl)amino]-1,3-thiazol-5-yl}phenoxy)-5-pyrimidinyl]urea,

(13) 1-[2-(3,4-dimethylphenyl)-5-(trifluoromethyl)-3-pyridinyl]-3-(2-{4-[2-(propylamino)-1,3-thiazol-5-yl]phenoxy}-5-pyrimidinyl)urea,

(14) 1-(2-{4-[2-(ethylamino)-1,3-thiazol-5-yl]phenoxy}-5-pyrimidinyl)-3-[2-(2-methylphenyl)-5-(trifluoromethyl)-3-pyridinyl]urea,

(15) 1-(2-{4-[2-(ethylamino)-1,3-thiazol-5-yl]phenoxy}-5-pyrimidinyl)-3-[2-phenoxy-5-(trifluoromethyl)-3-pyridinyl]urea,

(16) 1-(2-{4-[2-(ethylamino)-1,3-thiazol-5-yl]phenoxy}-5-pyrimidinyl)-3-[2-(6-methyl-3-pyridinyl)-5-(trifluoromethyl)phenyl]urea,

(17) 1-[2-(3,4-dimethylphenyl)-5-methyl-3-pyridinyl]-3-(2-{4-[2-(ethylamino)-1,3-thiazol-5-yl]phenoxy}-5-pyrimidinyl)urea,

(18) 1-[2-(3,4-dimethylphenyl)-3-pyridinyl]-3-(2-{4-[2-(ethylamino)-1,3-thiazol-5-yl]phenoxy}-5-pyrimidinyl)urea,

(19) 1-(2-{4-[2-(ethylamino)-1,3-thiazol-5-yl]phenoxy}-5-pyrimidinyl)-3-[2-(3-pyridinyl)-5-(trifluoromethyl)phenyl]urea,

(20) 1-(2-{4-[2-(ethylamino)-1,3-thiazol-5-yl]phenoxy}-5-pyrimidinyl)-3-[2-(1H-imidazol-1-yl)-5-(trifluoromethyl)phenyl]urea,

(21) 1-(2-{4-[2-(propylamino)-1,3-thiazol-5-yl]phenoxy}-5-pyrimidinyl)-3-[2-(3-pyridinyl)-5-(trifluoromethyl)phenyl]urea,

(22) 1-(6-{4-[2-(propylamino)-1,3-thiazol-5-yl]phenoxy}-3-pyridinyl)-3-[2-(3-pyridinyl)-5-(trifluoromethyl)phenyl]urea,

(23) 1-(2-{4-[2-(propylamino)-1,3-thiazol-5-yl]phenoxy}-5-pyrimidinyl)-3-[2-(1H-pyrazol-1-yl)-5-(trifluoromethyl)phenyl]urea,

(24) 1-(2-{4-[2-(propylamino)-1,3-thiazol-5-yl]phenoxy}-5-pyrimidinyl)-3-{5-(trifluoromethyl)-2-[3-(trifluoromethyl)-1H-pyrazol-1-yl]phenyl}urea,

(25) 1-[2-(1-methyl-1H-pyrazol-5-yl)-5-(trifluoromethyl)phenyl]-3-(2-{4-[2-(propylamino)-1,3-thiazol-5-yl]phenoxy}-5-pyrimidinyl)urea,

(26) 1-[2-(3-methyl-1H-pyrazol-1-yl)-5-(trifluoromethyl)phenyl]-3-(2-{4-[2-(propylamino)-1,3-thiazol-5-yl]phenoxy}-5-pyrimidinyl)urea,

(27) 1-[2-(4-methyl-1H-pyrazol-1-yl)-5-(trifluoromethyl)phenyl]-3-(2-{4-[2-(propylamino)-1,3-thiazol-5-yl]phenoxy}-5-pyrimidinyl)urea,

(28) 1-[2-(4-methyl-1H-1,2,3-triazol-1-yl)-5-(trifluoromethyl)phenyl]-3-(2-{4-[2-(propylamino)-1,3-thiazol-5-yl]phenoxy}-5-pyrimidinyl)urea,

(29) 1-(2-{4-[2-(propylamino)-1,3-thiazol-5-yl]phenoxy}-5-pyrimidinyl)-3-[2-(1H-pyrazol-1-yl)-4-(trifluoromethyl)phenyl]urea,

(30) 1-(2-{4-[2-(propylamino)-1,3-thiazol-5-yl]phenoxy}-5-pyrimidinyl)-3-[2-(3-pyridinyl)-4-(trifluoromethyl)phenyl]urea,

(31) 1-[5-chloro-2-(1H-pyrazol-1-yl)phenyl]-3-(2-{4-[2-(propylamino)-1,3-thiazol-5-yl]phenoxy}-5-pyrimidinyl)

(32) 1-[5-chloro-2-(3-pyridinyl)phenyl]-3-(2-{4-[2-(propylamino)-1,3-thiazol-5-yl]phenoxy}-5-pyrimidinyl)urea,

(33) 1-(6-{4-[2-(propylamino)-1,3-thiazol-5-yl]phenoxy}-3-pyridinyl)-3-[2-(1H-pyrazol-1-yl)-5-(trifluoromethyl)phenyl]urea,

(34) 1-(6-{4-[2-(propylamino)-1,3-thiazol-5-yl]phenoxy}-3-pyridinyl)-3-{5-(trifluoromethyl)-2-[3-(trifluoromethyl) pyrazol-1-yl]phenyl}urea,

(35) 1-[2-(1-methyl-1H-pyrazol-5-yl)-5-(trifluoromethyl)phenyl]-3-(6-{4-[2-(propylamino)-1,3-thiazol-5-yl]phenoxy}-3-pyridinyl)urea,

(36) 1-[2-(3-methyl-1H-pyrazol-1-yl)-5-(trifluoromethyl)phenyl]-3-(6-{4-[2-(propylamino)-1,3-thiazol-5-yl]phenoxy}-3-pyridinyl)urea,

(37) 1-[2-(4-methyl-1H-pyrazol-1-yl)-5-(trifluoromethyl)phenyl]-3-(6-{4-[2-(propylamino)-1,3-thiazol-5-yl]phenoxy}-3-pyridinyl)urea,

(38) 1-(6-{4-[2-(propylamino)-1,3-thiazol-5-yl]phenoxy}-3-pyridinyl)-3-[2-(1H-pyrazol-1-yl)-4-(trifluoromethyl)phenyl]urea,

(39) 1-(6-{4-[2-(propylamino)-1,3-thiazol-5-yl]phenoxy}-3-pyridinyl)-3-[2-(3-pyridinyl)-4-(trifluoromethyl)phenyl]urea,

(40) 1-[5-chloro-2-(1H-pyrazol-1-yl)phenyl]-3-(6-{4-[2-(propylamino)-1,3-thiazol-5-yl]phenoxy}-3-pyridinyl) urea,

(41) 1-[5-chloro-2-(3-pyridinyl)phenyl]-3-(6-{4-[2-(propylamino)-1,3-thiazol-5-yl]phenoxy}-3-pyridinyl)urea,

(42) 1-(2-{4-[2-(propylamino)-1,3-thiazol-5-yl]phenoxy}-5-pyrimidinyl)-3-[2-(2H-1,2,3-triazol-2-yl)-5-(trifluoromethyl)phenyl]urea,

(43) 1-[5-chloro-2-(1H-1,2,3-triazol-1-yl)phenyl]-3-(2-{4-[2-(propylamino)-1,3-thiazol-5-yl]phenoxy}-5-pyrimidinyl)urea,

(44) 1-[5-chloro-2-(2H-1,2,3-triazol-2-yl)phenyl]-3-(2-{4-[2-(propylamino)-1,3-thiazol-5-yl]phenoxy}-5-pyrimidinyl)urea,

(45) 1-(6-{4-[2-(propylamino)-1,3-thiazol-5-yl]phenoxy}-3-pyridinyl)-3-[2-(2H-1,2,3-triazol-2-yl)-5-(trifluoromethyl)phenyl]urea,

(46) 1-[5-chloro-2-(1H-1,2,3-triazol-1-yl)phenyl]-3-(6-{4-[2-(propylamino)-1,3-thiazol-5-yl]phenoxy}-3-pyridinyl)urea,

(47) 1-[5-chloro-2-(2H-1,2,3-triazol-2-yl)phenyl]-3-(6-{4-[2-(propylamino)-1,3-thiazol-5-yl]phenoxy}-3-pyridinyl)urea,

(48) 1-[2-(3-pyridinyl)-5-(trifluoromethyl)phenyl]-3-[2-(4-{2-[(tetrahydro-2H-pyran-4-ylmethyl)amino]-1,3-thiazol-5-yl}phenoxy)-5-pyrimidinyl]urea, or

(49) 1-{2-[3-(difluoromethyl)-1H-pyrazol-1-yl]-5-(trifluoromethyl)phenyl}-3-(2-{4-[2-(propylamino)-1,3-thiazol-5-yl]phenoxy}-5-pyrimidinyl)urea, a salt thereof, an N-oxide thereof, a solvate thereof or a prodrug thereof.

Among the compounds represented by the general formula (I), a compound represented by the following general formula (I-3-a) or general formula (I-3-b):

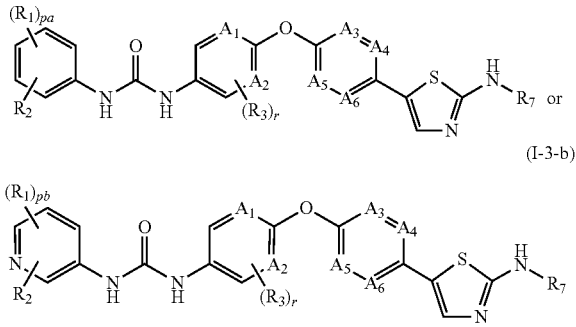

wherein all symbols represent the same meanings as those described in the above [1] and [6]; a salt thereof, an N-oxide thereof, a solvate thereof or a prodrug thereof is more preferred.

Among the compounds represented by the general formula (I), the compound represented by the general formula (I-3-a) or the compound represented by the general formula (I-3-b) is more preferably a compound represented by the following general formula (I-3-a-1), general formula (I-3-a-2), general formula (I-3-b-1) or general formula (I-3-b-2):

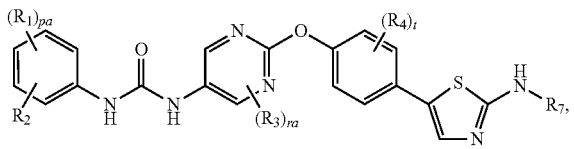

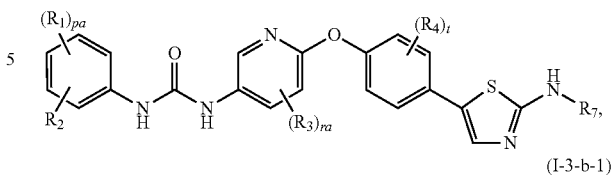

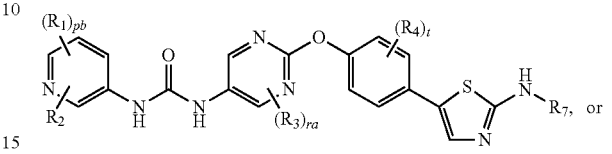

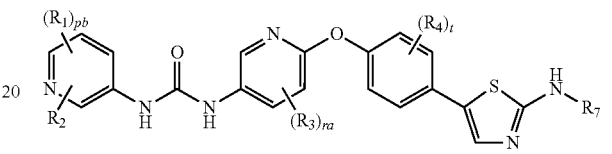

wherein ra represents an integer of 0 to 3; t represents an integer of 0 to 4; and other symbols represent the same meanings as those described in the above [1] and [6]; a salt thereof, an N-oxide thereof, a solvate thereof or a prodrug thereof.

Among the compounds represented by the general formula (I), the compound represented by the general formula (I-3-a-1), the compound represented by the general formula (I-3-a-2), the compound represented by the general formula (I-3-b-1) or the compound represented by the general formula (I-3-b-2) is preferably a compound having the general formula wherein $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_2$ is isopropyl, sec-butyl, tert-butyl, isobutyl, a hydrogen atom, a hydroxy group, a carboxyl group, 1-hydroxy-1-methylethyl, 2-hydroxypropyl, 3-hydroxy-3-methyl-1-butynyl, a methylsulfonyl group, a methylsulfonamide group or a dimethylsulfonamide group; $R_3$ is a fluorine, a chlorine, methyl, trifluoromethyl or a methoxy group; $R_4$ is a fluorine, a chlorine, methyl, trifluoromethyl or a methoxy group; $R_7$ is a C1-6 alkyl; pa is an integer of 0 to 2; pb is an integer of 0 to 2; ra is an integer of 0 to 1; and t is an integer of 0 to 2; a salt thereof, an N-oxide thereof, a solvate thereof or a prodrug thereof, more preferably a compound having the general formula wherein $R_1$ is a halogen, methyl, trifluoromethyl, tert-butyl, 1,1-difluoroethyl, isopropyl, cyclopropyl, oxetanyl or a difluoromethyl group; $R_2$ is isopropyl, sec-butyl, tert-butyl, isobutyl, a hydrogen atom, a hydroxy group, a carboxyl group, 1-hydroxy-1-methylethyl, 2-hydroxypropyl, 3-hydroxy-3-methyl-1-butynyl, a methylsulfonyl group, a methylsulfonamide group or a dimethylsulfonamide group; $R_3$ is a fluorine, a chlorine, methyl, trifluoromethyl or a methoxy group; $R_4$ is a fluorine, a chlorine, methyl, trifluoromethyl or a methoxy group; $R_7$ is a C1-6 alkyl; pa is an integer of 0 to 2; pb is an integer of 0 to 2; ra is an integer of 0 to 1; and t is an integer of 0 to 2; a salt thereof, an N-oxide thereof, a solvate thereof or a prodrug thereof, still more preferably a compound having the general formula wherein $R_1$ is a halogen, methyl or trifluoromethyl; $R_2$ is isopropyl, sec-butyl, tert-butyl, isobutyl, a hydrogen atom, a hydroxy group, a carboxyl group, 1-hydroxy-1-methylethyl, 2-hydroxypropyl, 3-hydroxy-3-methyl-1-butynyl, a methylsulfonyl group, a methylsulfonamide group or a dimethylsulfonamide group; $R_3$ is a fluorine, a chlorine, methyl, trifluoromethyl or a methoxy group; $R_4$ is a fluorine, a chlorine, methyl, trifluoromethyl or a methoxy group; $R_7$ is a C1-6 alkyl; pa is an integer of 0 to 2; pb is an integer of 0 to 2; ra is an integer of 0 to 1; and t is an integer of 0 to 2; a salt thereof, an N-oxide thereof, a solvate thereof or a prodrug thereof.

Among the compounds represented by the general formula (I), the compound represented by the general formula (I-3-a) or the compound represented by the general formula (I-3-b) is the most preferably:

(1)  1-(6-{4-[2-(ethylamino)-1,3-thiazol-5-yl]phenoxy}-5-pyridinyl)-3-[3-(trifluoromethyl)phenyl]urea,
(2)  1-(2-{4-[2-(ethylamino)-1,3-thiazol-5-yl]phenoxy}-5-pyrimidinyl)-3-[3-(trifluoromethyl)phenyl]urea,
(3)  1-(2-{4-[2-(ethylamino)-1,3-thiazol-5-yl]phenoxy}-5-pyrimidinyl)-3-[2-isopropyl-5-(trifluoromethyl)-3-pyridinyl]urea,
(4)  1-(2-{4-[2-(ethylamino)-1,3-thiazol-5-yl]phenoxy}-5-pyrimidinyl)-3-[4-methyl-3-(trifluoromethyl)phenyl]urea,
(5)  1-(2-{4-[2-(ethylamino)-1,3-thiazol-5-yl]phenoxy}-5-pyrimidinyl)-3-[4-(trifluoromethyl)phenyl]urea,
(6)  1-(2-{4-[2-(ethylamino)-1,3-thiazol-5-yl]phenoxy}-5-pyrimidinyl)-3-[3-fluoro-5-(trifluoromethyl)phenyl]urea,
(7)  1-[2-chloro-5-(trifluoromethyl)phenyl]-3-(2-{4-[2-(ethylamino)-1,3-thiazol-5-yl]phenoxy}-5-pyrimidinyl)urea,
(8)  1-[2-chloro-4-(trifluoromethyl)phenyl]-3-(2-{4-[2-(ethylamino)-1,3-thiazol-5-yl]phenoxy}-5-pyrimidinyl)urea,
(9)  1-(2-{4-[2-(ethylamino)-1,3-thiazol-5-yl]phenoxy}-5-pyrimidinyl)-3-[2-fluoro-3-(trifluoromethyl)phenyl]urea,
(10)  1-(2-{4-[2-(ethylamino)-1,3-thiazol-5-yl]phenoxy}-5-pyrimidinyl)-3-[2-fluoro-5-(trifluoromethyl)phenyl]urea,
(11)  1-[2-(4-{2-[(3-hydroxypropyl)amino]-1,3-thiazol-5-yl}phenoxy)-5-pyrimidinyl]-3-[3-(trifluoromethyl)phenyl]urea,
(12)  1-(2-{4-[2-(propylamino)-1,3-thiazol-5-yl]phenoxy}-5-pyrimidinyl)-3-[3-(trifluoromethyl)phenyl]urea,
(13)  1-[2-(4-{2-[(2-hydroxyethyl)amino]-1,3-thiazol-5-yl}phenoxy)-5-pyrimidinyl]-3-[3-(trifluoromethyl)phenyl]urea,
(14)  1-(2-{4-[2-(propylamino)-1,3-thiazol-5-yl]phenoxy}-5-pyrimidinyl)-3-[3-(trifluoromethyl)phenyl]urea,
(15)  1-{2-[4-(2-{[2-(4-morpholinyl)ethyl]amino}-1,3-thiazol-5-yl)phenoxy]-5-pyrimidinyl}-3-[3-(trifluoromethyl)phenyl]urea,
(16)  1-[2-(4-{2-[(2-hydroxypropyl)amino]-1,3-thiazol-5-yl}phenoxy)-5-pyrimidinyl]-3-[3-(trifluoromethyl)phenyl]urea,
(17) 1-[3-(difluoromethyl)phenyl]-3-(2-{4-[2-(ethylamino)-1,3-thiazol-5-yl]phenoxy}-5-pyrimidinyl)urea,
(18)  1-(3-acetylphenyl)-3-(2-{4-[2-(ethylamino)-1,3-thiazol-5-yl]phenoxy}-5-pyrimidinyl)urea,
(19)  1-(2-{4-[2-(ethylamino)-1,3-thiazol-5-yl]phenoxy}-5-pyrimidinyl)-3-(3-fluorophenyl)urea,
(20)  1-[4-chloro-3-(trifluoromethyl)phenyl]-3-(2-{4-[2-(ethylamino)-1,3-thiazol-5-yl]phenoxy}-5-pyrimidinyl)urea,
(21)  1-(2-{4-[2-(ethylamino)-1,3-thiazol-5-yl]phenoxy}-5-pyrimidinyl)-3-[2-methyl-5-(trifluoromethyl)phenyl]urea,
(22)  1-[3-chloro-5-(trifluoromethyl)phenyl]-3-(2-{4-[2-(ethylamino)-1,3-thiazol-5-yl]phenoxy}-5-pyrimidinyl)urea,
(23)  1-(2-{4-[2-(methylamino)-1,3-thiazol-5-yl]phenoxy}-5-pyrimidinyl)-3-[3-(trifluoromethyl)phenyl]urea,
(24)  1-(2-{4-[2-(isopropylamino)-1,3-thiazol-5-yl]phenoxy}-5-pyrimidinyl)-3-[3-(trifluoromethyl)phenyl]urea,
(25)  1-(2-{4-[2-(isobutylamino)-1,3-thiazol-5-yl]phenoxy}-5-pyrimidinyl)-3-[3-(trifluoromethyl)phenyl]urea,
(26)  1-(3-chlorophenyl)-3-(2-{4-[2-(ethylamino)-1,3-thiazol-5-yl]phenoxy}-5-pyrimidinyl)urea,
(27)  1-(2,5-dichlorophenyl)-3-(2-{4-[2-(ethylamino)-1,3-thiazol-5-yl]phenoxy}-5-pyrimidinyl)urea,
(28)  1-[2-(4-{2-[(cyclopropylmethyl)amino]-1,3-thiazol-5-yl}phenoxy)-5-pyrimidinyl]-3-[3-(trifluoromethyl)phenyl]urea,
(29)  1-(2-{4-[2-(cyclobutylamino)-1,3-thiazol-5-yl]phenoxy}-5-pyrimidinyl)-3-[3-(trifluoromethyl)phenyl]urea,
(30)  1-(2-{4-[2-(cyclopentylamino)-1,3-thiazol-5-yl]phenoxy}-5-pyrimidinyl)-3-[3-(trifluoromethyl)phenyl]urea,
(31)  1-(6-{4-[2-(ethylamino)-1,3-thiazol-5-yl]phenoxy}-3-pyridinyl)-3-[2-fluoro-5-(trifluoromethyl)phenyl]urea,
(32)  1-[2-chloro-5-(trifluoromethyl)phenyl]-3-(6-{4-[2-(ethylamino)-1,3-thiazol-5-yl]phenoxy}-3-pyridinyl)urea,
(33)  1-[2-chloro-4-(trifluoromethyl)phenyl]-3-(6-{4-[2-(ethylamino)-1,3-thiazol-5-yl]phenoxy}-3-pyridinyl)urea,
(34) 1-(2-{4-[2-(tetrahydro-3-furanylamino)-1,3-thiazol-5-yl]phenoxy}-5-pyrimidinyl)-3-[3-(trifluoromethyl)phenyl]urea,
(35)  1-(2-{4-[2-(3-oxetanylamino)-1,3-thiazol-5-yl]phenoxy}-5-pyrimidinyl)-3-[3-(trifluoromethyl)phenyl]urea,
(36) 1-{2-[4-(2-{[2-(3-oxetanyl)ethyl]amino}-1,3-thiazol-5-yl)phenoxy]-5-pyrimidinyl}-3-[3-(trifluoromethyl)phenyl]urea,
(37)  1-[2-chloro-5-(trifluoromethyl)phenyl]-3-(2-{4-[2-(propylamino)-1,3-thiazol-5-yl]phenoxy}-5-pyrimidinyl)urea,
(38)  1-[2-chloro-4-(trifluoromethyl)phenyl]-3-(2-{4-[2-(propylamino)-1,3-thiazol-5-yl]phenoxy}-5-pyrimidinyl)urea,
(39)  1-[4-methyl-3-(trifluoromethyl)phenyl]-3-(2-{4-[2-(propylamino)-1,3-thiazol-5-yl]phenoxy}-5-pyrimidinyl)urea,
(40)  1-(6-{4-[2-(propylamino)-1,3-thiazol-5-yl]phenoxy}pyridinyl)-3-[3-(trifluoromethyl)phenyl]urea,
(41)  1-(2-{4-[2-(ethylamino)-1,3-thiazol-5-yl]phenoxy}-5-pyrimidinyl)-3-[5-(trifluoromethyl)-3-pyridinyl]urea,
(42)  1-[2-chloro-5-(trifluoromethyl)-3-pyridinyl]-3-(2-{4-[2-(ethylamino)-1,3-thiazol-5-yl]phenoxy}-5-pyrimidinyl)urea,
(43)  1-[2-(4-{2-[(2-methoxyethyl)amino]-1,3-thiazol-5-yl}phenoxy)-5-pyrimidinyl]-3-[3-(trifluoromethyl)phenyl]urea,
(44)  1-(3,5-difluorophenyl)-3-(2-{4-[2-(ethylamino)-1,3-thiazol-5-yl]phenoxy}-5-pyrimidinyl)urea,
(45)  1-[2-(4-{2-[(tetrahydro-2H-pyran-4-ylmethyl)amino]thiazol-5-yl}phenoxy)-5-pyrimidinyl]-3-[3-(trifluoromethyl)phenyl]urea,
(46)  1-[6-(4-{2-[(2-methoxyethyl)amino]-1,3-thiazol-5-yl}phenoxy)-3-pyridinyl]-3-[3-(trifluoromethyl)phenyl]urea,
(47)  1-[2-fluoro-5-(trifluoromethyl)phenyl]-3-(2-{4-[2-(propylamino)-1,3-thiazol-5-yl]phenoxy}-5-pyrimidinyl)urea,
(48)  1-[2-methyl-5-(trifluoromethyl)phenyl]-3-(2-{4-[2-(propylamino)-1,3-thiazol-5-yl]phenoxy}-5-pyrimidinyl)urea,
(49)  1-(2,5-dichlorophenyl)-3-(2-{4-[2-(propylamino)-1,3-thiazol-5-yl]phenoxy}-5-pyrimidinyl)urea,

(50) 1-(2,4-dichlorophenyl)-3-(2-{4-[2-(propylamino)-1,3-thiazol-5-yl]phenoxy}-5-pyrimidinyl)urea,
(51) 1-(2,5-difluorophenyl)-3-(2-{4-[2-(propylamino)-1,3-thiazol-5-yl]phenoxy}-5-pyrimidinyl)urea,
(52) 1-[3-(difluoromethyl)phenyl]-3-(2-{4-[2-(propylamino)-1,3-thiazol-5-yl]phenoxy}-5-pyrimidinyl)urea,
(53) 1-[2-chloro-5-(trifluoromethyl)phenyl]-3-(6-{4-[2-(propylamino)-1,3-thiazol-5-yl]phenoxy}-3-pyridinyl)urea,
(54) 1-[2-fluoro-5-(trifluoromethyl)phenyl]-3-(6-{4-[2-(propylamino)-1,3-thiazol-5-yl]phenoxy}-3-pyridinyl)urea,
(55) 1-[2-methyl-5-(trifluoromethyl)phenyl]-3-(6-{4-[2-(propylamino)-1,3-thiazol-5-yl]phenoxy}-3-pyridinyl)urea,
(56) 1-(2,5-dichlorophenyl)-3-(6-{4-[2-(propylamino)-1,3-thiazol-5-yl]phenoxy}-3-pyridinyl)urea,
(57) 1-(2,4-dichlorophenyl)-3-(6-{4-[2-(propylamino)-1,3-thiazol-5-yl]phenoxy}-3-pyridinyl)urea,
(58) 1-(2,5-difluorophenyl)-3-(6-{4-[2-(propylamino)-1,3-thiazol-5-yl]phenoxy}-3-pyridinyl)urea,
(59) 1-[3-(difluoromethyl)phenyl]-3-(6-{4-[2-(propylamino)-1,3-thiazol-5-yl]phenoxy}-3-pyridinyl)urea,
(60) 1-[2-chloro-4-(trifluoromethyl)phenyl]-3-(6-{4-[2-(propylamino)-1,3-thiazol-5-yl]phenoxy}-3-pyridinyl)urea,
(61) 1-(3,5-difluorophenyl)-3-(2-{4-[2-(propylamino)-1,3-thiazol-5-yl]phenoxy}-5-pyrimidinyl)urea,
(62) N,N-dimethyl-2-{[(2-{4-[2-(propylamino)-1,3-thiazol-5-yl]phenoxy}-5-pyrimidinyl)carbamoyl]amino}-4-(trifluoromethyl)benzenesulfonamide, or
(63) 1-[2-(methylsulfonyl)-5-(trifluoromethyl)phenyl]-3-(2-{4-[2-(propylamino)-1,3-thiazol-5-yl]phenoxy}-5-pyrimidinyl)urea,
a salt thereof, an N-oxide thereof, a solvate thereof or a prodrug thereof.

Among the compounds represented by the general formula (I), a compound represented by the following general formula (I-4-a):

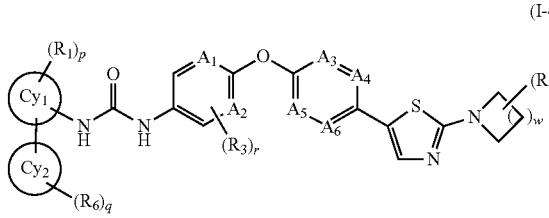
(I-4-a)

wherein all symbols represent the same meanings as those described in the above [1], a salt thereof, an N-oxide thereof, a solvate thereof or a prodrug thereof is more preferred, a compound represented by the following general formula (I-4-a-1) or general formula (I-4-a-2):

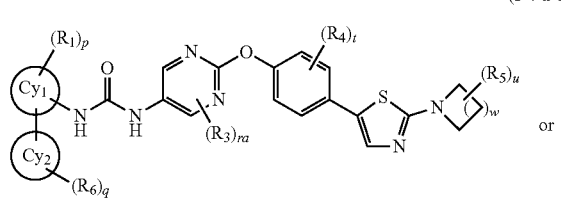
(I-4-a-1)

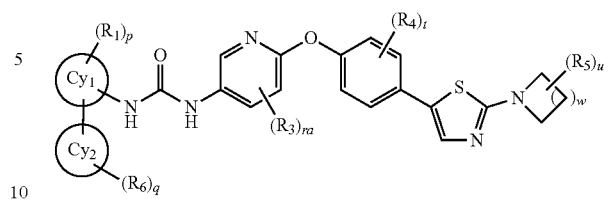
(I-4-a-2)

wherein ra represents an integer of 0 to 3; t represents an integer of 0 to 4; and other symbols represent the same meanings as those described in the above [1]; a salt thereof, an N-oxide thereof, a solvate thereof or a prodrug thereof is still more preferred and a compound represented by the following general formula (I-4-a-1-i), general formula (I-4-a-1-ii), general formula (I-4-a-2-i) or general formula (I-4-a-2-ii):

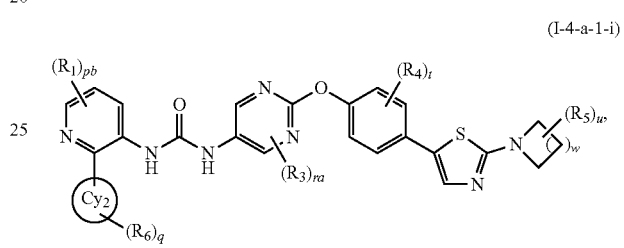
(I-4-a-1-i)

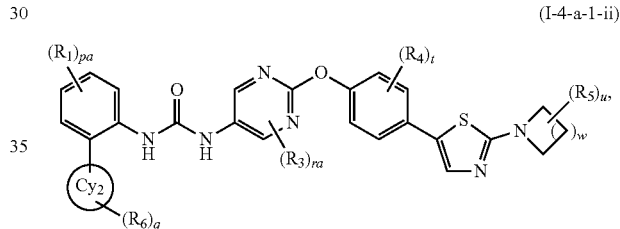
(I-4-a-1-ii)

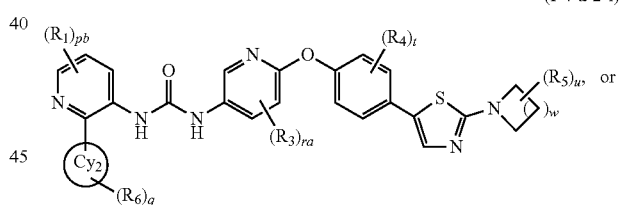
(I-4-a-2-i)

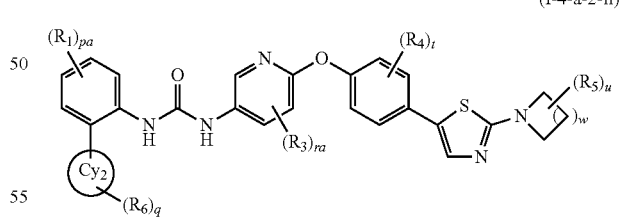
(I-4-a-2-ii)

wherein ra represents an integer of 0 to 3; t represents an integer of 0 to 4; and other symbols represent the same meanings as those described in the above [1] and [6]; a salt thereof, an N-oxide thereof, a solvate thereof or a prodrug thereof is particularly preferred.

Among the compounds represented by the general formula (I), the compound represented by the general formula (I-4-a-1-i), the compound represented by the general formula (I-4-a-1-ii), the compound represented by the general formula (I-4-a-2-i) or the compound represented by the general formula (I-4-a-2-ii) is preferably a compound having the general formula wherein the ring $Cy_2$ is a C3-10 monocyclic carbocycle or a 5- to 10-membered monocyclic heterocycle or bicyclic heterocycle; $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_3$ is a fluorine, a chlorine, methyl, trifluoromethyl or a methoxy group; $R_4$ is a fluorine, a chlorine, methyl, trifluoromethyl or a methoxy group; $R_5$ is a hydroxy group or a hydroxymethyl group; $R_6$ is (1) a halogen, (2) a hydroxy group, (3) a C1-4 alkyl, (4) a C1-4 alkyl substituted with a halogen, (5) a C1-4 alkyl substituted with a hydroxy group, (6) a C3-6 cycloalkyl, (7) a C1-4 alkoxy, (8) carboxyl, (9) —$CO_2$(C1-4 alkyl), (10) an acetylamide group, (11) a phosphonooxy group or (12) a sulfonamide group; pa is an integer of 0 to 2; pb is an integer of 0 to 2; q is an integer of 0 to 2; ra is an integer of 0 to 1; t is an integer of 0 to 2; u is an integer of 0 to 1; and w is an integer of 2 to 4; a salt thereof, an N-oxide thereof, a solvate thereof or a prodrug thereof, more preferably a compound having the general formula wherein the ring $Cy_2$ is cyclopropane, benzene, cyclohexane, indane, tetrahydronaphthalene, pyran, furan, thiophene, pyrrole, isoxazole, oxazole, isothiazole, thiazole, pyrazole, imidazole, triazole, pyridine, pyridone, pyridazine, pyrimidine, pyrazine, tetrahydropyran, tetrahydrothiopyran, piperidine, morpholine, thiomorpholine, tetrahydropyridine, benzodioxane, piperazine, perhydroindene, dihydrobenzofuran, dihydrobenzothiophene, indoline, benzodioxole, benzoxathiole, dihydrobenzoxazole, dihydrobenzothiazole, chromane, thiochromane, tetrahydroquinoline, dihydrobenzodioxine, dihydrobenzoxathiine, dihydrobenzoxazine, indole, benzofuran, benzothiophene, indazole or tetrahydronaphthalene; $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_3$ is a fluorine, a chlorine, methyl, trifluoromethyl or a methoxy group; $R_4$ is a fluorine, a chlorine, methyl, trifluoromethyl or a methoxy group; $R_5$ is a hydroxy group or a hydroxymethyl group; $R_6$ is (1) a halogen, (2) a hydroxy group, (3) a C1-4 alkyl, (4) a C1-4 alkyl substituted with a halogen, (5) a C1-4 alkyl substituted with a hydroxy group, (6) a C3-6 cycloalkyl, (7) a C1-4 alkoxy, (8) carboxyl, (9) —$CO_2$(C1-4 alkyl), (10) an acetylamide group, (11) a phosphonooxy group or (12) a sulfonamide group; pa is an integer of 0 to 2; pb is an integer of 0 to 2; q is an integer of 0 to 2; ra is an integer of 0 to 1; t is an integer of 0 to 2; u is an integer of 0 to 1; and w is an integer of 2 to 4; a salt thereof, an N-oxide thereof, a solvate thereof or a prodrug thereof, still more preferably a compound having the general formula wherein the ring $Cy_2$ is benzene, pyridine, pyrazole, imidazole or triazole; $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_3$ is a fluorine, a chlorine, methyl, trifluoromethyl or a methoxy group; $R_4$ is a fluorine, a chlorine, methyl, trifluoromethyl or a methoxy group; $R_5$ is a hydroxy group or a hydroxymethyl group; $R_6$ is (1) a halogen, (2) a hydroxy group, (3) a C1-4 alkyl, (4) a C1-4 alkyl substituted with a halogen, (5) a C1-4 alkyl substituted with a hydroxy group, (6) a C3-6 cycloalkyl, (7) a C1-4 alkoxy, (8) carboxyl, (9) —$CO_2$(C1-4 alkyl), (10) an acetylamide group, (11) a phosphonooxy group or (12) a sulfonamide group; pa is an integer of 0 to 2; pb is an integer of 0 to 2; q is an integer of 0 to 2; ra is an integer of 0 to 1; t is an integer of 0 to 2; u is an integer of 0 to 1; and w is an integer of 2 to 4; a salt thereof, an N-oxide thereof, a solvate thereof or a prodrug thereof.

Among the compounds represented by the general formula (I), the compound represented by the general formula (I-4-a-1) or the compound represented by the general formula (I-4-a-2) is the most preferably:

(1) 1-[2-(4-{2-[2-(2-hydroxy-2-propanyl)-1-pyrrolidinyl]-1,3-thiazol-5-yl}phenoxy)-5-pyrimidinyl]-3-[2-phenyl-5-(trifluoromethyl)-3-pyridinyl]urea, (2) 1-(2-{4-[2-(1-azetidinyl)-1,3-thiazol-5-yl]phenoxy}-5-pyrimidinyl)-3-[2-phenyl-5-(trifluoromethyl)-3-pyridinyl]urea, (3) 1-(2-{4-[2-(1-azetidinyl)-1,3-thiazol-5-yl]phenoxy}-5-pyrimidinyl)-3-[2-(3-pyridinyl)-5-(trifluoromethyl)phenyl]urea, (4) 1-(2-{4-[2-(1-azetidinyl)-1,3-thiazol-5-yl]phenoxy}-5-pyrimidinyl)-3-[5-phenyl-2-(trifluoromethyl)-4-pyridinyl]urea, (5) 1-(2-{4-[2-(1-azetidinyl)-1,3-thiazol-5-yl]phenoxy}-5-pyrimidinyl)-3-[2-(1H-1,2,3-triazol-1-yl)-5-(trifluoromethyl)phenyl]urea, or (6) 1-(2-{4-[2-(1-azetidinyl)-1,3-thiazol-5-yl]phenoxy}-5-pyrimidinyl)-3-[2-(1H-pyrazol-1-yl)-5-(trifluoromethyl)phenyl]urea, a salt thereof, an N-oxide thereof, a solvate thereof or a prodrug thereof.

Among the compounds represented by the general formula (I), a compound represented by the following general formula (I-5-a) or general formula (I-5-b):

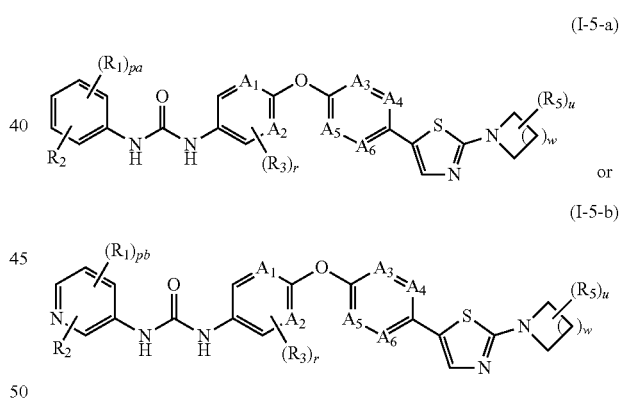

wherein all symbols represent the same meanings as those described in the above [1] and [6]; a salt thereof, an N-oxide thereof, a solvate thereof or a prodrug thereof is more preferred, and a compound represented by the following general formula (I-5-a-1), general formula (I-5-a-2), general formula (I-5-b-1) or general formula (I-5-b-2):

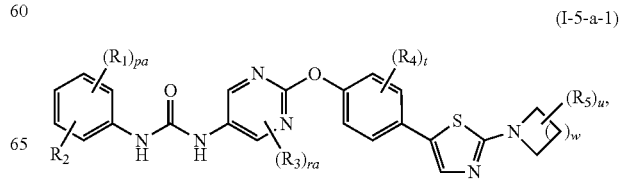

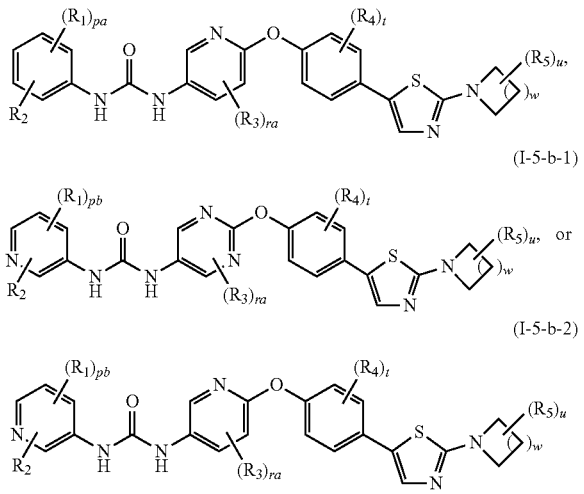

wherein ra represents an integer of 0 to 3; t represents an integer of 0 to 4; and other symbols represent the same meanings as those described in the above [1] and [6]; a salt thereof, an N-oxide thereof, a solvate thereof or a prodrug thereof is still more preferred.

Among the compounds represented by the general formula (I), the compound represented by the general formula (I-5-a-1), the compound represented by the general formula (I-5-a-2), the compound represented by the general formula (I-5-b-1) or the compound represented by the general formula (I-5-b-2) is preferably a compound having the general formula wherein $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_2$ is isopropyl, sec-butyl, tert-butyl, isobutyl, a hydrogen atom, a hydroxy group, a carboxyl group, 1-hydroxy-1-methylethyl, 2-hydroxypropyl, 3-hydroxy-3-methyl-1-butynyl, a methylsulfonyl group, a methylsulfonamide group or a dimethylsulfonamide group; $R_3$ is a fluorine, a chlorine, methyl, trifluoromethyl or a methoxy group; $R_4$ is a fluorine, a chlorine, methyl, trifluoromethyl or a methoxy group; $R_5$ is a halogen, a hydroxy group or a C1-4 alkyl group optionally substituted with a hydroxy group; pa is an integer of 0 to 2; pb is an integer of 0 to 2; ra is an integer of 0 to 1; t is an integer of 0 to 2; u is an integer of 0 to 1; and w is an integer of 2 to 4; a salt thereof, an N-oxide thereof, a solvate thereof or a prodrug thereof, more preferably a compound having the general formula wherein $R_1$ is a halogen, methyl, trifluoromethyl, tert-butyl, 1,1-difluoroethyl, isopropyl, cyclopropyl, oxetanyl or a difluoromethyl group; $R_2$ is isopropyl, sec-butyl, tert-butyl, isobutyl, a hydrogen atom, a hydroxy group, a carboxyl group, 1-hydroxy-1-methylethyl, 2-hydroxypropyl, 3-hydroxy-3-methyl-1-butynyl, a methylsulfonyl group, a methylsulfonamide group or a dimethylsulfonamide group; $R_3$ is a fluorine, a chlorine, methyl, trifluoromethyl or a methoxy group; $R_4$ is a fluorine, a chlorine, methyl, trifluoromethyl or a methoxy group; $R_5$ is a halogen, a hydroxy group or a C1-4 alkyl group optionally substituted with a hydroxy group; pa is an integer of 0 to 2; pb is an integer of 0 to 2; ra is an integer of 0 to 1; t is an integer of 0 to 2; u is an integer of 0 to 1; and w is an integer of 2 to 4; a salt thereof, an N-oxide thereof, a solvate thereof or a prodrug thereof, and still more preferably a compound having the general formula wherein $R_1$ is a halogen, methyl or trifluoromethyl; $R_2$ is isopropyl, sec-butyl, tert-butyl, isobutyl, a hydrogen atom, a hydroxy group, a carboxyl group, 1-hydroxy-1-methylethyl, 2-hydroxypropyl, 3-hydroxy-3-methyl-1-butynyl, a methylsulfonyl group, a methylsulfonamide group or a dimethylsulfonamide group; $R_3$ is a fluorine, a chlorine, methyl, trifluoromethyl or a methoxy group; $R_4$ is a fluorine, a chlorine, methyl, trifluoromethyl or a methoxy group; $R_5$ is a halogen, a hydroxy group or a C1-4 alkyl group optionally substituted with a hydroxy group; pa is an integer of 0 to 2; pb is an integer of 0 to 2; ra is an integer of 0 to 1; t is an integer of 0 to 2; u is an integer of 0 to 1; and w is an integer of 2 to 4; a salt thereof, an N-oxide thereof, a solvate thereof or a prodrug thereof.

Among the compounds represented by the general formula (I), the compound represented by the general formula (I-5-a) or the compound represented by the general formula (I-5-b) is the most preferably:

(1) 1-[2-(4-{2-[3-(hydroxymethyl)-1-pyrrolidinyl]-1,3-thiazol-5-yl}phenoxy)-5-pyrimidinyl]-3-[3-(trifluoromethyl)phenyl]urea,
(2) 1-(6-{4-[2-(1-pyrrolidinyl)-1,3-thiazol-5-yl]phenoxy}-3-pyridinyl)-3-[3-(trifluoromethyl)phenyl]urea,
(3) 1-(6-{4-[2-(1-piperidinyl)-1,3-thiazol-5-yl]phenoxy}-3-pyridinyl)-3-[3-(trifluoromethyl)phenyl]urea,
(4) 1-(2-{4-[2-(1-pyrrolidinyl)-1,3-thiazol-5-yl]phenoxy}-5-pyrimidinyl)-3-[3-(trifluoromethyl)phenyl]urea,
(5) 1-(2-{4-[2-(1-piperidinyl)-1,3-thiazol-5-yl]phenoxy}-5-pyrimidinyl)-3-[3-(trifluoromethyl)phenyl]urea,
(6) 1-(2-{4-[2-(1-azetidinyl)-1,3-thiazol-5-yl]phenoxy}-5-pyrimidinyl)-3-[3-(trifluoromethyl)phenyl]urea,
(7) 1-(2-{4-[2-(3-hydroxy-1-azetidinyl)-1,3-thiazol-5-yl]phenoxy}-5-pyrimidinyl)-3-[3-(trifluoromethyl)phenyl]urea,
(8) 1-(2-{4-[2-(1-azetidinyl)-1,3-thiazol-5-yl]phenoxy}-5-pyrimidinyl)-3-(2,6-difluorophenyl)urea,
(9) 1-(2-{4-[2-(1-azetidinyl)-1,3-thiazol-5-yl]phenoxy}-5-pyrimidinyl)-3-(2,4-difluorophenyl)urea,
(10) 1-(2-{4-[2-(1-azetidinyl)-1,3-thiazol-5-yl]phenoxy}-5-pyrimidinyl)-3-(3,5-difluorophenyl)urea,
(11) 1-(2-{4-[2-(1-azetidinyl)-1,3-thiazol-5-yl]phenoxy}-5-pyrimidinyl)-3-[3-fluoro-5-(trifluoromethyl)phenyl]urea,
(12) 1-(2-{4-[2-(1-azetidinyl)-1,3-thiazol-5-yl]phenoxy}-5-pyrimidinyl)-3-[4-methyl-3-(trifluoromethyl)phenyl]urea,
(13) 1-(2-{4-[2-(1-azetidinyl)-1,3-thiazol-5-yl]phenoxy}-5-pyrimidinyl)-3-[2-chloro-4-(trifluoromethyl)phenyl]urea,
(14) 1-(2-{4-[2-(1-azetidinyl)-1,3-thiazol-5-yl]phenoxy}-5-pyrimidinyl)-3-(2,5-difluorophenyl)urea,
(15) 1-(2-{4-[2-(1-azetidinyl)-1,3-thiazol-5-yl]phenoxy}-5-pyrimidinyl)-3-(3,4-difluorophenyl)urea,
(16) 1-(2-{4-[2-(1-azetidinyl)-1,3-thiazol-5-yl]phenoxy}-5-pyrimidinyl)-3-(2-fluorophenyl)urea,
(17) 1-(2-{4-[2-(3-hydroxy-3-methyl-1-azetidinyl)-1,3-thiazol-5-yl]phenoxy}-5-pyrimidinyl)-3-[3-(trifluoromethyl)phenyl]urea,
(18) 1-(2-{4-[2-(3,3-difluoro-1-azetidinyl)-1,3-thiazol-5-yl]phenoxy}-5-pyrimidinyl)-3-[3-(trifluoromethyl)phenyl]urea,
(19) 1-(2-{4-[2-(1-azetidinyl)-1,3-thiazol-5-yl]phenoxy}-5-pyrimidinyl)-3-(4-fluorophenyl)urea,
(20) 1-(2-{4-[2-(1-azetidinyl)-1,3-thiazol-5-yl]phenoxy}-5-pyrimidinyl)-3-[3-(difluoromethyl)phenyl]urea,
(21) 1-(2-{4-[2-(1-azetidinyl)-1,3-thiazol-5-yl]phenoxy}-5-pyrimidinyl)-3-(2,3,5-trifluorophenyl)urea,
(22) 1-(2-{4-[2-(1-azetidinyl)-1,3-thiazol-5-yl]phenoxy}-5-pyrimidinyl)-3-[2-chloro-5-(trifluoromethyl)phenyl]urea,

(23) 1-(2-{4-[2-(1-azetidinyl)-1,3-thiazol-5-yl]phenoxy}-5-pyrimidinyl)-3-(2,4, 6-trifluorophenyl)urea,

(24) 1-(2-{4-[2-(1-azetidinyl)-1,3-thiazol-5-yl]phenoxy}-5-pyrimidinyl)-3-[2-fluoro-5-(trifluoromethyl)phenyl]urea,

(25) 1-(2-{4-[2-(1-azetidinyl)-1,3-thiazol-5-yl]phenoxy}-5-pyrimidinyl)-3-(2,3-difluorophenyl)urea,

(26) 1-(2-{4-[2-(1-azetidinyl)-1,3-thiazol-5-yl]phenoxy}-5-pyrimidinyl)-3-(2,4,5-trifluorophenyl)urea,

(27) 1-(2-{4-[2-(1-azetidinyl)-1,3-thiazol-5-yl]phenoxy}-5-pyrimidinyl)-3-(2,3, 4-trifluorophenyl)urea,

(28) 1-(2-{4-[2-(1-azetidinyl)-1,3-thiazol-5-yl]phenoxy}-5-pyrimidinyl)-3-(2,3,5, 6-tetrafluorophenyl)urea,

(29) 1-(2-{4-[2-(1-azetidinyl)-1,3-thiazol-5-yl]phenoxy}-5-pyrimidinyl)-3-[2-methyl-5-(trifluoromethyl)phenyl]urea, or

(30) 1-(2-{4-[2-(1-azetidinyl)-1,3-thiazol-5-yl]phenoxy}-5-pyrimidinyl)-3-[2-(trifluoromethyl)-4-pyridinyl]urea, a salt thereof, an N-oxide thereof, a solvate thereof or a prodrug thereof.

Among the compounds represented by the general formula (I), a compound represented by the following general formula (I-6-a) or general formula (I-6-b):

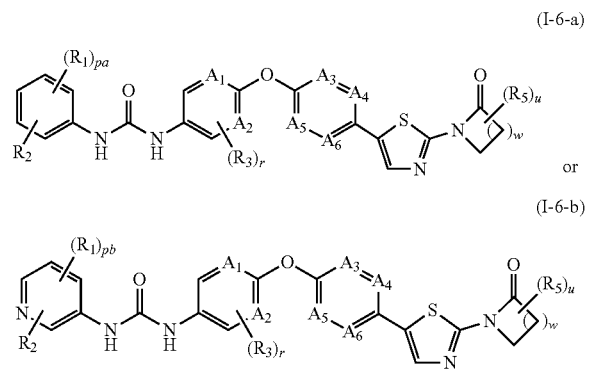

wherein all symbols represent the same meanings as those described in the above [1] and [6]; a salt thereof, an N-oxide thereof, a solvate thereof or a prodrug thereof is more preferred and a compound represented by the following general formula (I-6-a-1), general formula (I-6-a-2), general formula (I-6-b-1) or general formula (I-6-b-2):

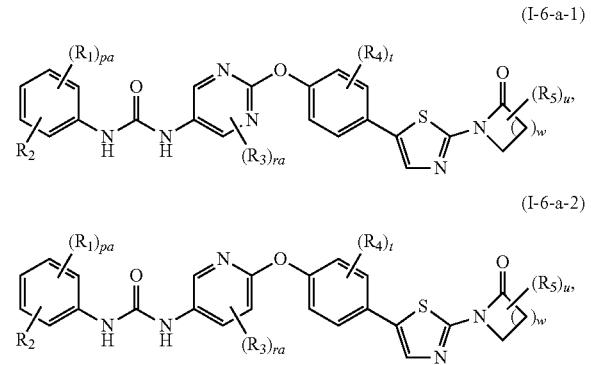

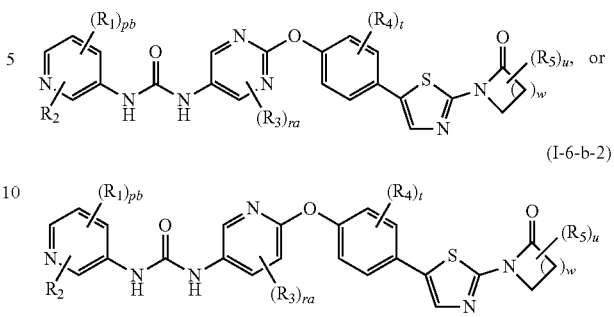

wherein ra represents an integer of 0 to 3; t represents an integer of 0 to 4; and other symbols represent the same meaning as those described in the above [1] and [6]; a salt thereof, an N-oxide thereof, a solvate thereof or a prodrug thereof is still more preferred.

Among the compounds represented by the general formula (I), the compound represented by the general formula (I-6-a-1), the compound represented by the general formula (I-6-a-2), the compound represented by the general formula (I-6-b-1) or the compound represented by the general formula (I-6-b-2) is preferably a compound having the general formula wherein $R_1$ is (1) a halogen, (2) a C1-4 alkyl, (3) a C1-4 alkyl substituted with a halogen, (4) cyclopropyl, (5) cyclobutyl, (6) cyclopropyl substituted with a halogen, (7) cyclobutyl substituted with a halogen, (8) oxetanyl or (9) an oxetanyl group substituted with a methyl group; $R_2$ is isopropyl, sec-butyl, tert-butyl, isobutyl, a hydrogen atom, a hydroxy group, a carboxyl group, 1-hydroxy-1-methylethyl, 2-hydroxypropyl, 3-hydroxy-3-methyl-1-butynyl, a methylsulfonyl group, a methylsulfonamide group or a dimethylsulfonamide group; $R_3$ is a fluorine, a chlorine, methyl, trifluoromethyl or a methoxy group; $R_4$ is a fluorine, a chlorine, methyl, trifluoromethyl or a methoxy group; $R_5$ is a halogen, a hydroxy group or a C1-4 alkyl group optionally substituted with a hydroxy group; pa is an integer of 0 to 2; pb is an integer of 0 to 2; ra is an integer of 0 to 1; t is an integer of 0 to 2; u is an integer of 0 to 1; and w is an integer of 2 to 4; a salt thereof, an N-oxide thereof, a solvate thereof or a prodrug thereof, more preferably a compound having the general formula wherein $R_1$ is a halogen, methyl, trifluoromethyl, tert-butyl, 1,1-difluoroethyl, isopropyl, cyclopropyl, oxetanyl or a difluoromethyl group; $R_2$ is isopropyl, sec-butyl, tert-butyl, isobutyl, a hydrogen atom, a hydroxy group, a carboxyl group, 1-hydroxy-1-methylethyl, 2-hydroxypropyl, 3-hydroxy-3-methyl-1-butynyl, a methylsulfonyl group, a methylsulfonamide group or a dimethylsulfonamide group; $R_3$ is a fluorine, a chlorine, methyl, trifluoromethyl or a methoxy group; $R_4$ is a fluorine, a chlorine, methyl, trifluoromethyl or a methoxy group; $R_5$ is a halogen, a hydroxy group or a C1-4 alkyl group optionally substituted with a hydroxy group; pa is an integer of 0 to 2; pb is an integer of 0 to 2; ra is an integer of 0 to 1; t is an integer of 0 to 2; u is an integer of 0 to 1; and w is an integer of 2 to 4; a salt thereof, an N-oxide thereof, a solvate thereof or a prodrug thereof and still more preferably a compound having the general formula wherein $R_1$ is a halogen, methyl or trifluoromethyl; $R_2$ is isopropyl, sec-butyl, tert-butyl, isobutyl, a hydrogen atom, a hydroxy group, a carboxyl group, 1-hydroxy-1-methylethyl, 2-hydroxypropyl, 3-hydroxy-3-methyl-1-butynyl, a methylsulfonyl group, a methylsulfonamide group or a dimethylsulfonamide group; $R_3$ is a fluorine, a chlorine, methyl, trifluoromethyl or a methoxy group; $R_4$ is a fluorine, a chlorine, methyl, trifluoromethyl or a methoxy group; $R_5$ is a halogen, a hydroxy group or a C1-4 alkyl group optionally substituted with a hydroxy group; pa is an integer of 0 to 2; pb is an integer of 0 to 2; ra is an integer of 0 to 1; t is an integer of 0 to 2; u is an integer of 0 to 1; and w is an integer of 2 to 4; a salt thereof, an N-oxide thereof, a solvate thereof or a prodrug thereof.

Among the compounds represented by the general formula (I), the compound represented by the general formula (I-6-a) or the compound represented by the general formula (I-6-b) is the most preferably:

(1) 1-[2-isopropyl-5-(trifluoromethyl)-3-pyridinyl]-3-(2-{4-[2-(2-oxo-1-pyrrolidinyl)-1,3-thiazol-5-yl]phenoxy}-5-pyrimidinyl)urea, (2) 1-[2-isopropyl-5-(trifluoromethyl)-3-pyridinyl]-3-(2-{4-[2-(2-oxo-1-piperidinyl)-1,3-thiazol-5-yl]phenoxy}-5-pyrimidinyl)urea, (3) 1-(2-{4-[2-(2-oxo-1-pyrrolidinyl)-1,3-thiazol-5-yl]phenoxy}-5-pyrimidinyl)-3-[3-(trifluoromethyl)phenyl]urea, (4) 1-[2-chloro-5-(trifluoromethyl)-3-pyridinyl]-3-(2-{4-[2-(2-oxo-1-pyrrolidinyl)-1,3-thiazol-5-yl]phenoxy}-5-pyrimidinyl)urea, (5) 1-(2-{4-[2-(2-oxo-1-pyrrolidinyl)-1,3-thiazol-5-yl]phenoxy}-5-pyrimidinyl)-3-[5-(trifluoromethyl)-3-pyridinyl]urea, (6) 1-[3-hydroxy-5-(trifluoromethyl)phenyl]-3-(2-{4-[2-(2-oxo-1-pyrrolidinyl)-1,3-thiazol-5-yl]phenoxy}-5-pyrimidinyl)urea, (7) 1-(2-{4-[2-(2-oxo-1-pyrrolidinyl)-1,3-thiazol-5-yl]phenoxy}-5-pyrimidinyl)-3-[4-(trifluoromethyl)-2-pyridinyl]urea, (8) 2-{[(2-{4-[2-(2-oxo-1-pyrrolidinyl)-1,3-thiazol-5-yl]phenoxy}-5-pyrimidinyl)carbamoyl]amino}-4-(trifluoromethyl)benzoic acid, (9) 1-[2-(2-hydroxy-2-propanyl)-5-(trifluoromethyl)phenyl]-3-(2-{4-[2-(2-oxo-1-pyrrolidinyl)-1,3-thiazol-5-yl]phenoxy}-5-pyrimidinyl)urea,

(10) 1-[3,5-bis(trifluoromethyl)phenyl]-3-(2-{4-[2-(2-oxo-1-pyrrolidinyl)-1,3-thiazol-5-yl]phenoxy}-5-pyrimidinyl)urea,

(11) 1-[2-(3-hydroxy-3-methyl-1-butyn-1-yl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,

(12) 1-[2-(2-hydroxy-2-propanyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,

(13) 1-[2-methoxy-5-(trifluoromethyl)-3-pyridinyl]-3-(2-{4-[2-(2-oxo-1-pyrrolidinyl)-1,3-thiazol-5-yl]phenoxy}-5-pyrimidinyl)urea,

(14) 1-(2-{3-methyl-4-[2-(2-oxo-1-pyrrolidinyl)-1,3-thiazol-5-yl]phenoxy}-5-pyrimidinyl)-3-[3-(trifluoromethyl)phenyl]urea,

(15) 1-[2-({6-[2-(2-oxo-1-pyrrolidinyl)-1,3-thiazol-5-yl]-3-pyridinyl}oxy)-5-pyrimidinyl]-3-[3-(trifluoromethyl)phenyl]urea,

(16) 1-[2-(4-{2-[3-(2-hydroxy-2-propanyl)-2-oxo-1-pyrrolidinyl]-1,3-thiazol-5-yl}phenoxy)-5-pyrimidinyl]-3-[3-(trifluoromethyl)phenyl]urea,

(17) 1-[3-(difluoromethyl)phenyl]-3-(2-{4-[2-(2-oxo-1-pyrrolidinyl)-1,3-thiazol-5-yl]phenoxy}-5-pyrimidinyl)urea,

(18) 1-[3-(1,1-difluoroethyl)phenyl]-3-(2-{4-[2-(2-oxo-1-pyrrolidinyl)-1,3-thiazol-5-yl]phenoxy}-5-pyrimidinyl)urea, or

(19) 1-[2-(4-{2-[3-(2-hydroxy-2-propanyl)-2-oxo-1-pyrrolidinyl]-1,3-thiazol-5-yl}phenoxy)-5-pyrimidinyl]-3-[2-(methylsulfonyl)-5-(trifluoromethyl)phenyl]urea, a salt thereof, an N-oxide thereof, a solvate thereof or a prodrug thereof.

Among the compounds represented by the general formula (I), other preferable compounds include:

(1) 1-(2-{4-[2-(2-oxo-1-pyrrolidinyl)-1,3-thiazol-5-yl]phenoxy}-5-pyrimidinyl)-3-[3-(trifluoromethyl)cyclohexyl]urea, (2) 1-(2-{4-[2-(2-oxo-1-pyrrolidinyl)-1,3-thiazol-5-yl]phenoxy})-5-pyrimidinyl)-3-[2-phenyl-5-(trifluoromethyl)cyclohexyl]urea, (3) 1-(2-{4-[2-(2-oxo-1-pyrrolidinyl)-1,3-thiazol-5-yl]phenoxy}-5-pyrimidinyl)-3-[2-(3-pyridinyl)-5-(trifluoromethyl)cyclohexyl]urea, (4) 1-(2-{4-[2-(2-oxo-1-pyrrolidinyl)-1,3-thiazol-5-yl]phenoxy}-5-pyrimidinyl)-3-[3-(3-pyridinyloxy)-5-(trifluoromethyl)phenyl]urea, (5) N-ethyl-N-[5-(4-{[5-({[2-phenyl-5-(trifluoromethyl)-3-pyridinyl]carbamoyl}amino)-2-pyridinyl]oxy}phenyl)-1,3-thiazol-2-yl]propanamide, (6) 1-(2-{4-[2-(2-oxo-1-pyrrolidinyl)-1,3-thiazol-5-yl]phenoxy}-5-pyrimidinyl)-3-[2-(3-pyridinyloxy)-5-(trifluoromethyl)phenyl]urea, (7) 1-(2-{4-[2-(dimethylamino)-1,3-thiazol-5-yl]phenoxy}-5-pyrimidinyl)-3-[3-(trifluoromethyl)phenyl]urea, (8) 1-[2-(cyclopropylcarbamoyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea, (9) 1-(2-{4-[2-(3-oxo-4-morpholinyl)-1,3-thiazol-5-yl]phenoxy}-5-pyrimidinyl)-3-[3-(trifluoromethyl)phenyl]urea,

(10) 1-(2-{4-[2-(dimethylamino)-1,3-thiazol-5-yl]phenoxy}-5-pyrimidinyl)-3-[2-(3-pyridinyl)-5-(trifluoromethyl)phenyl]urea,

(11) 1-(6-{4-[2-(dimethylamino)-1,3-thiazol-5-yl]phenoxy}-3-pyridinyl)-3-[3-(trifluoromethyl)phenyl]urea,

(12) 1-(2-{4-[2-(diethylamino)-1,3-thiazol-5-yl]phenoxy}-5-pyrimidinyl)-3-[3-(trifluoromethyl)phenyl]urea,

(13) 1-(6-{4-[2-(dimethylamino)-1,3-thiazol-5-yl]phenoxy}-3-pyridinyl)-3-[2-(3-pyridinyl)-5-(trifluoromethyl)phenyl]urea,

(14) 1-[2-chloro-5-(trifluoromethyl)phenyl]-3-(2-{4-[2-(dimethylamino)-1,3-thiazol-5-yl]phenoxy}-5-pyrimidinyl)urea,

(15) 1-{2-[4-(2-amino-1,3-thiazol-5-yl)phenoxy]-5-pyrimidinyl}-3-[2-(3-pyridinyl)-5-(trifluoromethyl)phenyl]urea,

(16) 1-[2-chloro-4-(trifluoromethyl)phenyl]-3-(6-{4-[2-(dimethylamino)-1,3-thiazol-5-yl]phenoxy}-3-pyridinyl)urea,

(17) 1-(2-{4-[2-(dipropylamino)-1,3-thiazol-5-yl]phenoxy}-5-pyrimidinyl)-3-[3-(trifluoromethyl)phenyl]urea,

(18) 1-[2-(4-{2-[ethyl(methyl)amino]-1,3-thiazol-5-yl}phenoxy)-5-pyrimidinyl]-3-[3-(trifluoromethyl)phenyl]urea,

(19) 1-[6-(4-{2-[(cyclopropylmethyl)(methyl)amino]-1,3-thiazol-5-yl}phenoxy)-3-pyridinyl]-3-[3-(trifluoromethyl)phenyl]urea,

(20) 1-(2-{4-[2-(4-morpholinyl)-1,3-thiazol-5-yl]phenoxy}-5-pyrimidinyl)-3-[3-(trifluoromethyl)phenyl]urea,

(21) 1-[6-(4-{2-[(cyclopropylmethyl)(methyl)amino]-1,3-thiazol-5-yl}phenoxy)-3-pyridinyl]-3-[3',4'-dimethyl-4-(trifluoromethyl)-2-biphenylyl]urea,

(22) 1-[6-(4-{2-[ethyl(methyl)amino]-1,3-thiazol-5-yl}phenoxy)-3-pyridinyl]-3-[3-(trifluoromethyl)phenyl]urea,

(23) 1-(2-{4-[2-(dimethylamino)-1,3-thiazol-5-yl]phenoxy}-5-pyrimidinyl)-3-[2-(1H-pyrazol-1-yl)-5-(trifluoromethyl)phenyl]urea,
(24) 1-(3,5-difluorophenyl)-3-(2-{4-[2-(dimethylamino)-1,3-thiazol-5-yl]phenoxy}-5-pyrimidinyl)urea, or
(25) 1-[2-chloro-4-(trifluoromethyl)phenyl]-3-(2-{4-[2-(dimethylamino)-1,3-thiazol-5-yl]phenoxy}-5-pyrimidinyl)urea, a salt thereof, an N-oxide thereof, a solvate thereof or a prodrug thereof.

All isomers are encompassed by the present invention unless specifically stated. For example, an alkyl group, an alkoxy group, an alkenyl group and an alkylene group comprise linear and branched groups. Further, double bonds, rings, isomers in fused rings (E, Z, cis and trans forms), isomers due to asymmetric carbons (R and S forms, α and β forms, enantiomers, diastereomers), optically active substances (D, L, d and l forms), polar substances by chromatographic separation (high-polarity substances, low-polarity substances), equilibrated compounds, rotational isomers, mixtures thereof with any proportions and racemic mixtures are all encompassed by the present invention. Isomers due to tautomeric properties are also encompassed by the present invention.

In the present invention, unless otherwise stated the symbol:

indicates that the bond projects below the plane of the paper (i.e. α-configuration), the symbol:

indicates that the bond projects above the plane of the paper (i.e. β-configuration), the symbol:

indicates that the bond is the α-configuration or the β-configuration, and the symbol:

indicates that the bond is a mixture of the α-configuration and the β-configuration as apparent to a person skilled in the art.

[Salts]

The compound represented by the general formula (I) may be converted to a salt according to well known methods.

The salt is preferably a pharmaceutically acceptable salt.
The salt is preferably water soluble.
The salt may include, for example, alkali metal salts, alkaline-earth metal salts, ammonium salts, amine salts and acid addition salts.

The alkali metal salt may include, for example, potassium and sodium.

The alkaline-earth metal salt may include, for example, calcium and magnesium.

The ammonium salt may include, for example, tetramethylammonium.

The amine salt may include, for example, triethylamine, methylamine, dimethylamine, cyclopentylamine, benzylamine, phenethylamine, piperidine, monoethanolamine, diethanolamine, tris(hydroxymethyl)aminomethane, lysine, arginine and N-methyl-D-glucamine.

The acid addition salt may include, for example, inorganic acid salts such as hydrochlorides, hydrobromides, hydroiodides, sulphates, phosphates and nitrates and organic acid salts such as acetates, lactates, tartrates, benzoates, citrates, methanesulfonates, ethanesulfonates, trifluoroacetates, benzenesulfonates, toluenesulfonates, isethionates, glucuronates and gluconates.

The present compound may be converted to an N-oxide according to any methods. The N-oxide represents the compound of the general formula (I) in which a nitrogen atom thereof is oxidized and may be, for example, the compound represented by the general formula (I) wherein the nitrogen atom in $A_1$, $A_2$, $A_3$, $A_4$, $A_5$ or $A_6$ which is independently =N— is oxidized. Alternatively, the N-oxide may be the compound represented by the general formula (I) wherein the nitrogen atom in $Cy_1$ and $Cy_2$ which are independently a nitrogen-containing heterocycle is oxidized. Further, the N-oxide may be the compound represented by the general formula (I) wherein the nitrogen atom in the $R_2$ and $R_6$ groups which are independently —NH(C1-3 alkyl) and —N(C1-3 alkyl)$_2$ groups is oxidized. Also, the N-oxide may be the compound represented by the general formula (I) wherein the nitrogen atom in the Z group and the nitrogen atom in the thiazole ring are oxidized.

The compound represented by the general formula (I) and a salt thereof may be converted to a solvate.

The solvate is preferably non-toxic and water soluble. Appropriate solvates may include, for example, solvates with water or an alcoholic solvent (e.g., ethanol).

[Prodrugs]

A prodrug of the compound represented by the general formula (I) refers to a compound that is converted to the compound represented by the general formula (I) by in vivo reaction with an enzyme or gastric acid. The prodrug of the compound represented by the general formula (I) may include, for example, compounds wherein an amino group in the compound represented by the general formula (I) is acylated, alkylated or phosphated (e.g., compounds wherein an amino group in the compound represented by the general formula (I) is derivatized to eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, acetoxymethyl or tert-butyl); compounds wherein a hydroxy group in the compound represented by the general formula (I) is acylated, alkylated, phosphated or borated (e.g., compounds wherein a hydroxy group in the compound represented by the general formula (I) is derivatized to acetyl, palmitoyl, propanoyl, pivaloyl, succinyl, fumaryl, alanyl or dimethylaminomethylcarbonyl); compounds wherein a carboxy group in the compound represented by the general formula (I) is esterified or amidated (e.g., compounds wherein a carboxy group in the compound represented by the general formula (I) is derivatized to ethyl ester, phenyl ester, carboxymethyl ester, dimethylaminomethyl ester, pivaloyloxymethyl ester, 1-{(ethoxycarbonyl)oxy}ethyl ester, phthalydyl ester, (5-methyl-2-oxo-1,3-dioxolen-4-yl)methyl ester, 1-{[(cyclohexyloxy)carbonyl]oxy}ethyl ester or methylamide) and the like. These compounds may be prepared according to the methods well known per se. The prodrug of the compound represented by the general formula (I) may be a hydrate or non-hydrate. The prodrug of the compound represented by the general formula (I) may be the one which is converted to the compound represented by the general formula (I) under physiological conditions described in "Iyakuhin no Kaihatsu (Development of Medicines)", vol. 7, "Bunshi Sekkei (Molecular Designs)", Hirokawa Shoten Co., 1990, pp. 163-198.

The atoms constituting the compound represented by the general formula (I) may respectively be substituted with isotopes thereof (e.g., $^2H$, $^3H$, $^{13}C$, $^{14}C$, $^{15}N$, $^6N$, $^{17}O$, $^{18}O$, $^{35}S$, $^{125}I$ and the like).

[Production Method of the Present Compound]

The present compound represented by the general formula (I) can be produced according to well known methods, for example the methods described hereinbelow, equivalent methods thereof or methods described in Examples. In the production methods described hereinbelow, starting compounds may be salts. The salts may include those described as pharmaceutically acceptable salts of the general formula (I).

The present compound of the general formula (I) wherein Y is an oxygen atom or an optionally oxidized sulfur atom can be prepared, for example, according to the following reaction scheme 1:

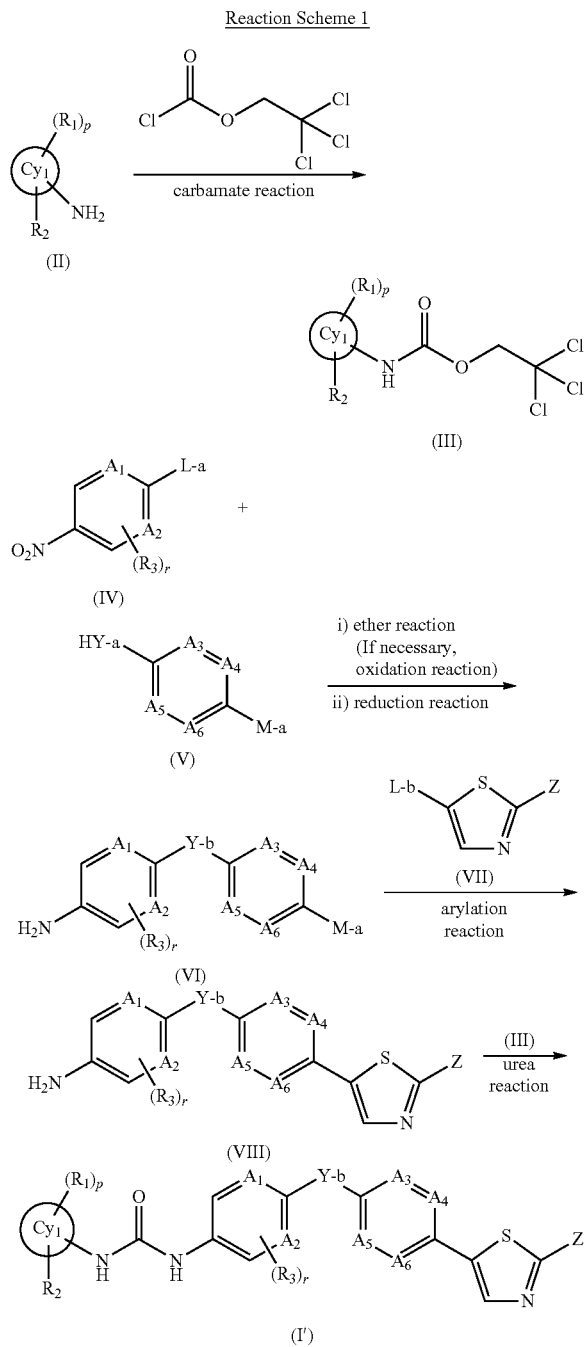

wherein L-a represents a halogen, M-a represents a halogen, a boronic acid group (—B(OH)$_2$) or a boronic ester group (—B(ORi)(ORii)(wherein Ri and Rii represent a C1-3 alkyl group and Ri and Rii may together form a ring), e.g., 4,4,5,5-tetramethyl-1,3,2-dioxaborolan-2-yl), Y-a represents an oxygen atom or a sulfur atom, Y-b represents an oxygen atom, a sulfur atom or an oxidized sulfur atom, L-b represents a halogen or a hydrogen atom and other symbols represent the same meanings as those described in the above [1].

The compound having the general formula (VI) wherein Y-b is an oxidized sulfur atom can be produced by oxidizing, in the above reaction scheme 1, the compound obtained after etherification reaction wherein Y-a is a sulfur atom according to the well known methods.

The present compound having a carboxyl group, a phosphonooxy group, a hydroxy group and an amino group can be produced by carrying out the reactions up to urea derivatization as indicated in the reaction scheme 1 with a compound which may be optionally protected with a protecting group conventionally used for the above-mentioned groups as described in, for example, "Comprehensive Organic Transformations: A Guide to Functional Group Preparations 2nd Edition (Richard C. Larock, John Wiley & Sons Inc, 1999)" followed by a well known deprotection reaction or the deprotection reaction described in, for example, "Comprehensive Organic Transformations: A Guide to Functional Group Preparations 2nd Edition (Richard C. Larock, John Wiley & Sons Inc, 1999)".

In the reaction scheme 1, the reaction step (carbamate derivatization reaction) of producing the compound represented by the general formula (III) from the compound represented by the general formula (II) is well known. The compound represented by the general formula (III) obtained thereby can be produced by, for example, allowing reaction of the compound represented by the general formula (II) with 2,2,2-trichloroethoxycarbonyl chloride in an organic solvent (e.g., pyridine, ethyl acetate, methylene chloride, dioxane, diethyl ether or an appropriately mixed solvent thereof) or in a mixed solvent of the organic solvent with water in the presence or absence of a base (e.g., 4-dimethylaminopyridine, pyridine, triethylamine, sodium hydrogen carbonate) at a temperature of about −20° C. to 80° C.

In the reaction scheme 1, the reaction step (etherification reaction, reduction reaction) of producing the compound represented by the general formula (VI) from the compound represented by the general formula (IV) is well known. The compound represented by the general formula (VI) obtained thereby can be produced by, for example, allowing reaction of the compound represented by the general formula (IV) and the compound represented by the general formula (V) in an organic solvent (e.g., dimethylsulfoxide, dimethylformamide, methanol, acetonitrile or an appropriately mixed solvent thereof) or in a mixed solvent of the organic solvent with water in the presence of a base (e.g., potassium fluoride, potassium carbonate, tripotassium phosphate, sodium hydroxide, sodium hydride) at a temperature of about 0° C. to 120° C. and subjecting the obtained compound to reaction under a hydrogen atmosphere in an organic solvent (e.g., methanol, ethanol, ethyl acetate, tetrahydrofuran, acetic acid, 1,2-dimethoxyethane or an appropriately mixed solvent thereof) or in a mixed solvent of the organic solvent with water in the presence of a catalyst (e.g., a silver catalyst (e.g., silver acetate), a platinum catalyst (e.g., platinum-carbon, platinum oxide), a rhodium catalyst (e.g., rhodium-carbon), an iron catalyst (e.g., iron acetate), a ruthenium catalyst (e.g., ruthenium-carbon), a palladium catalyst (e.g., palladium-carbon), a zinc catalyst (zinc bromide, zinc iodide, zinc acetate and the like), Raney nickel or an appropriately mixed catalyst thereof) at a temperature of from room temperature to about 80° C. or subjecting to reaction in an organic solvent (e.g., acetic acid, hydrochloric acid, ethanol, methanol, dimethylformamide, toluene or an appropriately mixed solvent thereof) or in a mixed solvent of the organic solvent with water in the presence of a catalyst (e.g., an iron catalyst (e.g., iron, iron chloride, iron-ammonium chloride), a zinc catalyst (e.g., zinc), a nickel catalyst (e.g., nickel chloride), an indium catalyst (e.g., indium), a tin catalyst (e.g., tin, tin chloride) or an appropriately mixed catalyst thereof) at a temperature of from room temperature to about 80° C.

In the reaction scheme 1, the reaction step (aryl derivatization reaction) of producing the compound represented by the general formula (VIII) from the compound represented by the general formula (VI) is well known. The compound represented by the general formula (VIII) obtained thereby can be produced by, for example, allowing reaction of the compound represented by the general formula (VI) and the compound represented by the general formula (VII) in an organic solvent (e.g., dimethylacetamide, dimethylformamide, an alcohol (e.g., methanol, ethanol), diethyl carbonate, dioxane, 1,2-dimethoxyethane, toluene or an appropriately mixed solvent thereof) or in a mixed solvent of the organic solvent with water, in the presence or absence of a base (e.g., cesium carbonate, potassium acetate, potassium carbonate, sodium carbonate, lithium-t-butoxide, silver carbonate, tripotassium phosphate, triethylamine or an appropriately mixed base thereof) in a catalyst (e.g., a palladium catalyst (e.g., palladium hydroxide, palladium acetate, bis(tri-t-butylphosphine)palladium, palladium(0)tetrakis(triphenylphosphine), bis(triphenylphosphine)dichloropalladium (II) or an appropriately mixed catalyst thereof)) at a temperature of from room temperature to about 120° C.

In the reaction scheme 1, the reaction step (urea derivatization reaction) of producing the present compound represented by the general formula (I') from the compound represented by the general formula (VIII) is the reaction carried out with the compound represented by the general formula (VIII) and the compound represented by the general formula (III) under the conditions described in Examples herein or under well known conditions.

In the reaction scheme 1, compounds used as starting materials and represented by the general formulae (II), (IV), (V) and (VII) are well known or can be easily produced according to well known methods, for example, the method described in "Comprehensive Organic Transformations: A Guide to Functional Group Preparations 2nd Edition (Richard C. Larock, John Wiley & Sons Inc, 1999)".

The present compound of the general formula (I) wherein Y is an oxygen atom or an optionally oxidized sulfur atom can be alternatively produced by subjecting to urea derivatization reaction the compound represented by the general formula (II) and a 2,2,2-trichloroethyl carbamate derivative produced from the compound represented by the general formula (VIII) in the reaction scheme 1 and 2,2,2-trichloroethoxycarbonyl chloride.

The present compound of the general formula (I) wherein Y is a methylene group can be produced, for example, through similar reaction steps as the reaction scheme 1 by using the compound represented by the general formula (XI) in the following reaction scheme 2 in place of the compound represented by the general formula (VI) in the reaction scheme 1:

Reaction Scheme 2

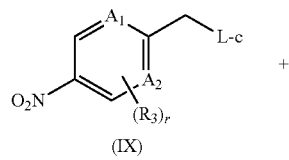

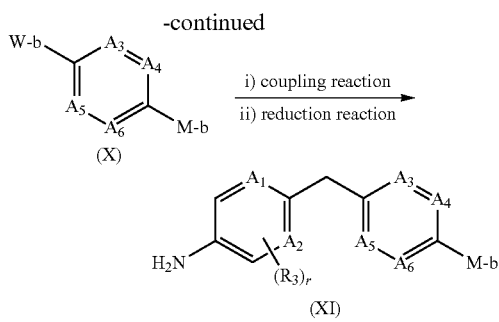

wherein L-c represents a leaving group (e.g., a halogen, mesylate or triflate), M-b represents a halogen, W-b represents a boronic acid group (—B(OH)$_2$) or a boronic ester group (–B(ORi) (ORii) (wherein Ri and Rii represent a C1-3 alkyl group and Ri and Rii may together form a ring), e.g., 4,4,5,5-tetramethyl-1,3,2-dioxaborolan-2-yl) or an alkylstannyl group (e.g., tributylstannyl) and other symbols represent the same meanings as those described in the above [1].

In the reaction scheme 2, the reaction step (coupling reaction, reduction reaction) of producing the compound represented by the general formula (XI) from the compound represented by the general formula (IX) is well known. The compound represented by the general formula (XI) obtained thereby can be produced by, for example, allowing reaction of the compound represented by the general formula (IX) with the compound represented by the general formula (X) in an organic solvent (e.g., dimethylacetamide, dimethylformamide, an alcohol (e.g., methanol, ethanol), diethyl carbonate, dioxane, 1,2-dimethoxyethane, toluene, xylene, tetrahydrofuran, methylene chloride, acetone, acetonitrile or an appropriately mixed solvent thereof) or in a mixed solvent of the organic solvent with water in the presence of absence of a base (e.g., cesium carbonate, potassium acetate, potassium carbonate, sodium carbonate, lithium-t-butoxide, silver carbonate, tripotassium phosphate, triethylamine or an appropriately mixed base thereof) in a catalyst (e.g., a palladium catalyst (e.g., palladium hydroxide, palladium acetate, bis(tri-t-butylphosphine)palladium, palladium(0)tetrakis(triphenylphosphine), bis(triphenylphosphine)dichloropalladium (II) or an appropriately mixed catalyst thereof)) at a temperature of from room temperature to about 120° C. and subjecting the obtained compound to reaction under a hydrogen atmosphere in an organic solvent (e.g., methanol, ethanol, ethyl acetate, tetrahydrofuran, acetic acid, 1,2-dimethoxyethane or an appropriately mixed solvent thereof) or in a mixed solvent of the organic solvent with water in the presence of a catalyst (e.g., a silver catalyst (e.g., silver acetate), a platinum catalyst (e.g., platinum-carbon, platinum oxide), a rhodium catalyst (e.g., rhodium-carbon), an iron catalyst (e.g., iron acetate), a ruthenium catalyst (e.g., ruthenium-carbon), a palladium catalyst (e.g., palladium-carbon), a zinc catalyst (zinc bromide, zinc iodide, zinc acetate and the like), Raney nickel or an appropriately mixed catalyst thereof) at a temperature of from room temperature to about 80° C. or to reaction in an organic solvent (e.g., acetic acid, hydrochloric acid, ethanol, methanol, dimethylformamide, toluene or an appropriately mixed solvent thereof) or in a mixed solvent of the organic solvent with water in the presence of a catalyst (e.g., an iron catalyst (e.g., iron, iron chloride, iron-ammonium chloride), a zinc catalyst (e.g., zinc), a nickel catalyst (e.g., nickel chloride), an indium catalyst (e.g., indium), a tin catalyst (e.g., tin, tin chloride) or an appropriately mixed catalyst thereof) at a temperature of from room temperature to about 80° C.

In reaction scheme 2, compounds used as starting materials and represented by the general formulae (IX) and (X) are well known or can be easily produced according to well known methods, for example, the method described in "Comprehensive Organic Transformations: A Guide to Functional Group Preparations 2nd Edition (Richard C. Larock, John Wiley & Sons Inc, 1999)".

The present compound of the general formula (I) wherein Y is C=O can be produced through similar reaction steps as the reaction scheme 1 by using the compound represented by the general formula (XIV) in the following reaction scheme 3 in place of the compound represented by the general formula (VI) in the reaction scheme 1:

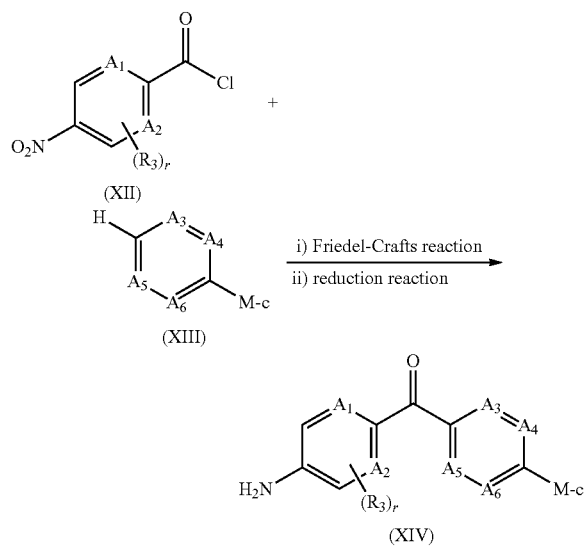

Reaction Scheme 3 wherein M-c represents a halogen and other symbols represent the same meanings as those described in the above [1].

In the reaction scheme 3, the reaction step (Friedel-Crafts reaction, reduction reaction) of producing the compound represented by the general formula (XIV) from the compound represented by the general formula (XII) is well known. The compound represented by the general formula (XIV) obtained thereby can be produced by, for example, allowing reaction of the compound represented by the general formula (XII) with the compound represented by the general formula (XIII) in an organic solvent (e.g., dichloroethane, trifluoromethanesulfonic acid, nitromethane) or in the absence of solvents in a catalyst (e.g., aluminium chloride, iron sulphate, hafnium triflate, bismuth triflate or an appropriately mixed catalyst thereof) at a temperature of from room temperature to about 150° C. and subjecting the obtained compound to reaction under a hydrogen atmosphere in an organic solvent (e.g., methanol, ethanol, ethyl acetate, tetrahydrofuran, acetic acid, 1,2-dimethoxyethane or an appropriately mixed solvent thereof) or in a mixed solvent of the organic solvent with water in the presence of a catalyst (e.g., a silver catalyst (e.g., silver acetate), a platinum catalyst (e.g., platinum-carbon, platinum oxide), a rhodium catalyst (e.g., rhodium-carbon), an iron catalyst (e.g., iron acetate), a ruthenium catalyst (e.g., ruthenium-carbon), a palladium catalyst (e.g., palladium-carbon), a zinc catalyst (zinc bromide, zinc iodide, zinc acetate and the like), Raney nickel or an appropriately mixed catalyst thereof) at a temperature of from room temperature to about 80° C. or to reaction in an organic solvent (e.g., acetic acid, hydrochloric acid, ethanol, methanol, dimethylformamide, toluene or an appropriately mixed solvent thereof) or in a mixed solvent of the organic solvent with water in the presence of a catalyst (e.g., an iron catalyst (e.g., iron, iron chloride, iron-ammonium chloride), a zinc catalyst (e.g., zinc), a nickel catalyst (e.g., nickel chloride), an indium catalyst (e.g., indium), a tin catalyst (e.g., tin, tin chloride) or an appropriately mixed catalyst thereof) at a temperature of from room temperature to about 80° C.

In the reaction scheme 3, compounds used as starting materials and represented by the general formulae (XII) and (XIII) are well known or can be easily produced according to well known methods, for example, the method described in "Comprehensive Organic Transformations: A Guide to Functional Group Preparations 2nd Edition (Richard C. Larock, John Wiley & Sons Inc, 1999)".

The present compounds represented by the general formula (I) other than those indicated above can be produced according to the methods described in Examples herein or to the combinations of well known methods, for example, the method described in "Comprehensive Organic Transformations: A Guide to Functional Group Preparations 2nd Edition (Richard C. Larock, John Wiley & Sons Inc, 1999)".

The respective reactions involving heating as described herein can be carried out, as apparent to a person skilled in the art, in a water bath, an oil bath, a sand bath or with microwave.

In the respective reactions as described herein, a reagent supported on a solid phase of a high-molecular weight polymer (e.g., polystyrene, polyacrylamide, polypropylene, polyethylene glycol) may be appropriately used.

In the respective reactions as described herein, reaction products can be purified by conventional purification means, e.g., by methods including distillation under normal or reduced pressure, high speed liquid chromatography using silica gel or magnesium silicate, thin layer chromatography, ion exchange resins, scavenger resins or column chromatography or washing and recrystallization. Purification may be carried out after each reaction step or may be carried out after more than one reaction steps.

[Toxicity]

The present compound has sufficiently low toxicity. The present compound does not cause, for example, hepatotoxicity or gastrointestinal dysfunction and has low brain transition. Thus the present compound can be used safely as a medicament.

[Application to Medicaments]

The present compound exhibits Trk-inhibiting activity and thus is useful as a prophylactic and/or therapeutic agent for Trk inhibition-mediated diseases e.g., pain, pruritus, lower urinary tract dysfunction, asthma, allergic rhinitis, inflammatory bowel disease and Chagas disease.

More specifically, pain may include, for example, pain of osteoarthritis, cancer pain, chronic low back pain, low back pain of osteoporosis, pain of bone fracture, pain of rheumatoid arthritis, neuropathic pain, postherpetic pain, pain of diabetic neuropathy, fibromyalgia, pain of pancreatitis, pain of interstitial cystitis, pain of endometriosis, pain of irritable bowel syndrome, migraine, pain of pulpitis and the like. Pruritus may include systemic cutaneous pruritus, localized cutaneous pruritus, senile cutaneous pruritus, gestational pruritus, pruritus ani, vulvar pruritus and the like. Inflammatory bowel disease may include, for example, ulcerative colitis, Crohn's disease and the like.

The present compound is particularly useful as a prophylactic and/or therapeutic agent for pain.

The present compound may be administered as a combination drug with another drug in order to:
1) complement and/or enhance the prophylactic and/or therapeutic effect of the compound;
2) improve the kinetics and absorption and reduce the dosage of the compound; and/or
3) alleviate the side effect of the compound.

The combination drug of the present compound and another drug may be administered in the form of one formulation containing both components or may be administered as separate formulations. Administration of separate formulations may include simultaneous administration and sequential administration. In the sequential administration, the present compound may be first administered followed by another drug or another drug may be first administered followed by the present compound. The respective manners of administration may be the same or different.

The disease for which the combination drug exhibits the prophylactic and/or therapeutic effect is not particularly limited and may be the disease which may complement and/or enhance the prophylactic and/or therapeutic effect of the present compound.

Another drug for complementing and/or enhancing the prophylactic and/or therapeutic effect of the present compound for pain may include, for example, acetaminophen, a nonsteroid antiinflammatory drug, an opioid, an antidepressant, an antiepileptic agent, an N-methyl-D-aspartate antagonist, a muscle relaxant, an antiarrhythmic agent, a steroid and a bisphosphonate.

The nonsteroid antiinflammatory drug may include, for example, sasapyrine, sodium salicylate, aspirin, aspirin formulations such as those containing aspirin-dialuminate, diflunisal, indomethacin, suprofen, ufenamate, dimethylisopropylazulene, bufexamac, felbinac, diclofenac, tolmetin sodium, Clinoril, fenbufen, nabumetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranoprofen, loxoprofen sodium, alminoprofen, zaltoprofen, mefenamic acid, aluminium mefenamate, tolfenamic acid, floctafenine, ketophenylbutazone, oxyphenbutazone, piroxicam, tenoxicam, ampiroxicam, Napageln ointment, epirizole, tiaramide hydrochloride, tinoridine hydrochloride, emorfazone, sulpyrine, Migrenin, Saridon, Sedes G, Amipylo-N, Sorbon, pilin cold remedies, acetaminophen, phenacetin, dimetotiazine mesilate, meloxicam, celecoxib, rofecoxib, valdecoxib, simetride-containing formulations and non-pilin cold remedies and the like.

The opioid may include, for example, codeine, fentanyl, hydromorphone, levorphanol, meperidine, methadone, morphine, oxycodone, oxymorphone, propoxyphene and the like.

The antidepressant may include, for example, tricyclic antidepressants (e.g., amitriptyline hydrochloride, imipramine hydrochloride, clomipramine hydrochloride, dosulepin hydrochloride, nortriptyline hydrochloride, lofepramine hydrochloride, trimipramine maleate, amoxapine), tetracyclic antidepressants (e.g., maprotiline hydrochloride, mianserin hydrochloride, setiptiline maleate), monoamine oxidase (MAO) inhibitors (safrazine hydrochloride), serotonin and noradrenaline reuptake inhibitors (SNRIs) (e.g., milnacipran hydrochloride, venlafaxine hydrochloride), selective serotonin reuptake inhibitors (SSRIs) (e.g., fluvoxamine maleate, paroxetine hydrochloride, fluoxetine hydrochloride, citalopram hydrochloride), serotonin reuptake inhibitors (e.g., trazodone hydrochloride) and the like.

The antiepileptic agent may include, for example, phenobarbital, Puridomin, phenytoin, ethosuximide, zonisamide, nitrazepam, clonazepam, carbamazepine, sodium valproate, acetazolamide, sulthiame and the like.

The N-methyl-D-aspartate antagonist may include, for example, ketamine hydrochloride, amantadine hydrochloride, memantine hydrochloride, dextromethorphan, methadone and the like.

The muscle relaxant may include, for example, succinylcholine, suxamethonium, vecuronium bromide, pancronium bromide, dantrolene sodium and the like.

The antiarrhythmic agent may include, for example, procainamide, disopyramide, cibenzoline, pirmenol, lidocaine, mexiletine, aprindine, pilsicainide, flecainide, propafenone, propranolol, atenolol, bisoprolol, amiodarone, sotalol, verapamil, diltiazem, bepridil and the like.

The steroid may include, for example, as medicines for external use, clobetasol propionate, diflorasone diacetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone propionate, triamcinolone acetonide, flumetasone pivalate, alclometasone dipropionate, clobetasone butyrate, prednisolone, beclometasone propionate, fludroxycortide and the like.

As medicines for internal use or for injection, cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone and the like may be included.

As inhalants, beclometasone propionate, fluticasone propionate, budesonide, flunisolide, triamcinolone, ST-126P, ciclesonide, dexamethasone palomitionate, momedasone furoate, prasterone sulfonate, deflazacort, methylprednisolone sleptanate, methylprednisolone sodium succinate and the like.

The bisphosphonate may include, for example, etidronate, pamidronate, alendronate, risedronate, zoledronate, minodronate and the like.

The mass ratio of the present compound and another drug is not particularly limited.

Another drug may be a combination of any two or more drugs.

Another drug for complementing and/or enhancing the prophylactic and/or therapeutic effect of the present compound may encompass not only those have been identified to date but also those will be identified in future based on the above mechanism.

The present compound or the combination drug of the present compound and another drug which is used for the purpose described above may be generally administered systemically or topically by oral or parenteral administration.

The dosage may vary according to age, weight, symptoms, therapeutic effect, mode of administration, treatment period and the like and may be one to several oral administrations a day within the range of 1 mg to 1000 mg per dose per adult or one to several parenteral administrations a day within the range of 0.1 mg to 100 mg per dose or intravenous continuous administration for 1 hour to 24 hours a day per adult.

As described above, the dosage may vary according to various conditions, thus the sufficient dosage may be of course lower than the amount described above or the amount higher than the above may be required.

The present compound or the combination drug of the present compound and another drug may be administered as an oral solid dosage form for internal use, an oral solution for internal use or an injection, an external preparation, a suppository, an ophthalmic solution or an inhalant for parenteral administration.

The oral solid dosage form for internal use may include tablets, pills, capsules, powders, granules and the like. Capsules may include hard capsules and soft capsules. Tablets may include sublingual tablets, oral patches, orally disintegrating tablets and the like.

In the solid dosage form for internal use, one or more active substances per se may be formulated or may be formulated after mixing thereof with an excipient (lactose, mannitol, glucose, microcrystalline cellulose, starch and the like), a binder (hydroxypropylcellulose, polyvinylpyrrolidone, magnesium aluminate metasilicate and the like), a disintegrant (calcium cellulose glycolate and the like), a lubricant (magnesium stearate and the like), a stabilizer, a solution adjuvant (glutamic acid, aspartic acid and the like) according to conventional methods. The solid dosage form may be optionally coated with a coating agent (sucrose, gelatin, hydroxypropylcellulose, hydroxypropyl methylcellulose phthalate and the like) and may be coated with two or more layers. The solid dosage form may further encompass capsules of an absorbable substance such as gelatin.

The oral solution for internal use may include pharmaceutically acceptable waters, suspensions, emulsions, syrups, elixirs and the like. In the solution, one or more active substances are dissolved, suspended or emulsified in a diluent of general use (purified water, ethanol or a mixed solution thereof). The solution may further contain a wetting agent, a suspending agent, an emulsifying agent, a sweetening agent, a flavouring agent, an aroma, a preservative, a buffering agent and the like.

The dosage form of the external preparation for parenteral administration may include, for example, ointments, gels, creams, fomentations, patches, liniments, atomized agents, inhalants, sprays, aerosols, ophthalmic solutions, nasal drops and the like. The dosage forms contain one or more active substances and may be prepared according to well known methods or formulations which are generally used.

Atomized agents, inhalants and sprays may contain, in addition to a diluent which is generally used, a stabilizer such as sodium hydrogen sulfate and a buffering agent that confers isotonicity, e.g., sodium chloride, sodium citrate or a isotonic agent such as citric acid. Methods for producing sprays are specifically described in, for example, U.S. Pat. Nos. 2,868, 691 and 3,095,355.

The injection for parenteral administration may encompass injections in the form of solution, suspension, emulsion and solid that is dissolved or suspended in a solvent upon use. The injection may be used by dissolving, suspending or emulsifying one or more active substances in a solvent. The solvent may be, for example, distilled water for injection, saline, vegetable oil, propylene glycol, polyethylene glycol, alcohols such as ethanol and combinations thereof. The injection may further contain a stabilizer, a solution adjuvant (glutamic acid, aspartic acid, Polysorbate 80® and the like), a suspending agent, an emulsifying agent, a soothing agent, a buffering agent, a preservative and the like. The injection may be produced by sterilization in the final step or through aseptic technique. Aseptic solid agents, e.g., lyophilized products may be manufactured and dissolved in sterilized or aseptic distilled water or other solvents for injection before use.

Other compositions for parenteral administration may include suppositories for rectal administration and pessaries for vaginal administration which contain one or more active substances and are formulated according to conventional methods.

The references described herein are incorporated herein by reference.

EXAMPLES

The present invention is explained below in detail based on Examples, but the present invention is not limited thereto.

Solvents given in parentheses concerning chromatographic separation and TLC each indicate the eluting solvent or the developing solvent employed, and the ratio is expressed in ratio by volume.

The solvents in parenthesis in NMR show the solvents used for measurement.

UPLC-MS/ELSD was carried out under the following conditions:

Column: Waters ACQUITY $C_{18}$ (particle diameter: $1.7 \times 10^{-6}$ m;

Column length: 30×2.1 mm I.D.);

Flow rate: 1.0 mL/min;

Column temperature: 40° C.;

Mobile phase (A): 0.1% trifluoroacetic acid aqueous solution;

mobile phase (B): 0.1% trifluoroacetic acid-acetonitrile solution;

Gradient (the ratio of mobile phase (A): mobile phase (B)):[0 min]95:5; [0.1 min]95:5; [1.2 min]5:95; [1.4 min] 5:95; [1.41 min]95:5; [1.5 min]95:5;

Detector: UV(PDA), ELSD, MS.

The compounds described herein were named by using a computer programme generally according to IUPAC nomenclature system or ACD/Name® or Chemdraw Ultra (version 12.0, Cambridge Soft).

Example 1

5-bromo-N-(5-bromothiazol-2-yl)pentanamide

To a solution of 5-bromothiazol-2-amine bromate (1 g) in methylene chloride (12 mL) was added a solution of pyridine (0.68 mL) and 5-bromopentanoyl chloride (0.54 mL) in methylene chloride (0.7 mL). The reaction mixture was stirred at room temperature for 2 hours. The reaction mixture was added with methanol (0.7 mL) and concentrated under reduced pressure. The obtained residue was added with 1 N hydrochloric acid (13 mL). The obtained solid was washed with tert-butyl methyl ether and dried to give the titled compound (1.06 g) having the following physical data.

TCL: Rf 0.50 (Hexane:Ethyl Acetate=3:1).

Example 2

1-(5-bromothiazol-2-yl)piperidin-2-one

To a solution of the compound prepared in Example 1 (1.06 g) in dimethylformamide (3.5 mL) was added potassium carbonate (860 mg) under ice bath. The reaction mixture was stirred at room temperature for 5 hours. The reaction mixture was added with water (60 mL) and stirred for 17 hours. The precipitated solid was washed with water (14 mL) and dried to give the titled compound (830 mg) having the following physical data.

TCL: Rf 0.53 (Hexane:Ethyl Acetate=3:1).

Example 3

1-(5-(4-hydroxyphenyl)thiazol-2-yl)piperidin-2-one

Under an argon atmosphere, the compound prepared in Example 2 (700 mg) was dissolved in a mixed solution (1:1, 14 mL) of tetrahydrofuran and 1,4-dioxane. The reaction mixture was added with (4-hydroxyphenyl)boronic acid (440 mg), tetrakis(triphenylphosphine)palladium (150 mg) and a tripotassium phosphate aqueous solution (2 mol/L, 2.7 mL) and stirred at 90° C. for 2 hours. To the reaction mixture was added water and the precipitated solid was collected by filtration. The obtained solid was washed with methanol and dried to give the titled compound (511 mg) having the following physical data.

TCL: Rf 0.38 (Hexane:Ethyl Acetate=1:1).

Example 4

1-(5-(4-((5-nitropyrimidin-2-yl)oxy)phenyl)thiazol-2-yl)piperidin-2-one

Sodium hydride (81 mg) was suspended in dimethylformamide (1.3 mL). The solution was cooled to 0° C. To the solution was added a solution of the compound prepared in Example 3 (530 mg) in dimethylformamide (3.3 mL). The reaction mixture was stirred for 30 minutes. To the mixture was added a solution of 2-chloro-5-nitropyrimidine in dimethylformamide (0.7 mL) and stirred for 15 minutes. To the reaction mixture was added water and the precipitated solid was collected by filtration and dried to obtain the titled compound (698 mg) having the following physical data.

TCL: 0.42 (Hexane:Ethyl Acetate=1:1).

Example 5

1-(5-(4-((5-aminopyrimidin-2-yl)oxy)phenyl)thiazol-2-yl)piperidin-2-one

Zinc (380 mg) was suspended in water (1.9 mL) to which a solution of ammonium chloride (310 mg) and the compound prepared in Example 4 (580 mg) in dimethylformamide (5.8 mL) was added and stirred at room temperature for 4 hours. The reaction mixture was added with water and filtered through Celite® and the filtrate was extracted with ethyl acetate. The obtained organic layer was dried over anhydrous sodium sulfate and concentrated under reduced pressure to give the titled compound (280 mg) having the following physical data.

TCL: Rf 0.21 (Hexane:Ethyl Acetate=1:4).

Example 6

3-nitro-5,6'-bis(trifluoromethyl)-2,3'-bipyridine

Under an argon atmosphere, to a solution of 2-chloro-3-nitro-5-(trifluoromethyl)pyridine (1 g) in 1,4-dioxane (15 mL) were added (6-(trifluoromethyl)pyridin-3-yl)boronic acid (925 mg), a solution of tricyclohexylphosphine in 15% toluene (2.0 mL), tris(dibenzylideneacetone)dipalladium (2.02 g) and a tripotassium phosphate aqueous solution (2 mol/L, 5.9 mL) and stirred overnight at 90° C. The reaction mixture was added with water and filtered through Celite® and the filtrate was extracted with ethyl acetate. The obtained organic layer was dried over anhydrous sodium sulfate and then concentrated under reduced pressure. The obtained residue was purified on silica gel column chromatography (hexane:ethyl acetate=85:15) to give the titled compound (1.15 g) having the following physical data.

TCL: Rf 0.34 (Hexane:Ethyl Acetate=9:1).

Example 7

5,6'-bis(trifluoromethyl)-[2,3'-bipyridin]-3-amine

The similar procedure as described in Example 5 was carried out with the compound prepared in Example 6 in place of the compound prepared in Example 4 to give the titled compound having the following physical data.

TCL: Rf 0.31 (Hexane:Ethyl Acetate=4:1).

Example 8

2,2,2-trichloroethyl(5,6'-bis(trifluoromethyl)-[2,3'-bipyridin]-3-yl)carbamate

To a solution of the compound prepared in Example 7 (863 mg) in tetrahydrofuran (9.4 mL) were added sodium hydrogen carbonate (708 mg) and 2,2,2-trichloroethyl chloroformate (378 μL) and stirred overnight. The reaction mixture was added with water and extracted with ethyl acetate. The obtained organic layer was washed with a saturated sodium chloride aqueous solution, dried over anhydrous sodium sulfate and then concentrated under reduced pressure. The obtained residue was purified on silica gel chromatography (hexane:ethyl acetate=9:1) to give the titled compound (1.15 g) having the following physical data.

TCL: Rf 0.53 (Hexane:Ethyl Acetate=4:1).

Example 9

1-[5,6'-bis(trifluoromethyl)-2,3'-bipyridin-3-yl]-3-(2-{4-[2-(2-oxo-1-piperidinyl)-1,3-thiazol-5-yl]phenoxy}-5-pyrimidinyl)urea

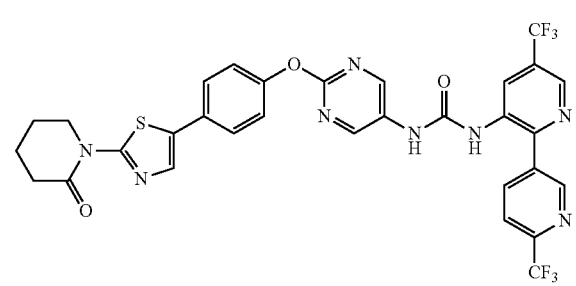 [SMILES: O=C(Nc1cnc(Oc2ccc(-c3cnc(N4CCCCC4=O)s3)cc2)nc1)Nc1cc(C(F)(F)F)cnc1-c1ccc(C(F)(F)F)nc1]

To a solution of the compound prepared in Example 8 (170 mg) in dimethylsulfoxide (1.2 mL) were added the compound prepared in Example 5 (120 mg) and 1-methylpyrrolidine (10 μL) and stirred overnight at 80° C. The reaction mixture was purified on silica gel column chromatography (methylene chloride:ethyl acetate=1:1) to give the present compound (77.5 mg) having the following physical data.

TCL: Rf 0.36 (Hexane:Ethyl Acetate=1:4);

1 H-NMR (DMSO-d$_6$): δ 1.82-1.99 (m, 4 H), 2.61 (t, 2 H), 4.07 (t, 2 H), 7.22 (d, 2 H), 7.66 (d, 2 H), 7.91 (s, 1 H), 8.10 (d, 1 H), 8.38-8.41 (m, 1 H), 8.67-8.82 (m, 5 H), 9.05 (s, 1 H), 9.24 (s, 1 H).

Example 10 tert-butyl thiazol-2-ylcarbamate

To a solution of thiazol-2-amine (200 mg) in N-methylpyrrolidone (2.3 mL) was added di-tert-butyl dicarbonate (480 mg) and the reaction mixture was stirred at room temperature for 17 hours. The reaction mixture was added with water (10 mL). The precipitated solid was collected by filtration. The solid was washed and dried to give the titled compound (390 mg) having the following physical data.
TCL: Rf 0.52 (Hexane:Ethyl Acetate=4:1).

Example 11 tert-butyl ethyl(thiazol-2-yl)carbamate

To a solution of the compound prepared in Example 10 (200 mg) in N-methylpyrrolidone (1 mL) were added tripotassium phosphate (212 mg) and iodoethane (172 mg). The reaction mixture was stirred at room temperature for 17 hours. The reaction mixture was added with water (15 mL) and extracted with tert-butyl methyl ether (15 mL). The obtained organic layer was washed with a saturated sodium chloride aqueous solution, dried over anhydrous sodium sulfate and then concentrated under reduced pressure to give the titled compound (211 mg) having the following physical data.
TCL: Rf 0.69 (Hexane:Ethyl Acetate=4:1).

Example 12

2-(4-bromophenoxy)-5-nitropyrimidine

To a solution of 4-bromophenol (200 mg) in tetrahydrofuran were added triethylamine (193 μL) and 2-chloro-5-nitropyrimidine (204 mg). The reaction mixture was stirred at room temperature for 3 hours. The reaction mixture was added to water (20 mL) and extracted with ethyl acetate (20 mL). The obtained organic layer was washed with a saturated sodium chloride aqueous solution, dried over anhydrous sodium sulfate and then concentrated under reduced pressure to give the titled compound (294 mg) having the following physical data.
TCL: Rf 0.44 (Hexane:Ethyl Acetate=4:1).

Example 13

2-(4-bromophenoxyl)pyrimidin-5-amine

Under an argon atmosphere, to a solution of 2-(4-bromophenoxy)-5-nitropyrimidine (400 mg) in tetrahydrofuran (20 mL)/methanol (20 mL) was added 3% platinum-carbon (200 mg). The reaction mixture was stirred under a hydrogen atmosphere at room temperature for 3 hours. The reaction mixture was filtered through Celite® to give the titled compound (363 mg) having the following physical data.
TCL: Rf 0.33 (Hexane:Ethyl Acetate=1:1).

Example 14 tert-butyl(5-(4-((5-aminopyrimidin-2-yl)oxy)phenyl)thiazol-2-yl)(ethyl)carbamate Under an argon atmosphere, to a solution of 2-(4-bromophenoxyl)pyrimidin-5-amine (233 mg) in dimethylacetamide (3 mL) were added the compound prepared in Example 11 (1 g), pivalic acid (54 mg), potassium carbonate (363 mg) and tricyclohexylphosphonium tetrafluoroborate (64 mg). The reaction mixture was added with palladium acetate (20 mg). The reaction mixture was stirred in a microwave at 120° C. for 1 hour. The reaction mixture was purified on silica gel column chromatography (hexane:ethyl acetate=1:2) to give the titled compound (173 mg) having the following physical data.
TCL: Rf 0.51 (Hexane:Ethyl Acetate=4:1).

Example 15

1-[5,6'-bis(trifluoromethyl)-2,3'-bipyridin-3-yl]-3-(2-{4-[2-(ethylamino)-1,3-thiazol-5-yl]phenoxy}-5-pyrimidinyl)urea

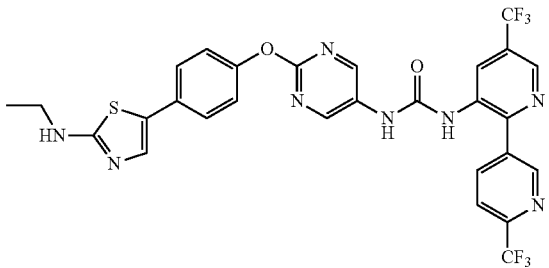 [SMILES: CCNc1ncc(-c2ccc(Oc3ncc(NC(=O)Nc4cc(C(F)(F)F)cnc4-c4ccc(C(F)(F)F)nc4)cn3)cc2)s1]

To a solution of the compound (138 mg) in methylene chloride (1.8 mL) that was obtained by carrying out the similar procedure as described in Example 9 with the compound prepared in Example 14 in place of the compound prepared in Example 5 was added trifluoroacetic acid (0.4 mL). The reaction mixture was stirred at room temperature for 6 hours. The reaction mixture was added with a saturated sodium hydrogen carbonate aqueous solution and extracted with ethyl acetate. The obtained organic layer was washed with a saturated sodium chloride aqueous solution. The obtained organic layer was dried over anhydrous sodium sulfate and then concentrated under reduced pressure. The obtained residue was washed with methylene chloride to give the present compound (96 mg) having the following physical data.
TCL: Rf 0.22 (Ethyl Acetate:Hexane=1:1);
$^1$H-NMR (DMSO-d$_6$): δ 1.16 (t, 3 H), 3.26 (m, 2 H), 7.13 (d, 2 H), 7.43-7.46 (m, 3 H), 7.72 (t, 1 H), 8.11 (d, 1 H), 8.40 (dd, 1 H), 8.66 (s, 2 H), 8.72 (s, 1 H), 8.79 (d, 1 H), 8.83 (d, 1 H), 9.06 (d, 1 H), 9.23 (s, 1 H).

Example 16

2,2,2-trichloroethyl(2-(3,4-dimethylphenyl)-5-(trifluoromethyl)pyridin-3-yl)carbamate The similar procedures as Example 6→Example 5→Example 8 were carried out with (3,4-dimethylphenyl)boronic acid in place of (6-(trifluoromethyl)pyridin-3-yl)boronic acid to give the titled compound having the following physical data.
TCL: Rf 0.62 (Hexane:Ethyl Acetate=4:1).

Example 17

1-[2-(3,4-dimethylphenyl)-5-(trifluoromethyl)-3-pyridinyl]-3-(2-{4-[2-(ethylamino)-1,3-thiazol-5-yl]phenoxy}-5-pyrimidinyl)urea The similar procedures as Example 9→Example 15 were carried out with the compound prepared in Example 16 in place of the compound prepared in Example 8 to give the present compound having the following physical data.

TCL: Rf 0.23 (Ethyl Acetate:Hexane=1:1);

$^1$H-NMR (DMSO-d$_6$): δ 1.16 (t, 3 H), 2.30 (s, 3 H), 2.30 (s, 3 H), 3.26 (m, 2 H), 7.13 (d, 2 H), 7.30-7.46 (m, 6 H), 7.72 (t, 1 H), 8.34 (s, 1 H), 8.66 (s, 2 H), 8.66 (s, 1 H), 8.78 (s, 1 H), 9.50 (s, 1 H).

Example 18 tert-butyl(5-bromothiazol-2-yl)(isopropyl)carbamate

The similar procedure as Example 11 was carried out with 2-iodopropane in place of iodoethane to give the titled compound having the following physical data.

TCL: Rf 0.59 (Hexane:Ethyl Acetate=9:1).

Example 19

1-(2-(4-bromophenoxyl)pyrimidin-5-yl)-3-(2-(3,4-dimethylphenyl)-5-(trifluoromethyl)pyridin-3-yl)urea The similar procedure as Example 9 was carried out with the compound prepared in Example 16 in place of the compound prepared in Example 8 and the compound prepared in Example 13 in place of the compound prepared in Example 7 to give the titled compound having the following physical data.

TCL: Rf 0.35 (Hexane:Ethyl Acetate=1:1).

Example 20

1-(2-(3,4-dimethylphenyl)-5-(trifluoromethyl)pyridin-3-yl)-3-(2-(4-(4,4,5,5-tetramethyl-1,3,2-dioxaborolan-2-yl)phenoxy)pyrimidin-5-yl)urea Under an argon atmosphere, to a solution of the compound prepared in Example 19 (270 mg) in dimethylsulfoxide (1.6 mL) were added bis(pinacolato)diboron (160 mg), potassium acetate (240 mg) and 1,1'-bis(diphenylphosphino)ferrocene-palladium (II) dichloride-dichloromethane complex (20 mg) and stirred at 80° C. for 3 hours. The reaction mixture was added with water and filtered through Celite® and the filtrate was extracted with ethyl acetate. The obtained organic layer was washed with water, dried over anhydrous sodium sulfate and then concentrated under reduced pressure. The obtained residue was washed with ethyl acetate to give the titled compound (213 mg) having the following physical data.

TCL: Rf 0.40 (Chloroform:Ethyl Acetate=9:1).

Example 21

1-[2-(3,4-dimethylphenyl)-5-(trifluoromethyl)-3-pyridinyl]-3-(2-{4-[2-(isopropylamino)-1,3-thiazol-5-yl]phenoxy}-5-pyrimidinyl)urea Under an argon atmosphere, to a solution of the compound prepared in Example 20 (200 mg) in 1,4-dioxane (1.1 mL) were added the compound prepared in Example 18 (127 mg), tetrakis(triphenylphosphine)palladium (19 mg) and a tripotassium phosphate aqueous solution (2 mol/L, 660 μL) and stirred at 80° C. for 1.5 hours. The reaction mixture was added with water and extracted with ethyl acetate. The obtained organic layer was washed with a saturated sodium chloride aqueous solution, dried over anhydrous sodium sulfate and then concentrated under reduced pressure. The obtained residue was purified on silica gel column chromatography (hexane:ethyl acetate=1:1) to give tert-butyl(5-(4-((5-(3-(2-(3,4-dimethylphenyl)-5-(trifluoromethyl)pyridin-3-yl)ureido)pyrimidin-2-yl)oxy)phenyl)thiazol-2-yl)(isopropyl)carbamate (134 mg). To a solution of the carbamate compound (134 mg) in methylene chloride (2 mL) was added trifluoroacetic acid (2 mL) and stirred for 1.5 hours. To a saturated sodium hydrogen carbonate aqueous solution was added the reaction mixture and the precipitated solid was collected by filtration. The obtained solid was washed with water and ethyl acetate and then dried to give the present compound (41.3 mg) having the following physical data.

TCL: Rf 0.27 (Hexane:Ethyl Acetate=1:1);

$^1$H-NMR (DMSO-d$_6$): δ 1.18 (d, 6 H), 2.31 (s, 6 H), 3.80 (m, 1 H), 7.13 (d, 2 H), 7.30-7.45 (m, 6 H), 7.64 (d, 1 H), 8.34 (s, 1 H), 8.66 (s, 2 H), 8.68 (s, 1 H), 8.78 (s, 1 H), 9.50 (s, 1 H).

Example 22

2,2,2-trichloroethyl(2-(p-tolyl)-5-(trifluoromethyl)pyridin-3-yl)carbamate

The similar procedures as Example 6→Example 5→Example 8 were carried out with (4-methylphenyl)boronic acid in place of (6-(trifluoromethyl)pyridin-3-yl)boronic acid to give the titled compound having the following physical data.

TCL: Rf 0.61 (Hexane:Ethyl Acetate=4:1).

Example 23

1-(2-{4-[2-(ethylamino)-1,3-thiazol-5-yl]phenoxy}-5-pyrimidinyl)-3-[2-(4-methylphenyl)-5-(trifluoromethyl)-3-pyridinyl]urea The similar procedures as Example 9→Example 15 were carried out with the compound prepared in Example 22 in place of the compound prepared in Example 8 to give the present compound having the following physical data.

TCL: Rf 0.49 (Hexane:Ethyl Acetate=1:4);

$^1$H-NMR (DMSO-d$_6$): δ 1.17 (t, 3 H), 2.40 (s, 3 H), 3.25 (m, 2 H), 7.13 (d, 2 H), 7.37 (d, 2 H), 7.43-7.47 (m, 3 H), 7.54 (d, 2 H), 7.72 (t, 1 H), 8.37 (s, 1 H), 8.65 (s, 2 H), 8.68 (s, 1 H), 8.75 (s, 1 H), 9.46 (s, 1 H).

Example 24

2,2,2-trichloroethyl(2-phenyl-5-(trifluoromethyl)pyridin-3-yl)carbamate

The similar procedures as Example 6→Example 5→Example 8 were carried out with phenylboronic acid in place of (6-(trifluoromethyl)pyridin-3-yl)boronic acid to give the titled compound having the following physical data.

TCL: Rf 0.64 (Hexane:Ethyl Acetate=4:1).

Example 25

1-(2-{4-[2-(ethylamino)-1,3-thiazol-5-yl]phenoxy}-5-pyrimidinyl)-3-[2-phenyl-5-(trifluoromethyl)-3-pyridinyl]urea The similar procedures as Example 9→Example 15 were carried out with the compound prepared in Example 24 in place of the compound prepared in Example 8 to give the present compound having the following physical data.

TCL: Rf 0.27 (Hexane:Ethyl Acetate=1:1);

$^1$H-NMR (DMSO-d$_6$): δ 1.16 (t, 3 H), 3.25 (m, 2 H), 7.12 (d, 2 H), 7.42-7.45 (m, 3 H), 7.52-7.58 (m, 3 H), 7.64-7.66 (m, 2 H), 7.71 (t, 1 H), 8.41 (s, 1 H), 8.65 (s, 2 H), 8.72 (s, 1 H), 8.75 (s, 1 H), 9.44 (s, 1 H).

Example 26

2,2,2-trichloroethyl(2-(m-tolyl)-5-(trifluoromethyl)pyridin-3-yl)carbamate

The similar procedures as Example 6→Example 5→Example 8 were carried out with m-tolylboronic acid in place of (6-(trifluoromethyl)pyridin-3-yl)boronic acid to give the titled compound having the following physical data.
TCL: Rf 0.64 (Hexane:Ethyl Acetate=4:1).

Example 27

1-(2-{4-[2-(ethylamino)-1,3-thiazol-5-yl]phenoxy}-5-pyrimidinyl)-3-[2-(3-methylphenyl)-5-(trifluoromethyl)-3-pyridinyl]urea The similar procedures as Example 9→Example 15 were carried out with the compound prepared in Example 26 in place of the compound prepared in Example 8 to give the present compound having the following physical data.
TCL: Rf 0.45 (Hexane:Ethyl Acetate=1:1);
$^1$H-NMR (DMSO-d$_6$): δ 1.16 (t, 3 H), 2.40 (s, 3 H), 3.25 (m, 2 H), 7.12 (d, 2 H), 7.33-7.45 (m, 7 H), 7.71 (t, 1 H), 8.36 (s, 1 H), 8.64 (s, 2 H), 8.69 (s, 1 H), 8.76 (s, 1 H), 9.48 (s, 1 H).

Example 28

5-(4-((5-aminopyrimidin-2-yl)oxy)phenyl)-N-(tert-butyl)thiazol-2-amine

The similar procedure as Example 14 was carried out with N-(tert-butyl)thiazol-2-amine in place of the compound prepared in Example 11 to give the titled compound having the following physical data.
TCL: Rf 0.33 (Hexane:Ethyl Acetate=1:2).

Example 29

1-[2-(3,4-dimethylphenyl)-5-(trifluoromethyl)-3-pyridinyl]-3-[2-(4-{2-[(2-methyl-2-propanyl)amino]-1,3-thiazol-5-yl}phenoxy)-5-pyrimidinyl]urea The similar procedure as Example 9 was carried out with the compound prepared in Example 28 in place of the compound prepared in Example 5 and the compound prepared in Example 16 in place of the compound prepared in Example 8 to give the present compound having the following physical data.
TCL: Rf 0.60 (Hexane:Ethyl Acetate=1:2);
$^1$H-NMR (DMSO-d$_6$): δ 1.37 (s, 9 H), 2.31 (s, 6 H), 7.12 (dd, 2 H), 7.30-7.43 (m, 6 H), 7.49 (s, 1 H), 8.33 (s, 1 H), 8.65 (s, 2 H), 8.67 (s, 1 H), 8.77 (dd, 1 H), 9.49 (s, 1 H).

Example 30 tert-butyl(5-bromothiazol-2-yl)(ethyl)carbamate

The similar procedures as Example 10→Example 11 were carried out with 5-bromothiazol-2-amine hydrobromide in place of thiazol-2-amine to give the titled compound having the following physical data.
TCL: Rf 0.45 (Hexane:Ethyl Acetate=19:1).

Example 31 tert-butyl ethyl(5-(4-hydroxyphenyl)thiazol-2-yl)carbamate

Under an argon atmosphere, the compound prepared in Example 30 (280 mg) was dissolved in a mixed solution of tetrahydrofuran and ethanol (1:1, 3 mL). To the solution were added (4-hydroxyphenyl)boronic acid (140 mg), tetrakis(triphenylphosphine)palladium (53 mg) and a tripotassium phosphate aqueous solution (2 mol/L, 140 mL) and stirred at 75° C. for 3 hours. The reaction mixture was further added with (4-hydroxyphenyl)boronic acid (12 mg) and tetrakis(triphenylphosphine)palladium (21 mg) and stirred for further 1.5 hours. The reaction mixture was added with a saturated ammonium chloride aqueous solution and extracted with ethyl acetate. The obtained organic layer was washed with a saturated sodium chloride aqueous solution, dried over anhydrous sodium sulfate and then concentrated under reduced pressure. The obtained residue was purified on silica gel column chromatography (hexane:ethyl acetate=9:1→3:1) to give the titled compound (211 mg) having the following physical data.
TCL: Rf 0.49 (Hexane:Ethyl Acetate=3:1).

Example 32 tert-butyl ethyl(5-(4-((5-nitropyridin-2-yl)oxy)phenyl)thiazol-2-yl)carbamate

To a solution of the compound prepared in Example 31 (741 mg) in dimethylformamide (8 mL) were added 2-chloro-5-nitropyridine (385 mg) and potassium carbonate (480 mg) and stirred at 90° C. for 1.5 hours. To the reaction mixture was added water and the precipitated solid was collected by filtration and dried to give the titled compound (1.04 g) having the following physical data.
TCL: Rf 0.58 (Hexane:Ethyl Acetate=3:1).

Example 33 tert-butyl(5-(4-((5-aminopyridin-2-yl)oxy)phenyl)thiazol-2-yl)(ethyl)carbamate

The similar procedure as Example 5 was carried out with the compound prepared in Example 32 in place of the compound prepared in Example 4 to give the titled compound having the following physical data.
TCL: Rf 0.20 (Hexane:Ethyl Acetate=3:2).

Example 34

1-[2-(3,4-dimethylphenyl)-5-(trifluoromethyl)-3-pyridinyl]-3-(6-{4-[2-(ethylamino)-1,3-thiazol-5-yl]phenoxy}-3-pyridinyl)urea

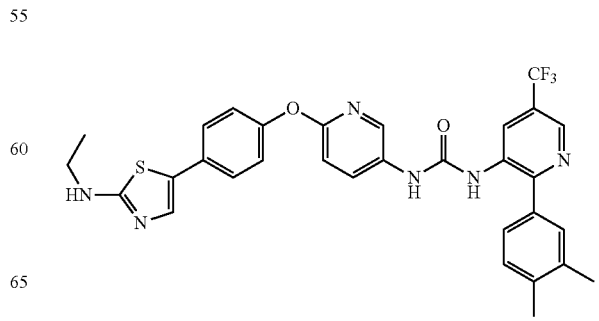

The similar procedures as Example 9→Example 15 were carried out with the compound prepared in Example 33 in place of the compound prepared in Example 5 and the compound prepared in Example 16 in place of the compound prepared in Example 8 to give the present compound having the following physical data.
TCL: Rf 0.47 (Hexane:Ethyl Acetate=1:2);
$^1$H-NMR (DMSO-d$_6$): δ 1.29 (t, 3 H), 2.25 (s, 3 H), 2.26 (s, 3 H), 3.22-3.37 (m, 2 H), 5.24 (br s, 1 H), 6.89 (s, 1 H), 7.07 (s, 2 H), 7.13-7.20 (m, 4 H), 7.23-7.27 (m, 1 H), 7.39 (d, 3 H), 7.82-7.95 (m, 2 H), 8.56 (d, 1 H), 8.92 (d, 1 H).

Example 35

1-(6-{4-[2-(ethylamino)-1,3-thiazol-5-yl]phenoxy}-3-pyridinyl)-3-[2-phenyl-5-(trifluoromethyl)-3-pyridinyl]urea The similar procedures as Example 9→Example 15 were carried out with the compound prepared in Example 33 in place of the compound prepared in Example 5 and the compound prepared in Example 24 in place of the compound prepared in Example 8 to give the present compound having the following physical data.
TCL: Rf 0.29 (Hexane:Ethyl Acetate=1:3);
$^1$H-NMR (CDCl$_3$): δ 1.31 (t, 3 H), 3.24-3.40 (m, 2 H), 5.47 (br s, 1 H), 6.85-7.00 (m, 3 H), 7.08 (d, 2 H), 7.24 (s, 1 H), 7.42 (d, 2 H), 7.45-7.53 (m, 5 H), 7.86 (dd, 1 H), 7.93 (d, 1 H), 8.61 (s, 1 H), 8.94 (s, 1 H).

Example 36

2,2,2-trichloroethyl(2-(3-(hydroxymethyl)phenyl)-5-(trifluoromethyl)pyridin-3-yl)carbamate The similar procedures as Example 6→Example 8 were carried out with (3-(hydroxymethyl)phenyl)boronic acid in place of (6-(trifluoromethyl)pyridin-3-yl)boronic acid and 2-chloro-5-(trifluoromethyl)pyridin-3-amine in place of 2-chloro-3-nitro-5-(trifluoromethyl)pyridine to give the titled compound having the following physical data.
TCL: Rf 0.57 (Hexane:Ethyl Acetate=1:1).

Example 37

1-(2-{4-[2-(ethylamino)-1,3-thiazol-5-yl]phenoxy}-5-pyrimidinyl)-3-{2-[3-(hydroxymethyl)phenyl]-5-(trifluoromethyl)-3-pyridinyl}urea The similar procedures as Example 9→Example 15 were carried out with the compound prepared in Example 36 in place of the compound prepared in Example 8 to give the present compound having the following physical data.
TCL: Rf 0.45 (Ethyl Acetate);
$^1$H-NMR (DMSO-d$_6$): δ 1.16 (t, 3 H), 3.25 (m, 2 H), 4.60 (d, 2 H), 5.30 (t, 1 H), 7.13 (d, 2 H), 7.42-7.52 (m, 6 H), 7.59 (s, 1 H), 7.72 (t, 1 H), 8.39 (s, 1 H), 8.65 (s, 2 H), 8.71 (s, 1 H), 8.76 (s, 1 H), 9.45 (s, 1 H).

Example 38

2,2,2-trichloroethyl(5-(trifluoromethyl)-[2,3'-bipyridin]-3-yl)carbamate

The similar procedures as Example 6→Example 8 were carried out with pyridin-3-ylboronic acid in place of (6-(trifluoromethyl)pyridin-3-yl)boronic acid and 2-chloro-5-(trifluoromethyl)pyridin-3-amine in place of 2-chloro-3-nitro-5-(trifluoromethyl)pyridine to give the titled compound having the following physical data.
TCL: Rf 0.67 (Ethyl Acetate).

Example 39

1-(2-{4-[2-(ethylamino)-1,3-thiazol-5-yl]phenoxy}-5-pyrimidinyl)-3-[5-(trifluoromethyl)-2,3'-bipyridin-3-yl]urea The similar procedures as Example 9→Example 15 were carried out with the compound prepared in Example 38 in place of the compound prepared in Example 8 to give the present compound having the following physical data.
TCL: Rf 0.60 (Ethyl Acetate:Methanol=19:1);
$^1$H-NMR (DMSO-d$_6$): δ 1.16 (t, 3 H), 3.25 (m, 2 H), 7.13 (d, 2 H), 7.42-7.46 (m, 3 H), 7.59 (dd, 1 H), 7.17 (t, 1 H), 8.07-8.09 (m, 1 H), 8.59 (s, 1 H), 8.65 (s, 2 H), 8.72-8.78 (m, 3 H), 8.85 (s, 1 H), 9.33 (s, 1 H).

Example 40 tert-butyl(5-bromothiazol-2-yl)(2-ethoxyethyl)carbamate

The similar procedures as Example 10→Example 11 were carried out with 5-bromothiazol-2-amine hydrobromide in place of thiazol-2-amine and 1-bromo-2-ethoxyethane in place of iodoethane to give the titled compound having the following physical data.
TCL: Rf 0.44 (Hexane:Ethyl Acetate=3:1).

Example 41

1-[2-(3,4-dimethylphenyl)-5-(trifluoromethyl)-3-pyridinyl]-3-[2-(4-{2-[(2-ethoxyethyl)amino]-1,3-thiazol-5-yl}phenoxy)-5-pyrimidinyl]urea The similar procedure as Example 21 was carried out with the compound prepared in Example 40 in place of the compound prepared in Example 18 to give the present compound having the following physical data.
TCL: Rf 0.34 (Ethyl Acetate);
$^1$H-NMR (DMSO-d$_6$): δ 1.12 (t, 3 H), 2.32 (s, 6 H), 3.40-3.54 (m, 6 H), 7.13 (d, 2 H), 7.30-7.63 (m, 6 H), 7.82 (t, 1 H), 7.37 (s, 1 H), 8.62 (s, 2 H), 8.66 (s, 1 H), 8.78 (s, 1 H), 9.50 (s, 1 H).

Example 42 tert-butyl(5-bromothiazol-2-yl)(propyl)carbamate

The similar procedures as Example 10→Example 11 were carried out with 5-bromothiazol-2-amine hydrobromide in place of thiazol-2-amine and 1-iodopropane in place of iodoethane to give the titled compound having the following physical data.
TCL: Rf 0.41 (Hexane:Ethyl Acetate=4:1).

Example 43

1-[2-(3,4-dimethylphenyl)-5-(trifluoromethyl)-3-pyridinyl]-3-(2-{4-[2-(propylamino)-1,3-thiazol-5-yl]phenoxy}-5-pyrimidinyl)urea The similar procedure as Example 21 was carried out with the compound prepared in Example 42 in place of the compound prepared in Example 18 to give the present compound having the following physical data.

TCL: Rf 0.55 (Ethyl Acetate);

$^1$H-NMR (DMSO-$d_6$): δ 0.91 (t, 3 H), 1.57 (m, 2 H), 2.34 (s, 6 H), 3.18 (m, 2 H), 7.13 (d, 2 H), 7.30-7.46 (m, 6 H), 7.76 (t, 1 H), 8.34 (s, 1 H), 8.63 (s, 2 H), 8.66 (s, 1 H), 8.77 (d, 1 H), 9.50 (s, 1 H).

Example 44

2,2,2-trichloroethyl(2-(o-tolyl)-5-(trifluoromethyl)pyridin-3-yl)carbamate

The similar procedures as Example 6→Example 5→Example 8 were carried out with o-tolylboronic acid in place of (6-(trifluoromethyl)pyridin-3-yl)boronic acid to give the titled compound having the following physical data.

TCL: Rf 0.67 (Hexane:Ethyl Acetate=4:1).

Example 45

1-(2-{4-[2-(ethylamino)-1,3-thiazol-5-yl]phenoxy}-5-pyrimidinyl)-3-[2-(2-methylphenyl)-5-(trifluoromethyl)-3-pyridinyl]urea The similar procedures as Example 9→Example 15 were carried out with the compound prepared in Example 44 in place of the compound prepared in Example 8 to give the present compound having the following physical data.

TCL: Rf 0.55 (Methylene Dichloride:Ethyl Acetate:Methanol=8:4:1);

$^1$H-NMR (DMSO-$d_6$): δ 1.16 (t, 3H), 2.06 (s, 3H), 3.20-3.30 (m, 2H), 7.12 (d, 2H), 7.28 (d, 1H), 7.34-7.50 (m, 6H), 7.71 (t, 1H), 7.97 (s, 1H), 8.63 (s, 2H), 8.66-8.70 (m, 1H), 8.86-8.90 (m, 1H), 9.50 (s, 1H).

Example 46

3-nitro-2-phenoxy-5-(trifluoromethyl)pyridine

To a solution of 2-chloro-3-nitro-5-(trifluoromethyl)pyridine (1280 mg) in dimethylformamide (18 mL) were added phenol (800 mg) and cesium carbonate (5530 mg). The reaction mixture was stirred at 60° C. for 3 hours. The reaction mixture was diluted with ethyl acetate and washed with water and a saturated sodium chloride aqueous solution. The obtained organic layer was dried over anhydrous magnesium sulfate and concentrated under reduced pressure. The obtained residue was purified on silica gel column chromatography (hexane:ethyl acetate=1:19) to give the titled compound (370 mg) having the following physical data.

TCL: Rf 0.41 (Ethyl Acetate:Hexane=1:19).

Example 47

2,2,2-trichloroethyl(2-phenoxy-5-(trifluoromethyl)pyridin-3-yl)carbamate

The similar procedures as Example 5→Example 8 were carried out with the compound prepared in Example 46 in place of the compound prepared in Example 4 to give the titled compound having the following physical data.

TCL: Rf 0.60 (Ethyl Acetate:Hexane=1:9).

Example 48

1-(2-{4-[2-(ethylamino)-1,3-thiazol-5-yl]phenoxy}-5-pyrimidinyl)-3-[2-phenoxy-5-(trifluoromethyl)-3-pyridinyl]urea

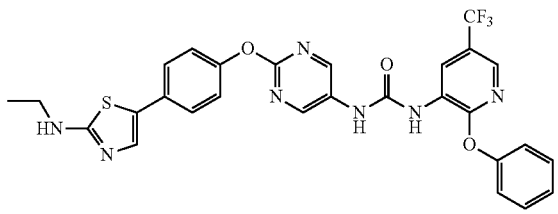 [SMILES: CCNc1ncc(-c2ccc(Oc3ncc(NC(=O)Nc4cc(C(F)(F)F)cnc4Oc4ccccc4)cn3)cc2)s1]

The similar procedures as Example 9→Example 15 were carried out with the compound prepared in Example 47 in place of the compound prepared in Example 8 to give the present compound having the following physical data.

TCL: Rf 0.20 (Ethyl Acetate:Hexane=1:1);

$^1$H-NMR (DMSO-$d_6$): δ 1.16 (t, 3 H), 3.21-3.30 (m, 2 H), 7.13-7.17 (m, 2 H), 7.24-7.32 (m, 3 H), 7.43-7.51 (m, 5 H), 7.72 (t, 1 H), 8.08-8.12 (m, 1 H), 8.73 (s, 2 H), 8.83 (d, 1 H), 9.20 (s, 1 H), 9.59 (s, 1 H).

Example 49

1-(5-(4-((5-aminopyrimidin-2-yl)oxy)phenyl)thiazol-2-yl)pyrrolidin-2-one

The similar procedures as Example 1→Example 2→Example 3→Example 4→Example 5 were carried out with 4-bromobutanoyl chloride in place of 5-bromopentanoyl chloride to give the titled compound having the following physical data.

TCL: Rf 0.52 (Methylene Dichloride:Ethyl Acetate:Methanol=8:4:1).

Example 50

1-[5,6'-bis(trifluoromethyl)-2,3'-bipyridin-3-yl]-3-(2-{4-[2-(2-oxo-1-pyrrolidinyl)-1,3-thiazol-5-yl]phenoxy}-5-pyrimidinyl)urea

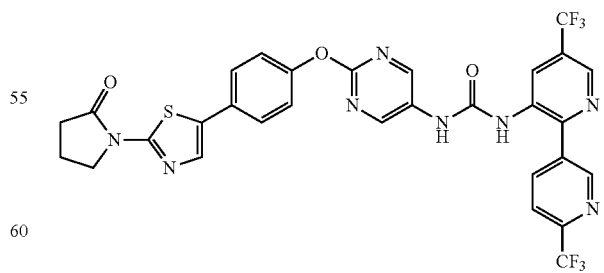

The similar procedure as Example 9 was carried out with the compound prepared in Example 49 in place of the compound prepared in Example 5 to give the present compound having the following physical data.

TCL: Rf 0.57 (Methylene Dichloride:Ethyl Acetate:Methanol=8:4:1);
$^1$H-NMR (DMSO-$d_6$): δ 2.10-2.24 (m, 2 H), 2.63 (t, 2 H), 4.04 (t, 2 H), 7.21 (d, 2 H), 7.66 (d, 2 H), 7.89 (s, 1 H), 8.10 (d, 1 H), 8.36-8.42 (m, 1 H), 8.66 (s, 2 H), 8.71 (s, 1 H), 8.78 (s, 1 H), 8.82 (s, 1 H), 9.04 (s, 1 H), 9.23 (s, 1 H).

Example 50-1

1-[2-(3,4-dimethylphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea The similar procedure as Example 9 was carried out with the compound prepared in Example 49 in place of the compound prepared in Example 5 and the compound prepared in Example 16 in place of the compound prepared in Example 8 to give the present compound having the following physical data.
TCL: Rf 0.62 (Methylene Dichloride:Ethyl Acetate:Methanol=8:4:1);
$^1$H-NMR (DMSO-$d_6$): δ 2.10-2.24 (m, 2 H), 2.31 (s, 6 H), 2.64 (t, 2 H), 4.05 (t, 2 H), 7.22 (d, 2 H), 7.30-7.38 (m, 2 H), 7.41 (s, 1 H), 7.67 (d, 2 H), 7.90 (s, 1 H), 8.35 (s, 1 H), 8.67 (s, 3 H), 8.77 (s, 1 H), 9.51 (s, 1 H).

Example 51

1-[12-(3,4-dimethylphenyl)-5-(trifluoromethyl)-3-pyridinyl]-3-(2-{4-[2-(2-oxo-1-piperidinyl)-1,3-thiazol-5-yl]phenoxy}-5-pyrimidinyl)urea The similar procedure as Example 9 was carried out with the compound prepared in Example 16 in place of the compound prepared in Example 8 to give the present compound having the following physical data.
TCL: Rf 0.58 (Methylene Dichloride:Ethyl Acetate=4:1);
$^1$H-NMR (DMSO-$d_6$): δ 1.80-2.00 (m, 4 H), 2.31 (s, 6 H), 2.61 (t, 2 H), 4.07 (t, 2 H), 7.22 (d, 2 H), 7.30-7.40 (m, 2 H), 7.41 (s, 1 H), 7.66 (d, 2 H), 7.91 (s, 1 H), 8.35 (s, 1 H), 8.67 (m, 3 H), 8.77 (s, 1 H), 9.51 (s, 1 H).

Example 52

1-(2-{4-[2-(2-oxo-1-piperidinyl)-1,3-thiazol-5-yl]phenoxy}-5-pyrimidinyl)-3-[2-phenyl-5-(trifluoromethyl)-3-pyridinyl]urea The similar procedure as Example 9 was carried out with the compound prepared in Example 24 in place of the compound prepared in Example 8 to give the present compound having the following physical data.
TCL: Rf 0.65 (Hexane:Ethyl Acetate=1:4);
$^1$H-NMR (DMSO-$d_6$): δ 1.75-1.98 (m, 4 H), 2.61 (t, 2 H), 4.07 (t, 2 H), 7.21 (d, 2 H), 7.50-7.64 (m, 3 H), 7.64-7.67 (m, 4 H), 7.90 (s, 1 H), 8.41 (s, 1 H), 8.66 (s, 2 H), 8.72 (s, 1 H), 8.75 (s, 1 H), 9.46 (s, 1 H).

Example 53

1-[2-(2-methylphenyl)-5-(trifluoromethyl)-3-pyridinyl]-3-(2-{4-[2-(2-oxo-1-piperidinyl)-1,3-thiazol-5-yl]phenoxy}-5-pyrimidinyl)urea The similar procedure as Example 9 was carried out with the compound prepared in Example 44 in place of the compound prepared in Example 8 to give the present compound having the following physical data.
TCL: Rf 0.65 (Hexane:Ethyl Acetate=1:4);
$^1$H-NMR (DMSO-$d_6$): δ 1.77-1.98 (m, 4 H), 2.07 (s, 3 H), 2.61 (t, 2 H), 4.07 (t, 2 H), 7.21 (d, 2 H), 7.27-7.50 (m, 4 H), 7.66 (d, 2 H), 7.91 (s, 1 H), 7.98 (s, 1 H), 8.65 (s, 2 H), 8.68 (s, 1 H), 8.88 (s, 1 H), 9.51 (s, 1 H).

Example 54

1-(2-{4-[2-(2-oxo-1-pyrrolidinyl)-1,3-thiazol-5-yl]phenoxy}-5-pyrimidinyl)-3-[2-phenyl-5-(trifluoromethyl)-3-pyridinyl]urea

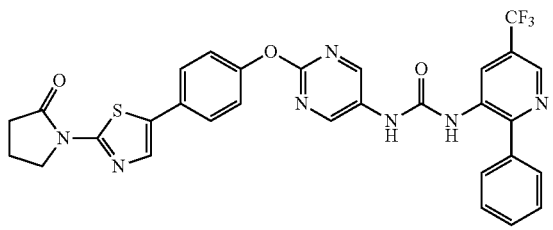 [SMILES: O=C(Nc1cnc(Oc2ccc(-c3cnc(N4CCCC4=O)s3)cc2)nc1)Nc1cc(C(F)(F)F)cnc1-c1ccccc1]

The similar procedure as Example 9 was carried out with the compound prepared in Example 49 in place of the compound prepared in Example 5 and the compound prepared in Example 24 in place of the compound prepared in Example 8 to give the present compound having the following physical data.
TCL: Rf 0.26 (Hexane:Ethyl Acetate=1:4);
$^1$H-NMR (DMSO-$d_6$): δ 2.16 (q, 2 H), 2.64 (t, 2 H), 4.04 (t, 2 H), 7.21 (d, 2 H), 7.54-7.67 (m, 7 H), 7.88 (s, 1 H), 8.41 (s, 1 H), 8.65 (s, 2 H), 8.71 (s, 1 H), 8.75 (s, 1 H), 9.45 (s, 1 H).

Example 55

1-[2-(2-methylphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea The similar procedure as Example 9 was carried out with the compound prepared in Example 49 in place of the compound prepared in Example 5 and the compound prepared in Example 44 in place of the compound prepared in Example 8 to give the present compound having the following physical data.
TCL: Rf 0.28 (Hexane:Ethyl Acetate=1:4);
$^1$H-NMR (DMSO-$d_6$): δ 2.06 (s, 3 H), 2.16 (q, 2 H), 2.64 (t, 2 H), 4.05 (t, 2 H), 7.20 (d, 2 H), 7.26-7.45 (m, 4 H), 7.66 (d, 2 H), 7.88 (s, 1 H), 7.97 (s, 1 H), 8.64 (s, 2 H), 8.67 (s, 1 H), 8.87 (s, 1 H), 9.51 (s, 1 H).

Example 56

1-[2-(4-methylphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea The similar procedure as Example 9 was carried out with the compound prepared in Example 49 in place of the compound prepared in Example 5 and the compound prepared in Example 22 in place of the compound prepared in Example 8 to give the present compound having the following physical data.

TCL: Rf 0.27 (Hexane:Ethyl Acetate=1:4);
$^1$H-NMR (DMSO-d$_6$): δ 2.17 (q, 2 H), 2.04 (s, 3 H), 2.64 (t, 2 H), 4.05 (t, 2 H), 7.22 (d, 2 H), 7.37 (d, 2 H), 7.55 (d, 2 H), 7.67 (d, 2 H), 7.89 (s, 1 H), 8.38 (s, 1 H), 8.67 (s, 2 H), 8.70 (s, 1 H), 8.76 (s, 1 H), 9.48 (s, 1 H).

Example 57

1-[2-(3-methylphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea The similar procedure as Example 9 was carried out with the compound prepared in Example 49 in place of the compound prepared in Example 5 and the compound prepared in Example 26 in place of the compound prepared in Example 8 to give the present compound having the following physical data.
TCL: Rf 0.31 (Hexane:Ethyl Acetate=1:4);
$^1$H-NMR (DMSO-d$_6$): δ 2.16 (q, 2 H), 2.40 (s, 3 H), 2.64 (t, 2 H), 4.05 (t, 2 H), 7.21 (d, 2 H), 7.30-7.45 (m, 4 H), 7.66 (d, 2 H), 7.89 (s, 1 H), 8.37 (s, 1 H), 8.66 (s, 2 H), 8.69 (s, 1 H), 8.76 (s, 1 H), 9.49 (s, 1 H).

Example 58

1-(5-bromothiazol-2-yl)azepan-2-one

The similar procedures as Example 1→Example 2 were carried out with 6-bromohexanoyl chloride in place of 5-bromopentanoyl chloride to give the titled compound having the following physical data.
TCL: Rf 0.56 (Hexane:Ethyl Acetate=3:1).

Example 59

1-[2-(3,4-dimethylphenyl)-5-(trifluoromethyl)-3-pyridinyl]-3-(2-{4-[2-(2-oxo-1-azepanyl)-1,3-thiazol-5-yl]phenoxy}-5-pyrimidinyl)urea

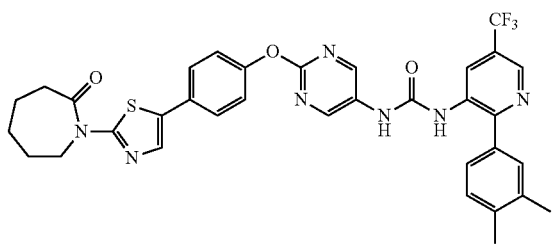 [SMILES: Cc1ccc(-c2ncc(C(F)(F)F)cc2NC(=O)Nc2cnc(Oc3ccc(-c4cnc(N5CCCCCC5=O)s4)cc3)nc2)cc1C]

The similar procedure as Example 21 was carried out with the compound prepared in Example 58 in place of the compound prepared in Example 18 to give the present compound having the following physical data.
TCL: Rf 0.82 (Ethyl Acetate);
$^1$H-NMR (DMSO-d$_6$): δ 1.74 (m, 6 H), 2.32 (s, 6 H), 2.83 (m, 2 H), 4.46 (m, 2 H), 7.25 (d, 2 H), 7.35 (m, 3 H), 7.42 (s, 1 H), 7.65 (d, 2 H), 7.87 (s, 1 H), 8.35 (s, 1 H) 8.67 (s, 2 H), 8.78 (s, 1 H), 9.51 (s, 1 H).

Example 60

2,2,2-trichloroethyl(2-(1-methyl-1H-pyrazol-4-yl)-5-(trifluoromethyl)pyridin-3-yl)carbamate The similar procedures as Example 6→Example 8 were carried out with 1-methyl-4-(4,4,5,5-tetramethyl-1,3,2-dioxaboron-2-yl)-1H-pyrazole in place of (6-(trifluoromethyl)pyridin-3-yl)boronic acid and 2-chloro-5-(trifluoromethyl)pyridin-3-amine in place of 2-chloro-3-nitro-5-(trifluoromethyl)pyridine to give the titled compound having the following physical data.
TCL: Rf 0.70 (Ethyl Acetate).

Example 61

1-[2-(1-methyl-1H-pyrazol-4-yl)-5-(trifluoromethyl)-3-pyridinyl]-3-(2-{4-[2-(2-oxo-1-piperidinyl)-1,3-thiazol-5-yl]phenoxy}-5-pyrimidinyl)urea The similar procedure as Example 9 was carried out with the compound prepared in Example 60 in place of the compound prepared in Example 8 to give the present compound having the following physical data.
TCL: Rf 0.63 (Ethyl Acetate);
$^1$H-NMR (DMSO-d$_6$): δ 1.75-1.98 (m, 4 H), 2.61 (t, 2 H), 3.93 (s, 3 H), 4.07 (t, 2 H), 7.23 (d, 2 H), 7.67 (d, 2 H), 7.91 (s, 1 H), 8.02 (s, 1 H), 8.35 (s, 1 H), 8.43 (s, 1 H), 8.58 (s, 1 H), 8.67 (s, 1 H), 8.73 (s, 2 H), 9.45 (s, 1 H).

Example 62

3-(tert-butyl)-1-(3,4-dimethylphenyl)-1H-pyrazol-5-amine

To a solution of pivaloylacetonitrile (400 mg) in toluene (10 mL) were added 3,4-dimethylphenylhydrazine hydrochloride (520 mg) and triethylamine (0.4 mL) and refluxed with heating for 5 hours. The reaction mixture was added with a saturated sodium hydrogen carbonate aqueous solution. The obtained organic layer was washed with a saturated sodium chloride aqueous solution. The obtained organic layer was dried over anhydrous sodium sulfate and then concentrated under reduced pressure. The obtained residue was purified on silica gel column chromatography (hexane:ethyl acetate=4:1) to give the titled compound (490 mg) having the following physical data.
TCL: Rf 0.41 (Hexane:Ethyl Acetate=4:1).

Example 63

2,2,2-trichloroethyl(3-(tert-butyl)-1-(3,4-dimethylphenyl)-1H-pyrazol-5-yl)carbamate The similar procedure as Example 8 was carried out with the compound prepared in Example 62 in place of the compound prepared in Example 7 to give the titled compound having the following physical data.
TCL: Rf 0.58 (Hexane:Ethyl Acetate=4:1).

Example 64

1-(3-(tert-butyl)-1-(3,4-dimethylphenyl)-1H-pyrazol-5-yl)-3-(2-(4-(4,4,5,5-tetramethyl-1,3,2-dioxaborolan-2-yl)phenoxy)pyrimidin-5-yl)urea The similar procedures as Example 9→Example 20 were carried out with the compound prepared in Example 63 in place of the compound prepared in Example 8 and the compound prepared in Example 13 in place of the compound prepared in Example 5 to give the titled compound having the following physical data.
TCL: Rf 0.56 (Methylene Dichloride:Ethyl Acetate=4:1).

Example 65

The similar procedure as Example 21 was carried out with the compound prepared in Example 64 in place of the compound prepared in Example 20 and corresponding 5-bromothiazole derivatives in place of the compound prepared in Example 18 to give the present compounds having the following physical data.

Example 65-1

1-[1-(3,4-dimethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea

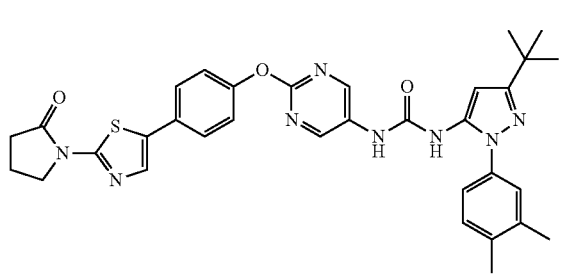 [SMILES: Cc1ccc(-n2nc(C(C)(C)C)cc2NC(=O)Nc2cnc(Oc3ccc(-c4cnc(N5CCCC5=O)s4)cc3)nc2)cc1C]

TCL: Rf 0.31 (Hexane:Ethyl Acetate=3:7);
$^1$H-NMR (DMSO-$d_6$): δ 1.25 (s, 9 H), 2.10-2.23 (m, 2 H), 2.27 (s, 6 H), 2.64 (t, 2 H), 4.05 (t, 2 H), 6.33 (s, 1 H), 7.15-7.28 (m, 5 H), 7.66 (d, 2 H), 7.89 (s, 1 H), 8.54 (s, 1 H), 8.64 (s, 2 H), 9.18 (s, 1 H).

Example 65-2

1-[1-(3,4-dimethylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.31 (Hexane:Ethyl Acetate=1:2);
$^1$H-NMR (DMSO-$d_6$): δ 1.26 (s, 9 H), 1.76-2.00 (m, 4 H), 2.27 (s, 6 H), 2.61 (t, 2 H), 4.07 (t, 2 H), 6.33 (s, 1 H), 7.16-7.29 (m, 5 H), 7.65 (d, 2 H), 7.91 (s, 1 H), 8.54 (s, 1 H), 8.65 (s, 2 H), 9.19 (s, 1 H).

Example 66

The similar procedures as Example 62→Example 63→Example 12→Example 13→Example 19→Example 20→Example 21 were carried out with corresponding hydrazine derivatives in place of (3,4-dimethylphenyl)hydrazine hydrochloride; 4-bromophenol or corresponding 4-bromophenol derivatives or 6-bromopyridin-3-ol in place of 4-bromophenol; and corresponding 5-bromothiazole derivatives in place of the compound prepared in Example 18 to give the present compounds having the following physical data.

Example 66-1

1-[1-(2,3-dihydro-1H-inden-5-yl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.58 (Methylene Dichloride:Ethyl Acetate:Methanol=8:4:1);
$^1$H-NMR (DMSO-$d_6$): δ 1.26 (s. 9 H), 2.00-2.22 (m, 4 H), 2.64 (t, 2 H), 2.84-2.97 (m, 4 H), 4.05 (t, 2 H), 6.33 (s, 1 H), 7.16-7.26 (m, 3 H), 7.27-7.36 (m, 2 H), 7.66 (d, 2 H), 7.89 (s, 1 H), 8.56 (s, 1 H), 8.65 (s, 2 H), 9.19 (s, 1 H).

Example 66-2

1-[1-(2,3-dihydro-1H-inden-5-yl)-3-(2-methyl-2-propanyl)-1H-pyrazol-5-yl]-3-(2-{2-fluoro-4-[2-(2-oxo-1-pyrrolidinyl)-1,3-thiazol-5-yl]phenoxy}-5-pyrimidinyl)urea

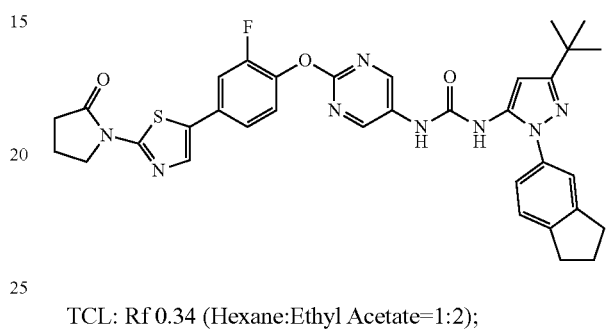

TCL: Rf 0.34 (Hexane:Ethyl Acetate=1:2);
$^1$H-NMR (DMSO-$d_6$): δ 1.26 (s, 9 H), 2.06 (t, 2 H), 2.14 (t, 2 H), 2.65 (t, 2 H), 2.89 (t, 2 H), 2.91 (t, 2 H), 4.05 (t, 2 H), 6.33 (s, 1 H), 7.21 (dd, 1 H), 7.32-7.46 (m, 4 H), 7.73 (dd, 1 H), 7.99 (s, 1 H), 8.56 (s, 1 H), 8.66 (s, 2 H), 9.20 (s, 1 H).

Example 66-3

1-[1-(2,3-dihydro-1H-inden-5-yl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.38 (Hexane:Ethyl Acetate=1:2);
$^1$H-NMR (DMSO-$d_6$): δ 1.26 (s, 9 H), 1.82 (m, 2 H), 1.93 (m, 2 H), 2.06 (m, 2 H), 2.61 (t, 2 H), 2.91 (m, 4 H), 4.06 (t, 2 H), 6.33 (s, 1 H), 7.21 (d, 3 H), 7.32 (m, 2 H), 7.65 (d, 2 H), 7.90 (s, 1 H), 8.56 (s, 1 H), 8.64 (s, 2 H), 9.18 (s, 1 H).

Example 66-4

1-[1-(2,3-dihydro-1H-inden-5-yl)-3-(2-methyl-2-propanyl)-1H-pyrazol-5-yl]-3-(2-{3-fluoro-4-[2-(2-oxo-1-pyrrolidinyl)-1,3-thiazol-5-yl]phenoxy}-5-pyrimidinyl)urea TCL: Rf 0.33 (Methanol:Ethyl Acetate=1:9);
$^1$H-NMR (DMSO-$d_6$): δ 1.26 (s, 9 H), 2.06 (m, 2 H), 2.17 (m, 2 H), 2.65 (t, 2 H), 2.90 (tt, 4 H), 4.06 (t, 2 H), 6.34 (s, 1 H), 7.11 (dd, 1 H), 7.22 (dd, 1 H), 7.32 (m, 3 H), 7.81 (t, 1 H), 7.95 (s, 1 H), 8.58 (s, 1 H), 8.68 (s, 2 H), 9.23 (s, 1 H).

Example 66-5

1-(2-{2-chloro-4-[2-(2-oxo-1-pyrrolidinyl)-1,3-thiazol-5-yl]phenoxy}-5-pyrimidinyl)-3-[1-(2,3-dihydro-1H-inden-5-yl)-3-(2-methyl-2-propanyl)-1H-pyrazol-5-yl]urea TCL: Rf 0.70 (Ethyl Acetate);
$^1$H-NMR (DMSO-$d_6$): δ 1.26 (s, 9 H), 2.06 (m, 2 H), 2.17 (m, 2 H), 2.65 (t, 2 H), 2.90 (m, 4 H), 4.06 (t, 2 H), 6.33 (s, 1

H), 7.21 (d, 1 H), 7.32-7.41 (m, 3 H) 7.63 (d, 1 H), 7.90 (s, 1 H), 8.01 (s, 1 H), 8.57 (s, 1 H), 8.65 (s, 2 H), 9.19 (s, 1 H).

Example 66-6

1-[1-(2,3-dihydro-1H-inden-5-yl)-3-(2-methyl-2-propanyl)-1H-pyrazol-5-yl]-3-(2-{4-[2-(2-oxo-1-azepanyl)-1,3-thiazol-5-yl]phenoxy}-5-pyrimidinyl)urea TCL: Rf 0.80 (Ethyl Acetate);
$^1$H-NMR (DMSO-d$_6$): δ 1.26 (s, 9 H), 1.73 (m, 6 H), 2.06 (m, 2 H), 2.81-2.94 (m, 6 H), 4.45 (t, 2 H), 6.33 (s, 1 H), 7.21 (d, 3 H), 7.32-7.47 (m, 2 H), 7.64 (d, 2 H), 7.86 (s, 1 H), 8.56 (s, 1 H), 8.65 (s, 2 H), 9.18 (s, 1 H).

Example 66-7

1-{1-[3-(hydroxymethyl)-4-methylphenyl]-3-(2-methyl-2-propanyl)-1H-pyrazol-5-yl}-3-(2-{4-[2-(2-oxo-1-pyrrolidinyl)-1,3-thiazol-5-yl]phenoxy}-5-pyrimidinyl)urea

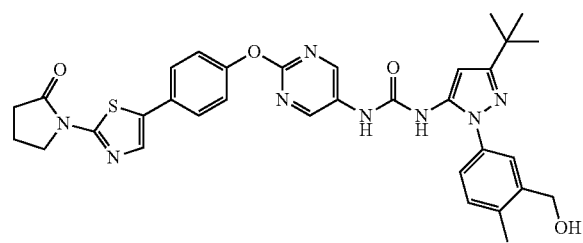 [SMILES: Cc1ccc(-n2nc(C(C)(C)C)cc2NC(=O)Nc2cnc(Oc3ccc(-c4cnc(N5CCCC5=O)s4)cc3)nc2)cc1CO]

TCL: Rf 0.57 (Ethyl Acetate:Methanol=9:1);
$^1$H-NMR (DMSO-d$_6$): δ 1.26 (s, 9 H), 2.16 (m, 2 H), 2.26 (s, 3 H), 2.64 (t, 2 H), 4.05 (t, 2 H), 4.53 (d, 2 H), 5.24 (t, 1 H), 6.33 (s, 1 H), 7.20-7.25 (m, 4 H), 7.48 (s, 1 H), 7.67 (d, 2 H), 7.89 (s, 1 H), 8.55 (s, 1 H), 8.65 (s, 2 H), 9.17 (s, 1 H).

Example 66-8

1-{1-[4-(hydroxymethyl)-3-methylphenyl]-3-(2-methyl-2-propanyl)-1H-pyrazol-5-yl}-3-(2-{4-[2-(2-oxo-1-pyrrolidinyl)-1,3-thiazol-5-yl]phenoxy}-5-pyrimidinyl)urea TCL: Rf 0.60 (Ethyl Acetate:Methanol=9:1);
$^1$H-NMR (DMSO-d$_6$): δ 1.26 (s, 9 H), 2.16 (m, 2 H), 2.28 (s, 3 H), 2.64 (t, 2 H), 4.05 (t, 2 H), 4.53 (d, 2 H), 5.20 (t, 1 H), 6.34 (s, 1 H), 7.20-7.29 (m, 4 H), 7.48 (d, 1 H), 7.67 (d, 2 H), 7.89 (s, 1 H), 8.57 (s, 1 H), 8.65 (s, 2 H), 9.21 (s, 1 H).

Example 66-9

1-{3-(2-methyl-2-propanyl)-1-[4-methyl-3-(trifluoromethyl)phenyl]-1H-pyrazol-5-yl}-3-(2-{4-[2-(2-oxo-1-pyrrolidinyl)-1,3-thiazol-5-yl]phenoxy}-5-pyrimidinyl)urea TCL: Rf 0.59 (Methylene Dichloride:Ethyl Acetate: Methanol=8:4:1);
$^1$H-NMR (DMSO-d$_6$): δ 1.27 (s, 9 H), 2.10-2.24 (m, 2 H), 2.49 (s, 3 H), 2.64 (t, 2 H), 4.05 (t, 2 H), 6.37 (s, 1 H), 7.21 (d, 2 H), 7.54-7.80 (m, 5 H), 7.89 (s, 1 H), 8.63 (s, 2 H), 8.69 (s, 1 H), 9.20 (s, 1 H).

Example 66-10

1-[3-(2-methyl-2-propanyl)-1-(3,4,5-trimethylphenyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.73 (Ethyl Acetate);
$^1$H-NMR (DMSO-d$_6$): δ 1.25 (s, 9 H), 1.83-2.00 (m, 4 H), 2.17 (s, 3 H), 2.30 (s, 6 H), 2.61 (t, 2 H), 4.07 (t, 2 H), 6.33 (s, 1 H), 7.10 (s, 2 H), 7.20 (d, 2 H), 7.65 (d, 2 H), 7.91 (s, 1 H) 8.51 (s, 1 H), 8.65 (s, 2 H), 9.19 (s, 1 H).

Example 66-11

1-[3-(2-methyl-2-propanyl)-1-(3,4,5-trimethylphenyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.80 (Ethyl Acetate);
$^1$H-NMR (DMSO-d$_6$): δ 1.26 (s, 9 H), 2.16 (m, 5 H), 2.29 (s, 6 H), 2.63 (t, 2 H), 4.05 (t, 2 H), 6.32 (s, 1 H), 7.10 (s, 2 H), 7.20 (d, 2 H), 7.65 (d, 2 H), 7.88 (s, 1 H) 8.51 (s, 1 H), 8.64 (s, 2 H), 9.18 (s, 1 H).

Example 66-12

1-[1-(4-fluorophenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.51 (Methylene Dichloride:Ethyl Acetate: Methanol=8:4:1);
$^1$H-NMR (DMSO-d$_6$): δ 1.27 (s, 9 H), 2.10-2.23 (m, 2 H), 2.64 (t, 2 H), 4.05 (t, 2 H), 6.35 (s, 1 H), 7.21 (d, 2 H), 7.35 (t, 2 H), 7.54 (dd, 2 H), 7.66 (d, 2 H), 7.89 (s, 1 H), 8.62 (s, 1 H), 8.65 (s, 2 H), 9.17 (s, 1 H).

Example 66-13

1-[1-(4-methoxy-3,5-dimethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.51 (Methylene Dichloride:Ethyl Acetate: Methanol=8:4:1);
$^1$H-NMR (DMSO-d$_6$): δ 1.25 (s, 9 H), 2.10-2.23 (m, 2 H), 2.27 (s, 6 H), 2.64 (t, 2 H), 3.69 (s, 3 H), 4.05 (t, 2 H), 5.75 (s, 1 H), 6.33 (s, 1 H), 7.14 (s, 1 H), 7.21 (d, 2 H), 7.66 (d, 2 H), 7.89 (s, 1 H), 8.57 (s, 1 H), 8.65 (s, 2 H), 9.18 (s, 1 H).

Example 66-14

1-{3-(2-methyl-2-propanyl)-1-[4-(trifluoromethyl)phenyl]-1H-pyrazol-5-yl}-3-(2-{4-[2-(2-oxo-1-pyrrolidinyl)-1,3-thiazol-5-yl]phenoxy}-5-pyrimidinyl)urea TCL: Rf 0.58 (Methylene Dichloride:Ethyl Acetate: Methanol=8:4:1);

¹H-NMR (DMSO-d₆): δ 1.28 (s, 9 H), 2.10-2.23 (m, 2 H), 2.64 (t, 2 H), 4.05 (t, 2 H), 6.41 (s, 1 H), 7.21 (d, 2 H), 7.66 (d, 2 H), 7.78 (d, 2 H), 7.70-7.82 (m, 3 H), 8.66 (s, 2 H), 8.80 (s, 1 H), 9.23 (s, 1 H).

Example 66-15

1-[3-(2-methyl-2-propanyl)-1-phenyl-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.51 (Methylene Dichloride:Ethyl Acetate:Methanol=8:4:1);
¹H-NMR (DMSO-d₆): δ 1.26 (s, 9 H), 2.10-2.23 (m, 2 H), 2.63 (t, 2 H), 4.04 (t, 2 H), 6.35 (s, 1 H), 7.20 (d, 2 H), 7.35-7.43 (m, 1 H), 7.47-7.53 (m, 4 H), 7.66 (d, 2 H), 7.88 (s, 1 H), 8.64 (s, 3 H), 9.19 (s, 1 H).

Example 66-16

1-[1-(4-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.49 (Methylene Dichloride:Ethyl Acetate:Methanol=8:4:1);
¹H-NMR (DMSO-d₆): δ 1.26 (s, 9 H), 2.10-2.23 (m, 2 H), 2.35 (s, 3 H), 2.63 (t, 2 H), 4.04 (t, 2 H), 6.32 (s, 1 H), 7.19 (d, 2 H), 7.29 (d, 2 H), 7.36 (d, 2 H), 7.65 (d, 2 H), 7.88 (s, 1 H), 8.56 (s, 1 H), 8.63 (s, 2 H), 9.18 (s, 1 H).

Example 66-17

1-[1-mesityl-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.51 (Methylene Dichloride:Ethyl Acetate:Methanol=8:4:1);
¹H-NMR (DMSO-d₆): δ 1.25 (s, 9 H), 1.87 (s, 6 H), 2.10-2.23 (m, 2 H), 2.32 (s, 3 H), 2.64 (t, 2 H), 4.05 (t, 2 H), 6.33 (s, 1 H), 7.04 (s, 2 H), 7.20 (d, 2 H), 7.66 (d, 2 H), 7.88 (s, 1 H), 8.28 (s, 1 H), 8.63 (s, 2 H), 9.03 (s, 1 H).

Example 66-18

1-[1-(2-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.51 (Methylene Dichloride:Ethyl Acetate:Methanol=8:4:1);
¹H-NMR (DMSO-d₆): δ 1.26 (s, 9 H), 1.99 (s, 3 H), 2.10-2.23 (m, 2 H), 2.64 (t, 2 H), 4.05 (t, 2 H), 6.33 (s, 1 H), 7.20 (d, 2 H), 7.28-7.44 (m, 4 H), 7.65 (d, 2 H), 7.88 (s, 1 H), 8.38 (s, 1 H), 8.62 (s, 2 H), 9.06 (s, 1 H).

Example 66-19

1-[1-(2,3-dihydro-1-benzofuran-5-yl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea

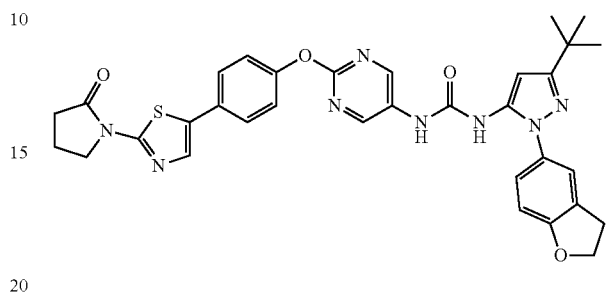

TCL: Rf 0.50 (Ethyl Acetate);
¹H-NMR (DMSO-d₆): δ 1.25 (s, 9 H), 2.16 (q, 2 H), 2.64 (t, 2 H), 3.23 (t, 2 H), 4.05 (t, 2 H), 4.59 (t, 2 H), 6.31 (s, 1 H), 6.86 (d, 1 H), 7.31-7.14 (m, 4 H), 7.67 (d, 2 H), 7.89 (s, 1 H), 8.50 (s, 1 H), 8.65 (s, 2 H), 9.17 (s, 1 H).

Example 66-20

1-[1-(2,3-dimethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.47 (Methylene Dichloride:Ethyl Acetate:Methanol=8:4:1);
¹H-NMR (DMSO-d₆): δ 1.25 (s, 9 H), 1.82 (s, 3 H), 2.10-2.23 (m, 2 H), 2.32 (s, 3 H), 2.64 (t, 2 H), 4.05 (t, 2 H), 6.34 (s, 1 H), 7.12-7.28 (m, 4 H), 7.30-7.36 (m, 1 H), 7.66 (d, 2 H), 7.88 (s, 1 H), 8.32 (s, 1 H), 8.62 (s, 2 H), 9.06 (s, 1 H).

Example 66-21

1-[1-(4-methoxyphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.44 (Methylene Dichloride:Ethyl Acetate:Methanol=8:4:1);
¹H-NMR (DMSO-d₆): δ 1.26 (s, 9 H), 2.10-2.23 (m, 2 H), 2.64 (t, 2 H), 3.80 (s, 3 H), 4.05 (t, 2 H), 6.31 (s, 1 H), 7.05 (d, 2 H), 7.20 (d, 2 H), 7.39 (d, 2 H), 7.66 (d, 2 H), 7.88 (s, 1 H), 8.52 (s, 1 H), 8.64 (s, 2 H), 9.17 (s, 1 H).

Example 66-22

1-[1-(4-fluoro-2-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.55 (Methylene Dichloride:Ethyl Acetate:Methanol=8:4:1);
¹H-NMR (DMSO-d₆): δ 1.25 (s, 9 H), 1.97 (s, 3 H), 2.10-2.24 (m, 2 H), 2.64 (t, 2 H), 4.04 (t, 2 H), 6.32 (s, 1 H), 7.14-7.24 (m, 3 H), 7.26-7.33 (m, 1 H), 7.35-7.42 (m, 1 H), 7.66 (d, 2 H), 7.88 (s, 1 H), 8.40 (s, 1 H), 8.62 (s, 2 H), 9.00 (s, 1 H).

Example 66-23

1-[1-(2-fluorophenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.62 (Methylene Dichloride:Ethyl Acetate:Methanol=8:4:1);
$^1$H-NMR (DMSO-$d_6$): δ 1.26 (s, 9 H), 2.10-2.24 (m, 2 H), 2.64 (t, 2 H), 4.05 (t, 2 H), 6.36 (s, 1 H), 7.20 (d, 2 H), 7.32-7.60 (m, 4 H), 7.66 (d, 2 H), 7.89 (s, 1 H), 8.61 (s, 1 H), 8.63 (s, 2 H), 9.04 (s, 1 H).

Example 66-24

1-[1-(2-fluoro-3-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.63 (Methylene Dichloride:Ethyl Acetate:Methanol=8:4:1);
$^1$H-NMR (DMSO-$d_6$): δ 1.25 (s, 9 H), 2.10-2.24 (m, 2 H), 2.32-2.36 (m, 3 H), 2.66 (t, 2 H), 4.05 (t, 2 H), 6.36 (s, 1 H), 7.18-7.28 (m, 3 H), 7.30-7.37 (m, 1 H), 7.40-7.48 (m, 1 H), 7.66 (d, 2 H), 7.89 (s, 1 H), 8.59 (s, 1 H), 8.65 (s, 2 H), 9.04 (s, 1 H).

Example 66-25

1-[1-(3-fluorophenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.64 (Methylene Dichloride:Ethyl Acetate:Methanol=8:4:1);
$^1$H-NMR (DMSO-$d_6$): δ 1.25 (s, 9 H), 2.10-2.24 (m, 2 H), 2.64 (t, 2 H), 4.05 (t, 2 H), 6.38 (s, 1 H), 7.21 (d, 2 H), 7.36-7.44 (m, 2 H), 7.48-7.70 (m, 4 H), 7.89 (s, 1 H), 8.62 (s, 2 H), 8.72 (s, 1 H), 9.24 (s, 1 H).

Example 66-26

1-[1-(2-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.33 (Ethyl Acetate:Hexane=2:1);
$^1$H-NMR (DMSO-$d_6$): δ 1.25 (s, 9 H), 1.83 (m, 2 H), 1.93 (m, 2 H), 1.99 (s, 3 H), 2.61 (t, 2 H), 4.06 (t, 2 H), 6.34 (s, 1 H), 7.21 (d, 2 H), 7.30-7.44 (m, 4 H), 7.66 (d, 2 H), 7.91 (s, 1 H), 8.39 (s, 1 H), 8.63 (s, 2 H), 9.06 (s, 1 H).

Example 66-27

Methyl 3-[3-(2-methyl-2-propanyl)-5-{[(2-{4-[2-(2-oxo-1-pyrrolidinyl)-1,3-thiazol-5-yl]phenoxy}-5-pyrimidinyl)carbamoyl]amino}-1H-pyrazol-1-yl]benzoate

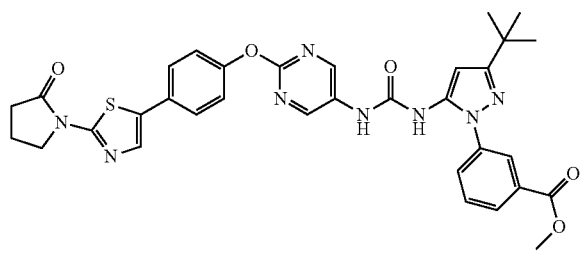 [SMILES: COC(=O)c1cccc(-n2nc(C(C)(C)C)cc2NC(=O)Nc2cnc(Oc3ccc(-c4cnc(N5CCCC5=O)s4)cc3)nc2)c1]

TCL: Rf 0.46 (Methylene Dichloride:Ethyl Acetate:Methanol=8:4:1);
$^1$H-NMR (DMSO-$d_6$): δ 1.28 (s, 9 H), 2.10-2.24 (m, 2 H), 2.64 (t, 2 H), 3.86 (s, 3 H), 4.05 (t, 2 H), 6.38 (s, 1 H), 7.18-7.25 (m, 2 H), 7.62-7.70 (m, 3 H), 7.82 (d, 1 H), 7.89 (s, 1 H), 7.94 (d, 1 H), 8.07 (s, 1 H), 8.64 (s, 2 H), 8.73 (s, 1 H), 9.20 (s, 1 H).

Example 66-28

N-{4-[3-(2-methyl-2-propanyl)-5-{[(2-{4-[2-(2-oxo-1-pyrrolidinyl)-1,3-thiazol-5-yl]phenoxy}-5-pyrimidinyl)carbamoyl]amino}-1H-pyrazol-1-yl]phenyl}acetamide

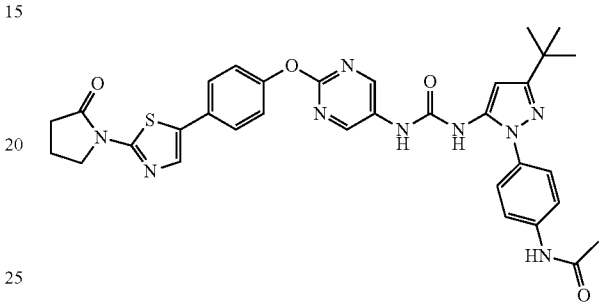

TCL: Rf 0.24 (Methylene Dichloride:Ethyl Acetate:Methanol=8:4:1);
$^1$H-NMR (DMSO-$d_6$): δ 1.26 (s, 9 H), 2.05 (s, 3 H), 2.10-2.24 (m, 2 H), 2.64 (t, 2 H), 4.05 (t, 2 H), 6.29 (s, 1 H), 7.20 (d, 2 H), 7.41 (d, 2 H), 7.60-7.75 (m, 4 H), 7.88 (s, 1 H), 8.65 (s, 2 H), 9.07 (br s, 1 H), 9.71 (br s, 1 H), 10.09 (s, 1 H).

Example 66-29

1-[1-(1,3-benzodioxol-5-yl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea

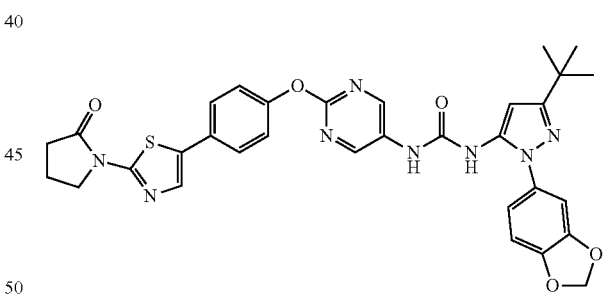

TCL: Rf 0.39 (Methylene Dichloride:Ethyl Acetate:Methanol=8:4:1);
$^1$H-NMR (DMSO-$d_6$): δ 1.25 (s, 9 H), 2.10-2.24 (m, 2 H), 2.64 (t, 2 H), 4.05 (t, 2 H), 6.10 (s, 2 H), 6.31 (s, 1 H), 6.52 (s, 1 H), 6.93 (dd, 1 H), 7.05 (t, 1 H), 7.21 (d, 2 H), 7.66 (d, 2 H), 7.89 (s, 1 H), 8.55 (s, 1 H), 8.65 (s, 2 H), 9.18 (s, 1 H).

Example 66-30

1-[3-(2-methyl-2-propanyl)-1-phenyl-1H-pyrazol-5-yl]-3-(2-{4-[2-(2-oxo-1-piperidinyl)-1,3-thiazol-5-yl]phenoxy}-5-pyrimidinyl)urea TCL: Rf 0.65 (Hexane:Ethyl Acetate=1:4);
$^1$H-NMR (DMSO-$d_6$): δ 1.27 (s, 9 H), 1.75-1.99 (m, 4 H), 2.61 (t, 2 H), 4.07 (s, 2 H), 6.36 (s, 1 H), 7.21 (d, 2 H), 7.35-7.40 (m, 1 H), 7.40-7.55 (m, 4 H), 7.65 (d, 2 H), 7.91 (s, 1 H), 8.65 (s, 1 H), 8.65 (s, 2 H), 9.20 (s, 1 H).

Example 66-31

1-[1-(2,3-dimethoxyphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.51 (Methylene Dichloride:Ethyl Acetate:Methanol=8:4:1);
$^1$H-NMR (DMSO-$d_6$): δ 1.25 (s, 9 H), 2.10-2.24 (m, 2 H), 2.64 (t, 2 H), 3.52 (s, 3 H), 3.87 (s, 3 H), 4.05 (t, 2 H), 6.33 (s, 1 H), 6.93-7.00 (m, 1 H), 7.17-7.26 (m, 4 H), 7.66 (d, 2 H), 7.89 (s, 1 H), 8.32 (s, 1 H), 8.64 (s, 2 H), 9.19 (s, 1 H).

Example 66-32

1-[1-(2-fluoro-4-methoxyphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.51 (Methylene Dichloride:Ethyl Acetate:Methanol=8:4:1);
$^1$H-NMR (DMSO-$d_6$): δ 1.25 (s, 9 H), 2.10-2.24 (m, 2 H), 2.64 (t, 2 H), 3.84 (s, 3 H), 4.05 (t, 2 H), 6.33 (s, 1 H), 6.90-6.96 (m, 1 H), 7.05-7.15 (m, 1 H), 7.21 (d, 2 H), 7.43 (t, 1 H), 7.66 (d, 2 H), 7.89 (s, 1 H), 8.55 (s, 1 H), 8.65 (s, 2 H), 9.03 (s, 1 H).

Example 66-33

1-{1-[2-fluoro-4-(trifluoromethyl)phenyl]-3-(2-methyl-2-propanyl)-1H-pyrazol-5-yl}-3-(2-{4-[2-(2-oxo-1-piperidinyl)-1,3-thiazol-5-yl]phenoxy}-5-pyrimidinyl)urea TCL: Rf 0.59 (Hexane:Ethyl Acetate=1:3);
$^1$H-NMR (CDCl$_3$): δ 1.30-1.38 (m, 9 H), 1.83-2.07 (m, 4 H), 2.55 (t, 2 H), 4.18 (t, 2 H), 6.42 (s, 1 H), 7.15 (d, 2 H), 7.19-7.28 (m, 1 H), 7.38-7.61 (m, 5 H), 7.64 (s, 1 H), 7.68 (s, 1 H), 8.60 (s, 2 H).

Example 66-34

1-[1-(2-chloro-4-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.35 (Hexane:Ethyl Acetate=1:3);
$^1$H-NMR (CDCl$_3$): δ 1.35 (s, 9 H), 1.88-2.07 (m, 4 H), 2.35 (s, 3 H), 2.68 (t, 2 H), 4.17 (t, 2 H), 6.34 (s, 1 H), 6.43 (s, 1 H), 7.03 (br s, 1 H), 7.12-7.21 (m, 3 H), 7.26-7.33 (m, 2 H), 7.58 (d, 2 H), 7.63 (s, 1 H), 8.55 (s, 2 H).

Example 66-35

1-[1-(2,5-dimethylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.68 (Methylene Dichloride:Ethyl Acetate:Methanol=8:4:1);
$^1$H-NMR (DMSO-$d_6$): δ 1.25 (s, 9 H), 1.77-1.88 (m, 2 H), 1.93 (s, 3 H), 2.33 (s, 3 H), 2.35-2.45 (m, 2 H), 2.61 (t, 2 H), 4.07 (t, 2 H), 6.33 (s, 1 H), 7.12-7.32 (m, 5 H), 7.65 (d, 2 H), 7.91 (s, 1 H), 8.37 (s, 1 H), 8.63 (s, 2 H), 9.08 (s, 1 H).

Example 66-36

1-[1-(2-fluorophenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.58 (Methylene Dichloride:Ethyl Acetate:Methanol=8:4:1);
$^1$H-NMR (DMSO-$d_6$): δ 1.26 (s, 9 H), 1.77-2.00 (m, 4 H), 2.61 (t, 2 H), 4.07 (t, 2 H), 6.36 (s, 1 H), 7.21 (d, 2 H), 7.33-7.60 (m, 4 H), 7.65 (d, 2 H), 7.91 (s, 1 H), 8.61 (s, 1 H), 8.64 (s, 2 H), 9.04 (s, 1 H).

Example 66-37

1-[1-(2-fluoro-4-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.61 (Methylene Dichloride:Ethyl Acetate:Methanol=8:4:1);
$^1$H-NMR (DMSO-$d_6$): δ 1.25 (s, 9 H), 1.77-2.00 (m, 4 H), 2.40 (s, 3 H), 2.61 (t, 2 H), 4.07 (t, 2 H), 6.34 (s, 1 H), 7.16-7.25 (m, 3 H), 7.30 (d, 1 H), 7.39 (t, 1 H), 7.65 (d, 2 H), 7.91 (s, 1 H), 8.56 (s, 1 H), 8.64 (s, 2 H), 9.05 (s, 1 H).

Example 66-38

1-[1-(4-fluorophenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.68 (Methylene Dichloride:Ethyl Acetate:Methanol=8:4:1);
$^1$H-NMR (DMSO-$d_6$): δ 1.27 (s, 9 H), 1.77-2.00 (m, 4 H), 2.61 (t, 2 H), 4.07 (t, 2 H), 6.35 (s, 1 H), 7.21 (d, 2 H), 7.35 (t, 2H), 7.50-7.59 (m, 2 H), 7.66 (d, 2 H), 7.91 (s, 1 H), 8.62 (s, 1 H), 8.65 (s, 2 H), 9.17 (s, 1 H).

Example 66-39

1-[1-(3-butoxyphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.59 (Hexane:Ethyl Acetate=1:3);
$^1$H-NMR (CDCl$_3$): δ 0.88-0.98 (m, 3 H), 1.35 (s, 9 H), 1.43 (dd, 2 H), 1.64-1.77 (m, 2 H), 1.83-2.05 (m, 4 H), 2.53 (t, 2 H), 3.91 (t, 1 H), 4.16 (t, 2 H), 6.43 (s, 1 H), 6.82-6.87 (m, 1H), 6.98-7.04 (m, 2 H), 7.10 (s, 1 H), 7.17 (d, 2 H), 7.22-7.30 (m, 2 H), 7.47 (s, 1 H), 7.53 (d, 2 H), 7.65 (s, 1 H), 8.61 (s, 2 H).

Example 66-40

1-[3-(2-methyl-2-propanyl)-1-(4-propylphenyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.67 (Hexane:Ethyl Acetate=1:3);
$^1$H-NMR (DMSO-$d_6$): δ 0.94 (t, 3 H), 1.36 (s, 9 H), 1.57-1.69 (m, 2 H), 1.86-2.07 (m, 4 H), 2.54-2.69 (m, 4 H), 4.17 (t, 2 H), 6.37 (s, 1 H), 6.53 (s, 1 H), 6.88 (br s, 1 H), 7.19 (d, 2 H), 7.24 (br s, 2 H), 7.35-7.41 (m, 2 H), 7.59 (d, 2 H), 7.65 (s, 1 H), 8.56 (s, 2 H).

Example 66-41

1-[1-(3-chloro-4-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.33 (Hexane:Ethyl Acetate=1:1);
$^1$H-NMR (DMSO-d$_6$): δ 1.26 (s, 9 H), 1.77-1.98 (m, 4 H), 2.36 (s, 3 H), 2.60 (t, 2 H), 4.06 (t, 2 H), 6.35 (s, 1 H), 7.20 (d, 2 H), 7.38-7.43 (m, 1H), 7.45-7.50 (m, 1H), 7.55-7.58 (m, 1H), 7.64 (d, 2 H), 7.90 (s, 1 H), 8.64 (s, 2 H), 8.66 (s, 1 H), 9.20 (s, 1 H).

Example 66-42

1-{3-(2-methyl-2-propanyl)-1-[4-(trifluoromethyl)phenyl]-1H-pyrazol-5-yl}-3-(2-{4-[2-(2-oxo-1-piperidinyl)-1,3-thiazol-5-yl]phenoxy}-5-pyrimidinyl)urea TCL: Rf 0.12 (Ethyl Acetate);
$^1$H-NMR (DMSO-d$_6$): δ 1.29 (s, 9 H), 1.83 (m, 2 H), 1.92 (m, 2H), 2.61 (t, 2 H), 4.67 (t, 2 H), 6.41 (s, 1 H), 7.19 (d, 2 H), 7.65 (d, 2 H), 7.77 (d, 2 H), 7.87 (d, 2 H), 7.90 (s, 1 H), 8.65 (s, 2 H), 8.79 (s, 1 H), 9.21 (s, 1 H).

Example 66-43

1-[1-(4-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.23 (Ethyl Acetate);
$^1$H-NMR (DMSO-d$_6$): δ 1.26 (s, 9 H), 1.83 (m, 2 H), 1.92 (m, 2H), 2.42 (s, 3 H), 2.61 (t, 2 H), 4.07 (t, 2 H), 6.33 (s, 1 H), 7.20 (dd, 2 H), 7.30 (d, 2 H), 7.37 (d, 2 H), 7.65 (dd, 2 H), 7.90 (s, 1 H), 8.56 (s, 1 H), 8.64 (s, 2 H), 9.18 (s, 1 H).

Example 66-44

1-[1-(3-methoxy-4-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.71 (Ethyl Acetate);
$^1$H-NMR (DMSO-d$_6$): δ 1.27 (s, 9 H), 1.85 (m, 2 H), 1.93 (m, 2H), 2.19 (s, 3 H), 2.61 (t, 2 H), 3.80 (s, 3 H), 4.07 (t, 2 H), 6.35 (s, 1 H), 6.97 (d, 1 H), 7.03 (s, 1 H) 7.20 (d, 2 H), 7.26 (d, 1 H), 7.65 (d, 2 H), 7.91 (s, 1 H), 8.55 (s, 1 H), 8.65 (s, 2 H), 9.24 (s, 1 H).

Example 66-45

1-[1-(3-methylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.63 (Ethyl Acetate);
$^1$H-NMR (DMSO-d$_6$): δ 1.27 (s, 9 H), 1.83 (m, 2 H), 1.93 (m, 2H), 2.37 (s, 3 H), 2.61 (t, 2 H), 4.07 (t, 2 H), 6.35 (s, 1 H), 7.20 (d, 3 H), 7.28 (m, 2 H) 7.39 (t, 1 H), 7.67 (d, 2 H), 7.91 (s, 1 H), 8.61 (s, 1 H), 8.65 (s, 2 H), 9.20 (s, 1 H).

Example 66-46

1-[1-(3,4-dihydro-2 H-chromen-6-yl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea

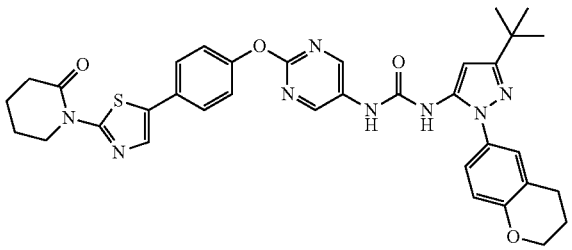 [SMILES: CC(C)(C)c1cc(NC(=O)Nc2cnc(Oc3ccc(-c4cnc(N5CCCCC5=O)s4)cc3)nc2)n(-c2ccc3c(c2)CCCO3)n1]

TCL: Rf 0.39 (Ethyl Acetate);
$^1$H-NMR (DMSO-d$_6$): δ 1.13 (s, 9 H), 1.71-1.85 (m, 6 H), 2.49 (t, 2 H), 2.65 (t, 2 H), 3.95 (t, 2 H), 4.05 (t, 2 H), 6.19 (s, 1H), 6.73 (d, 1 H), 7.04 (m, 2 H), 7.09 (d, 2 H) 7.54 (d, 2 H), 7.79 (s, 1 H), 8.39 (s, 1 H), 8.53 (s, 2 H), 9.06 (s, 1 H).

Example 66-47

1-{1-[4-(3-hydroxypropyl)phenyl]-3-(2-methyl-2-propanyl)-1H-pyrazol-5-yl}-3-(2-{4-[2-(2-oxo-1-piperidinyl)-1,3-thiazol-5-yl]phenoxy}-5-pyrimidinyl)urea TCL: Rf 0.50 (Ethyl Acetate);
$^1$H-NMR (DMSO-d$_6$): δ 1.27 (s, 9 H), 1.70-1.93 (m, 6 H), 2.59-2.72 (m, 4 H), 3.39 (q, 2 H), 4.07 (t, 2 H), 4.47 (t, 1 H), 6.35 (s, 1 H), 7.22 (m, 3 H), 7.32 (m, 2 H), 7.41 (t, 1 H), 7.65 (d, 2 H), 7.91 (s, 1 H), 8.61 (s, 1 H), 8.64 (s, 2 H), 9.21 (s, 1 H).

Example 66-48

1-[1-(3-methoxyphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.51 (Ethyl Acetate);
$^1$H-NMR (DMSO-d$_6$): δ 1.27 (s, 9 H), 1.83-1.94 (m, 4 H), 2.61 (t, 2 H), 3.79 (s, 3 H), 4.07 (t, 2 H), 6.36 (s, 1 H), 6.97 (dd, 1H), 7.08 (d, 2 H), 7.20 (d, 2 H), 7.41 (t, 1 H), 7.65 (d, 2 H), 7.91 (s, 1 H), 8.63 (s, 1 H), 8.65 (s, 2 H), 9.24 (s, 1 H).

Example 66-49

1-[1-(2,3-dihydro-1,4-benzodioxin-6-yl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea

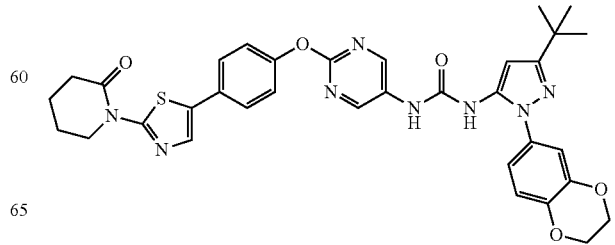

TCL: Rf 0.49 (Ethyl Acetate);

$^1$H-NMR (DMSO-d$_6$): δ 1.25 (s, 9 H), 1.80-2.00 (m, 4 H), 2.61 (t, 2 H), 4.14 (t, 2 H), 4.28 (s, 4 H), 6.31 (s, 1 H), 6.96 (m, 3H), 7.21 (d, 2 H), 7.63 (d, 2 H), 7.91 (s, 1 H), 8.61 (s, 1 H), 8.66 (s, 2 H), 9.19 (s, 1 H).

Example 66-50

1-[1-(2,5-dimethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.70 (Methylene Dichloride:Ethyl Acetate: Methanol=8:4:1);

$^1$H-NMR (DMSO-d$_6$): δ 1.27 (s, 9 H), 1.93 (s, 3 H), 2.10-2.23 (m, 2 H), 2.33 (s, 3 H), 2.64 (t, 2 H), 4.05 (t, 2 H), 6.33 (s, 1H), 7.12-7.30 (m, 5 H), 7.66 (d, 2 H), 7.88 (s, 1 H), 8.36 (s, 1 H), 8.63 (s, 2 H), 9.07 (s, 1 H).

Example 66-51

1-{1-[3-(2-hydroxyethyl)phenyl]-3-(2-methyl-2-propanyl)-1H-pyrazol-5-yl}-3-(2-{4-[2-(2-oxo-1-piperidinyl)-1,3-thiazol-5-yl]phenoxy}-5-pyrimidinyl)urea TCL: Rf 0.50 (Methylene Dichloride:Ethyl Acetate: Methanol=8:4:1);

$^1$H-NMR (DMSO-d$_6$): δ 1.27 (s, 9 H), 1.77-2.00 (m, 4 H), 2.61 (t, 2 H), 2.78 (t, 2 H), 3.55-3.68 (m, 2 H), 4.07 (t, 2 H), 4.65 (t, 1 H), 6.35 (s, 1 H), 7.17-7.27 (m, 3 H), 7.28-7.44 (m, 3H), 7.65 (d, 2 H), 7.91 (s, 1 H), 8.60 (s, 1 H), 8.64 (s, 2 H), 9.19 (s, 1 H).

Example 66-52

1-[1-(3,5-dimethyl-4-propoxyphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.80 (Methylene Dichloride:Ethyl Acetate: Methanol=8:4:1);

$^1$H-NMR (DMSO-d$_6$): δ 1.04 (t, 3 H), 1.25 (s, 9 H), 1.70-2.00 (m, 6 H), 2.26 (s, 6 H), 2.61 (t, 2 H), 3.73 (t, 2 H), 4.07 (t, 2H), 6.33 (s, 1 H), 7.13 (s, 2 H), 7.21 (d, 2 H), 7.65 (d, 2 H), 7.91 (s, 1 H), 8.57 (s, 1 H), 8.65 (s, 2 H), 9.17 (s, 1 H).

Example 66-53

1-[1-(3-isopropylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.78 (Methylene Dichloride:Ethyl Acetate: Methanol=8:4:1);

$^1$H-NMR (DMSO-d$_6$): δ 1.20 (d, 6 H), 1.27 (s, 9 H), 1.78-2.00 (m, 4 H), 2.61 (t, 2 H), 2.75-3.00 (m, 1 H), 4.07 (t, 2 H), 6.34 (s, 1 H), 7.20 (d, 2 H), 7.24-7.46 (m, 4 H), 7.65 (d, 2 H), 7.91 (s, 1 H), 8.59 (s, 1 H), 8.64 (s, 2 H), 9.20 (s, 1 H).

Example 66-54

1-[1-(2,3-dihydro-1-benzofuran-5-yl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea

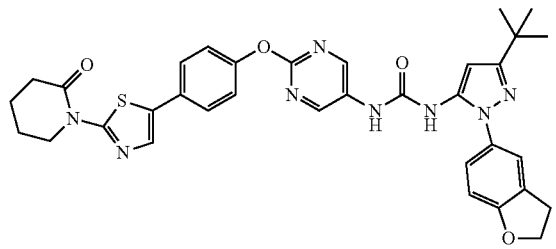 [SMILES: CC(C)(C)c1cc(NC(=O)Nc2cnc(Oc3ccc(-c4cnc(N5CCCCC5=O)s4)cc3)nc2)n(-c2ccc3c(c2)CCO3)n1]

TCL: Rf 0.65 (Methylene Dichloride:Ethyl Acetate: Methanol=8:4:1);

$^1$H-NMR (DMSO-d$_6$): δ 1.25 (s, 9 H), 1.78-2.00 (m, 4 H), 2.61 (t, 2 H), 3.23 (t, 2 H), 4.07 (t, 2 H), 4.59 (t, 2 H), 6.31 (s, 1H), 6.86 (d, 1 H), 7.13-7.26 (m, 3 H), 7.28-7.34 (m, 1 H), 7.65 (d, 2 H), 7.91 (s, 1 H), 8.50 (s, 1 H), 8.65 (s, 2 H), 9.17 (s, 1 H).

Example 66-55

1-[1-(2-chloro-6-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.22 (Methanol: Chloroform=1:19);

$^1$H-NMR (DMSO-d$_6$): δ 1.25 (s, 9 H), 1.97 (s, 3 H), 2.10-2.22 (m, 2 H), 2.64 (t, 2 H), 4.05 (t, 2 H), 6.36 (s, 1 H), 7.17-7.23 (m, 2 H), 7.38-7.56 (m, 3 H), 7.63-7.68 (m, 2 H), 7.88 (s, 1H), 8.45 (s, 1 H), 8.64 (s, 2 H), 8.93 (s, 1 H).

Example 66-56

1-[1-(3-fluoro-2-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.32 (Methanol: Chloroform=1:19);

$^1$H-NMR (DMSO-d$_6$): δ 1.26 (s, 9 H), 1.91 (d, 3 H), 2.11-2.21 (m, 2 H), 2.64 (t, 2 H), 4.05 (t, 2 H), 6.35 (s, 1 H), 7.17-7.24 (m, 3 H), 7.31-7.45 (m, 2 H), 7.63-7.69 (m, 2 H), 7.88 (s, 1H), 8.46 (s, 1 H), 8.63 (s, 2 H), 9.01 (s, 1 H).

Example 66-57

1-[1-(5-fluoro-2-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.40 (Methanol: Chloroform=1:19);

$^1$H-NMR (DMSO-d$_6$): δ 1.26 (s, 9 H), 1.96 (s, 3 H), 2.10-2.21 (m, 2 H), 2.64 (t, 2 H), 4.05 (t, 2 H), 6.34 (s, 1 H), 7.17-7.23 (m, 2 H), 7.26-7.34 (m, 2 H), 7.40-7.47 (m, 1 H), 7.63-7.68 (m, 2 H), 7.88 (s, 1 H), 8.47 (s, 1 H), 8.63 (s, 2 H), 9.03 (s, 1H).

Example 66-58

1-[1-(2-ethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.40 (Methanol: Chloroform=1:19);
$^1$H-NMR (DMSO-$d_6$): δ 1.00 (t, 3 H), 1.25 (s, 9 H), 2.11-2.22 (m, 2 H), 2.31 (q, 2 H), 2.64 (t, 2 H), 4.05 (t, 2 H), 6.34 (s, 1H), 7.18-7.23 (m, 2 H), 7.28-7.51 (m, 4 H), 7.62-7.68 (m, 2 H), 7.88 (s, 1 H), 8.36 (s, 1 H), 8.62 (s, 2 H), 9.07 (s, 1 H).

Example 66-59

1-[1-(2-methylphenyl)-3-(2-methyl-2-propanyl)-1H-pyrazol-5-yl]-3-(2-{4-[2-(2-oxo-1-azepanyl)-1,3-thiazol-5-yl]phenoxy}-5-pyrimidinyl)urea TCL: Rf 0.79 (Ethyl Acetate);
$^1$H-NMR (DMSO-$d_6$): δ 1.26 (s, 9 H), 1.73 (m, 6 H), 1.99 (s, 3H), 2.83 (m, 2 H), 4.45 (t, 2 H), 6.34 (s, 1 H), 7.20 (d, 2 H), 7.28-7.41 (m, 4 H), 7.64 (d, 2 H), 7.86 (s, 1 H) 8.38 (s, 1 H), 8.63 (s, 2 H), 9.06 (s, 1 H).

Example 66-60

1-[1-(2-chlorophenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.29 (Hexane:Ethyl Acetate=1:4);
$^1$H-NMR (DMSO-$d_6$): δ 1.25 (s, 9 H), 1.78-1.98 (m, 4 H), 2.60 (t, 2 H), 4.06 (t, 2 H), 6.35 (s, 1 H), 7.20 (d, 2 H), 7.51-7.72 (m, 6 H), 7.90 (s, 1 H), 8.51 (s, 1 H), 8.63 (s, 2 H), 8.99 (s, 1 H).

Example 66-61

1-{3-(2-methyl-2-propanyl)-1-[3-(trifluoromethyl)phenyl]-1H-pyrazol-5-yl}-3-(2-{4-[2-(2-oxo-1-piperidinyl)-1,3-thiazol-5-yl]phenoxy}-5-pyrimidinyl)urea TCL: Rf 0.38 (Hexane:Ethyl Acetate=1:2);
$^1$H-NMR (DMSO-$d_6$): δ 1.28 (s, 9 H), 1.77-1.98 (m, 4 H), 2.60 (t, 2 H), 4.06 (t, 2 H), 6.38 (s, 1 H), 7.20 (d, 2 H), 7.65 (d, 2H), 7.70-7.76 (m, 2 H), 7.82-7.89 (m, 2 H), 7.90 (s, 1 H), 8.61 (s, 2 H), 8.74 (s, 1 H), 9.22 (s, 1 H).

Example 66-62

1-[1-(3-ethylphenyl)-3-(2-methyl-2-propanyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.39 (Hexane:Ethyl Acetate=1:2);
$^1$H-NMR (DMSO-$d_6$): δ 1.18 (t, 3 H), 1.26 (s, 9 H), 1.77-1.98 (m, 4 H), 2.56-2.72 (m, 4 H), 4.06 (t, 2 H), 6.34 (s, 1 H), 7.17-7.45 (m, 6 H), 7.64 (d, 2 H), 7.90 (s, 1 H), 8.59 (s, 1 H), 8.63 (s, 2 H), 9.19 (s, 1 H).

Example 66-63

1-[1-(2-chloro-4-fluorophenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.65 (Methylene Dichloride:Ethyl Acetate: Methanol=8:4:1);
$^1$H-NMR (DMSO-$d_6$): δ 1.25 (s, 9 H), 2.10-2.23 (m, 2 H), 2.64 (t, 2 H), 4.05 (t, 2H), 6.35 (s, 1 H), 7.21 (d, 2 H), 7.37-7.47 (m, 1 H), 7.60-7.70 (m, 3 H), 7.71-7.78 (m, 1 H), 7.89 (s, 1H), 8.55 (s, 1 H), 8.65 (s, 2 H), 8.93 (s, 1 H).

Example 66-64

1-[1-(4-chloro-2-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.61 (Methylene Dichloride:Ethyl Acetate: Methanol=8:4:1);
$^1$H-NMR (DMSO-$d_6$): δ 1.25 (s, 9 H), 1.99 (s, 3 H), 2.16 (t, 2H), 2.64 (t, 2 H), 4.05 (t, 2 H), 6.34 (s, 1 H), 7.21 (d, 2 H), 7.33-7.45 (m, 2 H), 7.50-7.56 (m, 1 H), 7.66 (d, 2 H), 7.89 (s, 1 H), 8.44 (s, 1 H), 8.63 (s, 2 H), 9.00 (s, 1 H).

Example 66-65

1-[1-(3-methoxy-2,4-dimethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.59 (Methylene Dichloride:Ethyl Acetate: Methanol=8:4:1);
$^1$H-NMR (DMSO-$d_6$): δ 1.25 (s, 9 H), 1.85 (s, 3 H), 2.10-2.23 (m, 2 H), 2.31 (s, 3 H), 2.64 (t, 2 H), 3.71 (s, 3 H), 4.05 (t, 2H), 6.33 (s, 1 H), 7.02 (d, 1 H), 7.15-7.26 (m, 3 H), 7.66 (d, 2 H), 7.89 (s, 1 H), 8.34 (s, 1 H), 8.63 (s, 2 H), 9.06 (s, 1H).

Example 66-66

1-[1-(2-methoxyphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.53 (Methylene Dichloride:Ethyl Acetate: Methanol=8:4:1);
$^1$H-NMR (DMSO-$d_6$): δ 1.25 (s, 9 H), 2.10-2.24 (m, 2 H), 2.64 (t, 2 H), 3.79 (s, 3 H), 4.05 (t, 2 H), 6.32 (s, 1 H), 7.09 (td, 1H), 7.20 (d, 2 H), 7.26 (d, 1 H), 7.32 (dd, 1 H), 7.49 (td, 1H), 7.66 (d, 2 H), 7.88 (s, 1 H), 8.17 (s, 1 H), 8.64 (s, 2 H), 9.23 (s, 1 H).

Example 66-67

1-[1-(2-fluoro-5-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.61 (Methylene Dichloride:Ethyl Acetate: Methanol=8:4:1);
$^1$H-NMR (DMSO-$d_6$): δ 1.25 (s, 9 H), 2.10-2.23 (m, 2 H), 2.35 (s, 3 H), 2.64 (t, 2 H), 4.05 (t, 2 H), 6.35 (s, 1 H), 7.20 (d, 2H), 7.31-7.37 (m, 3 H), 7.66 (d, 2 H), 7.88 (s, 1 H), 8.59 (s, 1 H), 8.64 (s, 2 H), 9.04 (s, 1 H).

Example 66-68

1-[1-(2-chloro-5-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.60 (Methylene Dichloride:Ethyl Acetate: Methanol=8:4:1);
$^1$H-NMR (DMSO-$d_6$): δ 1.25 (s, 9 H), 2.10-2.23 (m, 2 H), 2.37 (s, 3 H), 2.64 (t, 2 H), 4.05 (t, 2 H), 6.34 (s, 1 H), 7.21 (d, 2H), 7.35-7.43 (m, 2 H), 7.54-7.60 (m, 1 H), 7.66 (d, 2 H), 7.89 (s, 1 H), 8.49 (s, 1 H), 8.65 (s, 2 H), 9.00 (s, 1 H).

Example 66-69

1-[1-(2-fluoro-4-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.60 (Methylene Dichloride:Ethyl Acetate:Methanol=8:4:1);
$^1$H-NMR (DMSO-$d_6$): δ 1.25 (s, 9 H), 2.10-2.23 (m, 2 H), 2.40 (s, 3 H), 2.64 (t, 2 H), 4.05 (t, 2 H), 6.35 (s, 1 H), 7.15-7.25 (m, 3 H), 7.25-7.35 (m, 1 H), 7.39 (t, 1 H), 7.66 (d, 2 H), 7.89 (s, 1 H), 8.56 (s, 1 H), 8.65 (s, 2 H), 9.05 (s, 1 H).

Example 66-70

1-[1-(3-fluoro-2,4-dimethylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.62 (Methylene Dichloride:Ethyl Acetate:Methanol=8:4:1);
$^1$H-NMR (DMSO-$d_6$): δ 1.25 (s, 9 H), 1.87 (d, 3 H), 2.10-2.23 (m, 2 H), 2.30 (d, 3 H), 2.64 (t, 2 H), 4.05 (t, 2 H), 6.34 (s, 1H), 7.10 (d, 1 H), 7.20 (d, 2 H), 7.27 (t, 1 H), 7.66 (d, 2 H), 7.88 (s, 1 H), 8.40 (s, 1 H), 8.63 (s, 2 H), 9.01 (s, 1 H).

Example 66-71

1-[1-(2-chloro-4-methylphenyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.61 (Methylene Dichloride:Ethyl Acetate:Methanol=8:4:1);
$^1$H-NMR (DMSO-$d_6$): δ 1.25 (s, 9 H), 2.10-2.23 (m, 2 H), 2.40 (s, 3 H), 2.64 (t, 2 H), 4.05 (t, 2 H), 6.33 (s, 1 H), 7.20 (d, 2H), 7.30-7.36 (m, 1 H), 7.42 (d, 1 H), 7.53 (s, 1 H), 7.66 (d, 2 H), 7.89 (s, 1 H), 8.46 (s, 1 H), 8.64 (s, 2 H), 9.01 (s, 1H).

Example 66-72

4-[3-(2-methyl-2-propanyl)-5-{[(2-{4-[2-(2-oxo-1-pyrrolidinyl)-1,3-thiazol-5-yl]phenoxy}-5-pyrimidinyl)carbamoyl]amino}-1H-pyrazol-1-yl]benzenesulfonamide

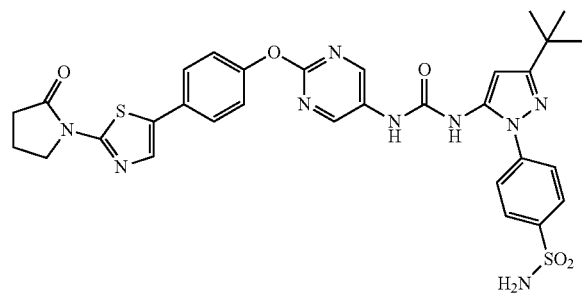 [SMILES: CC(C)(C)c1cc(NC(=O)Nc2cnc(Oc3ccc(-c4cnc(N5CCCC5=O)s4)cc3)nc2)n(-c2ccc(S(N)(=O)=O)cc2)n1]

TCL: Rf 0.48 (Methylene Dichloride:Ethyl Acetate:Methanol=8:4:1);
$^1$H-NMR (DMSO-$d_6$): δ 1.28 (s, 9 H), 2.10-2.23 (m, 2 H), 2.64 (t, 2 H), 4.05 (t, 2 H), 6.40 (s, 1 H), 7.21 (d, 2 H), 7.45 (s, 2H), 7.67 (d, 2 H), 7.73 (d, 2 H), 7.88-7.96 (m, 3 H), 8.66 (s, 2 H), 8.79 (s, 1 H), 9.23 (s, 1 H).

Examples 67-1 and -2

The similar procedures as Example 62→Example 63→Example 12→Example 13→Example 9→Example 20→Example 21 were carried out with (2-methylphenyl)hydrazine hydrochloride in place of (3,4-dimethylphenyl)hydrazine hydrochloride; 2-chloro-5-nitropyridine or 2-chloro-3-methyl-5-nitropyridine in place of 2-chloro-5-nitropyrimidine; and 1-(5-bromothiazol-2-yl)pyrrolidin-2-one in place of the compound prepared in Example 18 to give the present compounds having the following physical data.

Example 67-1

1-[1-(2-methylphenyl)-3-(2-methyl-2-propanyl)-1H-pyrazol-5-yl]-3-(6-{4-[2-(2-oxo-1-pyrrolidinyl)-1,3-thiazol-5-yl]phenoxy}-3-pyridinyl)urea TCL: Rf 0.49 (Ethyl Acetate);
$^1$H-NMR (DMSO-$d_6$): δ 1.25 (s, 9 H), 1.99 (s, 3 H), 2.16 (m, 2H), 2.63 (t, 2 H), 4.04 (t, 2 H), 6.33 (s, 1 H), 7.01 (d, 1 H), 7.11 (d, 2 H), 7.31-7.44 (m, 4 H), 7.63 (d, 2 H), 7.86 (s, 1H), 7.95 (dd, 1 H), 8.09 (d, 1 H), 8.23 (s, 1 H), 9.00 (s, 1H).

Example 67-2

1-(5-methyl-6-{4-[2-(2-oxo-1-pyrrolidinyl)-1,3-thiazol-5-yl]phenoxy}-3-pyridinyl)-3-[1-(2-methylphenyl)-3-(2-methyl-2-propanyl)-1H-pyrazol-5-yl]urea TCL: Rf 0.53 (Ethyl Acetate);
$^1$H-NMR (DMSO-$d_6$): δ 1.25 (s, 9 H), 1.99 (s, 3 H), 2.16 (m, 2H), 2.25 (s, 3 H), 2.63 (t, 2 H), 4.04 (t, 2 H), 6.34 (s, 1 H), 7.06 (d, 2 H), 7.31-7.44 (m, 4 H), 7.61 (d, 2 H), 7.84 (s, 1H), 7.86 (s, 1 H), 7.88 (s, 1 H), 8.22 (s, 1 H), 8.94 (s, 1 H).

Example 68

3-(tert-butyl)-1-(1-methyl-1H-indol-5-yl)-1H-pyrazol-5-amine

To a mixed solvent of dimethylformamide (8 mL) and pyridine (0.47 mL) were added 3-amino-5-tert-butylpyrazole (810 mg), N-methylindol-5-boronic acid (780 mg), copper (II) acetate (790 mg) and molecular sieves (400 mg). The reaction mixture was stirred overnight at room temperature. The reaction mixture was added with 10% aqueous ammonia and filtered through Celite®. The filtrate was added with ethyl acetate and separated. The obtained organic layer was washed with a saturated sodium chloride aqueous solution and dried over anhydrous sodium sulfate. The obtained residue was purified on silica gel column chromatography (hexane:ethyl acetate=7:3→1:1→1:4) to give the titled compound (577 mg) having the following physical data.
TCL: Rf 0.29 (Hexane:Ethyl Acetate=2:1).

Example 69

2,2,2-trichloroethyl (3-(tert-butyl)-(1-(1-methyl-1H-indol-5-yl)-1H-pyrazol-5-yl)carbamate The similar procedure as Example 8 was carried out with the compound prepared in Example 68 in place of the compound prepared in Example 7 to give the titled compound having the following physical data.
TCL: Rf 0.43 (Hexane:Ethyl Acetate=2:1).

Example 70

1-[1-(1-methyl-1H-indol-5-yl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea The similar procedures as Example 19→Example 20→Example 21 were carried out with the compound prepared in Example 69 in place of the compound prepared in Example 16 and 1-(5-bromothiazol-2-yl)pyrrolidin-2-one in place of the compound prepared in Example 18 to give the present compound having the following physical data.

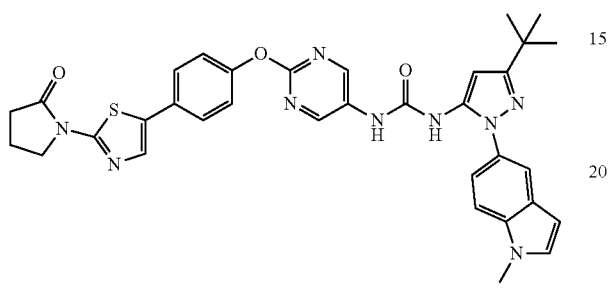

TCL: Rf 0.50 (Methylene Dichloride:Ethyl Acetate:Methanol=8:4:1);
$^1$H-NMR (DMSO-d$_6$): δ 1.27 (s, 9 H), 2.12-2.23 (m, 2 H), 2.64 (t, 2 H), 3.83 (s, 3 H), 4.05 (t, 2 H), 6.34 (s, 1 H), 6.52 (d, 1H), 7.17-7.24 (m, 3 H), 7.44 (d, 1 H), 7.56 (d, 1 H), 7.61 (d, 1 H), 7.66 (d, 2 H), 7.89 (s, 1 H), 8.47 (s, 1 H), 8.63 (s, 2H), 9.18 (s, 1 H).

Example 71

1-[1-(1-methyl-1H-indazol-5-yl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea The similar procedures as Example 68→Example 69→Example 19→Example 20→Example 21 were carried out with (1-methyl-1 H-indazol-5-yl)boronic acid in place of (1-methyl-1 H-indol-5-yl)boronic acid and 1-(5-bromothiazol-2-yl)pyrrolidin-2-one in place of the compound prepared in Example 18 to give the present compound having the following physical data.

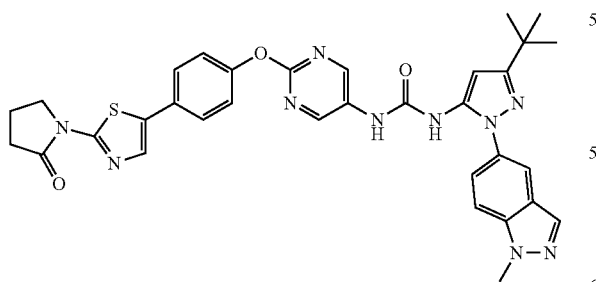

TCL: Rf 0.41 (Ethyl Acetate:Methanol=19:1);
$^1$H-NMR (DMSO-d$_6$): δ 9.14 (s, 1 H), 8.63 (s, 2 H), 8.57 (s, 1H), 8.14 (d, 1 H), 7.89 (s, 1 H), 7.86 (d, 1 H), 7.78 (d, 1 H), 7.62-7.70 (m, 2 H), 7.49 (dd, 1 H), 7.16-7.25 (m, 2 H), 6.37 (s, 1 H), 4.10 (s, 3 H), 4.01-4.09 (m, 2 H), 2.60-2.69 (m, 2 H), 2.10-2.24 (m, 2 H), 1.29 (s, 9 H).

Example 72

The similar procedures as Example 62→Example 63→Example 19→Example 20→Example 21 were carried out with corresponding nitrile derivatives in place of pivaloylacetonitrile; (3,4-dimethylphenyl)hydrazine hydrochloride or corresponding hydrazine derivatives in place of (3,4-dimethylphenyl)hydrazine hydrochloride; and corresponding 5-bromothiazole derivatives in place of the compound prepared in Example 18 to give the present compounds having the following physical data.

Example 72-1

1-[1-(2-methylphenyl)-3-(trifluoromethyl)-1H-pyrazol-5-yl]-3-(2-{4-[2-(2-oxo-1-pyrrolidinyl)-1,3-thiazol-5-yl]phenoxy}-5-pyrimidinyl)urea

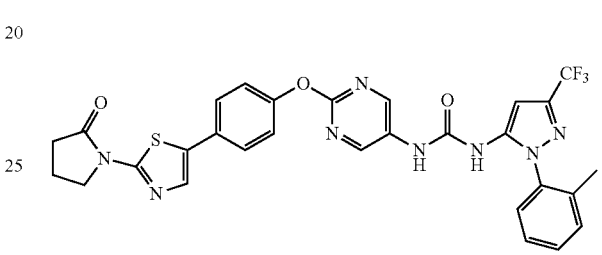

TCL: Rf 0.53 (Methylene Dichloride:Ethyl Acetate:Methanol=8:4:1);
$^1$H-NMR (DMSO-d$_6$): δ 2.01 (s, 3 H), 2.10-2.24 (m, 2 H), 2.64 (t, 2 H), 4.04 (t, 2 H), 6.85 (s, 1 H), 7.21 (d, 2 H), 7.40-7.57 (m, 4 H), 7.66 (d, 2 H), 7.89 (s, 1 H), 8.63 (s, 2 H), 8.82 (s, 1 H), 9.13 (s, 1 H).

Example 72-2

1-[1-(3,4-dimethylphenyl)-3-(trifluoromethyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.54 (Methylene Dichloride:Ethyl Acetate:Methanol=8:4:1);
$^1$H-NMR (DMSO-d$_6$): δ 2.10-2.24 (m, 2 H), 2.30 (s, 6 H), 2.64 (t, 2 H), 4.05 (t, 2 H), 6.85 (s, 1 H), 7.21 (d, 2 H), 7.25-7.40 (m, 3 H), 7.67 (d, 2 H), 7.89 (s, 1 H), 8.65 (s, 2 H), 8.91 (s, 1 H), 9.27 (s, 1 H).

Example 72-3

1-[3-(1,1-difluoroethyl)-1-(2-methylphenyl)-1H-pyrazol-5-yl]-3-(2-{4-[2-(2-oxo-1-pyrrolidinyl)-1,3-thiazol-5-yl]phenoxy}-5-pyrimidinyl)urea

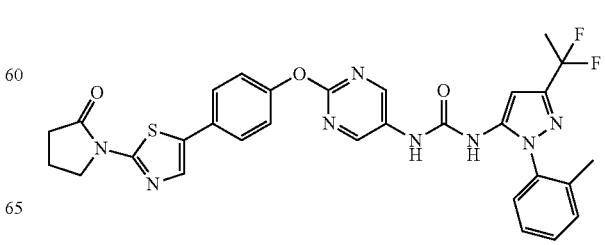

TCL: Rf 0.51 (Methylene Dichloride:Ethyl Acetate: Methanol=8:4:1);
$^1$H-NMR (DMSO-$d_6$): δ 1.97 (t, 3 H), 2.00 (s, 3 H), 2.10-2.24 (m, 2 H), 2.63 (t, 2 H), 4.04 (t, 2 H), 6.64 (s, 1 H), 7.20 (d, 2H), 7.36-7.54 (m, 4 H), 7.65 (d, 2 H), 7.88 (s, 1 H), 8.62 (s, 2 H), 8.65 (s, 1 H), 9.09 (s, 1 H).

Example 72-4

1-[1-(4-fluorophenyl)-3-(trifluoromethyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.59 (Methylene Dichloride:Ethyl Acetate: Methanol=8:4:1);
$^1$H-NMR (DMSO-$d_6$): δ 2.10-2.24 (m, 2 H), 2.64 (t, 2 H), 4.05 (t, 2 H), 6.88 (s, 1 H), 7.21 (d, 2 H), 7.45 (t, 2 H), 7.60-7.72 (m, 4 H), 7.89 (s, 1 H), 8.65 (s, 2 H), 8.97 (s, 1 H), 9.24 (s, 1 H).

Example 72-5

1-[1-(2-methylphenyl)-3-(trifluoromethyl)-1H-pyrazol-5-yl]-3-(2-{4-[2-(2-oxo-1-piperidinyl)-1,3-thiazol-5-yl]phenoxy})-5-pyrimidinyl)urea TCL: Rf 0.34 (Hexane:Ethyl Acetate=1:4);
$^1$H-NMR (DMSO-$d_6$): δ 1.83-1.99 (m, 4 H), 2.01 (s, 3 H), 2.61 (t, 2 H), 4.07 (t, 2 H), 6.85 (s, 1 H), 7.21 (d, 2 H), 7.43-7.64 (m, 4 H), 7.66 (d, 2 H), 7.91 (s, 1 H), 8.64 (s, 2 H), 8.21 (s, 1 H), 9.13 (s, 1 H).

Example 72-6

1-[3-(1,1-difluoroethyl)-1-(2-methylphenyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.34 (Hexane:Ethyl Acetate=1:4);
$^1$H-NMR (DMSO-$d_6$): δ 1.83-2.04 (m, 10 H), 2.61 (t, 2 H), 4.07 (t, 2 H), 6.65 (s, 1 H), 7.21 (d, 2 H), 7.30-7.50 (m, 4 H), 7.65 (d, 2 H), 7.91 (s, 1 H), 8.63 (s, 2 H), 8.66 (s, 1 H), 9.11 (s, 1 H).

Example 72-7

1-(3-cyclopropyl-1-phenyl-1H-pyrazol-5-yl)-3-(2-{4-[2-(2-oxo-1-pyrrolidinyl)-1,3-thiazol-5-yl]phenoxy}-5-pyrimidinyl)urea

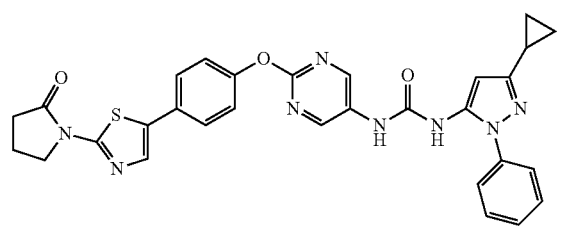 [SMILES: O=C(Nc1cnc(Oc2ccc(-c3cnc(N4CCCC4=O)s3)cc2)nc1)Nc1cc(C2CC2)nn1-c1ccccc1]

TCL: Rf 0.56 (Methylene Dichloride:Ethyl Acetate: Methanol=8:4:1);
$^1$H-NMR (DMSO-$d_6$): δ 0.65-0.75 (m, 2 H), 0.85-0.95 (m, 2 H), 1.80-1.95 (m, 1 H), 2.10-2.25 (m, 2 H), 2.64 (t, 2 H), 4.05 (t, 2 H), 6.16 (s, 1 H), 7.20 (d, 2 H), 7.34-7.44 (m, 1 H), 7.45-7.55 (m, 4 H), 7.66 (d, 2 H), 7.89 (s, 1 H), 8.60-8.70 (m, 3H), 9.15 (s, 1 H).

Example 73

The similar procedures as Example 62→Example 63→Example 19→Example 20→Example 21 were carried out with corresponding hydrazine derivatives in place of (3,4-dimethylphenyl)hydrazine hydrochloride and corresponding 5-bromothiazole derivatives in place of the compound prepared in Example 18 to give the present compounds having the following physical data.

Example 73-1

1-[1-(6-methoxy-3-pyridinyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea

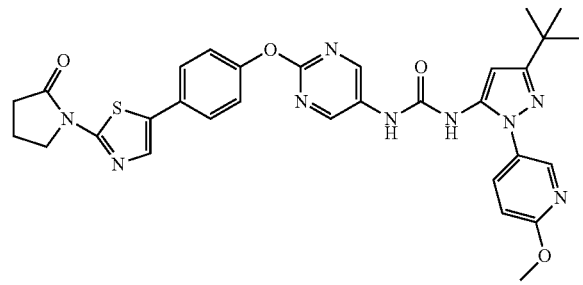 [SMILES: COc1ccc(-n2nc(C(C)(C)C)cc2NC(=O)Nc2cnc(Oc3ccc(-c4cnc(N5CCCC5=O)s4)cc3)nc2)cn1]

TCL: Rf 0.50 (Methylene Dichloride:Ethyl Acetate: Methanol=8:4:1);
$^1$H-NMR (DMSO-$d_6$): δ 1.26 (s, 9 H), 2.10-2.23 (m, 2 H), 2.64 (t, 2 H), 3.90 (s, 3 H), 4.05 (t, 2 H), 6.36 (s, 1 H), 6.97 (d, 1H), 7.21 (d, 2 H), 7.66 (d, 2 H), 7.82 (dd, 1 H), 7.89 (s, 1H), 8.29 (d, 1 H), 8.65 (s, 3 H), 9.14 (s, 1 H).

Example 73-2

1-[3-(2-methyl-2-propanyl)-1-(6-methyl-3-pyridinyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.34 (Methylene Dichloride:Ethyl Acetate: Methanol=8:4:1);
$^1$H-NMR (DMSO-$d_6$): δ 1.27 (s, 9 H), 2.10-2.23 (m, 2 H), 2.50 (s, 3 H), 2.64 (t, 2 H), 4.05 (t, 2 H), 6.37 (s, 1 H), 7.21 (d, 2H), 7.40 (d, 1 H), 7.66 (d, 2 H), 7.81 (dd, 1 H), 7.89 (s, 1H), 8.58 (d, 1 H), 8.64 (s, 2 H), 8.70 (s, 1 H), 9.18 (s, 1 H).

Example 73-3

1-[3-(2-methyl-2-propanyl)-1-(3-pyridinyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.46 (Methylene Dichloride:Ethyl Acetate: Methanol=8:4:1);
$^1$H-NMR (DMSO-$d_6$): δ 1.28 (s, 9 H), 2.10-2.23 (m, 2 H), 2.64 (t, 2 H), 4.05 (t, 2 H), 6.40 (s, 1 H), 7.21 (d, 2 H), 7.56 (dd, 1H), 7.66 (d, 2 H), 7.89 (s, 1 H), 7.92-8.00 (m, 1 H), 8.57 (d, 1 H), 8.64 (s, 2 H), 8.74-8.82 (m, 2 H), 9.22 (s, 1 H).

Example 73-4

1-[1-(6-isopropoxy-3-pyridinyl)-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea TCL: Rf 0.40 (Ethyl Acetate);
$^1$H-NMR (DMSO-$d_6$): δ 1.32-1.29 (m, 15 H), 2.16 (q, 2 H), 2.63 (t, 2 H), 4.05 (t, 2 H), 5.26 (m, 1 H), 6.35 (s, 1 H), 6.87 (d, 1 H), 7.20 (d, 2 H), 7.66 (d, 2 H), 7.78 (dd, 1 H), 7.88 (s, 1H), 8.25 (d, 1 H), 8.64 (m, 3 H), 9.13 (s, 1 H).

Example 73-5

1-[3-(2-methyl-2-propanyl)-1-(6-methyl-3-pyridinyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.63 (Ethyl Acetate:Methanol=19:1);
$^1$H-NMR (CD$_3$OD): δ 1.35 (s, 9 H), 1.86-2.11 (m, 4 H), 2.60 (s, 3 H), 2.69 (t, 2 H), 4.16 (t, 2 H), 6.42 (s, 1 H), 7.20 (d, 2H), 7.46 (d, 1 H), 7.65 (d, 2 H), 7.75 (s, 1 H), 7.89 (dd, 1H), 8.60 (d, 1 H), 8.62 (s, 2 H).

Example 73-6

1-[3-(2-methyl-2-propanyl)-1-(3-pyridinyl)-1H-pyrazol-5-yl]-3-(2-{4-[2-(2-oxo-1-piperidinyl)-1,3-thiazol-5-yl]phenoxy}-5-pyrimidinyl)urea TCL: Rf 0.21 (Ethyl Acetate);
$^1$H-NMR (DMSO-$d_6$): δ 1.28 (s, 9 H), 1.83 (m, 2 H), 1.93 (m, 2H), 2.61 (t, 2 H), 4.07 (t, 2 H), 6.40 (s, 1 H), 7.20 (dd, 2H), 7.55 (dd, 1 H) 7.64 (dd, 2 H), 7.90 (s, 1 H), 7.94 (m, 1H), 8.56 (dd, 1 H), 8.64 (s, 2 H), 8.75 (d, 1 H), 8.78 (s, 1H), 9.21 (s, 1 H).

Example 74

1-(2-{4-[2-(2-oxo-1-pyrrolidinyl)-1,3-thiazol-5-yl]phenoxy}-5-pyrimidinyl)-3-[2-(4-pyridinyl)-5-(trifluoromethyl)phenyl]urea The similar procedures as Example 8→Example 19→Example 20→Example 21 were carried out with 2-(pyridin-4-yl)-5-(trifluoromethyl)aniline in place of the compound prepared in Example 7 and 1-(5-bromothiazol-2-yl)pyrrolidin-2-one in place of the compound prepared in Example 18 to give the present compound having the following physical data.
TCL: Rf 0.27 (Methylene Dichloride:Ethyl Acetate:Methanol=8:4:1);
$^1$H-NMR (DMSO-$d_6$): δ 2.10-2.23 (m, 2 H), 2.64 (t, 2 H), 4.05 (t, 2 H), 7.21 (d, 2 H), 7.46-7.56 (m, 4 H), 7.67 (d, 2 H), 7.89 (s, 1 H), 8.23 (s, 1 H), 8.38 (s, 1 H), 8.64 (s, 2 H), 8.72 (d, 2 H), 9.25 (s, 1 H).

Example 75

1-(2-{4-[2-(ethylamino)-1,3-thiazol-5-yl]phenoxy}-5-pyrimidinyl)-3-[2-(6-methyl-3-pyridinyl)-5-(trifluoromethyl)phenyl]urea The similar procedures as Example 6→Example 5→Example 8→Example 19→Example 20→Example 21 were carried out with 2-bromo-5-(trifluoromethyl)aniline in place of 2-chloro-3-nitro-5-(trifluoromethyl)pyridine; 6-methylpyridin-3-boronic acid in place of (6-(trifluoromethyl)pyridin-3-yl)boronic acid; and tert-butyl(5-bromothiazol-2-yl)(ethyl)carbamate in place of the compound prepared in Example 18 to give the present compound having the following physical data.

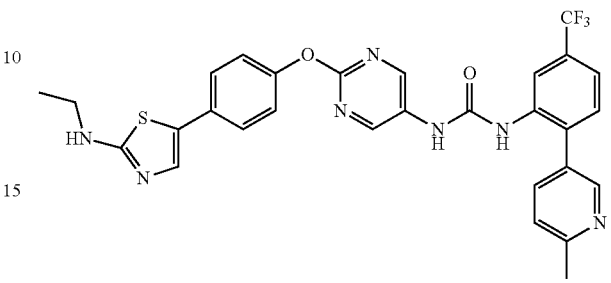

TCL: Rf 0.66 (Ethyl Acetate:Methanol=19:1);
$^1$H-NMR (DMSO-$d_6$): δ 1.16 (t, 3 H), 2.55 (s, 3 H), 3.25 (m, 2H), 7.12 (d, 2 H), 7.40-7.50 (m, 6 H), 7.71-7.77 (m, 2 H), 8.17 (s, 1 H), 8.40 (s, 1 H), 8.49 (s, 1 H), 8.63 (s, 2 H), 9.24 (s, 1 H).

Example 76

1-[2-(3,4-dimethylphenyl)-5-methyl-3-pyridinyl]-3-(2-{4-[2-(ethylamino)-1,3-thiazol-5-yl]phenoxy}-5-pyrimidinyl)urea The similar procedures as Example 6→Example 5→Example 8→Example 19-9 Example 20→Example 21 were carried out with 2-bromo-5-methyl-3-nitropyridine in place of 2-chloro-3-nitro-5-(trifluoromethyl)pyridine; 3,4-dimethylphenylboronic acid in place of (6-(trifluoromethyl)pyridin-3-yl)boronic acid; and tert-butyl(5-bromothiazol-2-yl)(ethyl)carbamate in place of the compound prepared in Example 18 to give the present compound having the following physical data.

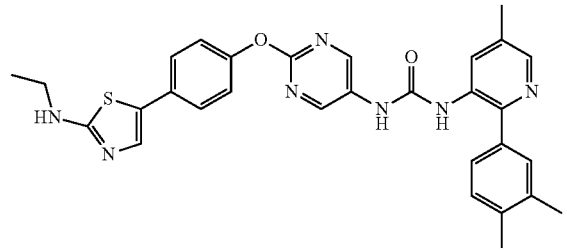 [SMILES: CCNc1ncc(-c2ccc(Oc3ncc(NC(=O)Nc4cc(C)cnc4-c4ccc(C)c(C)c4)cn3)cc2)s1]

TCL: Rf 0.52 (Ethyl Acetate);
$^1$H-NMR (DMSO-$d_6$): δ 1.16 (t, 3 H), 2.24 (s, 6 H), 2.32 (s, 3H), 3.26 (m, 2 H), 7.12 (d, 2 H), 7.25 (s, 2 H), 7.33 (s, 1 H), 7.42 (s, 1 H), 7.43 (d, 2 H), 7.71 (t, 1 H), 8.01 (s, 1 H), 8.13 (s, 1 H), 8.17 (s, 1 H), 8.64 (s, 2 H), 9.30 (s, 1 H).

Example 77

1-[2-(3,4-dimethylphenyl)-3-pyridinyl]-3-(2-{4-[2-(ethylamino)-1,3-thiazol-5-yl]phenoxy}-5-pyrimidinyl)urea The similar procedures as Example 6→Example 5→Example 8→Example 19→Example 20→Example 21 were carried out with 2-bromo-3-nitropyridine in place of 2-chloro-3-nitro-5-(trifluoromethyl)pyridine; 3,4-dimethylphenylboronic acid in place of (6-(trifluoromethyl)pyridin-3-yl)boronic acid; and tert-butyl(5-bromothiazol-2-yl)(ethyl)carbamate in place of the compound prepared in Example 18 to give the present compound having the following physical data.

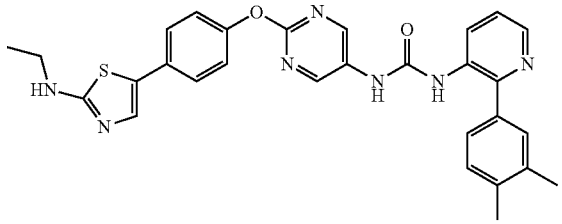 [SMILES: CCNc1ncc(-c2ccc(Oc3ncc(NC(=O)Nc4cccnc4-c4ccc(C)c(C)c4)cn3)cc2)s1]

TCL: Rf 0.55 (Ethyl Acetate);
¹H-NMR (DMSO-d₆): δ 1.16 (t, 3 H), 2.29 (s, 6 H), 3.24-3.32 (m, 2 H), 7.12 (d, 2 H), 7.27-7.34 (m, 4 H), 7.42 (s, 1 H), 7.44 (d, 2 H), 7.71 (t, 1 H), 8.06 (s, 1 H), 8.27 (dd, 1 H), 8.33 (dd, 1 H), 8.64 (s, 2 H), 9.31 (s, 1 H).

Example 78

1-[2-(4-morpholinyl)-5-(trifluoromethyl)phenyl]-3-(2-{4-[2-(2-oxo-1-piperidinyl)-1,3-thiazol-5-yl]phenoxy}-5-pyrimidinyl)urea The similar procedures as Example 8→Example 9 were carried out with 3-amino-4-(4-morpholino)benzotrifluoride in place of the compound prepared in Example 7 to give the present compound having the following physical data.
TCL: Rf 0.31 (Hexane:Ethyl Acetate=1:4);
¹H-NMR (DMSO-d₆): δ 1.75-2.00 (m, 4 H), 2.61 (t, 2 H), 3.80-3.90 (m, 4 H), 4.80-4.90 (m, 4 H), 4.07 (t, 2 H), 7.23 (d, 2 H), 7.24-7.36 (m, 2 H), 7.66 (d, 2 H), 7.91 (s, 1 H), 8.34 (s, 1H), 8.42 (s, 1 H), 8.73 (s, 2 H), 9.86 (s, 1 H).

Example 79

1-[2-(4-methyl-1-piperazinyl)-5-(trifluoromethyl)phenyl]-3-(2-{4-[2-(2-oxo-1-piperidinyl)-1,3-thiazol-5-yl]phenoxy}-5-pyrimidinyl)urea The similar procedures as Example 8→Example 9 were carried out with 2-(4-methylpiperazin-1-yl)-5-(trifluoromethyl)aniline in place of the compound prepared in Example 7 to give the present compound having the following physical data.
TCL: Rf 0.68 (Ethyl Acetate:Methanol:aqueous ammonia=9:1:0.5);
¹H-NMR (DMSO-d₆): δ 1.80-1.99 (m, 4 H), 2.28 (s, 3 H), 2.55-2.70 (m, 6 H), 3.80-3.90 (m, 4 H), 4.07 (t, 2 H), 7.23 (d, 2H), 7.30-7.40 (m, 2 H), 7.66 (d, 2 H), 7.91 (s, 1 H), 8.24 (s, 1 H), 8.34 (s, 1 H), 8.73 (s, 2 H), 9.89 (s, 1 H).

Example 80

The similar procedures as Example 62→Example 63→Example 19→Example 20→Example 21 were carried out with corresponding hydrazine derivatives in place of (3,4-dimethylphenyl)hydrazine hydrochloride and 1-(5-bromothiazol-2-yl)pyrrolidin-2-one in place of the compound prepared in Example 18 to give the present compounds having the following physical data.

Example 80-1

1-[3-(2-methyl-2-propanyl)-1-(1,2,3,4-tetrahydro-2-naphthalenyl)-1H-pyrazol-5-yl]-3-(2-{4-[2-(2-oxo-1-pyrrolidinyl)-1,3-thiazol-5-yl]phenoxy}-5-pyrimidinyl)urea

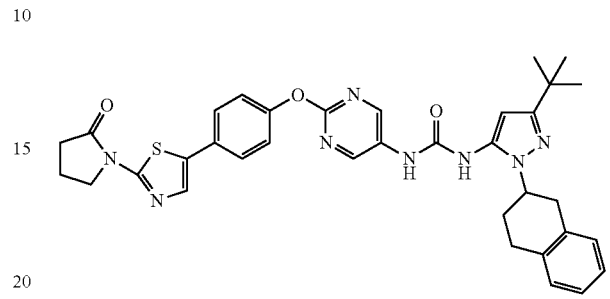

TCL: Rf 0.64 (Ethyl Acetate);
¹H-NMR (DMSO-d₆): δ 1.22 (s, 9 H), 2.00-2.25 (m, 4 H), 2.64 (t, 2 H), 2.88-3.04 (m, 3 H), 3.16-3.22 (m, 1 H), 4.05 (t, 2 H), 4.38 (m, 1 H), 6.08 (s, 1 H), 7.08-7.13 (m, 4 H), 7.21 (d, 2H), 7.67 (d, 2 H), 7.89 (s, 1 H), 8.68 (s, 2 H), 8.71 (s, 1 H), 9.01 (s, 1 H).

Example 80-2

1-[3-(2-methyl-2-propanyl)-1-(tetrahydro-2H-pyran-4-yl)-1H-pyrazol-5-yl]-3-(2-{4-[2-(2-oxo-1-pyrrolidinyl)-1,3-thiazol-5-yl]phenoxy}-5-pyrimidinyl)urea

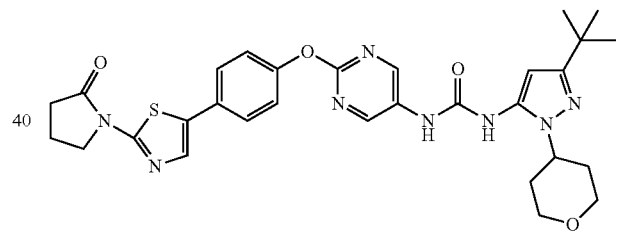

TCL: Rf 0.34 (Ethyl Acetate:Methanol=9:1);
¹H-NMR (DMSO-d₆): δ 1.21 (s, 9 H), 1.76 (m, 2 H), 2.01 (m, 2H), 2.16 (m, 2 H), 2.64 (t, 2 H), 3.40 (m, 2 H), 3.95 (m, 2 H), 4.05 (t, 2 H), 4.20 (m, 1 H), 6.03 (s, 1 H), 7.22 (d, 2 H), 7.68 (d, 2 H), 7.89 (s, 1 H), 8.65 (s, 1 H), 8.70 (s, 2 H), 9.06 (s, 1 H).

Example 80-3

1-[1-cyclohexyl-3-(2-methyl-2-propanyl)-1H-pyrazol-5-yl]-3-(2-{4-[2-(2-oxo-1-pyrrolidinyl)-1,3-thiazol-5-yl]phenoxy}-5-pyrimidinyl)urea

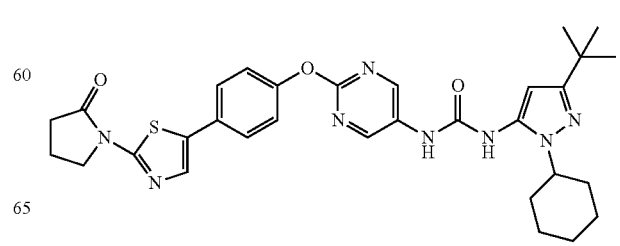

TCL: Rf 0.63 (Methylene Dichloride:Ethyl Acetate:Methanol=8:4:1);
$^1$H-NMR (DMSO-$d_6$): δ 1.20 (s, 9 H), 1.15-1.40 (m, 4 H), 1.57-1.88 (m, 6 H), 2.10-2.23 (m, 2 H), 2.64 (t, 2 H), 3.86-4.00 (m, 1 H), 4.05 (t, 2 H), 6.01 (s, 1 H), 7.22 (d, 2 H), 7.67 (d, 2H), 7.90 (s, 1 H), 8.60 (s, 1 H), 8.71 (s, 2 H), 9.03 (s, 1 H).

Example 81

1-(2-{4-[2-(ethylamino)-1,3-thiazol-5-yl]phenoxy}-5-pyrimidinyl)-3-[2-(3-pyridinyl)-5-(trifluoromethyl)phenyl]urea The similar procedures as Example 8→Example 19→Example 20→Example 21 were carried out with 2-(pyridin-2-yl)-5-(trifluoromethyl)aniline in place of the compound prepared in Example 7 and tert-butyl(5-bromothiazol-2-yl)(ethyl)carbamate in place of the compound prepared in Example 18 to give the present compound having the following physical data.

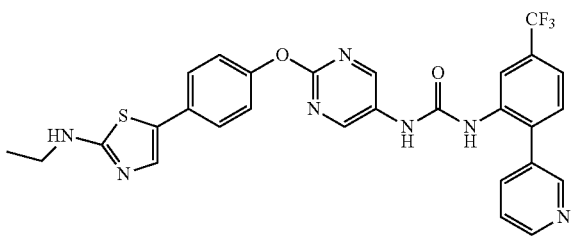 [SMILES: CCNc1ncc(-c2ccc(Oc3ncc(NC(=O)Nc4cc(C(F)(F)F)ccc4-c4cccnc4)cn3)cc2)s1]

TCL: Rf 0.54 (Ethyl Acetate:Hexane=9:1);
$^1$H-NMR (DMSO-$d_6$): δ 1.16 (t, 3 H), 3.26 (m, 2 H), 7.13 (d, 2H), 7.42-7.58 (m, 6 H), 7.72 (t, 1 H), 7.89 (dt, 1 H), 8.23 (s, 1 H), 8.38 (s, 1 H), 8.62 (s, 2 H), 8.65 (dd, 1 H), 8.68 (dd, 1 H), 9.22 (s, 1 H).

Example 82

1-[2-cyclohexyl-5-(trifluoromethyl)-3-pyridinyl]-3-(2-{4-[2-(2-oxo-1-pyrrolidinyl)-1,3-thiazol-5-yl]phenoxy}-5-pyrimidinyl)urea The similar procedures as Example 8→Example 19→Example 20→Example 21 were carried out with 2-cyclohexyl-5-(trifluoromethyl)-pyridin-3-amine in place of the compound prepared in Example 7 and 1-(5-bromothiazol-2-yl)pyrrolidin-2-one in place of the compound prepared in Example 18 to give the present compound having the following physical data.

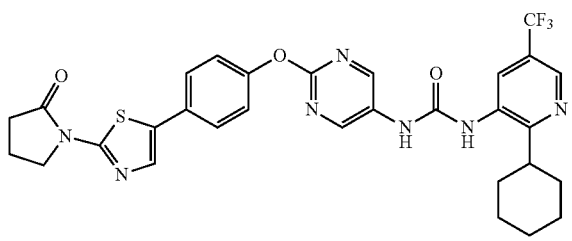 [SMILES: O=C(Nc1cnc(Oc2ccc(-c3cnc(N4CCCC4=O)s3)cc2)nc1)Nc1cc(C(F)(F)F)cnc1C1CCCCC1]

TCL: Rf 0.60 (Methylene Dichloride:Ethyl Acetate:Methanol=8:4:1);
$^1$H-NMR (DMSO-$d_6$): δ 1.20-1.70 (m, 6 H), 1.70-1.90 (m, 4 H), 2.10-2.23 (m, 2 H), 2.64 (t, 2 H), 2.95-3.07 (m, 1 H), 4.05 (t, 2 H), 7.23 (d, 2 H), 7.68 (d, 2 H), 7.90 (s, 1 H), 8.51 (s, 1H), 8.61 (s, 2 H), 8.75 (s, 2 H), 9.33 (s, 1 H).

Example 83

1-[2-(3,4-dimethylphenyl)-5-methyl-3-pyridinyl]-3-(2-{4-[2-(2-oxo-1-pyrrolidinyl)-1,3-thiazol-5-yl]phenoxy}-5-pyrimidinyl)urea The similar procedures as Example 6→Example 5→Example 8→Example 19→Example 20→Example 21 were carried out with 2-bromo-5-methyl-3-nitropyridine in place of 2-chloro-3-nitro-5-(trifluoromethyl)pyridine; 3,4-dimethylphenylboronic acid in place of (6-(trifluoromethyl)pyridin-3-yl)boronic acid; and 1-(5-bromothiazol-2-yl)pyrrolidin-2-one in place of the compound prepared in Example 18 to give the present compound having the following physical data.

TCL: Rf 0.53 (Ethyl Acetate);
$^1$H-NMR (DMSO-$d_6$): δ 2.14 (m, 2 H), 2.28 (s, 3 H), 2.32 (s, 6H), 2.64 (t, 2 H), 4.05 (t, 2 H), 7.20-7.33 (m, 5 H), 7.65 (dd, 2 H), 7.89 (d, 1 H), 8.02 (s, 1 H), 8.13 (s, 1 H), 8.18 (s, 1H), 8.66 (s, 2 H), 9.32 (s, 1 H).

Example 84

The similar procedures as Example 8→Example 12→Example 13→Example 19→Example 20→Example 21 were carried out with corresponding amine derivatives in place of the compound prepared in Example 7; corresponding 5-bromothiazole derivatives in place of the compound prepared in Example 18; 2-chloro-5-nitropyrimidine or 2-chloro-5-nitropyridine in place of 2-chloro-5-nitropyrimidine; and 4-bromophenol or 6-bromopyridin-3-ol in place of 4-bromophenol to give the present compounds having the following physical data.

Example 84-1

1-[2-(3,4-dimethylphenyl)-3-pyridinyl]-3-(2-{4-[2-(2-oxo-1-pyrrolidinyl)-1,3-thiazol-5-yl]phenoxy}-5-pyrimidinyl)urea TCL: Rf 0.69 (Ethyl Acetate);
$^1$H-NMR (DMSO-$d_6$): δ 2.12 (m, 2 H), 2.28 (s, 6 H), 2.60 (t, 2H), 4.03 (t, 2 H), 7.17 (d, 2 H), 7.23-7.32 (m, 4 H), 7.62 (d, 2 H), 7.85 (d, 1 H), 8.03 (s, 1 H), 8.24 (d, 1 H), 8.29 (d, 1H), 8.62 (s, 2 H), 9.29 (s, 1 H).

Example 84-2

1-(3-isopropyl-1-phenyl-1H-pyrazol-5-yl)-3-(2-{4-[2-(2-oxo-1-pyrrolidinyl)-1,3-thiazol-5-yl]phenoxy}-5-pyrimidinyl)urea

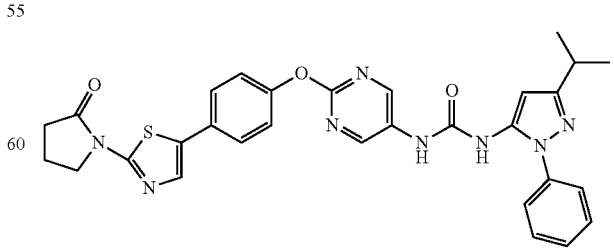

TCL: Rf 0.55 (Methylene Dichloride:Ethyl Acetate:Methanol=8:4:1);

¹H-NMR (DMSO-d₆): δ 1.22 (d, 6 H), 2.10-2.23 (m, 2 H), 2.64 (t, 2 H), 2.80-2.95 (m, 1 H), 4.05 (t, 2 H), 6.31 (s, 1 H), 7.20 (d, 2 H), 7.34-7.44 (m, 1 H), 7.46-7.54 (m, 4 H), 7.66 (d, 2H), 7.88 (s, 1 H), 8.62-8.68 (m, 3 H), 9.17 (s, 1 H).

Example 84-3

1-(2-{4-[2-(2-oxo-1-pyrrolidinyl)-1,3-thiazol-5-yl]phenoxy}-5-pyrimidinyl)-3-[2-(3-pyridinyl)-5-(trifluoromethyl)phenyl]urea TCL: Rf 0.26 (Ethyl Acetate:Methanol=19:1);
¹H-NMR (DMSO-d₆): δ 2.16 (q, 2 H), 2.61 (t, 2 H), 4.05 (t, 2H), 7.21 (d, 2 H), 7.46-7.57 (m, 3 H), 7.66 (d, 2 H), 7.82-7.92 (m, 2 H), 8.23 (s, 1 H), 8.38 (s, 1 H), 8.63-8.68 (m, 4H), 9.23 (s, 1 H).

Example 84-4

1-(6-{4-[2-(2-oxo-1-pyrrolidinyl)-1,3-thiazol-5-yl]phenoxy}-3-pyridinyl)-3-[2-(4-pyridinyl)-5-(trifluoromethyl)phenyl]urea TCL: Rf 0.17 (Ethyl Acetate:Methanol=19:1);
¹H-NMR (DMSO-d₆): δ 2.16 (q, 2 H), 2.64 (t, 2 H), 4.04 (t, 2H), 7.02 (d, 1 H), 7.11 (d, 2 H), 7.46-7.54 (m, 4 H), 7.64 (d, 2 H), 7.86 (s, 1 H), 7.98 (dd, 1 H), 8.09-8.10 (m, 2 H), 8.42 (s, 1 H), 8.72 (d, 2 H), 9.19 (s, 1 H).

Example 84-5

1-[6'-methyl-5-(trifluoromethyl)-2,3'-bipyridin-3-yl]-3-(6-{4-[2-(2-oxo-1-pyrrolidinyl)-1,3-thiazol-5-yl]phenoxy}-3-pyridinyl)urea

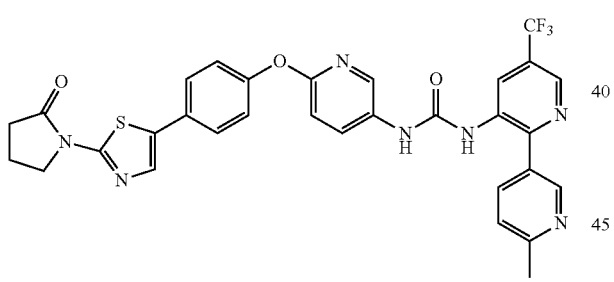

TCL: Rf 0.35 (Ethyl Acetate:Methanol=19:1);
¹H-NMR (DMSO-d₆): δ 2.16 (q, 2 H), 2.60 (s, 3 H), 2.63 (t, 2H), 4.04 (t, 2 H), 7.04 (d, 1 H), 7.12 (d, 2 H), 7.45 (d, 1 H), 7.64 (d, 2 H), 7.89 (s, 1 H), 7.96 (dd, 1 H), 8.01 (dd, 1 H), 8.12 (d, 1 H), 8.42 (d, 1 H), 8.68-8.76 (m, 2 H), 8.78 (s, 1H), 9.30 (s, 1 H).

Example 84-6

1-(6-{4-[2-(2-oxo-1-pyrrolidinyl)-1,3-thiazol-5-yl]phenoxy}-3-pyridinyl)-3-[2-(3-pyridinyl)-5-(trifluoromethyl)phenyl]urea TCL: Rf 0.23 (Ethyl Acetate:Methanol=19:1);
¹H-NMR (DMSO-d₆): δ 2.16 (q, 2 H), 2.64 (t, 2 H), 4.04 (t, 2H), 7.02 (d, 1 H), 7.11 (d, 2 H), 7.44-7.52 (m, 2 H), 7.56 (dd, 1 H), 7.64 (d, 2 H), 7.86-7.91 (2 H), 7.98 (dd, 1 H), 8.08-8.09 (m, 2 H), 8.42 (s, 1 H), 8.65 (d, 1 H), 8.68 (dd, 1 H), 9.17 (s, 1 H).

Example 84-7

1-(6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea TCL: Rf 0.58 (Ethyl Acetate:Methanol=19:1);
¹H-NMR (DMSO-d₆): δ 2.16 (q, 2 H), 2.64 (t, 2 H), 4.04 (s, 2H), 7.04 (d, 1 H), 7.12 (d, 2 H), 7.55-7.67 (m, 7 H), 7.87 (s, 1 H), 8.01 (dd, 1 H), 8.12 (d, 1 H), 8.29 (s, 1 H), 8.70 (s, 1H), 8.79 (s, 1 H), 9.40 (s, 1 H).

Example 84-8

1-(6-{4-[2-(2-oxo-1-pyrrolidinyl)-1,3-thiazol-5-yl]phenoxy}-3-pyridinyl)-3-[5-(trifluoromethyl)-2,4'-bipyridin-3-yl]urea TCL: Rf 0.11 (Ethyl Acetate);
¹H-NMR (DMSO-d₆): δ 2.16 (t, 2 H), 2.64 (t, 2 H), 4.04 (t, 2H), 7.04 (d, 1 H), 7.12 (d, 2 H), 7.63-7.68 (m, 4 H), 7.87 (s, 1 H), 8.00 (dd, 1 H), 8.11 (d, 1 H), 8.42 (s, 1 H), 8.76 (m, 4H), 9.30 (s, 1 H).

Example 84-9

1-[2-(4-methylphenyl)-5-(trifluoromethyl)-3-pyridinyl]-3-(6-{4-[2-(2-oxo-1-pyrrolidinyl)-1,3-thiazol-5-yl]phenoxy}-3-pyridinyl)urea TCL: Rf 0.72 (Ethyl Acetate:Methanol=19:1);
¹H-NMR (DMSO-d₆): δ 2.16 (q, 2 H), 2.40 (s, 3 H), 2.64 (t, 2H), 4.03 (t, 2 H), 7.04 (d, 1 H), 7.12 (d, 2 H), 7.38 (d, 2 H), 7.54 (d, 2 H), 7.64 (d, 2 H), 7.89 (s, 1 H), 8.02 (dd, 1 H), 8.11 (d, 1 H), 8.26 (s, 1 H), 8.67 (s, 1 H), 8.79 (s, 1 H), 9.42 (s, 1 H).

Example 84-10

1-[2-(6-methyl-3-pyridinyl)-5-(trifluoromethyl)phenyl]-3-(6-{4-[2-(2-oxo-1-pyrrolidinyl)-1,3-thiazol-5-yl]phenoxy}-3-pyridinyl)urea TCL: Rf 0.28 (Ethyl Acetate:Methanol=19:1);
¹H-NMR (DMSO-d₆): δ 2.16 (q, 2 H), 2.55 (s, 3 H), 2.64 (t, 2H), 4.04 (t, 2 H), 7.02 (d, 1 H), 7.11 (d, 2 H), 7.41-7.48 (m, 3 H), 7.64 (d, 2 H), 7.77 (dd, 1 H), 7.86 (s, 1 H), 8.11 (dd, 1 H), 8.06 (s, 1 H), 8.09 (d, 1 H), 8.44 (s, 1 H), 8.50 (d, 1H), 9.21 (s, 1 H).

Example 84-11

1-[1-oxido-2-phenyl-5-(trifluoromethyl)-3-pyridinyl]-3-(2-{4-[2-(2-oxo-1-pyrrolidinyl)-1,3-thiazol-5-yl]phenoxy}-5-pyrimidinyl)urea

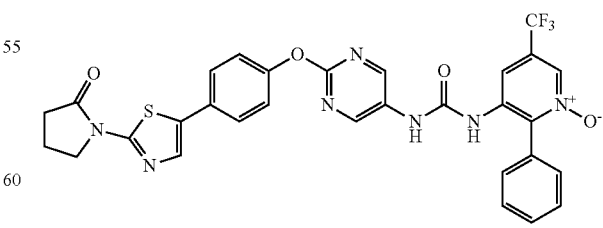

TCL: Rf 0.20 (Ethyl Acetate:Methanol=19:1);
¹H-NMR (DMSO-d₆): δ 2.18 (q, 2 H), 2.64 (t, 2 H), 4.04 (t, 2H), 7.21 (d, 2 H), 7.42-7.44 (m, 2 H), 7.57-7.59 (m, 3 H), 7.66 (d, 2 H), 7.86-7.89 (m, 2 H), 8.43 (s, 1 H), 8.57 (s, 1H), 8.61 (s, 2 H), 9.55 (s, 1 H).

Example 84-12

1-(6-{4-[2-(2-oxo-1-pyrrolidinyl)-1,3-thiazol-5-yl]phenoxy}-3-pyridinyl)-3-{5-(trifluoromethyl)-2-[6-(trifluoromethyl)-3-pyridinyl]phenyl}urea TCL: Rf 0.53 (Hexane:Ethyl Acetate=1:2);
$^1$H-NMR (DMSO-$d_6$): δ 2.16 (t, 2 H), 2.64 (t, 2 H), 4.04 (t, 2H), 7.00 (d, 1 H), 7.10 (d, 2 H), 7.54 (s, 2 H), 7.63 (d, 2 H), 7.86 (s, 1 H), 7.96 (dd, 1 H), 8.06 (m, 2 H), 8.20 (m, 2 H), 8.41 (s, 1 H), 8.85 (d, 1 H), 9.04 (s, 1 H).

Example 84-13

1-[2-(6-methyl-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.24 (Ethyl Acetate:Methanol=19:1);
$^1$H-NMR (DMSO-$d_6$): δ 2.16 (q, 2 H), 2.53 (s, 3 H), 2.64 (t, 2H), 4.05 (t, 2 H), 7.21 (d, 2 H), 7.41-7.52 (m, 3 H), 7.67 (d, 2 H), 7.76 (dd, 1 H), 7.89 (s, 1 H), 8.19 (s, 1 H), 8.41 (s, 1H), 8.50 (d, 1 H), 8.65 (s, 2 H), 9.27 (s, 1 H).

Example 84-14

1-(6-{4-[2-(2-oxo-1-pyrrolidinyl)-1,3-thiazol-5-yl]phenoxy}-3-pyridinyl)-3-[5-(trifluoromethyl)-2,3'-bipyridin-3-yl]urea TCL: Rf 0.15 (Ethyl Acetate:Methanol=19:1);
$^1$H-NMR (DMSO-$d_6$): δ 2.16 (q, 2 H), 2.64 (t, 2 H), 4.04 (t, 2H), 7.03 (d, 1 H), 7.12 (d, 2 H), 7.57-7.66 (m, 3 H), 7.98 (s, 1 H), 8.00 (dd, 1 H), 8.06-8.12 (m, 2 H), 8.45 (s, 1 H), 8.72 (dd, 1 H), 8.76 (s, 1 H), 8.78 (s, 1 H), 8.85 (s, 1 H), 9.28 (s, 1 H).

Example 84-15

1-[2-(6-methoxy-3-pyridinyl)-5-(trifluoromethyl)phenyl]-3-(6-{4-[2-(2-oxo-1-pyrrolidinyl)-1,3-thiazol-5-yl]phenoxy}-3-pyridinyl)urea TCL: Rf 0.54 (Hexane:Ethyl Acetate=1:2);
$^1$H-NMR (DMSO-$d_6$): δ 2.16 (t, 2 H), 2.64 (t, 2 H), 3.92 (s, 3H), 4.04 (t, 2 H), 6.98 (d, 1 H), 7.03 (d, 1 H), 7.13 (d, 2 H), 7.43 (d, 2 H), 7.63 (d, 2 H), 7.78 (dd, 1 H), 7.86 (s, 1 H), 8.00 (m, 2 H), 8.10 (d, 1 H), 8.23 (d, 1 H), 8.45 (s, 1 H), 9.20 (s, 1 H).

Example 84-16

1-[2-(3-hydroxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea TCL: Rf 0.31 (Methanol: Chloroform=1:19);
$^1$H-NMR (DMSO-$d_6$): δ 2.10-2.22 (m, 2 H), 2.64 (t, 2 H), 4.01-4.08 (m, 2 H), 6.88-6.94 (m, 1 H), 6.97-7.06 (m, 2 H), 7.19-7.24 (m, 2 H), 7.35 (t, 1 H), 7.63-7.69 (m, 2 H), 7.89 (s, 1H), 8.36 (s, 1 H), 8.66-8.70 (m, 3 H), 8.73-8.77 (m, 1 H), 9.53 (s, 1 H), 9.72 (s, 1 H).

Example 84-17

1-(2-{4-[2-(2-oxo-1-pyrrolidinyl)-1,3-thiazol-5-yl]phenoxy}-5-pyrimidinyl)-3-[5-(trifluoromethyl)-2,3'-bipyridin-3-yl]urea TCL: Rf 0.41 (Ethyl Acetate:Methanol=4:1);
$^1$H-NMR (DMSO-$d_6$): δ 2.16 (q, 2 H), 2.64 (t, 2 H), 4.05 (t, 2H), 7.21 (d, 2 H), 7.56-7.60 (m, 1 H), 7.66 (d, 2 H), 7.89 (s, 1 H), 8.04-8.10 (m, 1 H), 8.59 (s, 1 H), 8.66 (s, 2 H), 8.72 (dd, 1 H), 8.74-8.79 (m, 2 H), 8.83-8.84 (m, 1 H), 9.34 (s, 1H).

Example 84-18

1-[2-(1-oxido-4-pyridinyl)-5-(trifluoromethyl)phenyl]-3-(6-{4-[2-(2-oxo-1-pyrrolidinyl)-1,3-thiazol-5-yl]phenoxy}-3-pyridinyl)urea TCL: Rf 0.59 (Chloroform:Methanol=9:1);
$^1$H-NMR (DMSO-$d_6$): δ 2.16 (q, 2 H), 2.64 (t, 2 H), 4.04 (t, 2H), 7.03 (d, 1 H), 7.12 (d, 2 H), 7.56-7.53 (m, 4 H), 7.64 (d, 2 H), 7.87 (s, 1 H), 8.00 (dd, 1 H), 8.11-8.15 (m, 2 H), 8.32-8.41 (m, 3 H), 9.17 (s, 1 H).

Example 84-19

1-(6-{4-[2-(2-oxo-1-pyrrolidinyl)-1,3-thiazol-5-yl]phenoxy}-3-pyridinyl)-3-[4-(trifluoromethyl)-2-biphenylyl]urea TCL: Rf 0.60 (Ethyl Acetate);
$^1$H-NMR (DMSO-$d_6$): δ 2.16 (q, 2 H), 2.64 (t, 2 H), 4.04 (t, 2H), 7.02 (d, 1 H), 7.11 (d, 2 H), 7.39-7.56 (m, 7 H), 7.64 (d, 2 H), 7.86 (s, 1 H), 7.95 (s, 1 H), 8.00 (dd, 1 H), 8.10 (d, 1H), 8.43 (s, 1 H), 9.31 (s, 1 H).

Example 84-20

1-[2-(4-hydroxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea TCL: Rf 0.68 (Ethyl Acetate:Methanol=19:1);
$^1$H-NMR (DMSO-$d_6$): δ 2.16 (q, 2 H), 2.64 (t, 2 H), 4.05 (t, 2H), 6.92 (d, 2 H), 7.21 (d, 2 H), 7.50 (d, 2 H), 7.67 (d, 2 H), 7.89 (s, 1 H), 8.37 (s, 1 H), 8.65 (s, 1 H), 8.67 (s, 2 H), 8.71 (s, 1 H), 9.49 (s, 1 H), 9.88 (s, 1 H).

Example 84-21

1-[2-(1-oxido-4-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.42 (Ethyl Acetate:Methanol:aqueous ammonia=9:1:0.5);
$^1$H-NMR (DMSO-$d_6$): δ 2.16 (q, 2 H), 2.64 (t, 2 H), 4.05 (t, 2H), 7.21 (d, 2 H), 7.50-7.52 (m, 4 H), 7.66 (d, 2 H), 7.89 (s, 1 H), 8.27 (s, 1 H), 8.32-8.36 (m, 3 H), 8.66 (s, 2 H), 9.20 (s, 1 H).

Example 84-22

1-[2-(1-oxido-3-pyridinyl)-5-(trifluoromethyl)phenyl]-3-(6-{4-[2-(2-oxo-1-pyrrolidinyl)-1,3-thiazol-5-yl]phenoxy}-3-pyridinyl)urea TCL: Rf 0.38 (Ethyl Acetate:Methanol:aqueous ammonia=9:1:0.5);
$^1$H-NMR (DMSO-$d_6$): δ 2.16 (q, 2 H), 2.64 (t, 2 H), 4.04 (t, 2H), 7.03 (d, 1 H), 7.11 (d, 2 H), 7.38 (d, 1 H), 7.49-7.58 (m, 3 H), 7.64 (d, 2 H), 7.86 (s, 1 H), 8.00 (dd, 1 H), 8.11 (d, 1H), 8.14 (s, 1 H), 8.30-8.33 (m, 2 H), 8.44 (s, 1 H), 9.15 (s, 1 H).

Example 84-23

1-[2-(1-oxido-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.34 (Ethyl Acetate:Methanol:aqueous ammonia=9:1:0.5);
$^1$H-NMR (DMSO-d$_6$): δ 2.16 (q, 2 H), 2.64 (t, 2 H), 4.05 (t, 2H), 7.22 (d, 2 H), 7.36-7.39 (m, 1 H), 7.51-7.57 (m, 3 H), 7.67 (d, 2 H), 7.90 (s, 1 H), 8.28-8.33 (m, 3 H), 8.41 (s, 1H), 8.66 (s, 2 H), 9.23 (s, 1 H).

Example 84-24

1-[2-(2-methoxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea TCL: Rf 0.54 (Ethyl Acetate);
$^1$H-NMR (DMSO-d$_6$): δ 2.16 (t, 2 H), 2.64 (t, 2 H), 3.75 (s, 3 H), 4.05 (t, 2 H), 7.14 (t, 1 H), 7.21 (m, 3 H), 7.37 (dd, 1 H), 7.55 (dt, 1 H), 7.66 (d, 2 H), 7.89 (s, 2 H), 8.67 (s, 3 H), 8.77 (d, 1 H), 9.61 (s, 1 H).

Example 84-25

1-[2-(3-methoxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea TCL: Rf 0.43 (Hexane:Ethyl Acetate=1:2);
$^1$H-NMR (DMSO-d$_6$): δ 2.16 (t, 2 H), 2.64 (t, 2 H), 3.81 (s, 3H), 4.05 (t, 2 H), 7.08 (d, 1 H), 7.19 (m, 4 H), 7.48 (t, 1 H), 7.66 (d, 2 H), 7.90 (s, 1 H), 8.38 (s, 1 H), 8.67 (s, 2 H), 8.71 (s, 1 H), 8.79 (s, 1 H), 9.52 (s, 1 H).

Example 84-26

1-[2-(2-hydroxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea TCL: Rf 0.53 (Hexane:Ethyl Acetate=1:2);
$^1$H-NMR (DMSO-d$_6$): δ 2.16 (t, 2 H), 2.64 (t, 2 H), 4.05 (t, 2H), 7.00 (m, 2 H), 7.21 (d, 2 H), 7.30-7.34 (m, 2 H), 7.67 (d, 2 H), 7.89 (s, 1 H), 8.04 (br, 1 H), 8.65 (s, 1 H), 8.67 (s, 2H), 8.76 (s, 1 H), 9.75 (s, 1 H), 10.2 (br s, 1 H).

Example 84-27

1-(1-oxido-6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea TCL: Rf 0.44 (Ethyl Acetate:Methanol:aqueous ammonia=9:1:0.5);
$^1$H-NMR (DMSO-d$_6$): δ 2.15 (q, 2 H), 2.63 (t, 2 H), 4.02 (t, 2H), 6.93 (d, 2 H), 7.27 (dd, 1 H), 7.35 (d, 1 H), 7.55-7.69 (m, 7 H), 7.84 (s, 1 H), 8.47 (s, 1 H), 8.66 (d, 1 H), 8.70 (s, 1H), 8.75 (s, 1 H), 9.73 (s, 1 H).

Example 84-28

1-[2-(4-methoxyphenyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea TCL: Rf 0.56 (Ethyl Acetate);
$^1$H-NMR (DMSO-d$_6$): δ 2.15 (q, 2 H), 2.64 (t, 2 H), 3.80 (s, 3H), 4.05 (t, 2 H), 7.11 (d, 2 H), 7.22 (d, 2 H), 7.60-7.69 (m, 4 H), 7.90 (s, 1 H), 8.41 (s, 1 H), 8.68-8.73 (m, 4 H), 9.47 (s, 1 H).

Example 84-29

1-[2-({6-[2-(2-oxo-1-pyrrolidinyl)-1,3-thiazol-5-yl]-3-pyridinyl}oxy)-5-pyrimidinyl]-3-[2-phenyl-5-(trifluoromethyl)-3-pyridinyl]urea TCL: Rf 0.20 (Ethyl Acetate);
$^1$H-NMR (DMSO-d$_6$): δ 2.19 (t, 2 H), 2.35 (t, 2 H), 4.14 (t, 2H), 7.26 (d, 1 H), 7.30 (m, 3 H), 7.52 (dd, 1 H), 7.58-7.62 (m, 2 H), 7.75 (s, 1 H), 7.81 (s, 1 H), 8.21 (d, 1 H), 8.39 (s, 1H), 8.60 (s, 1 H), 8.71 (s, 2 H), 8.84 (s, 1 H).

Example 84-30

1-[2-cyclohexyl-5-(trifluoromethyl)-3-pyridinyl]-3-(2-{4-[2-(2-oxo-1-piperidinyl)-1,3-thiazol-5-yl]phenoxy}-5-pyrimidinyl)urea TCL: Rf 0.64 (Hexane:Ethyl Acetate=1:4);
$^1$H-NMR (DMSO-d$_6$): δ 1.20-1.99 (m, 14 H), 2.61 (t, 2 H), 3.00 (m, 1 H), 4.07 (t, 2 H), 7.23 (d, 2 H), 7.66 (d, 2 H), 7.91 (s, 1 H), 8.49-8.50 (m, 2 H), 8.60 (s, 2 H), 8.74 (s, 2 H), 9.33 (s, 1 H).

Example 84-31

1-[1-(2,3-dihydro-1H-inden-5-yl)-3-(2-methyl-2-propanyl)-1H-pyrazol-5-yl]-3-(4-{4-[2-(2-oxo-1-piperidinyl)-1,3-thiazol-5-yl]phenoxy}phenyl)urea

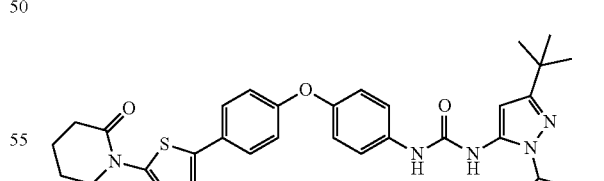

TCL: Rf 0.56 (Hexane:Ethyl Acetate=4:6);
$^1$H-NMR (DMSO-d$_6$): δ 1.25 (s, 9 H), 1.78-1.98 (m, 4 H), 2.06 (q, 2 H), 2.59 (t, 2 H), 2.85-2.95 (m, 4 H), 4.05 (t, 2 H), 6.33 (s, 1 H), 6.94-7.02 (m, 4 H), 7.19-7.24 (m, 1 H), 7.29-7.38 (m, 2 H), 7.41 (d, 2 H), 7.58 (d, 2 H), 7.83 (s, 1 H), 8.29 (s, 1H), 9.02 (s, 1 H).

Example 84-32

1-[3-(2-methyl-2-propanyl)-1-phenyl-1H-pyrazol-5-yl]-3-(6-{4-[2-(2-oxo-1-piperidinyl)-1,3-thiazol-5-yl]phenoxy}-3-pyridinyl)urea TCL: Rf 0.59 (Ethyl Acetate);
$^1$H-NMR (DMSO-$d_6$): δ 1.26 (s, 9 H), 1.82-1.95 (m, 4 H), 2.60 (t, 2 H), 4.06 (t, 2 H), 6.36 (s, 1 H), 7.01 (d, 1 H), 7.10 (dd, 2H), 7.29 (m, 1 H), 7.51 (dd, 4 H), 7.62 (dd, 2 H), 7.88 (s, 1H), 7.95 (dd, 1 H), 8.12 (d, 1 H), 8.49 (s, 1 H), 9.12 (s, 1H).

Example 84-33

1-(6-{4-[2-(2-oxo-1-piperidinyl)-1,3-thiazol-5-yl]phenoxy}-3-pyridinyl)-3-[2-phenyl-5-(trifluoromethyl)-3-pyridinyl]urea TCL: Rf 0.65 (Ethyl Acetate);
$^1$H-NMR (DMSO-$d_6$): δ 1.82-1.95 (m, 4 H), 2.61 (t, 2 H), 4.04 (t, 2 H), 7.04 (d, 1 H), 7.12 (d, 2 H), 7.53-7.67 (m, 7 H), 7.88 (s, 1 H), 8.00 (dd, 1 H), 8.10 (d, 1 H), 8.29 (s, 1 H), 8.70 (s, 1 H), 8.79 (s, 1 H), 9.40 (s, 1 H).

Example 84-34

1-(6-{4-[2-(2-oxo-1-piperidinyl)-1,3-thiazol-5-yl]phenoxy}-3-pyridinyl)-3-[2-(4-pyridinyl)-5-(trifluoromethyl)phenyl]urea TCL: Rf 0.27 (Ethyl Acetate:Methanol=19:1);
$^1$H-NMR (DMSO-$d_6$): δ 1.82-1.98 (m, 4 H), 2.60 (t, 2 H), 4.06 (t, 2 H), 7.02 (d, 1 H), 7.11 (d, 2 H), 7.48-7.50 (m, 4 H), 7.63 (d, 2 H), 7.88 (s, 1 H), 7.98 (dd, 1 H), 8.09-8.11 (m, 2 H), 8.42 (s, 1 H), 8.72 (d, 2 H), 9.23 (s, 1 H).

Example 84-35

1-(6-{4-[2-(2-oxo-1-piperidinyl)-1,3-thiazol-5-yl]phenoxy}-3-pyridinyl)-3-[2-(3-pyridinyl)-5-(trifluoromethyl)phenyl]urea TCL: Rf 0.51 (Ethyl Acetate:Methanol=19:1);
$^1$H-NMR (DMSO-$d_6$): δ 1.81-2.00 (m, 4 H), 2.60 (t, 2 H), 4.06 (t, 2 H), 7.01 (d, 1 H), 7.10 (d, 2 H), 7.40-7.50 (m, 2 H), 7.56 (dd, 1 H), 7.62 (d, 2 H), 7.87-7.90 (m, 2 H), 7.97 (dd, 1 H), 8.08 (d, 1 H), 8.11 (s, 1 H), 8.41 (s, 1 H), 8.63-8.67 (m, 2H), 9.21 (s, 1 H).

Example 84-36

1-(2-{4-[2-(2-oxo-1-piperidinyl)-1,3-thiazol-5-yl]phenoxy}-5-pyrimidinyl)-3-[5-(trifluoromethyl)-2,4'-bipyridin-3-yl]urea TCL: Rf 0.19 (Ethyl Acetate);
$^1$H-NMR (DMSO-$d_6$): δ 1.82-1.98 (m, 4 H), 2.61 (t, 2 H), 4.07 (t, 2 H), 7.22 (d, 2 H), 7.67 (m, 4 H), 7.91 (s, 1 H), 8.65 (br s, 1 H), 8.67 (s, 2 H), 8.76 (m, 4 H), 9.35 (br s, 1 H).

Example 84-37

1-(2-{4-[2-(2-oxo-1-piperidinyl)-1,3-thiazol-5-yl]phenoxy}-5-pyrimidinyl)-3-[2-(3-pyridinyl)-5-(trifluoromethyl)phenyl]urea TCL: Rf 0.53 (Ethyl Acetate:Methanol=19:1);
$^1$H-NMR (DMSO-$d_6$): δ 1.80-2.00 (m, 4 H), 2.61 (t, 2 H), 4.07 (t, 2 H), 7.21 (d, 2 H), 7.47-7.58 (m, 3 H), 7.66 (d, 2 H), 7.82-7.91 (m, 2 H), 8.24 (s, 1 H), 8.38 (s, 1 H), 8.64-8.68 (m, 4H), 9.24 (s, 1 H).

Example 84-38

1-(2-{4-[2-(2-oxo-1-piperidinyl)-1,3-thiazol-5-yl]phenoxy}-5-pyrimidinyl)-3-[5-(trifluoromethyl)-2,3'-bipyridin-3-yl]urea TCL: Rf 0.16 (Ethyl Acetate);
$^1$H-NMR (DMSO-$d_6$): δ 1.82-1.94 (m, 4 H), 2.61 (t, 2 H), 4.07 (t, 2 H), 7.22 (d, 2 H), 7.57 (dd, 1 H), 7.65 (d, 2 H), 7.91 (s, 1H), 8.08 (d, 1 H), 8.61 (br s, 1 H), 8.66 (s, 2 H), 8.71 (dd, 1 H), 8.76 (d, 2 H), 8.85 (d, 1 H), 9.35 (br s, 1 H).

Example 84-39

1-(2-{4-[2-(2-oxo-1-piperidinyl)-1,3-thiazol-5-yl]phenoxy}-5-pyrimidinyl)-3-[2-(4-pyridinyl)-5-(trifluoromethyl)phenyl]urea TCL: Rf 0.32 (Ethyl Acetate:Methanol=19:1);
$^1$H-NMR (DMSO-$d_6$): δ 1.80-1.98 (m, 4 H), 2.61 (t, 2 H), 4.07 (t, 2 H), 7.21 (d, 2 H), 7.46-7.56 (m, 4 H), 7.66 (d, 2 H), 7.91 (s, 1 H), 8.23 (s, 1 H), 8.38 (s, 1 H), 8.64 (s, 2 H), 8.72 (d, 2 H), 9.23 (s, 1 H).

Example 84-40

1-[2-(6-methyl-3-pyridinyl)-5-(trifluoromethyl)phenyl]-3-(2-{4-[2-(2-oxo-1-piperidinyl)-1,3-thiazol-5-yl]phenoxy}-5-pyrimidinyl)urea TCL: Rf 0.66 (Ethyl Acetate:Methanol=19:1);
$^1$H-NMR (DMSO-$d_6$): δ 1.75-2.00 (m, 4 H), 2.55 (s, 3 H), 2.61 (t, 2 H), 4.07 (t, 2 H), 7.21 (d, 2 H), 7.41-7.52 (m, 3 H), 7.66 (d, 2 H), 7.75-7.78 (m, 1 H), 7.91 (s, 1 H), 8.19 (s, 1 H), 8.41 (s, 1 H), 8.50 (s, 1 H), 8.65 (s, 2 H), 9.27 (s, 1 H).

Example 84-41

1-[2-isopropyl-5-(trifluoromethyl)-3-pyridinyl]-3-(2-{4-[2-(2-oxo-1-pyrrolidinyl)-1,3-thiazol-5-yl]phenoxy}-5-pyrimidinyl)urea TCL: Rf 0.59 (Methylene Dichloride:Ethyl Acetate:Methanol=8:4:1);
$^1$H-NMR (DMSO-$d_6$): δ 1.23 (d, 6 H), 2.10-2.23 (m, 2 H), 2.64 (t, 2 H), 3.30-3.45 (m, 1 H), 4.05 (t, 2 H), 7.24 (d, 2 H), 7.68 (d, 2 H), 7.89 (s, 1 H), 8.52-8.56 (m, 1 H), 8.63 (d, 2 H), 8.74 (s, 2 H), 9.34 (s, 1 H).

Example 84-42

1-[2-isopropyl-5-(trifluoromethyl)-3-pyridinyl]-3-(2-{4-[2-(2-oxo-1-piperidinyl)-1,3-thiazol-5-yl]phenoxy}-5-pyrimidinyl)urea TCL: Rf 0.40 (Hexane:Ethyl Acetate=1:4);
$^1$H-NMR (DMSO-$d_6$): δ 1.24 (d, 6 H), 1.83-1.98 (m, 4 H), 2.61 (t, 2 H), 3.34 (m, 1 H), 4.07 (t, 2 H), 7.23 (d, 2 H), 7.67 (d, 2H), 7.92 (s, 1 H), 8.55 (s, 1 H), 8.62 (s, 1 H), 8.70 (s, 1 H), 8.74 (s, 2 H), 9.43 (s, 1 H).

Example 85

The similar procedure as Example 9 was carried out with corresponding amine derivatives in place of the compound prepared in Example 5 and corresponding carbamate derivatives in place of the compound prepared in Example 8 to give the present compounds having the following physical data. Alternatively, the similar procedure as Example 21 was carried out with corresponding 5-bromothiazole derivatives in place of the compound prepared in Example 18 and corresponding boronate ester derivatives in place of the compound prepared in Example 20 to give the present compounds having the following physical data.

Example 85-1

3-[3-{[(2{4-[2-(2-oxo-1-pyrrolidinyl)-1,3-thiazol-5-pyrimidinyl)carbamoyl]amino}-5-(trifluoromethyl)-2-pyridinyl]phenyl dihydrogen phosphate

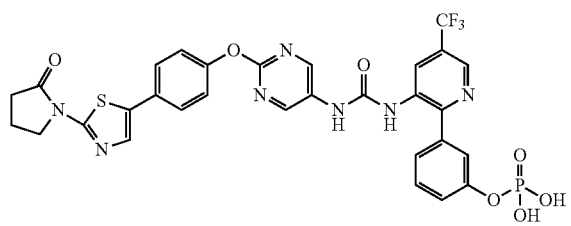 [SMILES: O=C(Nc1cnc(Oc2ccc(-c3cnc(N4CCCC4=O)s3)cc2)nc1)Nc1cc(C(F)(F)F)cnc1-c1cccc(OP(=O)(O)O)c1]

TCL: Rf 0.23 (Ethyl Acetate:Acetic acid:Water=6:1:1);
$^1$H-NMR (DMSO-$d_6$): δ 2.11-2.21 (m, 2 H), 2.61-2.67 (m, 2 H), 4.05 (t, 2 H), 7.19-7.25 (m, 2 H), 7.28-7.33 (m, 1 H), 7.41-7.57 (m, 3 H), 7.64-7.70 (m, 2 H), 7.90 (s, 1 H), 8.49 (s, 1H), 8.68 (s, 2 H), 8.72-8.78 (m, 2 H), 9.45 (s, 1 H).

Example 85-2

1-(2-{4-[2-(2-oxo-1-pyrrolidinyl)-1,3-thiazol-5-yl]phenoxy}-5-pyrimidinyl)-3-[3-(trifluoromethyl)phenyl]urea

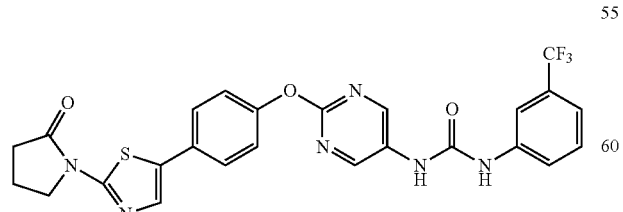

TCL: Rf 0.26 (Ethyl Acetate);
$^1$H-NMR (DMSO-$d_6$): δ 2.11-2.23 (m, 2 H), 2.64 (t, 2 H), 4.05 (t, 2 H), 7.23 (d, 2 H), 7.33 (dd, 1 H), 7.51 (t, 1 H), 7.62 (dd, 1 H), 7.68 (d, 2 H), 7.90 (s, 1 H), 7.97 (s, 1 H), 8.73 (s, 2H), 8.98 (s, 1 H), 9.31 (s, 1 H).

Example 85-3

1-[6-({6-[2-(2-oxo-1-pyrrolidinyl)-1,3-thiazol-5-yl]-3-pyridinyl}oxy)-3-pyridinyl]-3-[2-phenyl-5-(trifluoromethyl)-3-pyridinyl]urea TCL: Rf 0.66 (Ethyl Acetate:Methanol=9:1);
$^1$H-NMR (DMSO-$d_6$): δ 2.13-2.27 (m, 2 H), 2.64 (t, 2 H), 4.05 (t, 2 H), 7.19 (d, 1 H), 7.53-7.67 (m, 6 H), 7.98 (d, 1 H), 8.04 (dd, 1 H), 8.09 (d, 1 H), 8.15 (s, 1 H), 8.29 (s, 1 H), 8.37 (d, 1 H), 8.70 (s, 1 H), 8.78 (s, 1 H), 9.42 (s, 1 H).

Example 85-4

1-[2-(4-{2-[(4S)-4-hydroxy-2-oxo-1-pyrrolidinyl]-1,3-thiazol-5-yl}phenoxy)-5-pyrimidinyl]-3-[2-phenyl-5-(trifluoromethyl)-3-pyridinyl]urea

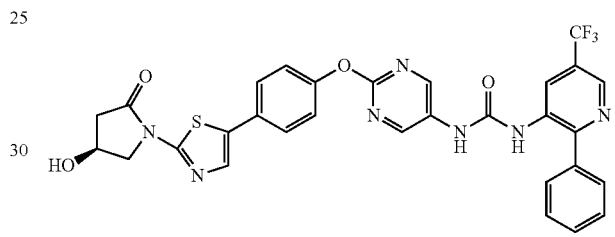

TCL: Rf 0.20 (Ethyl Acetate);
$^1$H-NMR (DMSO-$d_6$): δ 2.38-2.50 (m, 1 H), 2.99 (dd, 1 H), 3.95 (d, 1 H), 4.14 (dd, 1 H), 4.45-4.53 (m, 1 H), 5.49 (d, 1 H), 7.19-7.25 (m, 2 H), 7.49-7.60 (m, 3 H), 7.63-7.70 (m, 4 H), 7.89 (s, 1 H), 8.42 (s, 1 H), 8.67 (s, 2 H), 8.71-8.78 (m, 2H), 9.47 (s, 1 H).

Example 85-5

1-(2-{2-fluoro-4-[2-(2-oxo-1-pyrrolidinyl)-1,3-thiazol-5-yl]phenoxy}-5-pyrimidinyl)-3-[2-phenyl-5-(trifluoromethyl)-3-pyridinyl]urea TCL: Rf 0.50 (Ethyl Acetate);
$^1$H-NMR (DMSO-$d_6$): δ 2.11-2.23 (m, 2 H), 2.64 (t, 2 H), 4.09 (t, 2 H), 7.40-7.67 (m, 7 H), 7.75 (dd, 1 H), 7.99 (s, 1 H), 8.43 (s, 1 H), 8.67 (s, 2 H), 8.72 (d, 1 H), 8.74 (d, 1 H), 9.47 (s, 1 H).

Example 85-6

1-(2-{2-fluoro-4-[2-(2-oxo-1-pyrrolidinyl)-1,3-thiazol-5-yl]phenoxy}-5-pyrimidinyl)-3-[2-(3-pyridinyl)-5-(trifluoromethyl)phenyl]urea TCL: Rf 0.43 (Ethyl Acetate);
$^1$H-NMR (DMSO-$d_6$): δ 2.11-2.24 (m, 2 H), 2.64 (t, 2 H), 4.09 (t, 2 H), 7.37-7.51 (m, 5 H), 7.56 (dd, 1 H), 7.79 (dd, 1 H), 7.90 (dt, 1 H), 7.99 (s, 1 H), 8.25 (s, 1 H), 8.39 (s, 1 H), 8.64 (s, 2 H), 8.67 (dd, 1 H), 9.25 (s, 1 H).

Example 85-7

1-[2-chloro-5-(trifluoromethyl)-3-pyridinyl]-3-(2-{4-[2-(2-oxo-1-pyrrolidinyl)-1,3-thiazol-5-yl]phenoxy}-5-pyrimidinyl)urea TCL: Rf 0.36 (Hexane:Ethyl Acetate=1:2);
$^1$H-NMR (DMSO-$d_6$): δ 2.10-2.24 (m, 2 H), 2.64 (t, 2 H), 4.05 (t, 2 H), 7.24 (d, 2 H), 7.68 (d, 2 H), 7.90 (s, 1 H), 8.49 (s, 1H), 8.77 (s, 2 H), 8.87 (s, 1 H), 8.95 (d, 1 H), 9.78 (s, 1 H).

Example 85-8

1-(2-{4-[2-(2-oxo-1-pyrrolidinyl)-1,3-thiazol-5-yl]phenoxy}-5-pyrimidinyl)-3-[5-(trifluoromethyl)-3-pyridinyl]urea

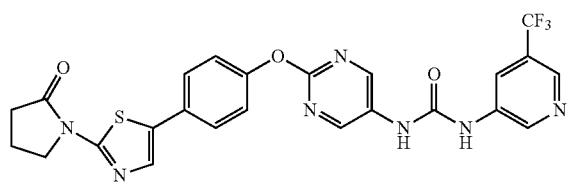 [SMILES: O=C(Nc1cnc(Oc2ccc(-c3cnc(N4CCCC4=O)s3)cc2)nc1)Nc1cncc(C(F)(F)F)c1]

TCL: Rf 0.54 (Hexane:Ethyl Acetate=1:2);
$^1$H-NMR (DMSO-$d_6$): δ 2.11-2.24 (m, 2 H), 2.64 (t, 2 H), 4.05 (t, 2 H), 7.24 (d, 2 H), 7.68 (d, 2 H), 7.90 (s, 1 H), 8.39 (s, 1H), 8.57 (s, 1 H), 8.73 (s, 2 H), 8.82 (d, 1 H), 9.20 (s, 1 H), 9.53 (s, 1 H).

Example 85-9

1-[3-hydroxy-5-(trifluoromethyl)phenyl]-3-(2-{4-[2-(2-oxo-1-pyrrolidinyl)-1,3-thiazol-5-yl]phenoxy}-5-pyrimidinyl)urea

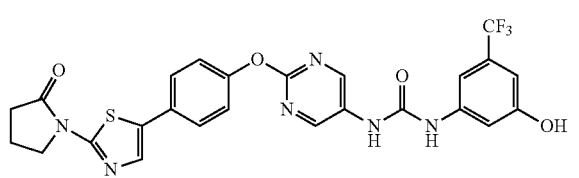 [SMILES: O=C(Nc1cnc(Oc2ccc(-c3cnc(N4CCCC4=O)s3)cc2)nc1)Nc1cc(O)cc(C(F)(F)F)c1]

TCL: Rf 0.79 (Ethyl Acetate:Methanol=10:1);
$^1$H-NMR (DMSO-$d_6$): δ 2.16 (quint, 2 H), 2.64 (t, 2 H), 4.05 (t, 2 H), 6.65 (s, 1 H), 7.16-7.31 (m, 4 H), 7.62-7.71 (m, 2 H), 7.90 (s, 1 H), 8.71 (s, 2 H), 8.89 (s, 1 H), 9.20 (s, 1 H), 10.1 (s, 1 H).

Example 85-10

1-[2-cyclopropyl-5-(trifluoromethyl)-3-pyridinyl]-3-(2-{4-[2-(2-oxo-1-pyrrolidinyl)-1,3-thiazol-5-yl]phenoxy}-5-pyrimidinyl)urea

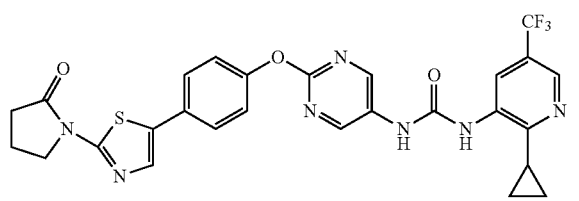 [SMILES: O=C(Nc1cnc(Oc2ccc(-c3cnc(N4CCCC4=O)s3)cc2)nc1)Nc1cc(C(F)(F)F)cnc1C1CC1]

TCL: Rf 0.43 (Ethyl Acetate);
$^1$H-NMR (DMSO-$d_6$): δ 1.08 (t, 4 H), 2.12-2.23 (m, 2 H), 2.27-2.30 (m, 1 H), 2.64 (t, 2 H), 4.05 (t, 2 H), 7.24 (d, 2 H), 7.68 (d, 2 H), 7.90 (s, 1 H), 8.48 (d, 2 H), 8.74 (s, 2 H), 8.91 (s, 1 H), 9.37 (s, 1 H).

Example 85-11

1-(2-{4-[2-(2-oxo-1-pyrrolidinyl)-1,3-thiazol-5-yl]phenoxy})-5-pyrimidinyl)-3-[4-(trifluoromethyl)-2-pyridinyl]urea TCL: Rf 0.42 (Ethyl Acetate);
$^1$H-NMR (DMSO-$d_6$): δ 2.11-2.24 (m, 2 H), 2.64 (t, 2 H), 4.05 (t, 2 H), 7.24 (d, 2 H), 7.39 (dd, 1 H), 7.68 (d, 2 H), 7.90 (s, 1H), 7.99 (s, 1 H), 8.54 (d, 1 H), 8.78 (s, 2 H), 9.90 (s, 1 H), 9.94 (s, 1 H).

Example 85-12

1-[2-(1-oxido-3-pyridinyl)-5-(trifluoromethyl)-3-pyridinyl]-3-(6-{4-[2-(2-oxo-1-pyrrolidinyl)-1,3-thiazol-5-yl]phenoxy}-3-pyridinyl)urea

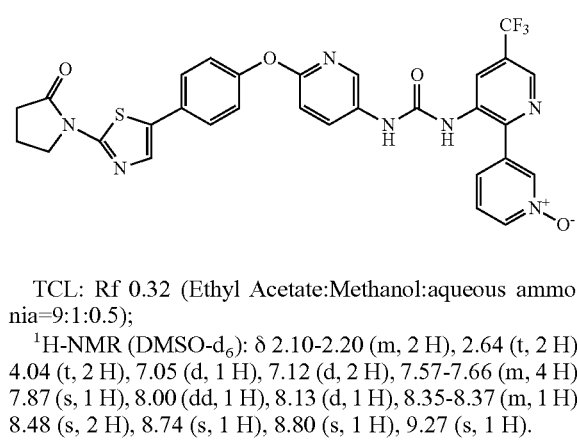

TCL: Rf 0.32 (Ethyl Acetate:Methanol:aqueous ammonia=9:1:0.5);
$^1$H-NMR (DMSO-$d_6$): δ 2.10-2.20 (m, 2 H), 2.64 (t, 2 H), 4.04 (t, 2 H), 7.05 (d, 1 H), 7.12 (d, 2 H), 7.57-7.66 (m, 4 H), 7.87 (s, 1 H), 8.00 (dd, 1 H), 8.13 (d, 1 H), 8.35-8.37 (m, 1 H), 8.48 (s, 2 H), 8.74 (s, 1 H), 8.80 (s, 1 H), 9.27 (s, 1 H).

Example 85-13

1-[2-(1-oxido-3-pyridinyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea TCL: Rf 0.18 (Ethyl Acetate:Methanol:aqueous ammonia=9:1:0.5);
$^1$H-NMR (DMSO-$d_6$): δ 2.10-2.25 (m, 2 H), 2.64 (t, 2 H), 4.05 (t, 2 H), 7.22 (d, 2 H), 7.57-7.60 (m, 2 H), 7.67 (d, 2 H), 7.90 (s, 1 H), 8.34-8.37 (m, 1 H), 8.48 (s, 1 H), 8.62 (s, 1 H), 8.68 (s, 2 H), 8.77-8.78 (m, 2 H), 9.34 (s, 1 H).

Example 85-14

1-(6-{2-fluoro-4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea TCL: Rf 0.50 (Ethyl Acetate);
$^1$H-NMR (DMSO-$d_6$): δ 2.11-2.23 (m, 2 H), 2.64 (t, 2 H), 4.05 (t, 2 H), 7.11 (d, 1 H), 7.31 (t, 1 H), 7.45 (dd, 1 H), 7.53-7.60 (m, 3 H), 7.64 (dd, 1 H), 7.70 (dd, 2 H), 7.98 (s, 1 H), 8.02-8.08 (m, 1 H), 8.29 (s, 1 H), 8.70 (s, 1 H), 8.78 (s, 1 H), 9.38 (s, 1 H).

Example 85-15

1-(6-{2-fluoro-4-[2-(2-oxo-1-pyrrolidinyl)-1,3-thiazol-5-yl]phenoxy}-3-pyridinyl)-3-[2-(3-pyridinyl)-5-(trifluoromethyl)phenyl]urea TCL: Rf 0.46 (Ethyl Acetate);
$^1$H-NMR (DMSO-$d_6$): δ 2.11-2.22 (m, 2 H), 2.64 (t, 2 H), 4.05 (t, 2 H), 7.10 (d, 1 H), 7.30 (t, 1 H), 7.46 (dd, 1 H), 7.48 (s, 2H), 7.56 (dd, 1 H), 7.71 (dd, 1 H), 7.88 (dt, 1 H), 7.98 (d, 2H), 8.02 (d, 1 H), 8.09 (s, 1 H), 8.42 (s, 1 H), 8.64 (d, 1 H), 8.68 (d, 1 H), 9.15 (s, 1 H).

Example 85-16

1-[2-(4-{2-[2-(2-hydroxy-2-propanyl)-1-pyrrolidinyl]-1,3-thiazol-5-yl}phenoxy)-5-pyrimidinyl]-3-[2-phenyl-5-(trifluoromethyl)-3-pyridinyl]urea

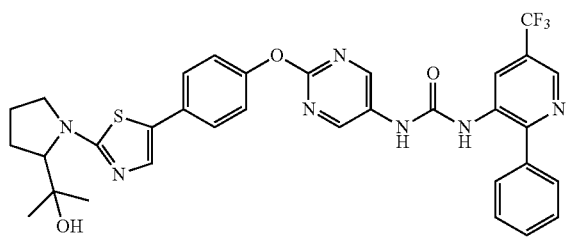 [SMILES: CC(C)(O)C1CCCN1c1ncc(-c2ccc(Oc3ncc(NC(=O)Nc4cc(C(F)(F)F)cnc4-c4ccccc4)cn3)cc2)s1]

TCL: Rf 0.35 (Chloroform:Methanol=19:1);
$^1$H-NMR (DMSO-$d_6$): δ 0.94 (s, 6 H), 1.56-1.72 (m, 1 H), 1.83-2.16 (m, 3 H), 3.35-3.54 (m, 2 H), 3.65 (t, 1 H), 7.09-7.15 (m, 2 H), 7.21 (s, 1 H), 7.35-7.50 (m, 5 H), 7.58-7.64 (m, 3 H), 8.61-8.68 (m, 4 H), 8.86 (d, 1 H), 8.90 (s, 1H).

Example 85-17

1-[2-(2-methyl-4-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.47 (Ethyl Acetate);
$^1$H-NMR (DMSO-$d_6$): δ 2.11-2.22 (m, 2H), 2.54 (s, 3 H), 2.64 (t, 2 H), 4.05 (t, 2 H), 7.22 (d, 2 H), 7.27 (d, 1 H), 7.35 (s, 1H), 7.44-7.52 (m, 2 H), 7.67 (d, 2 H), 7.89 (s, 1 H), 8.17 (s, 1 H), 8.42 (s, 1 H), 8.59 (d, 1 H), 8.65 (s, 2 H), 9.29 (s, 1H).

Example 85-18

1-(2-{4-[2-(2-oxo-1-pyrrolidinyl)-1,3-thiazol-5-yl]phenoxy}-5-pyrimidinyl)-3-[2-(4-piperidinyl)-5-(trifluoromethyl)phenyl]urea

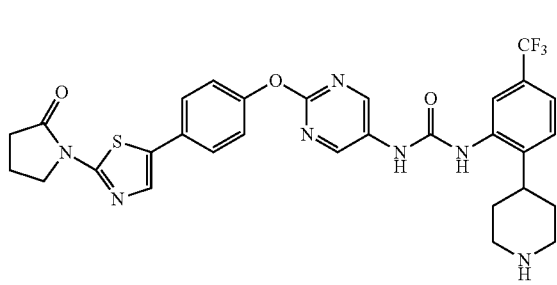 [SMILES: O=C(Nc1cnc(Oc2ccc(-c3cnc(N4CCCC4=O)s3)cc2)nc1)Nc1cc(C(F)(F)F)ccc1C1CCNCC1]

TCL: Rf 0.19 (Ethyl Acetate:Methanol:aqueous ammonia=9:1:0.5);
$^1$H-NMR (DMSO-$d_6$): δ 1.40-1.70 (m, 4 H), 2.10-2.20 (m, 2 H), 2.61-2.75 (m, 4 H), 2.85-3.10 (m, 3 H), 4.05 (t, 2 H), 7.22 (d, 2 H), 7.39-7.48 (m, 2 H), 7.67 (d, 2 H), 7.89 (s, 1 H), 8.05 (s, 1 H), 8.55 (s, 1 H), 8.73 (s, 2 H), 9.40 (s, 1 H).

Example 85-19

1-(2-{4-[2-(2-oxo-1-pyrrolidinyl)-1,3-thiazol-5-yl]phenoxy}-5-pyrimidinyl)-3-[2-(1,2,3,6-tetrahydro-4-pyridinyl)-5-(trifluoromethyl)phenyl]urea TCL: Rf 0.29 (Ethyl Acetate:Methanol:aqueous ammonia=9:1:0.5);
$^1$H-NMR (DMSO-$d_6$): δ 2.14-2.20 (m, 4 H), 2.64 (t, 2 H), 2.94-2.99 (m, 2 H), 3.38 (s, 2 H), 4.05 (t, 2 H), 5.83 (s, 1 H), 7.22 (d, 2 H), 7.25-7.40 (m, 2 H), 7.67 (d, 2H), 7.89 (s, 1H), 8.09 (s, 1 H), 8.30 (s, 1 H), 8.71 (s, 2 H), 9.60 (s, 1 H).

Example 85-20

1-(4-methyl-6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea TCL: Rf 0.51 (Ethyl Acetate);
$^1$H-NMR (DMSO-$d_6$): δ 2.10-2.23 (m, 5 H), 2.64 (t, 2 H), 4.05 (t, 2 H), 6.96 (s, 1 H), 7.11 (d, 2 H), 7.52-7.57 (m, 3 H), 7.66 (d, 3 H), 7.69 (dd, 1 H), 7.86 (s, 1 H), 8.24 (s, 1 H), 8.52 (s, 1 H), 8.59 (s, 1 H), 8.69 (s, 2 H).

Example 85-21

1-(4-methyl-6-{4-[2-(2-oxo-1-pyrrolidinyl)-1,3-thiazol-5-yl]phenoxy}-3-pyridinyl)-3-[2-(3-pyridinyl)-5-(trifluoromethyl)phenyl]urea TCL: Rf 0.46 (Ethyl Acetate);
$^1$H-NMR (DMSO-$d_6$): δ 2.10-2.24 (m, 2 H), 2.17 (s, 3 H), 2.64 (t, 2 H), 4.05 (t, 2 H), 6.94 (s, 1 H), 7.11 (d, 2 H), 7.49 (s, 2H), 7.56 (dd, 1 H), 7.64 (d, 2 H), 7.86 (s, 1 H), 7.90 (dd, 1H), 8.19 (s, 1 H), 8.30 (d, 2 H), 8.37 (s, 1 H), 8.67 (d, 2 H).

Example 85-22

1-[2-(1-methyl-4-piperidinyl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.21 (Ethyl Acetate:Methanol:aqueous ammonia=9:1:0.5);
$^1$H-NMR (DMSO-$d_6$): δ 1.60-1.80 (m, 4 H), 1.98-2.20 (m, 7 H), 2.60-2.90 (m, 5 H), 4.05 (t, 2 H), 7.23 (d, 2 H), 7.41 (d, 1H), 7.50 (d, 1 H), 7.68 (d, 2 H), 7.90 (s, 1 H), 8.05 (s, 1 H), 8.44 (s, 1 H), 8.73 (s, 2 H), 9.28 (s, 1 H).

Example 85-23

1-(2-{4-[2-(2-oxo-1-pyrrolidinyl)-1,3-thiazol-5-yl]phenoxy}-5-pyrimidinyl)-3-[2-(1H-pyrazol-3-yl)-5-(trifluoromethyl)phenyl]urea

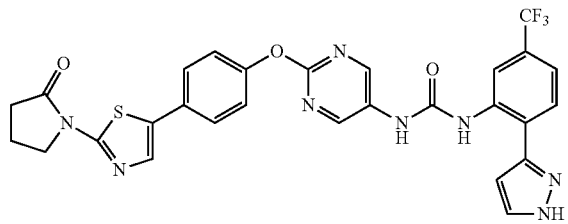 [SMILES: O=C(Nc1cnc(Oc2ccc(-c3cnc(N4CCCC4=O)s3)cc2)nc1)Nc1cc(C(F)(F)F)ccc1-c1cc[nH]n1]

TCL: Rf 0.19 (Ethyl Acetate);
¹H-NMR (DMSO-$d_6$): δ 2.23-2.32 (m, 2 H), 2.71 (s, 2 H), 4.18 (t, 2 H), 5.95 (d, 1 H), 7.16 (d, 2 H), 7.26 (s, 2 H), 7.40 (d, 2H), 7.52-7.60 (m, 3 H), 7.89 (s, 1 H), 8.55 (s, 2 H), 8.85 (s, 1 H), 9.29 (d, 1 H).

Example 85-24

1-(2-methyl-6-{4-[2-(2-oxo-1-pyrrolidinyl)-1,3-thiazol-5-yl]phenoxy}-3-pyridinyl)-3-[2-(3-pyridinyl)-5-(trifluoromethyl)phenyl]urea TCL: Rf 0.35 (Ethyl Acetate:Methanol=19:1);
¹H-NMR (DMSO-$d_6$): δ 2.13-2.22 (m, 5 H), 2.63 (t, 2 H), 4.04 (t, 2 H), 6.84 (d, 1 H), 7.10 (d, 2 H), 7.49 (s, 2 H), 7.57 (dd, 1H), 7.62 (d, 2 H), 7.86 (s, 1 H), 7.89-7.93 (m, 1 H), 8.01 (d, 1 H), 8.32 (s, 1 H), 8.34 (s, 1 H), 8.41 (s, 1 H), 8.66-8.68 (m, 2 H).

Example 85-25

1-(2-{4-[2-(2-oxo-1-pyrrolidinyl)-1,3-thiazol-5-yl]phenoxy}-5-pyrimidinyl)-3-[3-(trifluoromethyl)cyclohexyl]urea TCL: Rf 0.41 (Ethyl Acetate);
¹H-NMR (DMSO-$d_6$): δ 1.08-2.05 (m, 9 H), 2.16 (m, 2 H), 2.64 (t, 2 H), 3.55 (m, 1 H), 4.05 (t, 2 H), 6.43 (d, 1 H), 7.19 (d, 2H), 7.65 (d, 2 H), 7.88 (s, 1 H), 8.56 (s, 1 H), 8.62 (s, 2 H).

Example 85-26

2-{[(2-{4-[2-(2-oxo-1-pyrrolidinyl)-1,3-thiazol-5-yl]phenoxy}-5-pyrimidinyl)carbamoyl]amino}-4-(trifluoromethyl)benzoic acid

TCL: Rf 0.48 (Ethyl Acetate:Methanol: Acetic acid=9:1:0.1);
¹H-NMR (DMSO-$d_6$): δ 2.11-2.23 (m, 2 H), 2.64 (t, 2 H), 4.05 (t, 2 H), 7.23 (d, 2 H), 7.40 (d, 1 H), 7.67 (d, 2 H), 7.89 (s, 1H), 8.14 (d, 1 H), 8.73 (s, 2 H), 8.80 (s, 1 H), 10.3 (s, 1 H), 10.7 (s, 1 H), 14.1 (s, 1 H).

Example 85-27

1-[2-(2-hydroxy-2-propanyl)-5-(trifluoromethyl)phenyl]-3-(2-{4-[2-(2-oxo-1-pyrrolidinyl)-1,3-thiazol-5-yl]phenoxy}-5-pyrimidinyl)urea

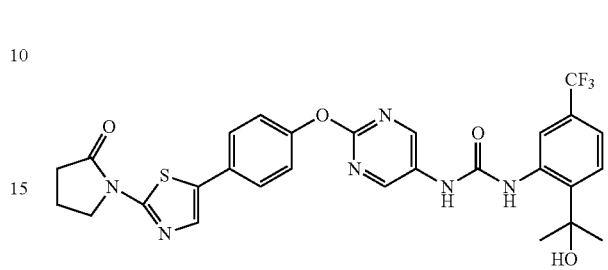

TCL: Rf 0.54 (Ethyl Acetate);
¹H-NMR (DMSO-$d_6$): δ 1.57 (s, 6 H), 2.10-2.23 (m, 2 H), 2.64 (t, 2 H), 4.05 (t, 2 H), 6.21 (s, 1 H), 7.22 (d, 2 H), 7.29 (d, 1H), 7.47 (d, 1 H), 7.67 (d, 2 H), 7.89 (s, 1 H), 8.36 (s, 1 H), 8.73 (s, 2 H), 9.88 (s, 1 H), 10.0 (s, 1 H).

Example 85-28

1-(2-methyl-6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea TCL: Rf 0.70 (Ethyl Acetate:Methanol=19:1);
¹H-NMR (DMSO-$d_6$): δ 2.10-2.25 (m, 5 H), 2.64 (t, 2 H), 4.05 (t, 2 H), 6.86 (d, 1 H), 7.11 (d, 2 H), 7.55-7.71 (m, 7 H), 7.87 (s, 1 H), 8.06 (d, 1 H), 8.57 (s, 1 H), 8.63 (s, 1 H), 8.71 (s, 2 H).

Example 85-29

1-[2-(1H-imidazol-1-yl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.34 (Ethyl Acetate);
¹H-NMR (DMSO-$d_6$): δ 2.10-2.23 (m, 2 H), 2.64 (t, 2 H), 4.05 (t, 2 H), 7.19 (d, 2 H), 7.23 (s, 1 H), 7.49 (s, 1 H), 7.54 (s, 2H), 7.67 (d, 2 H), 7.90 (s, 1 H), 7.97 (s, 1 H), 8.32 (s, 1 H), 8.50 (s, 1 H), 8.66 (s, 2 H), 9.42 (s, 1 H).

Example 85-30

1-[3,5-bis(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.54 (Ethyl Acetate);
¹H-NMR (DMSO-$d_6$): δ 2.10-2.22 (m, 2 H), 2.64 (t, 2 H), 4.05 (t, 2 H), 7.24 (d, 2 H), 7.62-7.72 (m, 3 H), 7.90 (s, 1 H), 8.14 (s, 2 H), 8.72 (s, 2 H), 9.20 (s, 1 H), 9.66 (s, 1 H).

Example 85-31

1-(2-{4-[2-(2-oxo-1-pyrrolidinyl)-1,3-thiazol-5-yl]phenoxy}-5-pyrimidinyl)-3-[2-phenyl-5-(trifluoromethyl)cyclohexyl]urea TCL: Rf 0.62 (Ethyl Acetate);
¹H-NMR (DMSO-$d_6$): δ 1.34-1.87 (m, 8 H), 2.10-2.25 (m, 2 H), 2.64 (t, 2 H), 3.85-4.00 (m, 1 H), 4.05 (t, 2 H), 6.22 (d, 1H), 7.11-7.20 (m, 3 H), 7.22-7.34 (m, 4 H), 7.64 (d, 2 H), 7.88 (s, 1 H), 8.45 (s, 1 H), 8.51 (s, 2 H).

Example 85-32

1-(2-{4-[2-(2-methyl-5-oxo-1-pyrrolidinyl)-1,3-thiazol-5-yl]phenoxy}-5-pyrimidinyl)-3-[2-phenyl-5-(trifluoromethyl)-3-pyridinyl]urea TCL: Rf 0.54 (Ethyl Acetate);
$^1$H-NMR (DMSO-$d_6$): δ 1.41 (d, 3 H), 1.77-1.88 (m, 1 H), 2.29-2.58 (m, 2 H), 2.81-2.90 (m, 1 H), 4.60-4.71 (m, 1 H), 7.22 (d, 2 H), 7.52-7.60 (m, 3 H), 7.63-7.70 (m, 4 H), 7.90 (s, 1 H), 8.43 (s, 1 H), 8.67 (s, 2 H), 8.71-8.78 (m, 2 H), 9.47 (s, 1H).

Example 85-33

1-(2-{4-[2-(2-methyl-5-oxo-1-pyrrolidinyl)-1,3-thiazol-5-yl]phenoxy}-5-pyrimidinyl)-3-[2-(3-pyridinyl)-5-(trifluoromethyl)phenyl]urea

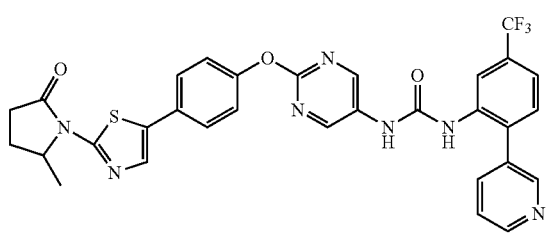 [SMILES: CC1CCC(=O)N1c1ncc(-c2ccc(Oc3ncc(NC(=O)Nc4cc(C(F)(F)F)ccc4-c4cccnc4)cn3)cc2)s1]

TCL: Rf 0.14 (Ethyl Acetate);
$^1$H-NMR (DMSO-$d_6$): δ 1.42 (d, 3 H), 1.76-1.91 (m, 1 H), 2.32-2.58 (m, 2 H), 2.78-2.93 (m, 1 H), 4.60-4.70 (m, 1 H), 7.19-7.25 (m, 2 H), 7.47-7.58 (m, 3 H), 7.64-7.69 (m, 2 H), 7.86-7.92 (m, 2 H), 8.24 (s, 1 H), 8.38 (s, 1 H), 8.62-8.72 (m, 4H), 9.25 (s, 1 H).

Example 85-34

1-(2-{4-[2-(2-oxo-1-pyrrolidinyl)-1,3-thiazol-5-yl]phenoxy}-5-pyrimidinyl)-3-[2-(3-pyridinyl)-5-(trifluoromethyl)cyclohexyl]urea TCL: Rf 0.74 (Ethyl Acetate);
$^1$H-NMR (DMSO-$d_6$): δ 1.38-2.21 (m, 8 H), 2.11-2.24 (m, 2 H), 2.64 (t, 2 H), 3.92-4.03 (m, 1 H), 4.05 (t, 2 H), 6.34 (d, 1H), 7.17 (d, 2 H), 7.30 (dd, 1 H), 7.58-7.70 (m, 3 H), 7.89 (s, 1 H), 8.37 (dd, 1 H), 8.45 (s, 2 H), 8.50 (s, 2 H).

Example 85-35

1-[5-(2-methyl-2-propanyl)-2-(3-pyridinyl)phenyl]-3-(2-{4-[2-(2-oxo-1-pyrrolidinyl)-1,3-thiazol-5-yl]phenoxy}-5-pyrimidinyl)urea

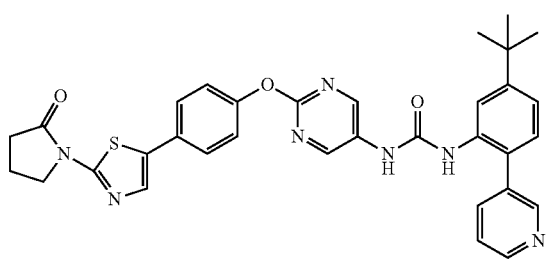 [SMILES: CC(C)(C)c1ccc(-c2cccnc2)c(NC(=O)Nc2cnc(Oc3ccc(-c4cnc(N5CCCC5=O)s4)cc3)nc2)c1]

TCL: Rf 0.27 (Ethyl Acetate:Methanol=9:1);
$^1$H-NMR (DMSO-$d_6$): δ 1.31 (s, 9 H), 2.11-2.21 (m, 2 H), 2.66 (t, 2 H), 4.05 (t, 2 H), 7.19-7.28 (m, 4 H), 7.48 (dd, 1 H), 7.66 (d, 2 H), 7.79-7.85 (m, 2 H), 7.89 (s, 1 H), 8.06 (s, 1 H), 8.56-8.60 (m, 4 H), 9.03 (s, 1 H).

Example 85-36

1-(5-methyl-6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea TCL: Rf 0.61 (Ethyl Acetate:Methanol=9:1);
$^1$H-NMR (DMSO-$d_6$): δ 2.10-2.28 (m, 5 H), 2.63 (t, 2 H), 4.04 (t, 2 H), 7.07 (d, 2 H), 7.54-7.66 (m, 7 H), 7.85-7.93 (m, 3 H), 8.27 (s, 1 H), 8.69 (s, 1 H), 8.79 (s, 1 H), 9.39 (s, 1 H).

Example 85-37

1-(5-methyl-6-{4-[2-(2-oxo-1-pyrrolidinyl)-1,3-thiazol-5-yl]phenoxy}-3-pyridinyl)-3-[2-(3-pyridinyl)-5-(trifluoromethyl)phenyl]urea TCL: Rf 0.56 (Ethyl Acetate);
$^1$H-NMR (DMSO-$d_6$): δ 2.10-2.27 (m, 5 H), 2.63 (t, 2 H), 4.04 (t, 2 H), 7.06 (d, 2 H), 7.47-7.62 (m, 5 H), 7.84-7.93 (m, 4 H), 8.07 (s, 1 H), 8.43 (s, 1 H), 8.63-8.68 (m, 2 H), 9.11 (s, 1H).

Example 85-38

1-[2-(1-methyl-6-oxo-1,6-dihydro-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea

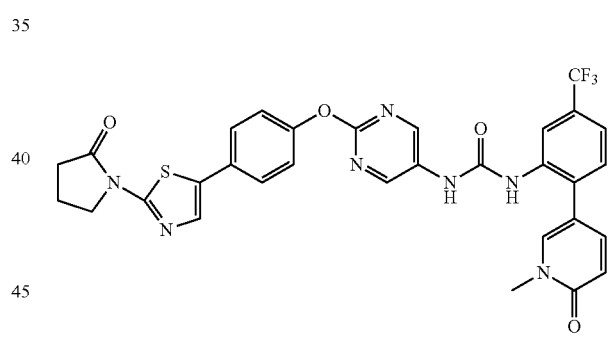

TCL: Rf 0.65 (Ethyl Acetate:Methanol=9:1);
$^1$H-NMR (DMSO-$d_6$): δ 2.10-2.21 (m, 2 H), 2.64 (t, 2 H), 3.49 (s, 3 H), 4.05 (t, 2 H), 6.53 (d, 1 H), 7.23 (d, 2 H), 7.44 (d, 2H), 7.47 (dd, 1 H), 7.67 (dd, 2 H), 7.90 (s, 1 H), 7.95 (d, 1H), 8.25 (s, 1 H), 8.43 (s, 1 H), 8.69 (s, 2 H), 9.31 (s, 1 H).

Example 85-39

1-(6-{4-[2-(ethylamino)-1,3-thiazol-5-yl]phenoxy}-3-pyridinyl)-3-[3-(trifluoromethyl)phenyl]urea

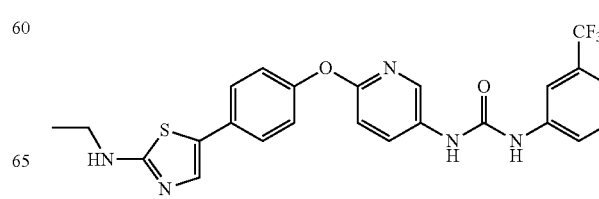

TCL: Rf 0.75 (Ethyl Acetate:Methanol=19:1);
$^1$H-NMR (DMSO-d$_6$): δ 1.16 (t, 3 H), 3.20-3.32 (m, 2 H), 6.99-7.06 (m, 3 H), 7.30 (d, 1 H), 7.39-7.59 (m, 5 H), 7.69 (t, 1H), 7.97-8.01 (m, 2 H), 8.18 (d, 1 H), 8.88 (s, 1 H), 9.14 (s, 1 H).

Example 85-40

1-(2-{4-[2-(ethylamino)-1,3-thiazol-5-yl]phenoxy}-5-pyrimidinyl)-3-[3-(trifluoromethyl)phenyl]urea TCL: Rf 0.48 (Methylene Dichloride:Ethyl Acetate: Methanol=8:4:1);
$^1$H-NMR (DMSO-d$_6$): δ 1.17 (t, 3 H), 3.20-3.30 (m, 2 H), 7.14 (d, 2 H), 7.32 (d, 1 H), 7.42-7.55 (m, 4 H), 7.62 (d, 1 H), 7.72 (t, 1 H), 8.97 (s, 1 H), 8.70 (s, 2 H), 9.03 (s, 1 H), 9.35 (s, 1 H).

Example 85-41

1-(2-{4-[2-(2-oxo-1-pyrrolidinyl)-1,3-thiazol-5-yl]phenoxy}-5-pyrimidinyl)-3-[3-(3-pyridinyloxy)-5-(trifluoromethyl)phenyl]urea

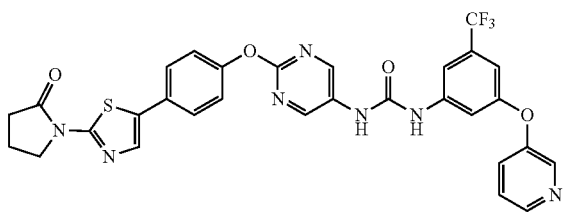 [SMILES: O=C(Nc1cnc(Oc2ccc(-c3cnc(N4CCCC4=O)s3)cc2)nc1)Nc1cc(Oc2cccnc2)cc(C(F)(F)F)c1]

TCL: Rf 0.44 (Ethyl Acetate);
$^1$H-NMR (DMSO-d$_6$): δ 2.11-2.24 (m, 2 H), 2.64 (t, 2 H), 4.05 (t, 2 H), 6.99 (s, 1 H), 7.23 (d, 2 H), 7.36 (s, 1 H), 7.47 (dd, 1H), 7.56 (dt, 1 H), 7.64-7.70 (m, 3 H), 7.90 (s, 1H), 8.42-8.50 (m, 2 H), 8.68 (s, 2 H), 8.98 (s, 1 H), 9.43 (s, 1 H).

Example 85-42

1-[2-(3-hydroxy-3-methyl-1-butyn-1-yl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea

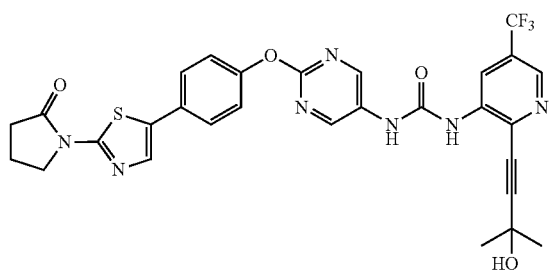 [SMILES: CC(C)(O)C#Cc1ncc(C(F)(F)F)cc1NC(=O)Nc1cnc(Oc2ccc(-c3cnc(N4CCCC4=O)s3)cc2)nc1]

TCL: Rf 0.45 (Ethyl Acetate);
$^1$H-NMR (DMSO-d$_6$): δ 1.55 (s, 6 H), 2.10-2.23 (m, 2 H), 2.64 (t, 2 H), 4.05 (t, 2 H), 5.72 (s, 1 H), 7.23 (d, 2 H), 7.67 (dd, 2H), 7.90 (s, 1 H), 8.47 (s, 1 H), 8.59 (d, 1 H), 8.68 (d, 1 H), 8.74 (s, 2 H), 9.89 (s, 1 H).

Example 85-43

1-[2-(2-hydroxy-2-propanyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea TCL: Rf 0.54 (Ethyl Acetate);
$^1$H-NMR (DMSO-d$_6$): δ 1.58 (s, 6 H), 2.11-2.24 (m, 2 H), 2.64 (t, 2 H), 4.05 (t, 2 H), 6.44 (s, 1 H), 7.23 (d, 2 H), 7.68 (d, 2H), 7.90 (s, 1 H), 8.50 (d, 1 H), 8.74 (s, 2 H), 8.78 (d, 1 H), 10.0 (s, 1 H), 10.2 (s, 1 H).

Example 85-44

N-ethyl-N-[5-(4-{[5-({([2-phenyl-5-(trifluoromethyl)-3-pyridinyl]carbamoyl}amino)-2-pyridinyl]oxy}phenyl)-1,3-thiazol-2-yl]propanamide

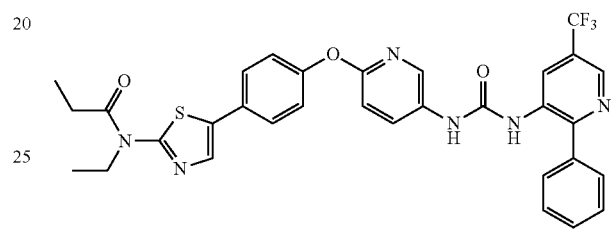

TCL: Rf 0.29 (Hexane:Ethyl Acetate=1:1);
$^1$H-NMR (DMSO-d$_6$): δ 1.16 (t, 3 H), 1.28 (t, 3 H), 2.75 (q, 2H), 4.19 (q, 2 H), 7.04 (d, 1 H), 7.13 (d, 2 H), 7.53-7.67 (m, 7 H), 7.86 (s, 1 H), 8.01 (dd, 1 H), 8.11 (d, 1 H), 8.29 (s, 1H), 8.70 (d, 1 H), 8.79 (s, 1 H), 9.40 (s, 1 H).

Example 85-45

1-[2-(6-oxo-1,6-dihydro-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.23 (Ethyl Acetate);
$^1$H-NMR (DMSO-d$_6$): δ 2.11-2.22 (m, 2 H), 2.64 (t, 2 H), 4.05 (t, 2 H), 6.46 (d, 1 H), 7.23 (d, 2 H), 7.46 (s, 1 H), 7.48 (dd, 2H), 7.67 (d, 2 H), 7.90 (s, 1 H), 8.23 (s, 1 H), 8.38 (s, 1 H), 8.69 (s, 2 H), 9.33 (s, 1 H), 11.9 (s, 1 H).

Example 85-46

1-[2-methoxy-5-(trifluoromethyl)-3-pyridinyl]-3-(2-{4-[2-(2-oxo-1-pyrrolidinyl)-1,3-thiazol-5-yl]phenoxy}-5-pyrimidinyl)urea

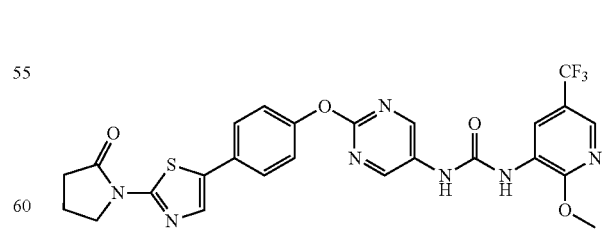

TCL: Rf 0.56 (Ethyl Acetate);
$^1$H-NMR (DMSO-d$_6$): δ 2.11-2.21 (m, 2 H), 2.64 (t, 2 H), 3.49 (s, 3 H), 4.06 (t, 2 H), 7.23 (d, 2 H), 7.67 (dd, 2 H), 7.90 (s, 1H), 8.19 (s, 1 H), 8.66 (d, 1 H), 8.72 (s, 2 H), 8.84 (s, 1 H), 9.61 (s, 1 H).

Example 85-47

1-[5-(3-oxetanyl)-2-phenyl-3-pyridinyl]-3-(2-{4-[2-(2-oxo-1-pyrrolidinyl)-1,3-thiazol-5-yl]phenoxy}-5-pyrimidinyl)urea

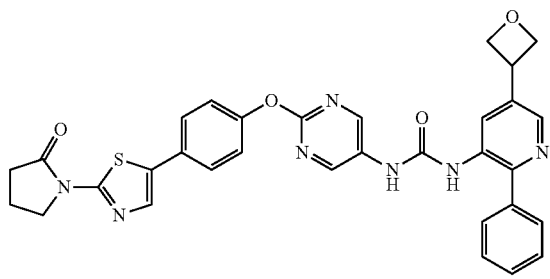 [SMILES: O=C(Nc1cnc(Oc2ccc(-c3cnc(N4CCCC4=O)s3)cc2)nc1)Nc1cc(C2COC2)cnc1-c1ccccc1]

TCL: Rf 0.35 (Ethyl Acetate);
$^1$H-NMR (DMSO-$d_6$): δ 2.13-2.24 (m, 2 H), 2.64 (t, 2 H), 4.05 (t, 2 H), 4.33 (m, 1 H), 4.65 (t, 2 H), 4.98 (dd, 2 H), 7.22 (d, 2H), 7.44-7.53 (m, 3 H), 7.60 (dd, 2 H), 7.67 (d, 2 H), 7.89 (s, 1 H), 8.21 (s, 1 H), 8.39 (d, 2 H), 8.66 (s, 2 H), 9.31 (s, 1H).

Example 85-48

1-(2-{4-[2-(2-oxo-1-azetidinyl)-1,3-thiazol-5-yl]phenoxy)}-5-pyrimidinyl)-3-[2-(3-pyridinyl)-5-(trifluoromethyl)phenyl]urea

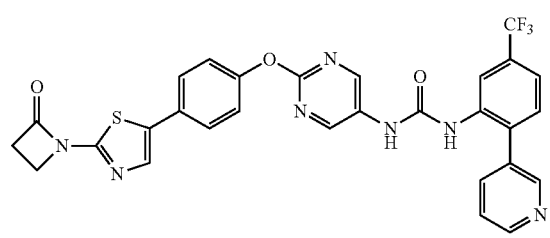 [SMILES: O=C(Nc1cnc(Oc2ccc(-c3cnc(N4CCC4=O)s3)cc2)nc1)Nc1cc(C(F)(F)F)ccc1-c1cccnc1]

TCL: Rf 0.24 (Chloroform:Methanol=19:1);
$^1$H-NMR (DMSO-$d_6$): δ 3.24-3.27 (m, 2 H), 3.87 (t, 2H), 7.20-7.25 (m, 2 H), 7.47-7.58 (m, 3H), 7.63-7.69 (m, 2 H), 7.85 (s, 1H), 7.89 (dt, 1 H), 8.24 (s, 1H), 8.38 (s, 1 H), 8.62-8.68 (m, 4H), 9.24 (s, 1 H).

Example 85-49

1-(2-{4-[2-(ethylamino)-1,3-thiazol-5-yl]phenoxy}-5-pyrimidinyl)-3-[2-isopropyl-5-(trifluoromethyl)-3-pyridinyl]urea

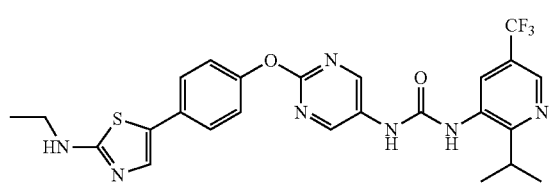 [SMILES: CCNc1ncc(-c2ccc(Oc3ncc(NC(=O)Nc4cc(C(F)(F)F)cnc4C(C)C)cn3)cc2)s1]

TCL: Rf 0.25 (Hexane:Ethyl Acetate=1:4);
$^1$H-NMR (DMSO-$d_6$): δ 1.14-1.25 (m, 9 H), 3.20-3.40 (m, 3H), 7.14 (d, 2 H), 7.43-7.46 (m, 3H), 7.72 (t, 1 H), 8.54 (s, 1H), 8.61 (s, 1 H), 8.65 (s, 1 H), 8.72 (s, 2H), 9.33 (s, 1 H).

Example 85-50

1-(2-{4-[2-(2-oxo-1-pyrrolidinyl)-1,3-thiazol-5-yl]phenoxy}-5-pyrimidinyl)-3-[2-(3-pyridinyloxy)-5-(trifluoromethyl)phenyl]urea TCL: Rf 0.56 (Ethyl Acetate:Methanol=9:1);
$^1$H-NMR (DMSO-$d_6$): δ 2.11-2.23 (m, 2 H), 2.64 (t, 2H), 4.05 (t, 2 H), 7.01 (d, 1H), 7.23 (d, 2 H), 7.32 (dd, 1H), 7.49 (dd, 1 H), 7.64 (dd, 1 H), 7.68 (d, 2 H), 7.89 (s, 1 H), 8.47 (d, 1H), 8.54 (d, 1 H), 8.65 (s, 1 H), 8.71 (s, 2 H), 9.02 (s, 1 H), 9.48 (s, 1 H).

Example 85-51

1-[5-(3-oxetanyl)-2-(3-pyridinyl)phenyl]-3-(2-{4-[2-(2-oxo-1-pyrrolidinyl)-1,3-thiazol-5-yl]phenoxy}-5-pyrimidinyl)urea TCL: Rf 0.52 (Ethyl Acetate:Methanol=9:1);
$^1$H-NMR (DMSO-$d_6$): δ 2.09-2.23 (m, 2 H), 2.64 (t, 2 H), 4.05 (t, 2 H), 4.25-4.34 (m, 1 H), 4.63 (t, 2 H), 4.97 (dd, 2 H), 7.20 (d, 2 H), 7.27 (s, 2 H), 7.49 (dd, 2 H), 7.66 (d, 2 H), 7.81 (d, 1 H), 7.88 (s, 2 H), 8.08 (s, 1 H), 8.58 (s, 2 H), 8.62 (s, 2 H), 9.08 (s, 1 H).

Example 85-52

1-(2-{3-methyl-4-[2-(2-oxo-1-pyrrolidinyl)-1,3-thiazol-5-yl]phenoxy}-5-pyrimidinyl)-3-[2-(3-pyridinyl)-5-(trifluoromethyl)phenyl]urea TCL: Rf 0.34 (Ethyl Acetate:Methanol=9:1);
$^1$H-NMR (DMSO-$d_6$): δ 2.11-2.24 (m, 2 H), 2.37 (s, 3 H), 2.63 (t, 2 H), 4.06 (t, 2 H), 7.05 (dd, 1 H), 7.14 (d, 1 H), 7.40 (d, 1 H), 7.50 (d, 2 H), 7.55-7.60 (m, 3 H), 7.89 (dd, 1 H), 8.24 (s, 1 H), 8.37 (s, 1 H), 8.64 (s, 2 H), 8.67 (dd, 1 H), 9.24 (s, 1 H).

Example 85-53

1-(2-{3-methyl-4-[2-(2-oxo-1-pyrrolidinyl)-1,3-thiazol-5-yl]phenoxy}-5-pyrimidinyl)-3-[3-(trifluoromethyl)phenyl]urea TCL: Rf 0.35 (Ethyl Acetate:Methanol=9:1);
$^1$H-NMR (DMSO-$d_6$): δ 2.11-2.23 (m, 2 H), 2.38 (s, 3 H), 2.63 (t, 2 H), 4.06 (t, 2 H), 7.05 (dd, 1 H), 7.16 (d, 1 H), 7.32 (dd, 1 H), 7.42 (d, 1 H), 7.51 (t, 1 H), 7.57 (s, 1 H), 7.60 (dd, 1 H), 7.97 (s, 1 H), 8.71 (s, 2 H), 8.98 (s, 1 H), 9.31 (s, 1 H).

Example 85-54

1-[2-(4-{2-[4-(hydroxymethyl)-2-oxo-1-pyrrolidinyl]-1,3-thiazol-5-yl}phenoxy)-5-pyrimidinyl]-3-[2-(3-pyridinyl)-5-(trifluoromethyl)phenyl]urea

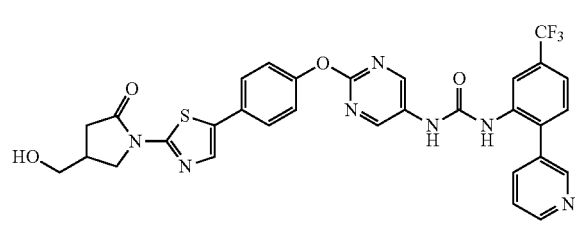 [SMILES: O=C(Nc1cnc(Oc2ccc(-c3cnc(N4CC(CO)CC4=O)s3)cc2)nc1)Nc1cc(C(F)(F)F)ccc1-c1cccnc1]

Example 85-55

1-[2-({6-[2-(2-oxo-1-pyrrolidinyl)-1,3-thiazol-5-yl]-3-pyridinyl}oxy)-5-pyrimidinyl]-3-[3-(trifluoromethyl)phenyl]urea TCL: Rf 0.43 (Ethyl Acetate);
$^1$H-NMR (DMSO-$d_6$): δ 2.16 (m, 2 H), 2.64 (t, 2 H), 4.06 (t, 2H), 7.32 (d, 1 H), 7.52 (t, 1 H), 7.61 (d, 1 H), 7.75 (dd, 1 H), 7.96 (s, 1 H), 8.03 (d, 1 H), 8.18 (s, 1 H), 8.46 (d, 1 H), 8.73 (s, 2H), 9.01 (s, 1 H), 9.31 (s, 1 H).

Example 85-56

1-[2-({6-[2-(2-oxo-1-pyrrolidinyl)-1,3-thiazol-5-yl]-3-pyridinyl}oxy)-5-pyrimidinyl]-3-[2-(3-pyridinyl)-5-(trifluoromethyl)phenyl]urea TCL: Rf 0.36 (Ethyl Acetate);
$^1$H-NMR (DMSO-$d_6$): δ 2.16 (m, 2 H), 2.64 (t, 2 H), 4.05 (t, 2 H), 7.46-7.60 (m, 3 H), 7.73 (dd, 1 H), 7.87-7.93 (m, 1 H), 8.02 (d, 1 H), 8.17 (s, 1 H), 8.24 (s, 1 H), 8.37 (s, 1 H), 8.44 (d, 1 H), 8.63-8.74 (m, 4 H), 9.26 (s, 1 H).

Example 85-57

1-(2-{4-[2-(dimethylamino)-1,3-thiazol-5-yl]phenoxy}-5-pyrimidinyl)-3-[3-(trifluoromethyl)phenyl]urea

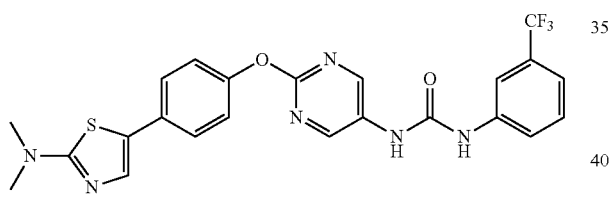

TCL: Rf 0.44 (Ethyl Acetate);
$^1$H-NMR (DMSO-$d_6$): δ 3.07 (s, 6 H), 7.15 (d, 2 H), 7.31 (d, 1 H), 7.45-7.66 (m, 5 H), 7.96 (s, 1 H), 8.70 (s, 2 H), 8.95 (s, 1 H), 9.28 (s, 1 H).

Example 85-58

1-[2-(cyclopropylcarbonyl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea

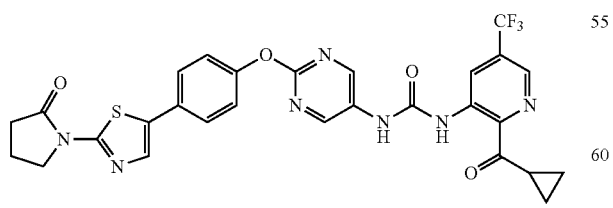

TCL: Rf 0.59 (Ethyl Acetate);
$^1$H-NMR (CDCl$_3$): δ 1.25 (d, 4 H), 2.30 (m, 2 H), 2.75 (t, 2 H), 3.74 (m, 1 H), 4.20 (t, 2 H), 7.24 (d, 2 H), 7.31 (s, 1 H), 7.58 (s, 1 H), 7.62 (d, 2 H), 8.59 (s, 1 H), 8.73 (s, 2 H), 9.28 (s, 1 H), 11.5 (s, 1 H).

Example 85-59

1-(2-{4-[2-(ethylamino)-1,3-thiazol-5-yl]phenoxy}-5-pyrimidinyl)-3-[4-methyl-3-(trifluoromethyl)phenyl]urea TCL: Rf 0.29 (Chloroform:Methanol=10:1);
$^1$H-NMR (DMSO-$d_6$): δ 1.16 (t, 3 H), 2.36 (s, 3 H), 3.20-3.32 (m, 2 H), 7.14 (d, 2 H), 7.33 (d, 1 H), 7.41-7.48 (m, 3 H), 7.51-7.56 (m, 1 H), 7.72 (t, 1 H), 7.87-7.90 (m, 1 H), 8.69 (s, 2 H), 8.94 (s, 1 H), 9.20 (s, 1 H).

Example 85-60

1-(2-{4-[2-(ethylamino)-1,3-thiazol-5-yl]phenoxy}-5-pyrimidinyl)-3-[4-(trifluoromethyl)phenyl]urea

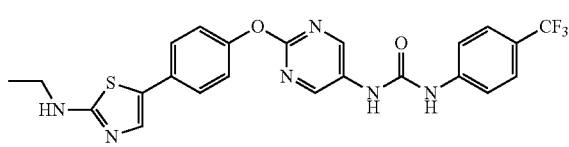 [SMILES: CCNc1ncc(-c2ccc(Oc3ncc(NC(=O)Nc4ccc(C(F)(F)F)cc4)cn3)cc2)s1]

TCL: Rf 0.18 (Chloroform:Methanol=10:1);
$^1$H-NMR (DMSO-$d_6$): δ 1.17 (t, 3 H), 3.21-3.34 (m, 2 H), 7.14 (d, 2 H), 7.42-7.49 (m, 3 H), 7.60-7.75 (m, 5 H), 8.71 (s, 2 H), 9.12 (s, 1 H), 9.49 (s, 1 H).

Example 85-61

1-(2-{4-[2-(ethylamino)-1,3-thiazol-5-yl]phenoxy}-5-pyrimidinyl)-3-[3-fluoro-5-(trifluoromethyl)phenyl]urea TCL: Rf 0.16 (Chloroform:Methanol=10:1);
$^1$H-NMR (DMSO-$d_6$): δ 1.17 (t, 3 H), 3.21-3.31 (m, 2 H), 7.12-7.18 (m, 2 H), 7.22-7.28 (m, 1 H), 7.42-7.49 (m, 3 H), 7.59-7.66 (m, 1 H), 7.68-7.75 (m, 2 H), 8.70 (s, 2 H), 9.10 (s, 1 H), 9.52 (s, 1 H).

Example 85-62

1-[2-chloro-5-(trifluoromethyl)phenyl]-3-(2-{4-[2-(ethylamino)-1,3-thiazol-5-yl]phenoxy}-5-pyrimidinyl)urea TCL: Rf 0.16 (Chloroform:Methanol=10:1);
$^1$H-NMR (DMSO-$d_6$): δ 1.17 (t, 3 H), 3.22-3.34 (m, 2 H), 7.12-7.18 (m, 2 H), 7.36-7.48 (m, 4 H), 7.67-7.76 (m, 2 H), 8.55 (d, 1 H), 8.72 (s, 2 H), 8.83 (s, 1 H), 9.81 (s, 1 H).

Example 85-63

1-[2-chloro-4-(trifluoromethyl)phenyl]-3-(2-{4-[2-(ethylamino)-1,3-thiazol-5-yl]phenoxy}-5-pyrimidinyl)urea TCL: Rf 0.18 (Chloroform:Methanol=10:1);
$^1$H-NMR (DMSO-$d_6$): δ 1.17 (t, 3 H), 3.20-3.34 (m, 2 H), 7.12-7.18 (m, 2 H), 7.42-7.48 (m, 3 H), 7.65-7.76 (m, 2 H), 7.86-7.90 (m, 1 H), 8.42 (d, 1 H), 8.72 (s, 2 H), 8.80 (s, 1 H), 9.80 (s, 1 H).

Example 85-64

1-(2-{4-[2-(ethylamino)-1,3-thiazol-5-yl]phenoxy}-5-pyrimidinyl)-3-[2-fluoro-3-(trifluoromethyl)phenyl]urea TCL: Rf 0.24 (Chloroform:Methanol=10:1);
$^1$H-NMR (DMSO-d$_6$): δ 1.16 (t, 3 H), 3.20-3.34 (m, 2 H), 7.12-7.18 (m, 2 H), 7.32-7.48 (m, 5 H), 7.72 (t, 1 H), 8.33-8.40 (m, 1 H), 8.72 (s, 2 H), 9.03 (s, 1 H), 9.28 (s, 1 H).

Example 85-65

1-(2-{4-[2-(ethylamino)-1,3-thiazol-5-yl]phenoxy}-5-pyrimidinyl)-3-[2-fluoro-5-(trifluoromethyl)phenyl]urea TCL: Rf 0.24 (Chloroform:Methanol=10:1);
$^1$H-NMR (DMSO-d$_6$): δ 1.16 (t, 3 H), 3.20-3.34 (m, 2 H), 7.11-7.18 (m, 2 H), 7.34-7.54 (m, 5 H), 7.72 (t, 1 H), 8.50-8.55 (m, 1 H), 8.71 (s, 2 H), 9.14 (s, 1 H), 9.43 (s, 1 H).

Example 85-66

1-[2-(3-oxetanyl)-5-(trifluoromethyl)phenyl]-3-(2-{4-[2-(2-oxo-1-pyrrolidinyl)-1,3-thiazol-5-yl]phenoxy}-5-pyrimidinyl)urea

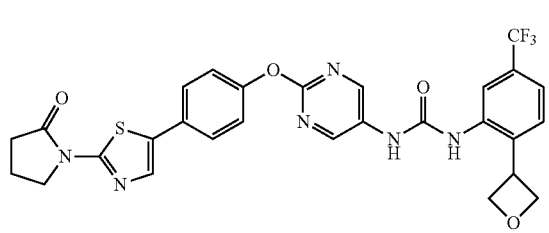 [SMILES: O=C(Nc1cnc(Oc2ccc(-c3cnc(N4CCCC4=O)s3)cc2)nc1)Nc1cc(C(F)(F)F)ccc1C1COC1]

TCL: Rf 0.64 (Ethyl Acetate:Methanol=19:1);
$^1$H-NMR (DMSO-d$_6$): δ 2.10-2.20 (m, 2 H), 2.49-2.64 (m, 2 H), 4.05 (t, 2 H), 4.40-4.60 (m, 1 H), 4.64 (t, 2 H), 4.96 (t, 2 H), 7.22 (d, 2 H), 7.52 (d, 1 H), 7.65-7.72 (m, 3 H), 7.89 (s, 1 H), 7.97 (s, 1 H), 8.34 (s, 1 H), 8.71 (s, 2 H), 9.19 (s, 1 H).

Example 85-67

1-(2-{4-[2-(2-oxo-1-pyrrolidinyl)-1,3-thiazol-5-yl]phenoxy}-5-pyrimidinyl)-3-[2-(1H-pyrazol-1-yl)-5-(trifluoromethyl)phenyl]urea TCL: Rf 0.34 (Ethyl Acetate);
$^1$H-NMR (DMSO-d$_6$): δ 2.16 (m, 2 H), 2.64 (t, 2 H), 4.05 (t, 2 H), 6.73 (t, 1 H), 7.23 (d, 2 H), 7.52 (dd, 1 H), 7.67 (d, 2 H), 7.75 (d, 1 H), 7.89 (s, 1 H), 7.95 (d, 1 H), 8.41 (d, 1 H), 8.57-8.61 (m, 1 H), 8.69 (s, 2 H), 9.70 (s, 1 H), 9.96 (s, 1 H).

Example 85-68

1-[5-fluoro-2-(1H-imidazol-1-yl)phenyl]-3-(2-{4-[2-(2-oxo-1-pyrrolidinyl)-1,3-thiazol-5-yl]phenoxy}-5-pyrimidinyl)urea TCL: Rf 0.33 (Ethyl Acetate);
$^1$H-NMR (DMSO-d$_6$): δ 2.17 (t, 2 H), 2.62-2.68 (m, 2 H), 4.06 (t, 2 H), 6.99-7.38 (m, 6 H), 7.67 (d, 2 H), 7.75-7.90 (m, 2 H), 7.99-8.10 (m, 2 H), 8.65 (s, 2 H), 9.43 (s, 1 H).

Example 85-69

1-(2-{4-[2-(3-oxo-4-morpholinyl)-1,3-thiazol-5-yl]phenoxy}-5-pyrimidinyl)-3-[3-(trifluoromethyl)phenyl]urea

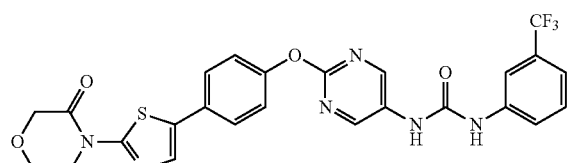

TCL: Rf 0.68 (Ethyl Acetate);
$^1$H-NMR (DMSO-d$_6$): δ 4.04-4.14 (m, 4 H), 4.41 (s, 2 H), 7.21-7.27 (m, 2 H), 7.29-7.34 (m, 1 H), 7.51 (t, 1 H), 7.58-7.64 (m, 1 H), 7.66-7.72 (m, 2 H), 7.94-7.98 (m, 2 H), 8.71 (s, 2 H), 9.06 (s, 1 H), 9.38 (s, 1 H).

Example 85-70

1-[2-(4-{2-[(3-hydroxypropyl)amino]-1,3-thiazol-5-yl}phenoxy)-5-pyrimidinyl]-3-[3-(trifluoromethyl)phenyl]urea

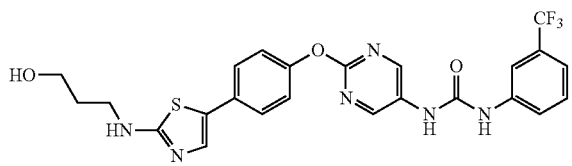 [SMILES: O=C(Nc1cnc(Oc2ccc(-c3cnc(NCCCO)s3)cc2)nc1)Nc1cccc(C(F)(F)F)c1]

TCL: Rf 0.51 (Ethyl Acetate);
$^1$H-NMR (DMSO-d$_6$): δ 1.91 (m, 2 H), 3.34 (t, 2 H), 4.17 (t, 2 H), 7.14 (d, 2 H), 7.31 (d, 1 H), 7.43 (s, 1 H), 7.44 (d, 2 H), 7.53 (t, 1 H), 7.60 (d, 1 H), 7.80 (t, 1 H), 7.96 (s, 1 H), 8.22 (s, 1 H), 8.70 (s, 2 H), 8.95 (s, 1 H), 9.29 (s, 1 H).

Example 85-71

1-(2-{4-[2-(propylamino)-1,3-thiazol-5-yl]phenoxy}-5-pyrimidinyl)-3-[3-(trifluoromethyl)phenyl]urea TCL: Rf 0.68 (Ethyl Acetate);
$^1$H-NMR (DMSO-d$_6$): δ 0.91 (m, 3 H), 1.58 (m, 2 H), 3.19 (q, 2 H), 7.14 (d, 2 H), 7.32 (d, 1 H), 7.41-7.57 (m, 4 H), 7.61 (d, 1 H), 7.75 (t, 1 H), 7.96 (s, 1 H), 8.69 (s, 2 H), 8.96 (s, 1 H), 9.29 (s, 1 H).

Example 85-72

1-[2-(4-{2-[(2-hydroxyethyl)amino]-1,3-thiazol-5-yl}phenoxy)-5-pyrimidinyl]-3-[3-(trifluoromethyl)phenyl]urea TCL: Rf 0.35 (Ethyl Acetate);
$^1$H-NMR (DMSO-d$_6$): δ 3.28-3.38 (m, 2 H), 3.55 (q, 2 H), 4.76 (t, 1 H), 7.14 (d, 2 H), 7.31 (d, 1 H), 7.41-7.56 (m, 4 H), 7.61 (d, 1 H), 7.75 (t, 1 H), 7.96 (s, 1 H), 8.69 (s, 2 H), 8.95 (s, 1 H), 9.28 (s, 1 H).

Example 85-73

1-(2-{4-[2-(butylamino)-1,3-thiazol-5-yl]phenoxy}-5-pyrimidinyl)-3-[3-(trifluoromethyl)phenyl]urea TCL: Rf 0.80 (Ethyl Acetate);
$^1$H-NMR (DMSO-d$_6$): δ 0.90 (t, 3 H), 1.36 (m, 2 H), 1.54 (m, 2 H), 3.24 (q, 2 H), 7.14 (d, 2 H), 7.31 (d, 1 H), 7.41-7.57 (m, 4 H), 7.60 (d, 1 H), 7.72 (t, 1 H), 7.96 (s, 1 H), 8.69 (s, 2 H), 8.96 (s, 1 H), 9.29 (s, 1 H).

Example 85-74

1-{2-[4-(2-{[2-(4-morpholinyl)ethyl]amino}-1,3-thiazol-5-yl)phenoxy]-5-pyrimidinyl}-3-[3-(trifluoromethyl)phenyl]urea

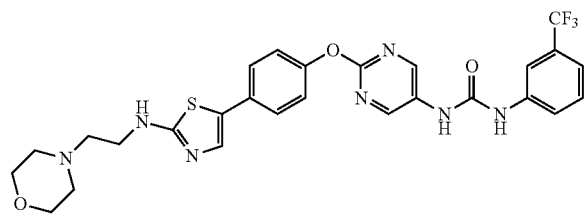 [SMILES: O=C(Nc1cnc(Oc2ccc(-c3cnc(NCCN4CCOCC4)s3)cc2)nc1)Nc1cccc(C(F)(F)F)c1]

TCL: Rf 0.57 (Ethyl Acetate:Methanol=9:1);
$^1$H-NMR (DMSO-d$_6$): δ 2.49 (m, 6 H), 3.39 (q, 2 H), 3.57 (t, 4 H), 7.14 (d, 2 H), 7.32 (d, 1 H), 7.40-7.55 (m, 4 H), 7.58-7.73 (m, 2 H), 7.96 (s, 1 H), 8.69 (s, 2 H), 8.96 (s, 1 H), 9.29 (s, 1 H).

Example 85-75

1-[2-(4-methyl-1H-imidazol-1-yl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.38 (Ethyl Acetate);
$^1$H-NMR (DMSO-d$_6$): δ 2.16 (m, 2 H), 2.20 (s, 3 H), 2.64 (t, 2 H), 4.04 (t, 2 H), 7.16 (s, 1 H), 7.22 (d, 2 H), 7.46-7.55 (m, 2 H), 7.67 (d, 2 H), 7.81 (s, 1 H), 7.89 (s, 1 H), 8.33 (s, 1 H), 8.51 (s, 1 H), 8.66 (s, 2 H), 9.43 (s, 1 H).

Example 85-76

1-(2-{4-[2-(2-oxo-1-pyrrolidinyl)-1,3-thiazol-5-yl]phenoxy}-5-pyrimidinyl)-3-[2-(1H-1,2,3-triazol-1-yl)-5-(trifluoromethyl)phenyl]urea TCL: Rf 0.54 (Ethyl Acetate);
$^1$H-NMR (DMSO-d$_6$): δ 2.16 (m, 2 H), 2.64 (t, 2 H), 4.05 (t, 2 H), 7.22 (d, 2 H), 7.58-7.78 (m, 4 H), 7.89 (s, 1 H), 8.09 (s, 1 H), 8.57 (s, 1 H), 8.64-8.75 (m, 4 H), 9.64 (s, 1 H).

Example 85-77

1-[2-(4-{2-[3-(2-hydroxy-2-propanyl)-2-oxo-1-pyrrolidinyl]-1,3-thiazol-5-yl}phenoxy)-5-pyrimidinyl]-3-[2-(3-pyridinyl)-5-(trifluoromethyl)phenyl]urea TCL: Rf 0.51 (Ethyl Acetate:Methanol=9:1);
$^1$H-NMR (CDCl$_3$): δ 1.29 (s, 3 H), 1.35 (s, 3 H), 1.99-2.14 (m, 1 H), 2.33-2.46 (m, 1 H), 2.93 (t, 1 H), 3.85-4.02 (m, 2 H), 4.21-4.33 (m, 1 H), 7.14-7.25 (m, 3 H), 7.36-7.47 (m, 3 H), 7.51-7.63 (m, 3 H), 7.78-7.84 (m, 1 H), 8.21-8.26 (m, 1 H), 8.43 (s, 1 H), 8.57 (s, 2 H), 8.68 (s, 1 H), 8.90 (s, 1 H).

Example 85-78

1-[2-(4-{2-[3-(2-hydroxy-2-propanyl)-2-oxo-1-pyrrolidinyl]-1,3-thiazol-5-yl}phenoxy)-5-pyrimidinyl]-3-[3-(trifluoromethyl)phenyl]urea TCL: Rf 0.17 (Hexane:Ethyl Acetate=1:4);
$^1$H-NMR (CDCl$_3$+CD$_3$OD): δ 1.26 (s, 3 H), 1.30 (s, 3 H), 1.95-2.13 (m, 1 H), 2.30-2.42 (m, 1 H), 2.89 (t, 1 H), 3.87-3.97 (m, 1 H), 4.15-4.25 (m, 1 H), 7.14-7.27 (m, 3 H), 7.37 (t, 1 H), 7.52-7.66 (m, 5 H), 8.64 (s, 2 H).

Example 85-79

1-[2-(2-methyl-1H-imidazol-1-yl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.45 (Ethyl Acetate);
$^1$H-NMR (DMSO-d$_6$): δ 2.12 (s, 3 H), 2.16 (m, 2 H), 2.64 (t, 2 H), 4.05 (t, 2 H), 7.04 (d, 1 H), 7.20-7.29 (m, 3 H), 7.46-7.57 (m, 2 H), 7.67 (d, 2 H), 7.89 (s, 1 H), 8.19 (s, 1 H), 8.64 (s, 1 H), 8.66 (s, 2 H), 9.48 (s, 1 H).

Example 85-80

1-[2-(4-{2-[(2-hydroxypropyl)amino]-1,3-thiazol-5-yl}phenoxy)-5-pyrimidinyl]-3-[3-(trifluoromethyl)phenyl]urea

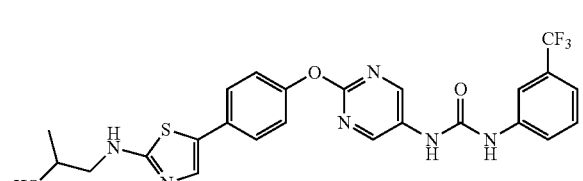

TCL: Rf 0.54 (Ethyl Acetate);
$^1$H-NMR (DMSO-d$_6$): δ 1.08 (d, 3 H), 3.18 (t, 2 H), 3.81 (m, 1 H), 4.78 (d, 1 H), 7.14 (d, 2 H), 7.32 (d, 1 H), 7.42 (s, 1 H), 7.45 (d, 2 H), 7.53 (t, 1 H), 7.62 (d, 1 H), 7.76 (t, 1 H), 7.97 (s, 1 H), 8.69 (s, 2 H), 8.98 (s, 1 H), 9.31 (s, 1 H).

Example 85-81

1-[3-(difluoromethyl)phenyl]-3-(2-{4-[2-(2-oxo-1-pyrrolidinyl)-1,3-thiazol-5-yl]phenoxy}-5-pyrimidinyl)urea

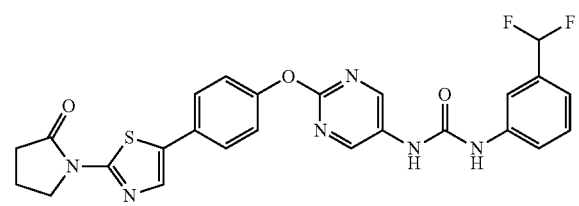 [SMILES: O=C(Nc1cnc(Oc2ccc(-c3cnc(N4CCCC4=O)s3)cc2)nc1)Nc1cccc(C(F)F)c1]

TCL: Rf 0.30 (Ethyl Acetate);
$^1$H-NMR (DMSO-d$_6$): δ 2.12-2.21 (m, 2 H), 2.64 (t, 2 H), 4.05 (t, 2 H), 6.81-7.24 (m, 4 H), 7.41 (t, 1 H), 7.51 (d, 1 H), 7.64-7.69 (m, 2 H), 7.77 (s, 1 H), 7.89 (s, 1 H), 8.71 (s, 2 H), 8.90 (s, 1 H), 9.16 (s, 1 H).

Example 85-82

1-[3-(1,1-difluoroethyl)phenyl]-3-(2-{4-[2-(2-oxo-1-pyrrolidinyl)-1,3-thiazol-5-yl]phenoxy}-5-pyrimidinyl)urea

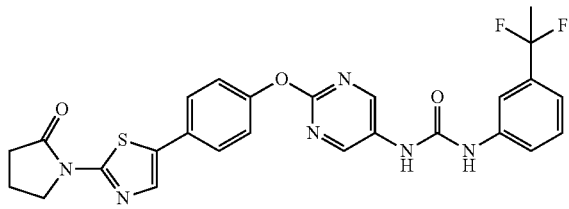 [SMILES: CC(F)(F)c1cccc(NC(=O)Nc2cnc(Oc3ccc(-c4cnc(N5CCCC5=O)s4)cc3)nc2)c1]

TCL: Rf 0.30 (Ethyl Acetate);
$^1$H-NMR (DMSO-$d_6$): δ 1.93 (t, 3 H), 2.11-2.21 (m, 2 H), 2.64 (t, 2 H), 4.05 (t, 2 H), 7.15 (d, 1 H), 7.22 (d, 2 H), 7.38 (t, 1 H), 7.49 (d, 1 H), 7.66 (d, 2 H), 7.72 (s, 1 H), 7.89 (s, 1 H), 8.71 (s, 2 H), 8.89 (s, 1 H), 9.13 (s, 1 H).

Example 85-83

1-[3-(difluoromethyl)phenyl]-3-(2-{4-[2-(ethylamino)-1,3-thiazol-5-yl]phenoxy}-5-pyrimidinyl)urea TCL: Rf 0.56 (Ethyl Acetate);
$^1$H-NMR (DMSO-$d_6$): δ 1.17 (t, 3 H), 3.21-3.27 (m, 2 H), 6.81-7.18 (m, 4 H), 7.39-7.53 (m, 5 H), 7.72 (t, 1 H), 7.77 (s, 1 H), 8.71 (s, 2 H), 8.89 (s, 1 H), 9.15 (s, 1 H).

Example 85-84

1-(3-acetylphenyl)-3-(2-{4-[2-(ethylamino)-1,3-thiazol-5-yl]phenoxy}-5-pyrimidinyl)urea

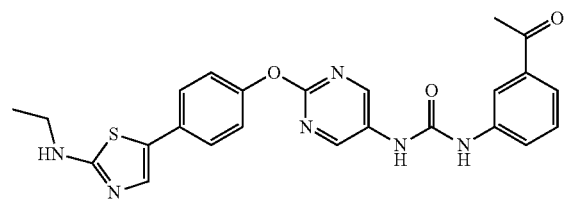 [SMILES: CCNc1ncc(-c2ccc(Oc3ncc(NC(=O)Nc4cccc(C(C)=O)c4)cn3)cc2)s1]

TCL: Rf 0.52 (Ethyl Acetate);
$^1$H-NMR (DMSO-$d_6$): δ 1.18 (t, 3 H), 2.56 (s, 3 H), 3.22-3.30 (m, 2 H), 7.13-7.17 (m, 2 H), 7.42-7.47 (m, 4 H), 7.59-7.63 (m, 1 H), 7.74-7.68 (m, 2 H), 8.03 (t, 1 H), 8.71 (s, 2 H), 8.89 (s, 1 H), 9.17 (s, 1 H).

Example 85-85

1-(2-{4-[2-(ethylamino)-1,3-thiazol-5-yl]phenoxy}-5-pyrimidinyl)-3-(3-fluorophenyl)urea

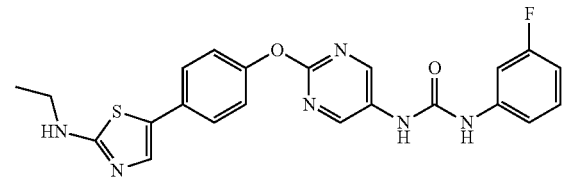 [SMILES: CCNc1ncc(-c2ccc(Oc3ncc(NC(=O)Nc4cccc(F)c4)cn3)cc2)s1]

TCL: Rf 0.32 (Chloroform:Methanol=10:1);
$^1$H-NMR (DMSO-$d_6$): δ 1.16 (t, 3 H), 3.21-3.32 (m, 2 H), 6.79 (td, 1 H), 7.11-7.17 (m, 3 H), 7.26-7.34 (m, 1 H), 7.42-7.49 (m, 4 H), 7.72 (t, 1 H), 8.69 (s, 2 H), 8.90 (s, 1 H), 9.16 (s, 1 H).

Example 85-86

1-[4-chloro-3-(trifluoromethyl)phenyl]-3-(2-{4-[2-(ethylamino)-1,3-thiazol-5-yl]phenoxy}-5-pyrimidinyl)urea TCL: Rf 0.29 (Chloroform:Methanol=10:1);
$^1$H-NMR (DMSO-$d_6$): δ 1.16 (t, 3 H), 3.20-3.32 (m, 2 H), 7.14 (d, 2 H), 7.41-7.48 (m, 3 H), 7.59-7.74 (m, 3 H), 8.04-8.08 (m, 1 H), 8.69 (s, 2 H), 9.03 (s, 1 H), 9.43 (s, 1 H).

Example 85-87

1-(2-{4-[2-(ethylamino)-1,3-thiazol-5-yl]phenoxy}-5-pyrimidinyl)-3-[2-methyl-5-(trifluoromethyl)phenyl]urea TCL: Rf 0.29 (Chloroform:Methanol=10:1);
$^1$H-NMR (DMSO-$d_6$): δ 1.16 (t, 3 H), 2.34 (s, 3 H), 3.20-3.32 (m, 2 H), 7.10-7.18 (m, 2 H), 7.24-7.30 (m, 1 H), 7.36-7.48 (m, 4 H), 7.68-7.76 (m, 1 H), 8.20 (s, 1 H), 8.74 (s, 2 H), 9.17 (s, 1 H), 10.4 (s, 1 H).

Example 85-88

1-[3-chloro-5-(trifluoromethyl)phenyl]-3-(2-{4-[2-(ethylamino)-1,3-thiazol-5-yl]phenoxy}-5-pyrimidinyl)urea TCL: Rf 0.32 (Chloroform:Methanol=10:1);
$^1$H-NMR (DMSO-$d_6$): δ 1.17 (t, 3 H), 3.20-3.33 (m, 2 H), 7.14 (d, 2 H), 7.38-7.49 (m, 4 H), 7.67-7.76 (m, 1 H), 7.84 (s, 2 H), 8.70 (s, 2 H), 9.35 (s, 1 H), 9.67 (s, 1 H).

Example 85-89

1-[2-(1H-imidazol-1-yl)-5-(trifluoromethyl)phenyl]-3-[2-({6-[2-(2-oxo-1-pyrrolidinyl)-1,3-thiazol-5-yl]-3-pyridinyl}oxy)-5-pyrimidinyl]urea TCL: Rf 0.44 (Ethyl Acetate:Methanol=9:1);
$^1$H-NMR (DMSO-$d_6$): δ 2.15 (quint, 2 H), 2.63 (t, 2 H), 4.05 (t, 2 H), 7.18 (s, 1 H), 7.46-7.56 (m, 3 H), 7.72-7.77 (m, 1 H), 7.96 (s, 1 H), 8.01 (d, 1 H), 8.17 (s, 1 H), 8.32 (s, 1 H), 8.43-8.47 (m, 1 H), 8.48 (s, 1 H), 8.67 (s, 2 H), 9.44 (s, 1 H).

Example 85-90

1-(2-{4-[2-(dimethylamino)-1,3-thiazol-5-yl]phenoxy}-5-pyrimidinyl)-3-[2-(3-pyridinyl)-5-(trifluoromethyl)phenyl]urea TCL: Rf 0.30 (Ethyl Acetate);
$^1$H-NMR (DMSO-$d_6$): δ 3.08 (s, 6 H), 7.14 (d, 2 H), 7.46-7.60 (m, 6 H), 7.87-7.93 (m, 1 H), 8.34 (s, 1 H), 8.36 (s, 1 H), 8.61-8.74 (m, 4 H), 9.34 (s, 1 H).

Example 85-91

1-[2-(3-pyridinyl)-5-(trifluoromethyl)phenyl]-3-[2-(4-{2-[(tetrahydro-2H-pyran-4-ylmethyl)amino]-1,3-thiazol-5-yl}phenoxy)-5-pyrimidinyl]urea

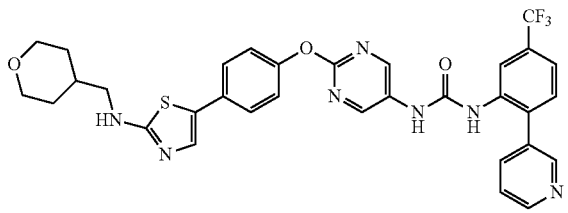 [SMILES: O=C(Nc1cnc(Oc2ccc(-c3cnc(NCC4CCOCC4)s3)cc2)nc1)Nc1cc(C(F)(F)F)ccc1-c1cccnc1]

TCL: Rf 0.30 (Ethyl Acetate);
$^1$H-NMR (DMSO-$d_6$): δ 1.14-1.23 (m, 2 H), 1.62 (d, 2 H), 1.84 (m, 1 H), 3.13 (t, 2 H), 3.21-3.30 (m, 2 H), 3.85 (dd, 2 H), 7.12 (d, 2 H), 7.38-7.60 (m, 6 H), 7.82 (t, 1 H), 7.86-7.92 (m, 1 H), 8.22 (s, 1 H), 8.37 (s, 1 H), 8.60-8.70 (m, 4 H), 9.21 (s, 1 H).

Example 85-92

1-(2-{4-[2-(ethylamino)-1,3-thiazol-5-yl]phenoxy}-5-pyrimidinyl)-3-[2-(1H-imidazol-1-yl)-5-(trifluoromethyl)phenyl]urea TCL: Rf 0.60 (Ethyl Acetate:Methanol=9:1);
$^1$H-NMR (DMSO-$d_6$): δ 1.16 (t, 3 H), 3.24 (q, 2 H), 7.10 (s, 1 H), 7.11 (d, 2 H), 7.39-7.56 (m, 6 H), 7.72 (br s, 1 H), 7.96 (s, 1 H), 8.29 (s, 1 H), 8.42 (s, 1 H), 8.65 (s, 2 H), 10.0 (br s, 1 H).

Example 85-93

1-(2-{4-[2-(2-oxo-1-pyrrolidinyl)-1,3-thiazol-5-yl]phenoxy}-5-pyrimidinyl)-3-[2-(4H-1,2,4-triazol-4-yl)-5-(trifluoromethyl)phenyl]urea TCL: Rf 0.40 (Ethyl Acetate);
$^1$H-NMR (CDCl$_3$): δ 2.30 (m, 2 H), 2.74 (t, 2 H), 4.20 (t, 2 H), 7.23 (d, 2 H), 7.59-7.77 (m, 5 H), 7.91 (d, 1 H), 8.16 (s, 1 H), 8.44 (s, 1 H), 8.54 (s, 1 H), 8.80 (s, 2 H), 9.42 (s, 1 H).

Example 85-94

1-(6-{4-[2-(dimethylamino)-1,3-thiazol-5-yl]phenoxy}-3-pyridinyl)-3-[3-(trifluoromethyl)phenyl]urea TCL: Rf 0.28 (Hexane:Ethyl Acetate=1:2);
$^1$H-NMR (DMSO-$d_6$): δ 3.06 (s, 6 H), 6.99-7.08 (m, 3 H), 7.30 (d, 1 H), 7.44-7.64 (m, 5 H), 7.97-8.01 (m, 2 H), 8.18 (d, 1 H), 8.87 (s, 1 H), 9.12 (s, 1 H).

Example 85-95

1-(2-{4-[2-(diethylamino)-1,3-thiazol-5-yl]phenoxy}-5-pyrimidinyl)-3-[3-(trifluoromethyl)phenyl]urea TCL: Rf 0.22 (Chloroform:Methanol=19:1);
$^1$H-NMR (DMSO-$d_6$): δ 1.18 (t, 6 H), 3.47 (q, 4 H), 7.12-7.18 (m, 2 H), 7.30-7.35 (m, 1 H), 7.45-7.54 (m, 4 H), 7.59-7.64 (m, 1 H), 7.95-7.99 (m, 1 H), 8.71 (s, 2 H), 8.97 (s, 1 H), 9.31 (s, 1 H).

Example 85-96

1-(6-{4-[2-(dimethylamino)-1,3-thiazol-5-yl]phenoxy}-3-pyridinyl)-3-[2-(3-pyridinyl)-5-(trifluoromethyl)phenyl]urea TCL: Rf 0.61 (Ethyl Acetate:Methanol=9:1);
$^1$H-NMR (DMSO-$d_6$): δ 3.06 (s, 6 H), 6.98 (d, 1 H), 7.02-7.06 (m, 2 H), 7.42-7.48 (m, 4 H), 7.51 (s, 1 H), 7.53-7.58 (m, 1 H), 7.86-7.90 (m, 1 H), 7.96 (dd, 1 H), 8.06-8.07 (m, 2 H), 8.41 (s, 1 H), 8.63-8.68 (m, 2 H), 9.15 (s, 1 H).

Example 85-97

1-[2-(4-{2-[3-(hydroxymethyl)-1-pyrrolidinyl]-1,3-thiazol-5-yl}phenoxy)-5-pyrimidinyl]-3-[3-(trifluoromethyl)phenyl]urea

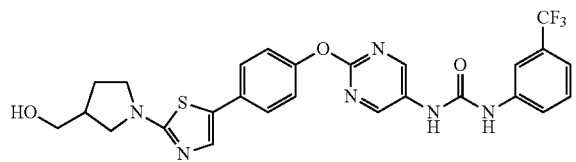 [SMILES: O=C(Nc1cnc(Oc2ccc(-c3cnc(N4CCC(CO)C4)s3)cc2)nc1)Nc1cccc(C(F)(F)F)c1]

TCL: Rf 0.31 (Ethyl Acetate:Methanol=9:1);
$^1$H-NMR (DMSO-$d_6$): δ 1.48 (m, 1 H), 1.93 (m, 1 H), 2.11 (br s, 1 H), 3.32-3.50 (m, 3 H), 3.58-3.79 (m, 2 H), 4.03 (dd, 1 H), 4.80 (s, 1 H), 7.17 (d, 1 H), 7.24 (s, 1 H), 7.30 (d, 2 H), 7.32 (d, 2 H), 7.50 (t, 2 H), 7.62 (d, 1 H), 7.98 (s, 1 H), 8.72 (s, 2 H), 9.43 (s, 1 H), 9.70 (s, 1 H).

Example 85-98

1-(2-{4-[2-(methylamino)-1,3-thiazol-5-yl]phenoxy}-5-pyrimidinyl)-3-[3-(trifluoromethyl)phenyl]urea TCL: Rf 0.51 (Ethyl Acetate);
$^1$H-NMR (DMSO-$d_6$): δ 2.84 (d, 3 H), 7.14 (d, 2 H), 7.32 (d, 1 H), 7.45 (d, 1 H), 7.50 (d, 2 H), 7.50-7.67 (m, 3 H), 7.97 (s, 1 H), 8.70 (s, 2 H), 8.97 (s, 1 H), 9.31 (s, 1 H).

Example 85-99

1-(2-{4-[2-(isopropylamino)-1,3-thiazol-5-yl]phenoxy}-5-pyrimidinyl)-3-[3-(trifluoromethyl)phenyl]urea TCL: Rf 0.69 (Ethyl Acetate);
$^1$H-NMR (DMSO-$d_6$): δ 1.18 (d, 6 H), 3.80 (m, 1 H), 7.14 (d, 2 H), 7.32 (d, 1 H), 7.41 (s, 1 H), 7.45 (d, 2 H), 7.51 (t, 1 H), 7.61 (s, 1 H), 7.66 (d, 1 H), 7.97 (s, 1 H), 8.70 (s, 1 H), 8.96 (s, 1 H), 9.30 (s, 1 H).

Example 85-100

1-(2-{4-[2-(isobutylamino)-1,3-thiazol-5-yl]phenoxy}-5-pyrimidinyl)-3-[3-(trifluoromethyl)phenyl]urea TCL: Rf 0.75 (Ethyl Acetate);
$^1$H-NMR (DMSO-$d_6$): δ 0.90 (d, 6 H), 1.88 (m, 1 H), 3.06 (t, 2 H), 7.14 (d, 2 H), 7.32 (d, 1 H), 7.41 (s, 1 H), 7.45 (d, 2 H), 7.51 (t, 1 H), 7.61 (d, 1 H), 7.80 (t, 1 H), 7.97 (s, 1 H), 8.70 (s, 1 H), 8.97 (s, 1 H), 9.30 (s, 1 H).

Example 85-101

1-(3-chlorophenyl)-3-(2-{4-[2-(ethylamino)-1,3-thiazol-5-yl]phenoxy}-5-pyrimidinyl)urea TCL: Rf 0.80 (Ethyl Acetate);
¹H-NMR (DMSO-d₆): δ 1.17 (t, 3 H), 3.21-3.34 (m, 2 H), 7.00-7.07 (m, 1 H), 7.11-7.17 (m, 2 H), 7.27-7.33 (m, 2 H), 7.41-7.48 (m, 3 H), 7.65-7.75 (m, 2 H), 8.69 (s, 2 H), 9.05 (s, 1 H), 9.25 (s, 1 H).

Example 85-102

1-(2,5-dichlorophenyl)-3-(2-{4-[2-(ethylamino)-1,3-thiazol-5-yl]phenoxy}-5-pyrimidinyl)urea

TCL: Rf 0.76 (Ethyl Acetate);
¹H-NMR (DMSO-d₆): δ 1.17 (t, 3 H), 3.21-3.34 (m, 2 H), 7.10-7.18 (m, 3 H), 7.42-7.52 (m, 4 H), 7.72 (t, 1 H), 8.25 (d, 1 H), 8.65 (s, 1 H), 8.71 (s, 2 H), 9.69 (s, 1 H).

Example 85-103

1-[2-chloro-5-(trifluoromethyl)phenyl]-3-(2-{4-[2-(dimethylamino)-1,3-thiazol-5-yl]phenoxy}-5-pyrimidinyl)urea TCL: Rf 0.30 (Hexane:Ethyl Acetate=1:2);
¹H-NMR (DMSO-d₆): δ 3.07 (s, 6 H), 7.16 (d, 2 H), 7.39 (dd, 1 H), 7.49 (d, 2 H), 7.55 (s, 1 H), 7.72 (d, 1 H), 8.56 (d, 1 H), 8.72 (s, 2 H), 8.77 (s, 1 H), 9.69 (s, 1 H).

Example 85-104

1-{2-[4-(2-amino-1,3-thiazol-5-yl)phenoxy]-5-pyrimidinyl}-3-[2-(3-pyridinyl)-5-(trifluoromethyl)phenyl]urea

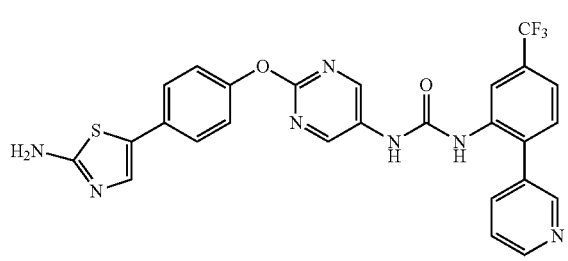 [SMILES: Nc1ncc(-c2ccc(Oc3ncc(NC(=O)Nc4cc(C(F)(F)F)ccc4-c4cccnc4)cn3)cc2)s1]

TCL: Rf 0.66 (Ethyl Acetate:Methanol=9:1);
¹H-NMR (CDCl₃): δ 7.10-7.14 (m, 2 H), 7.23 (s, 1 H), 7.45-7.62 (m, 5 H), 7.93-7.97 (m, 1 H), 8.54 (s, 1 H), 8.60-8.63 (m, 4 H).

Example 85-105

1-[2-(4-{2-[(cyclopropylmethyl)amino]-1,3-thiazol-5-yl}phenoxy)-5-pyrimidinyl]-3-[3-(trifluoromethyl)phenyl]urea

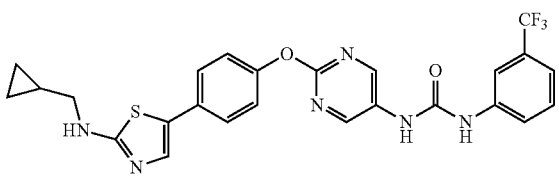 [SMILES: O=C(Nc1cnc(Oc2ccc(-c3cnc(NCC4CC4)s3)cc2)nc1)Nc1cccc(C(F)(F)F)c1]

TCL: Rf 0.79 (Ethyl Acetate)
¹H-NMR (DMSO-d₆): δ 0.22 (q, 2 H), 0.46 (q, 2 H), 1.07 (m, 1 H), 3.13 (t, 2 H), 7.14 (d, 2 H), 7.32 (d, 1 H), 7.41 (s, 1 H), 7.45 (d, 2 H), 7.50 (t, 1 H), 7.61 (d, 1 H), 7.84 (t, 1 H), 7.96 (s, 1 H), 8.69 (s, 2 H), 8.95 (s, 1 H), 9.29 (s, 1 H).

Example 85-106

1-(2-{4-[2-(cyclobutylamino)-1,3-thiazol-5-yl]phenoxy}-5-pyrimidinyl)-3-[3-(trifluoromethyl)phenyl]urea TCL: Rf 0.79 (Ethyl Acetate);
¹H-NMR (DMSO-d₆): δ 1.68 (m, 2 H), 1.94 (m, 2 H), 2.31 (m, 2 H), 4.06 (m, 1 H), 7.14 (d, 2 H), 7.32 (d, 1 H), 7.42 (s, 1 H), 7.45 (d, 2 H), 7.50 (t, 1 H), 7.61 (d, 1 H), 7.96 (s, 1 H), 8.03 (d, 1 H), 8.69 (s, 2 H), 8.96 (s, 1 H), 9.29 (s, 1 H).

Example 85-107

1-(2-{4-[2-(cyclopentylamino)-1,3-thiazol-5-yl]phenoxy}-5-pyrimidinyl)-3-[3-(trifluoromethyl)phenyl]urea TCL: Rf 0.79 (Ethyl Acetate);
¹H-NMR (DMSO-d₆): δ 1.52 (m, 4 H), 1.67 (m, 2 H), 1.93 (m, 2 H), 3.94 (m, 1 H), 4.06 (m, 1 H), 7.14 (d, 2 H), 7.32 (d, 1 H), 7.42 (s, 1 H), 7.45 (d, 2 H), 7.50 (t, 1 H), 7.61 (d, 1 H), 7.76 (d, 1 H), 7.96 (s, 1 H), 8.70 (s, 2 H), 8.95 (s, 1 H), 9.29 (s, 1 H).

Example 85-108

1-[2-chloro-4-(trifluoromethyl)phenyl]-3-(6-{4-[2-(dimethylamino)-1,3-thiazol-5-yl]phenoxy}-3-pyridinyl)urea TCL: Rf 0.48 (Hexane:Ethyl Acetate=1:2);
¹H-NMR (DMSO-d₆): δ 3.06 (s, 6 H), 7.03 (s, 1 H), 7.05-7.10 (m, 2 H), 7.45-7.49 (m, 2 H), 7.53 (s, 1 H), 7.68 (dd, 1 H), 7.87 (d, 1 H), 8.02 (dd, 1 H), 8.20 (d, 1 H), 8.44 (d, 1 H), 8.67 (s, 1 H), 9.68 (s, 1 H).

Example 85-109

1-(6-{4-[2-(ethylamino)-1,3-thiazol-5-yl]phenoxy}-3-pyridinyl)-3-[2-fluoro-5-(trifluoromethyl)phenyl]urea TCL: Rf 0.60 (Ethyl Acetate);
¹H-NMR (DMSO-d₆): δ 1.16 (t, 3 H), 3.23-3.27 (m, 2 H), 7.00-7.07 (m, 3 H), 7.36-7.39 (m, 5 H), 7.66-7.76 (m, 1 H), 8.03 (dd, 1 H), 8.17 (d, 1 H), 8.56 (d, 1 H), 8.97 (s, 1 H), 9.25 (s, 1 H).

Example 85-110

1-[2-chloro-5-(trifluoromethyl)phenyl]-3-(6-{4-[2-(ethylamino)-1,3-thiazol-5-yl]phenoxy}-3-pyridinyl)urea TCL: Rf 0.62 (Ethyl Acetate);
$^1$H-NMR (DMSO-$d_6$): δ 1.16 (t, 3 H), 3.21-3.27 (m, 2 H), 7.01-7.08 (m, 3 H), 7.36-7.45 (m, 4 H), 7.68-7.73 (m, 2 H), 8.04 (dd, 1 H), 8.17 (d, 1 H), 8.60 (s, 1 H), 8.66 (s, 1 H), 9.63 (s, 1 H).

Example 85-111

1-[2-chloro-4-(trifluoromethyl)phenyl]-3-(6-{4-[2-(ethylamino)-1,3-thiazol-5-yl]phenoxy}-3-pyridinyl)urea TCL: Rf 0.64 (Ethyl Acetate);
$^1$H-NMR (DMSO-$d_6$): δ 1.16 (t, 3 H), 3.21-3.27 (m, 2 H), 7.02-7.08 (m, 3 H), 7.40-7.44 (m, 3 H), 7.66-7.71 (m, 2 H), 7.87 (s, 1 H), 8.02 (d, 1 H), 8.19 (d, 1 H), 8.45 (d, 1 H), 8.67 (s, 1 H), 9.68 (s, 1 H).

Example 85-112

1-(2-{4-[2-(tetrahydro-3-furanylamino)-1,3-thiazol-5-yl]phenoxy}-5-pyrimidinyl)-3-[3-(trifluoromethyl)phenyl]urea

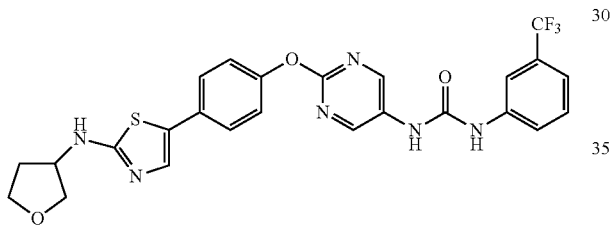

TCL: Rf 0.22 (Chloroform:Methanol=9:1);
$^1$H-NMR (DMSO-$d_6$): δ 1.79-1.90 (m, 1 H), 2.11-2.24 (m, 1 H), 3.61 (dd, 1 H), 3.67-3.86 (m, 3 H), 4.21-4.31 (m, 1 H), 7.12-7.18 (m, 2 H), 7.30-7.35 (m, 1 H), 7.43-7.54 (m, 4 H), 7.58-7.64 (m, 1 H), 7.95-8.01 (m, 2 H), 8.70 (s, 2 H), 8.98 (s, 1 H), 9.31 (s, 1 H).

Example 85-113

1-(2-{4-[2-(3-oxetanylamino)-1,3-thiazol-5-yl]phenoxy}-5-pyrimidinyl)-3-[3-(trifluoromethyl)phenyl]urea TCL: Rf 0.17 (Chloroform:Methanol=9:1);
$^1$H-NMR (DMSO-$d_6$): δ 3.36-3.56 (m, 2 H), 3.70 (dd, 1 H), 3.91 (t, 1 H), 4.34-4.45 (m, 1 H), 4.78 (t, 1 H), 7.13-7.19 (m, 2 H), 7.30-7.38 (m, 3 H), 7.47-7.55 (m, 2 H), 7.58-7.64 (m, 1 H), 7.95-8.00 (m, 1 H), 8.70 (s, 2 H), 8.98 (s, 1 H), 9.31 (s, 1 H).

Example 85-114

1-[6'-methyl-5-(trifluoromethyl)-2,3'-bipyridin-3-yl]-3-(2-{4-[2-(2-oxo-1-pyrrolidinyl)-1,3-thiazol-5-yl]phenoxy}-5-pyrimidinyl)urea TCL: Rf 0.58 (Ethyl Acetate:Methanol=9:1);
$^1$H-NMR (DMSO-$d_6$): δ 2.10-2.23 (m, 2 H), 2.57 (s, 3 H), 2.64 (t, 2 H), 4.05 (t, 2 H), 7.21 (d, 2 H), 7.44 (d, 1 H), 7.67 (d, 2 H), 7.89 (s, 1 H), 7.95 (dd, 1 H), 8.54 (d, 1 H), 8.67 (s, 2 H), 8.71 (dd, 1 H), 8.75 (s, 2 H), 9.35 (s, 1 H).

Example 85-115

1-(2-{4-[2-(dipropylamino)-1,3-thiazol-5-yl]phenoxy}-5-pyrimidinyl)-3-[3-(trifluoromethyl)phenyl]urea TCL: Rf 0.80 (Ethyl Acetate);
$^1$H-NMR (DMSO-$d_6$): δ 0.89 (t, 6 H), 1.55-1.75 (m, 4 H), 3.25-3.50 (m, 4 H), 7.14 (d, 2 H), 7.32 (d, 1 H), 7.46 (d, 2 H), 7.49 (s, 1 H), 7.50 (t, 1 H), 7.59 (d, 1 H), 7.96 (s, 1 H), 8.70 (s, 2 H), 8.95 (s, 1 H), 9.29 (s, 1 H).

Example 85-116

1-{2-[4-(2-{[2-(3-oxetanyl)ethyl]amino}-1,3-thiazol-5-yl)phenoxy]-5-pyrimidinyl}-3-[3-(trifluoromethyl)phenyl]urea TCL: Rf 0.33 (Ethyl Acetate);
$^1$H-NMR (DMSO-$d_6$): δ 1.92 (q, 2 H), 2.95-3.10 (m, 1 H), 3.19 (q, 2 H), 4.27 (t, 2 H), 4.64 (dd, 2 H), 7.14 (dd, 2 H), 7.32 (d, 1 H), 7.43 (s, 1 H), 7.45 (d, 2 H), 7.51 (t, 1 H), 7.62 (d, 1 H), 7.73 (t, 1 H), 7.97 (s, 1 H), 8.70 (s, 2 H), 8.96 (s, 1 H), 9.30 (s, 1 H).

Example 85-117

1-[2-chloro-5-(trifluoromethyl)phenyl]-3-(2-{4-[2-(propylamino)-1,3-thiazol-5-yl]phenoxy}-5-pyrimidinyl)urea

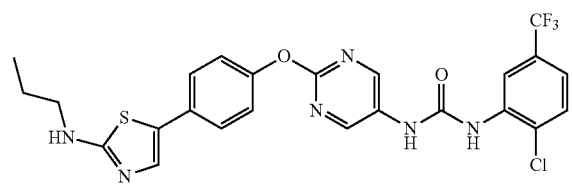 [SMILES: CCCNc1ncc(-c2ccc(Oc3ncc(NC(=O)Nc4cc(C(F)(F)F)ccc4Cl)cn3)cc2)s1]

TCL: Rf 0.56 (Ethyl Acetate:Methanol=9:1);
$^1$H-NMR (DMSO-$d_6$): δ 0.91 (t, 3 H), 1.51-1.63 (m, 2 H), 3.15-3.23 (m, 2 H), 7.13-7.17 (m, 2 H), 7.38-7.48 (m, 4 H), 7.71-7.78 (m, 2 H), 8.56 (d, 1 H), 8.72 (s, 2 H), 8.77 (s, 1 H), 9.69 (s, 1 H).

Example 85-118

1-[2-chloro-4-(trifluoromethyl)phenyl]-3-(2-{4-[2-(propylamino)-1,3-thiazol-5-yl]phenoxy}-5-pyrimidinyl)urea TCL: Rf 0.73 (Ethyl Acetate:Methanol=9:1);
$^1$H-NMR (DMSO-$d_6$): δ 0.91 (t, 3 H), 1.51-1.63 (m, 2 H), 3.16-3.23 (m, 2 H), 7.13-7.17 (m, 2 H), 7.42-7.48 (m, 3 H), 7.68 (dd, 1 H), 7.76 (t, 1 H), 7.88 (d, 1 H), 8.42 (d, 1 H), 8.72 (s, 2 H), 8.79 (s, 1 H), 9.75 (s, 1 H).

Example 85-119

1-[4-methyl-3-(trifluoromethyl)phenyl]-3-(2-{4-[2-(propylamino)-1,3-thiazol-5-yl]phenoxy}-5-pyrimidinyl)urea TCL: Rf 0.56 (Ethyl Acetate:Methanol=9:1);
$^1$H-NMR (DMSO-$d_6$): δ 0.91 (t, 3 H), 1.51-1.63 (m, 2 H), 2.36 (d, 3 H), 3.16-3.23 (m, 2 H), 7.12-7.17 (m, 2 H), 7.33 (d, 1 H), 7.42-7.47 (m, 3 H), 7.53 (dd, 1 H), 7.76 (t, 1 H), 7.88 (d, 1 H), 8.69 (s, 2 H), 8.90 (s, 1 H), 9.17 (s, 1 H).

Example 85-120

1-(2-{4-[2-(propylamino)-1,3-thiazol-5-yl]phenoxy}-5-pyrimidinyl)-3-[2-(3-pyridinyl)-5-(trifluoromethyl)phenyl]urea TCL: Rf 0.40 (Ethyl Acetate:Methanol=9:1);
$^1$H-NMR (DMSO-$d_6$): δ 0.91 (t, 3 H), 1.51-1.63 (m, 2 H), 3.16-3.23 (m, 2 H), 7.10-7.15 (m, 2 H), 7.41-7.57 (m, 6 H), 7.75 (t, 1 H), 7.87-7.91 (m, 1 H), 8.22 (s, 1 H), 8.38 (s, 1 H), 8.62-8.68 (m, 4 H), 9.22 (s, 1 H).

Example 85-121

1-(6-{4-[2-(propylamino)-1,3-thiazol-5-yl]phenoxy}-3-pyridinyl)-3-[2-(3-pyridinyl)-5-(trifluoromethyl)phenyl]urea TCL: Rf 0.10 (Ethyl Acetate);
$^1$H-NMR (DMSO-$d_6$): δ 0.91 (t, 3 H), 1.51-1.63 (m, 2 H), 3.16-3.21 (m, 2 H), 6.96-7.04 (m, 3 H), 7.38-7.60 (m, 6 H), 7.73 (s, 1 H), 7.92 (d, 1 H), 7.96 (d, 1 H), 8.09 (d, 1 H), 8.37-8.50 (m, 2 H), 8.63-8.66 (m, 2 H), 9.46 (s, 1 H).

Example 85-122

1-(6-{4-[2-(propylamino)-1,3-thiazol-5-yl]phenoxy}-3-pyridinyl)-3-[3-(trifluoromethyl)phenyl]urea TCL: Rf 0.48 (Ethyl Acetate);
$^1$H-NMR (DMSO-$d_6$): δ 0.91 (t, 3 H), 1.53-1.60 (m, 2 H), 3.16-3.22 (m, 2 H), 6.99-7.07 (m, 3 H), 7.28-7.57 (m, 6 H), 7.72-7.75 (m, 1 H), 7.98-8.01 (m, 2 H), 8.19 (d, 1 H), 8.91 (s, 1 H), 9.16 (s, 1 H).

Example 85-123

1-(2-{4-[2-(ethylamino)-1,3-thiazol-5-yl]phenoxy}-5-pyrimidinyl)-3-[5-(trifluoromethyl)-3-pyridinyl]urea TCL: Rf 0.43 (Dichloromethane:Methanol=9:1);
$^1$H-NMR (DMSO-$d_6$): δ 1.17 (t, 3 H), 3.21-3.29 (m, 2 H), 7.12-7.17 (m, 2 H), 7.43-7.47 (m, 3 H), 7.72 (t, 1 H), 8.38 (t, 1 H), 8.58 (d, 1 H), 8.71 (s, 2 H), 8.82 (d, 1 H), 9.18 (s, 1 H), 9.52 (s, 1 H).

Example 85-124

1-[2-(4-{2-[3-(2-hydroxy-2-propanyl)-2-oxo-1-pyrrolidinyl]-1,3-thiazol-5-yl}phenoxy)-5-pyrimidinyl]-3-[2-phenyl-5-(trifluoromethyl)-3-pyridinyl]urea TCL: Rf 0.28 (Chloroform:Methanol=19:1);
$^1$H-NMR (DMSO-$d_6$): δ 1.25 (s, 3 H), 1.28 (s, 3 H), 2.20-2.29 (m, 2 H), 2.78 (t, 1 H), 3.84-3.94 (m, 1 H), 3.98-4.08 (m, 1 H), 4.65 (s, 1 H), 7.20-7.26 (m, 2 H), 7.49-7.60 (m, 3 H), 7.64-7.70 (m, 4 H), 7.89 (s, 1 H), 8.42 (s, 1 H), 8.67 (s, 2 H), 8.71-8.78 (m, 2 H), 9.47 (s, 1 H).

Example 85-125

1-(6-{4-[2-(1-pyrrolidinyl)-1,3-thiazol-5-yl]phenoxy}-3-pyridinyl)-3-[3-(trifluoromethyl)phenyl]urea TCL: Rf 0.12 (Hexane:Ethyl Acetate=1:1);
$^1$H-NMR (DMSO-$d_6$): δ 1.96-2.00 (m, 4 H), 3.38-3.42 (m, 4 H), 7.00-7.07 (m, 3 H), 7.29-7.60 (m, 6 H), 7.98-8.01 (m, 2 H), 8.19 (d, 1 H), 8.88 (s, 1 H), 9.13 (s, 1 H).

Example 85-126

1-(6-{4-[2-(1-piperidinyl)-1,3-thiazol-5-yl]phenoxy}-3-pyridinyl)-3-[3-(trifluoromethyl)phenyl]urea TCL: Rf 0.46 (Hexane:Ethyl Acetate=1:1);
$^1$H-NMR (DMSO-$d_6$): δ 1.55-1.65 (s, 6 H), 3.44 (s, 4 H), 7.00-7.08 (m, 3 H), 7.30 (d, 1 H), 7.45-7.60 (m, 5 H), 7.98-8.02 (m, 2 H), 8.19 (d, 1 H), 8.88 (s, 1 H), 9.13 (s, 1 H).

Example 85-127

1-[2-chloro-5-(trifluoromethyl)-3-pyridinyl]-3-(2-{4-[2-(ethylamino)-1,3-thiazol-5-yl]phenoxy}-5-pyrimidinyl)urea TCL: Rf 0.48 (Dichloromethane:Methanol=9:1);
$^1$H-NMR (DMSO-$d_6$): δ 1.16 (t, 3 H), 3.21-3.29 (m, 2 H), 7.15 (d, 2 H), 7.43-7.47 (m, 3 H), 7.72 (t, 1 H), 8.48 (d, 1 H), 8.73 (s, 2 H), 8.88 (d, 1 H), 8.95 (s, 1 H), 9.77 (s, 1 H).

Example 85-128

1-[2-(4-{2-[ethyl(methyl)amino]-1,3-thiazol-5-yl}phenoxy)-5-pyrimidinyl]-3-[3-(trifluoromethyl)phenyl]urea TCL: Rf 0.32 (Hexane:Ethyl Acetate=1:2);
$^1$H-NMR (DMSO-$d_6$): δ 1.15 (t, 3 H), 3.03 (s, 3 H), 3.47-3.54 (m, 2 H), 7.13-7.17 (m, 2 H), 7.32 (d, 1 H), 7.46-7.53 (m, 4 H), 7.61 (d, 1 H), 7.96 (s, 1 H), 8.70 (s, 2 H), 8.96 (s, 1 H), 9.29 (s, 1 H).

Example 85-129

1-[2-(4-{2-[(2-methoxyethyl)amino]-1,3-thiazol-5-yl}phenoxy)-5-pyrimidinyl]-3-[3-(trifluoromethyl)phenyl]urea

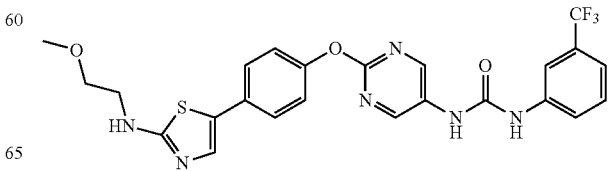

TCL: Rf 0.58 (Dichloromethane:Methanol=9:1);

¹H-NMR (DMSO-d₆): δ 3.27 (s, 3 H), 3.41-3.51 (m, 4 H), 7.12-7.16 (m, 2 H), 7.32 (d, 1 H), 7.41-7.59 (m, 4 H), 7.61 (d, 1 H), 7.82 (t, 1 H), 7.96 (s, 1 H), 8.69 (s, 2 H), 8.95 (s, 1 H), 9.29 (s, 1 H).

Example 85-130

1-[5-fluoro-2-(3-pyridinyl)phenyl]-3-(2-{4-[2-(2-oxo-1-pyrrolidinyl)-1,3-thiazol-5-yl]phenoxy}-5-pyrimidinyl)urea TCL: Rf 0.34 (Ethyl Acetate);
¹H-NMR (DMSO-d₆): δ 2.10-2.23 (m, 2 H), 2.64 (t, 2 H), 4.05 (t, 2 H), 7.01 (dt, 1 H), 7.21 (d, 2 H), 7.29 (dd, 1 H), 7.51 (dd, 1 H), 7.66 (d, 2 H), 7.80 (m, 3 H), 8.10 (s, 1 H), 8.55-8.68 (m, 4 H), 9.22 (s, 1 H).

Example 85-131

1-(3,5-difluorophenyl)-3-(2-{4-[2-(ethylamino)-1,3-thiazol-5-yl]phenoxy}-5-pyrimidinyl)urea TCL: Rf 0.75 (Ethyl Acetate);
¹H-NMR (DMSO-d₆): δ 1.17 (t, 3 H), 3.22-3.30 (m, 2 H), 6.82 (dt, 1 H), 7.12-7.25 (m, 4 H), 7.42-7.47 (m, 3 H), 7.72 (t, 1 H), 8.69 (s, 2 H), 9.01 (s, 1 H), 9.35 (s, 1 H).

Example 85-132

1-[6-(4-{2-[(cyclopropylmethyl)(methyl)amino]-1,3-thiazol-5-yl}phenoxy)-3-pyridinyl]-3-[3-(trifluoromethyl)phenyl]urea TCL: Rf 0.49 (Hexane:Ethyl Acetate=1:2);
¹H-NMR (DMSO-d₆): δ 0.27-0.32 (m, 2H), 0.46-0.51 (m, 2H), 1.03-1.16 (m, 1H), 3.10 (s, 3H), 3.35 (d, 2H), 7.00-7.09 (m, 3H), 7.30 (d, 1H), 7.44-7.53 (m, 4H), 7.59 (d, 1H), 7.98 (d, 1H), 8.01 (d, 1H), 8.19 (d, 1H), 8.87 (s, 1H), 9.13 (s, 1H).

Example 85-133

1-(5-methoxy-6-{4-[2-(2-oxo-1-pyrrolidinyl)-1,3-thiazol-5-yl]phenoxy}-3-pyridinyl)-3-[2-phenyl-5-(trifluoromethyl)-3-pyridinyl]urea

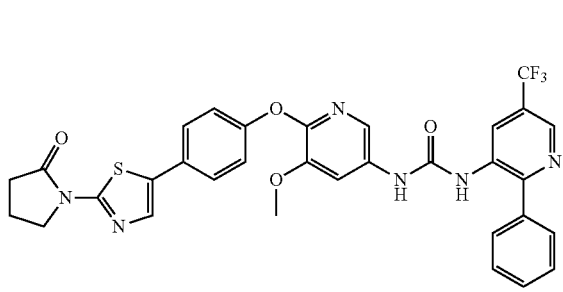 [SMILES: COc1cc(NC(=O)Nc2cc(C(F)(F)F)cnc2-c2ccccc2)cnc1Oc1ccc(-c2cnc(N3CCCC3=O)s2)cc1]

TCL: Rf 0.67 (Ethyl Acetate);
¹H-NMR (DMSO-d₆): δ 2.11-2.21 (m, 2 H), 2.63 (t, 2 H), 3.84 (s, 3 H), 4.04 (t, 2 H), 7.01-7.07 (m, 2 H), 7.51-7.68 (m, 8 H), 7.78 (d, 1 H), 7.84 (s, 1 H), 8.30 (s, 1 H), 8.69-8.73 (m, 1 H), 8.78-8.83 (m, 1 H), 9.46 (s, 1 H).

Example 85-134

1-[2-(4-{2-[(tetrahydro-2H-pyran-4-ylmethyl)amino]-1,3-thiazol-5-yl}phenoxy)-5-pyrimidinyl]-3-[3-(trifluoromethyl)phenyl]urea TCL: Rf 0.49 (Ethyl Acetate);
¹H-NMR (DMSO-d₆): δ 1.14-1.23 (m, 2 H), 1.62 (d, 2 H), 1.75-1.95 (m, 1 H), 3.14 (t, 2 H), 3.25 (dd, 2 H), 3.85 (dd, 2 H), 7.14 (d, 2 H), 7.32 (d, 1 H), 7.41-7.55 (m, 4 H), 7.61 (d, 1 H), 7.82 (t, 1 H), 7.96 (s, 1 H), 8.69 (s, 2 H), 8.95 (s, 1 H), 9.29 (s, 1 H).

Example 85-135

1-[2-(2-methyl-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.34 (Ethyl Acetate);
¹H-NMR (DMSO-d₆): δ 2.10-2.21 (m, 2 H), 2.24 (s, 3 H), 2.64 (t, 2 H), 4.15 (t, 2 H), 7.21 (d, 2 H), 7.35-7.43 (m, 2 H), 7.47 (d, 1 H), 7.62 (dd, 1 H), 7.66 (d, 2 H), 7.86 (s, 1 H), 7.89 (s, 1 H), 8.52 (s, 1 H), 8.59 (dd, 1 H), 8.64 (s, 2 H), 9.28 (s, 1 H).

Example 85-136

1-[2-(4-methyl-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.34 (Ethyl Acetate);
¹H-NMR (DMSO-d₆): δ 2.07 (s, 3 H), 2.10-2.21 (m, 2 H), 2.64 (t, 2 H), 4.15 (t, 2 H), 7.21 (d, 2 H), 7.38 (d, 1 H), 7.43 (d, 1 H), 7.48 (dd, 1 H), 7.66 (d, 2 H), 7.89 (s, 1 H), 7.90 (s, 1 H), 8.36 (s, 1 H), 8.50 (s, 1 H), 8.56 (d, 1 H), 8.63 (s, 2 H), 9.26 (s, 1 H).

Example 85-137

1-(2-{4-[2-(1-pyrrolidinyl)-1,3-thiazol-5-yl]phenoxy}-5-pyrimidinyl)-3-[3-(trifluoromethyl)phenyl]urea

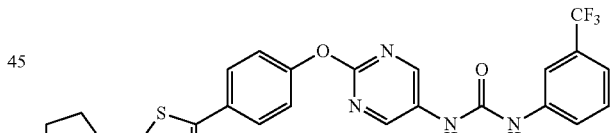

TCL: Rf 0.50 (Hexane:Ethyl Acetate=1:1);
¹H-NMR (DMSO-d₆): δ 1.92-2.03 (m, 4 H), 3.36-3.48 (m, 4 H), 7.15 (d, 2 H), 7.32 (d, 1 H), 7.47-7.63 (m, 5 H), 7.97 (s, 1 H), 8.70 (s, 2 H), 9.00 (s, 1 H), 9.32 (s, 1 H).

Example 85-138

1-(2-{4-[2-(1-piperidinyl)-1,3-thiazol-5-yl]phenoxy}-5-pyrimidinyl)-3-[3-(trifluoromethyl)phenyl]urea TCL: Rf 0.25 (Hexane:Ethyl Acetate=1:1);
¹H-NMR (DMSO-d₆): δ 1.52-1.67 (m, 6 H), 3.40-3.50 (m, 4 H), 7.16 (d, 2 H), 7.31 (d, 1 H), 7.47-7.62 (m, 5 H), 7.96 (s, 1 H), 8.70 (s, 2 H), 8.96 (s, 1 H), 9.29 (s, 1 H).

Example 85-139

1-(2-{4-[2-(4-morpholinyl)-1,3-thiazol-5-yl]phenoxy}-5-pyrimidinyl)-3-[3-(trifluoromethyl)phenyl]urea TCL: Rf 0.14 (Hexane:Ethyl Acetate=1:1);
$^1$H-NMR (DMSO-$d_6$): δ 3.37-3.45 (m, 4 H), 3.67-3.76 (m, 4 H), 7.18 (d, 2 H), 7.32 (d, 1 H), 7.51-7.65 (m, 5 H), 7.97 (s, 1 H), 8.71 (s, 2 H), 8.97 (s, 1 H), 9.30 (s, 1 H).

Example 85-140

1-(5-fluoro-2,3'-bipyridin-3-yl)-3-(2-{4-[2-(2-oxo-1-pyrrolidinyl)-1,3-thiazol-5-yl]phenoxy}-5-pyrimidinyl)urea TCL: Rf 0.19 (Ethyl Acetate);
$^1$H-NMR (DMSO-$d_6$): δ 2.10-2.20 (m, 2 H), 2.65 (t, 2 H), 4.07 (t, 2 H), 7.21 (d, 2 H), 7.54 (dd, 1 H), 7.66 (d, 2 H), 7.86 (s, 1 H), 7.97-8.00 (m, 1 H), 8.31 (dd, 1 H), 8.42 (d, 1 H), 8.46 (s, 1 H), 8.66-8.67 (m, 3 H), 8.76 (d, 1 H), 9.30 (s, 1 H).

Example 85-141

1-(2-{4-[2-(1-azetidinyl)-1,3-thiazol-5-yl]phenoxy}-5-pyrimidinyl)-3-[3-(trifluoromethyl)phenyl]urea TCL: Rf 0.64 (Ethyl Acetate);
$^1$H-NMR (DMSO-$d_6$): δ 2.39-2.44 (m, 2 H), 4.03 (t, 4 H), 7.16 (d, 2 H), 7.32 (d, 1 H), 7.48-7.63 (m, 5 H), 7.97 (s, 1 H), 8.70 (s, 2 H), 8.96 (s, 1 H), 9.30 (s, 1 H).

Example 85-142

1-[6-(4-{2-[(cyclopropylmethyl)(methyl)amino]-1,3-thiazol-5-yl}phenoxy)-3-pyridinyl]-3-[3',4'-dimethyl-4-(trifluoromethyl)-2-biphenylyl]urea TCL: Rf 0.45 (Hexane:Ethyl Acetate=1:1);
$^1$H-NMR (DMSO-$d_6$): δ 0.27-0.32 (m, 2 H), 0.46-0.52 (m, 2 H), 1.03-1.16 (m, 1 H), 2.29 (s, 6 H), 3.10 (s, 3 H), 3.35 (d, 2 H), 6.97-7.06 (m, 3 H), 7.14 (dd, 1 H), 7.20 (s, 1 H), 7.29-7.50 (m, 6 H), 7.88 (s, 1 H), 7.99 (dd, 1 H), 8.08 (d, 1 H), 8.47 (s, 1 H), 9.35 (s, 1 H).

Example 85-143

1-[2-(5-methyl-3-pyridinyl)-5-(trifluoromethyl)phenyl]-3-(2-{4-[2-(2-oxo-1-pyrrolidinyl)-1,3-thiazol-5-yl]phenoxy}-5-pyrimidinyl)urea TCL: Rf 0.35 (Ethyl Acetate);
$^1$H-NMR (DMSO-$d_6$): δ 2.10-2.22 (m, 2 H), 2.38 (s, 3 H), 2.64 (t, 2 H), 4.05 (t, 2 H), 7.21 (d, 2 H), 7.42-7.52 (m, 2 H), 7.66 (d, 2 H), 7.70 (s, 1 H), 7.88 (s, 1 H), 8.18 (s, 1 H), 8.42 (dd, 2 H), 8.51 (s, 1 H), 8.64 (s, 2 H), 9.27 (s, 1 H).

Example 85-144

1-[6-(4-{2-[ethyl(methyl)amino]-1,3-thiazol-5-yl}phenoxy)-3-pyridinyl]-3-[3-(trifluoromethyl)phenyl]urea TCL: Rf 0.49 (Ethyl Acetate);
$^1$H-NMR (DMSO-$d_6$): δ 1.15 (t, 3 H), 3.03 (s, 3 H), 3.49 (q, 2 H), 7.01 (d, 1 H), 7.06 (d, 2 H), 7.29 (d, 1 H), 7.45-7.70 (m, 5 H), 7.97 (s, 1 H), 8.01 (d, 1 H), 8.18 (d, 1 H), 8.87 (s, 1 H), 9.12 (s, 1 H).

Example 85-145

1-[6-(4-{2-[(2-methoxyethyl)amino]-1,3-thiazol-5-yl}phenoxy)-3-pyridinyl]-3-[3-(trifluoromethyl)phenyl]urea TCL: Rf 0.49 (Ethyl Acetate);
$^1$H-NMR (DMSO-$d_6$): δ 3.27 (s, 3 H), 3.40-3.50 (m, 4 H), 6.98 (d, 1 H), 7.04 (d, 2 H), 7.26 (d, 1 H), 7.38 (s, 1 H), 7.44 (d, 2 H), 7.47 (t, 1 H), 7.65 (d, 1 H), 7.79 (t, 1 H), 7.97-8.05 (m, 2 H), 8.24 (d, 1 H), 8.42 (s, 1 H), 10.3 (br s, 1 H).

Example 85-146

1-(2-{4-[2-(dimethylamino)-1,3-thiazol-5-yl]phenoxy}-5-pyrimidinyl)-3-[2-(1H-pyrazol-1-yl)-5-(trifluoromethyl)phenyl]urea TCL: Rf 0.62 (Methylene Dichloride:Ethyl Acetate:Methanol=8:4:1);
$^1$H-NMR (DMSO-$d_6$): δ 3.07 (s, 6H), 6.67 (t, 1 H), 7.15 (d, 2 H), 7.45-7.55 (m, 4 H), 7.75 (d, 1 H), 7.95 (d, 1 H), 8.41 (d, 1 H), 8.58 (d, 1 H), 8.68 (s, 2 H), 9.69 (s, 1 H), 9.94 (s, 1 H).

Example 85-147

1-(3,5-difluorophenyl)-3-(2-{4-[2-(dimethylamino)-1,3-thiazol-5-yl]phenoxy}-5-pyrimidinyl)urea TCL: Rf 0.35 (Ethyl Acetate);
$^1$H-NMR (DMSO-$d_6$): δ 3.07 (s, 6H), 6.81 (tt, 1H), 7.12-7.24 (m, 4H), 7.49 (d, 2H), 7.55 (s, 1H), 8.69 (s, 2H), 9.01 (s, 1H), 9.34 (s, 1H).

Example 85-148

1-[2-chloro-4-(trifluoromethyl)phenyl]-3-(2-{4-[2-(dimethylamino)-1,3-thiazol-5-yl]phenoxy}-5-pyrimidinyl)urea TCL: Rf 0.27 (Hexane:Ethyl Acetate=1:2);
$^1$H-NMR (DMSO-$d_6$): δ 3.07 (s, 6 H), 7.17 (d, 2 H), 7.50 (d, 2 H), 7.55 (s, 1 H), 7.69 (dd, 1 H), 7.89 (d, 1 H), 8.42 (d, 1 H), 8.72 (s, 2 H), 8.79 (s, 1 H), 9.75 (s, 1 H).

Example 85-149

1-[5-fluoro-2-(4-pyridinyl)phenyl]-3-(2-{4-[2-(2-oxo-1-pyrrolidinyl)-1,3-thiazol-5-yl]phenoxy}-5-pyrimidinyl)urea TCL: Rf 0.35 (Ethyl Acetate);
$^1$H-NMR (DMSO-$d_6$): δ 2.11-2.22 (m, 2 H), 2.64 (t, 2 H), 4.05 (t, 2 H), 7.03 (tt, 1 H), 7.22 (d, 2 H), 7.31 (dd, 1 H), 7.44

(d, 2 H), 7.66 (d, 2 H), 7.83-7.91 (m, 2 H), 8.13 (s, 1 H), 8.64 (s, 2 H), 8.66-8.72 (m, 2 H), 9.23 (s, 1 H).

Example 85-150

1-(2-{4-[2-(3-hydroxy-1-azetidinyl)-1,3-thiazol-5-yl]phenoxy}-5-pyrimidinyl)-3-[3-(trifluoromethyl)phenyl]urea

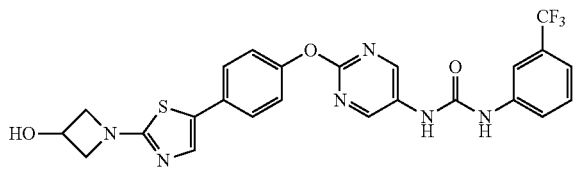 [SMILES: O=C(Nc1cnc(Oc2ccc(-c3cnc(N4CC(O)C4)s3)cc2)nc1)Nc1cccc(C(F)(F)F)c1]

TCL: Rf 0.37 (Ethyl Acetate);
¹H-NMR (DMSO-d₆): δ 3.77-3.81 (m, 2 H), 4.21-4.25 (m, 2 H), 4.55-4.70 (m, 1 H), 5.83 (d, 1 H), 7.16 (d, 2 H), 7.31 (d, 1 H), 7.48-7.62 (m, 4 H), 7.96 (s, 1 H), 8.70 (s, 2 H), 8.96 (s, 1 H), 9.29 (s, 1 H).

Example 85-151

1-[2-(1-methyl-1H-imidazol-4-yl)-5-(trifluoromethyl)-3-pyridinyl]-3-(2-{4-[2-(2-oxo-1-pyrrolidinyl)-1,3-thiazol-5-yl]phenoxy}-5-pyrimidinyl)urea TCL: Rf 0.44 (Ethyl Acetate);
¹H-NMR (DMSO-d₆): δ 2.10-2.22 (m, 2 H), 2.64 (t, 2 H), 3.80 (s, 3 H), 4.05 (t, 2 H), 7.24 (d, 2 H), 7.68 (d, 2 H), 7.89 (s, 1 H), 7.97 (d, 2 H), 8.49 (d, 1 H), 8.76 (s, 2 H), 8.93 (d, 1 H), 10.1 (s, 1 H), 12.0 (s, 1 H).

Example 85-152

1-(2-{4-[2-(2-oxo-1-pyrrolidinyl)-1,3-thiazol-5-yl]phenoxy})-5-pyrimidinyl)-3-[5-(trifluoromethyl)-2,2'-bipyridin-3-yl]urea TCL: Rf 0.18 (Ethyl Acetate);
¹H-NMR (DMSO-d₆): δ 2.10-2.20 (m, 2 H), 2.64 (t, 2 H), 4.05 (t, 2 H), 7.24 (d, 2 H), 7.61-7.69 (m, 3 H), 7.90 (s, 1 H), 8.08-8.14 (m, 1 H), 8.57 (d, 1 H), 8.70-8.80 (m, 4 H), 9.12-9.17 (m, 1 H), 10.2 (s, 1 H), 12.8 (s, 1 H).

Example 85-153

1-(2-{4-[2-(1-azetidinyl)-1,3-thiazol-5-yl]phenoxy}-5-pyrimidinyl)-3-(2,6-difluorophenyl)urea TCL: Rf 0.69 (Ethyl Acetate);
¹H-NMR (DMSO-d₆): δ 2.36-2.58 (m, 2 H), 4.03 (t, 4 H), 7.16 (m, 4 H), 7.25-7.40 (m, 1 H), 7.48 (d, 2 H), 7.53 (s, 1 H), 8.40 (s, 1 H), 8.68 (s, 2 H), 9.16 (s, 1 H).

Example 85-154

1-(2-{4-[2-(1-azetidinyl)-1,3-thiazol-5-yl]phenoxy}-5-pyrimidinyl)-3-(2,4-difluorophenyl)urea TCL: Rf 0.75 (Ethyl Acetate);
¹H-NMR (DMSO-d₆): δ 2.36-2.58 (m, 2 H), 4.03 (t, 4 H), 7.04 (dt, 1 H), 7.16 (d, 2 H), 7.31 (dt, 1 H), 7.49 (d, 2 H), 7.54 (s, 1 H), 7.92-8.02 (m, 1 H), 8.70 (s, 3 H), 9.14 (s, 1 H).

Example 85-155

1-[5-fluoro-2-(2-pyridinyl)phenyl]-3-(2-{4-[2-(2-oxo-1-pyrrolidinyl)-1,3-thiazol-5-yl]phenoxy}-5-pyrimidinyl)urea TCL: Rf 0.67 (Ethyl Acetate);
¹H-NMR (DMSO-d₆): δ 2.10-2.22 (m, 2 H), 2.64 (t, 2 H), 4.05 (t, 2 H), 6.85-7.02 (m, 1 H), 7.22 (d, 2 H), 7.45-7.50 (m, 1 H), 7.68 (d, 2 H), 7.80-8.05 (m, 4 H), 8.11 (dd, 1 H), 8.70 (s, 2 H), 8.71 (d, 1 H), 9.88 (s, 1 H), 11.7 (s, 1 H).

Example 85-156

1-(2-{4-[2-(1-azetidinyl)-1,3-thiazol-5-yl]phenoxy})-5-pyrimidinyl)-3-(3, 5-difluorophenyl)urea TCL: Rf 0.73 (Ethyl Acetate);
¹H-NMR (DMSO-d₆): δ 2.39-2.49 (m, 2 H), 4.03 (t, 4 H), 6.81 (t, 1 H), 7.15-7.21 (m, 4 H), 7.48-7.54 (m, 3 H), 8.69 (s, 2 H), 9.02 (s, 1 H), 9.35 (s, 1 H).

Example 85-157

1-(2-{4-[2-(1-azetidinyl)-1,3-thiazol-5-yl]phenoxy}-5-pyrimidinyl)-3-[3-fluoro-5-(trifluoromethyl)phenyl]urea TCL: Rf 0.69 (Ethyl Acetate);
¹H-NMR (DMSO-d₆): δ 2.37-2.49 (m, 2 H), 4.03 (t, 4 H), 7.16 (d, 2 H), 7.25 (d, 1 H), 7.49-7.70 (m, 5 H), 8.70 (s, 2 H), 9.09 (s, 1 H), 9.50 (s, 1 H).

Example 85-158

1-(2-{4-[2-(1-azetidinyl)-1,3-thiazol-5-yl]phenoxy}-5-pyrimidinyl)-3-[4-methyl-3-(trifluoromethyl)phenyl]urea TCL: Rf 0.69 (Ethyl Acetate);
¹H-NMR (DMSO-d₆): δ 2.36-2.49 (m, 5 H), 4.03 (t, 4 H), 7.16 (d, 2 H), 7.34 (d, 1 H), 7.48-7.54 (m, 4 H), 7.88 (s, 1 H), 8.69 (d, 2 H), 8.91 (s, 1 H), 9.17 (s, 1 H).

Example 85-159

1-(2-{4-[2-(1-azetidinyl)-1,3-thiazol-5-yl]phenoxy}-5-pyrimidinyl)-3-[2-chloro-4-(trifluoromethyl)phenyl]urea TCL: Rf 0.67 (Ethyl Acetate);
¹H-NMR (DMSO-d₆): δ 2.39-2.44 (m, 2 H), 4.03 (t, 4 H), 7.17 (d, 2 H), 7.47-7.54 (m, 3 H), 7.65-7.75 (m, 1 H), 7.88 (s, 1 H), 8.41-8.43 (m, 1 H), 8.73 (s, 2 H), 9.04 (br s, 1 H), 9.60 (br s, 1 H).

Example 85-160

1-(2-{4-[2-(1-azetidinyl)-1,3-thiazol-5-yl]phenoxy}-5-pyrimidinyl)-3-(2,5-difluorophenyl)urea

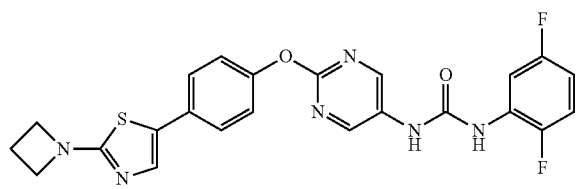 [SMILES: O=C(Nc1cnc(Oc2ccc(-c3cnc(N4CCC4)s3)cc2)nc1)Nc1cc(F)ccc1F]

TCL: Rf 0.60 (Ethyl Acetate);
$^1$H-NMR (DMSO-$d_6$): δ 2.42 (quin, 2 H), 4.03 (t, 4 H), 6.79-6.90 (m, 1 H), 7.17 (d, 2 H), 7.29 (ddd, 1 H), 7.50 (d, 2 H), 7.54 (s, 1 H), 7.96 (ddd, 1 H), 8.71 (s, 2 H), 8.95 (s, 1 H), 9.25 (s, 1 H).

Example 85-161

1-(2-{4-[2-(1-azetidinyl)-1,3-thiazol-5-yl]phenoxy}-5-pyrimidinyl)-3-(3,4-difluorophenyl)urea TCL: Rf 0.50 (Ethyl Acetate);
$^1$H-NMR (DMSO-$d_6$): δ 2.42 (quin, 2 H), 4.03 (t, 4 H), 7.10-7.20 (m, 3 H), 7.31 (dd, 1 H), 7.49 (d, 2 H), 7.54 (s, 1 H), 7.63 (ddd, 1 H), 8.68 (s, 2 H), 8.95-9.60 (br s, 2 H).

Example 85-162

1-(2-{4-[2-(1-azetidinyl)-1,3-thiazol-5-yl]phenoxy}-5-pyrimidinyl)-3-(2-fluorophenyl)urea TCL: Rf 0.62 (Ethyl Acetate);
$^1$H-NMR (DMSO-$d_6$): δ 2.42 (quin, 2 H), 4.03 (t, 4 H), 6.98-7.08 (m, 1 H), 7.10-7.30 (m, 4 H), 7.50 (d, 2 H), 7.54 (s, 1 H), 8.06 (dt, 1 H), 8.71 (s, 2 H), 8.73 (s, 1 H), 9.19 (s, 1 H).

Example 85-163

1-(2-{4-[2-(3-hydroxy-3-methyl-1-azetidinyl)-1,3-thiazol-5-yl]phenoxy}-5-pyrimidinyl)-3-[3-(trifluoromethyl)phenyl]urea TCL: Rf 0.52 (Ethyl Acetate);
$^1$H-NMR (DMSO-$d_6$): δ 1.44 (s, 3 H), 3.87-3.93 (m, 4 H), 5.77 (s, 1 H), 7.16 (d, 2 H), 7.31 (d, 1 H), 7.49-7.65 (m, 5 H), 7.97 (s, 1 H), 8.71 (s, 2 H), 9.22 (s, 1 H), 9.53 (s, 1 H).

Example 85-164

1-(2-{4-[2-(3,3-difluoro-1-azetidinyl)-1,3-thiazol-5-yl]phenoxy}-5-pyrimidinyl)-3-[3-(trifluoromethyl)phenyl]urea TCL: Rf 0.50 (Hexane:Ethyl Acetate=1:2);
$^1$H-NMR (DMSO-$d_6$): δ 4.52 (t, 4 H), 7.18 (d, 2 H), 7.30 (d, 1 H), 7.47-7.64 (m, 5 H), 7.94-7.97 (m, 1 H), 8.70 (s, 2 H), 8.99 (s, 1 H), 9.31 (s, 1 H).

Example 85-165

1-(2-{4-[2-(1-azetidinyl)-1,3-thiazol-5-yl]phenoxy}-5-pyrimidinyl)-3-(4-fluorophenyl)urea TCL: Rf 0.63 (Ethyl Acetate);
$^1$H-NMR (DMSO-$d_6$): δ 2.38-2.54 (m, 2 H), 4.03 (t, 4 H), 7.06-7.19 (m, 4 H), 7.41-7.58 (m, 4 H), 8.65 (s, 1 H), 8.69 (s, 2 H), 8.86 (s, 1 H), 8.94 (s, 1 H).

Example 85-166

1-(2-{4-[2-(1-azetidinyl)-1,3-thiazol-5-yl]phenoxy}-5-pyrimidinyl)-3-[2-phenyl-5-(trifluoromethyl)-3-pyridinyl]urea TCL: Rf 0.45 (Hexane:Ethyl Acetate=1:4);
$^1$H-NMR (DMSO-$d_6$): δ 2.40-2.49 (m, 2 H), 4.03 (t, 4 H), 7.14 (d, 2 H), 7.47-7.66 (m, 8 H), 8.41 (s, 1 H), 8.65 (s, 2 H), 8.72 (s, 1 H), 8.75 (s, 1 H), 9.44 (s, 1 H).

Example 85-167

1-(2-{4-[2-(1-azetidinyl)-1,3-thiazol-5-yl]phenoxy}-5-pyrimidinyl)-3-[1-(2-methylphenyl)-3-(2-methyl-2-propanyl)-1H-pyrazol-5-yl]urea

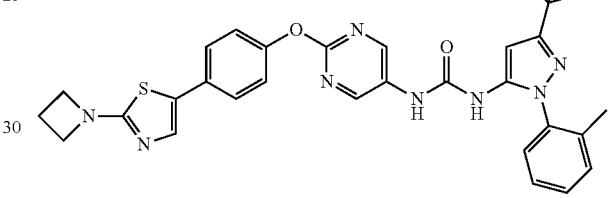

TCL: Rf 0.44 (Hexane:Ethyl Acetate=1:4);
$^1$H-NMR (DMSO-$d_6$): δ 1.26 (t, 9 H), 1.99 (s, 3 H), 2.40-2.49 (m, 2 H), 4.03 (t, 4 H), 6.33 (s, 1 H), 7.13 (d, 2 H), 7.28-7.53 (m, 7 H), 8.37 (s, 1 H), 8.61 (s, 2 H), 9.04 (s, 1 H).

Example 85-168

1-(2-{4-[2-(1-azetidinyl)-1,3-thiazol-5-yl]phenoxy}-5-pyrimidinyl)-3-[2-(3-pyridinyl)-5-(trifluoromethyl)phenyl]urea TCL: Rf 0.58 (Ethyl Acetate:Methanol=19:1);
$^1$H-NMR (DMSO-$d_6$): δ 2.40-2.49 (m, 2 H), 4.03 (t, 4 H), 7.14 (d, 2 H), 7.47-7.57 (m, 6 H), 7.87-7.89 (m, 1 H), 8.22 (s, 1 H), 8.37 (s, 1 H), 8.62-8.67 (m, 4 H), 9.22 (s, 1 H).

Example 85-169

1-(2-{4-[2-(1-azetidinyl)-1,3-thiazol-5-yl]phenoxy}-5-pyrimidinyl)-3-[3-(difluoromethyl)phenyl]urea TCL: Rf 0.44 (Hexane:Ethyl Acetate=1:4);
$^1$H-NMR (DMSO-$d_6$): δ 2.40-2.49 (m, 2 H), 4.03 (t, 4 H), 6.99 (s, 1 H), 7.14-7.18 (m, 3 H), 7.38-7.54 (m, 5 H), 7.76 (s, 1 H), 8.70 (s, 2 H), 8.89 (s, 1 H), 9.15 (s, 1 H).

Example 85-170

1-(2-{4-[2-(1-azetidinyl)-1,3-thiazol-5-yl]phenoxy}-5-pyrimidinyl)-3-(2,3,5-trifluorophenyl)urea TCL: Rf 0.59 (Hexane:Ethyl Acetate=1:4);

¹H-NMR (DMSO-d₆): δ 2.40-2.49 (m, 2 H), 4.13 (t, 4 H), 7.15-7.22 (m, 3 H), 7.54 (d, 2 H), 7.69 (s, 1 H), 7.78-7.85 (m, 1 H), 8.71 (s, 2 H), 9.22 (s, 1 H), 9.41 (s, 1 H).

Example 85-171

1-(2-{4-[2-(1-azetidinyl)-1,3-thiazol-5-yl]phenoxy}-5-pyrimidinyl)-3-[2-chloro-5-(trifluoromethyl)phenyl]urea TCL: Rf 0.49 (Hexane:Ethyl Acetate=1:4);
¹H-NMR (DMSO-d₆): δ 2.40-2.49 (m, 2 H), 4.03 (t, 4 H), 7.16 (d, 2 H), 7.37-7.40 (m, 1 H), 7.48-7.54 (m, 3 H), 7.72 (d, 1 H), 8.55 (s, 1 H), 8.72 (s, 2 H), 8.80 (s, 1 H), 9.70 (s, 1 H).

Example 85-172

1-(2-{4-[2-(1-azetidinyl)-1,3-thiazol-5-yl]phenoxy}-5-pyrimidinyl)-3-(2,4,6-trifluorophenyl)urea TCL: Rf 0.49 (Hexane:Ethyl Acetate=1:4);
¹H-NMR (DMSO-d₆): δ 2.35-2.49 (m, 2 H), 4.03 (t, 4 H), 7.14 (d, 2 H), 7.26 (t, 2 H), 7.48 (d, 2 H), 7.53 (s, 1 H), 8.40 (s, 1 H), 8.67 (s, 2 H), 9.20 (s, 1 H).

Example 85-173

1-(2-{4-[2-(1-azetidinyl)-1,3-thiazol-5-yl]phenoxy}-5-pyrimidinyl)-3-[2-fluoro-5-(trifluoromethyl)phenyl]urea TCL: Rf 0.50 (Hexane:Ethyl Acetate=1:4);
¹H-NMR (DMSO-d₆): δ 2.35-2.49 (m, 2 H), 4.03 (t, 4 H), 7.16 (d, 2 H), 7.38-7.54 (m, 5 H), 8.52 (d, 1 H), 8.72 (s, 2 H), 9.19 (s, 2 H).

Example 85-174

1-(2-{4-[2-(1-azetidinyl)-1,3-thiazol-5-yl]phenoxy}-5-pyrimidinyl)-3-(2,3-difluorophenyl)urea TCL: Rf 0.57 (Hexane:Ethyl Acetate=1:2);
¹H-NMR (DMSO-d₆): δ 2.38-2.50 (m, 2 H), 4.03 (t, 4 H), 7.02-7.21 (m, 4 H), 7.49 (d, 2 H), 7.54 (s, 1 H), 7.86 (t, 1 H), 8.71 (s, 2 H), 8.94 (s, 1 H), 9.23 (s, 1 H).

Example 85-175

1-(2-{4-[2-(1-azetidinyl)-1,3-thiazol-5-yl]phenoxy}-5-pyrimidinyl)-3-(2,4,5-trifluorophenyl)urea TCL: Rf 0.36 (Hexane:Ethyl Acetate=1:2);
¹H-NMR (DMSO-d₆): δ 2.37-2.50 (m, 2 H), 4.03 (t, 4 H), 7.16 (d, 2 H), 7.51 (d, 2 H), 7.54 (s, 1 H), 7.59-7.70 (m, 1 H), 8.00-8.17 (m, 1 H), 8.70 (s, 2 H), 8.91 (s, 1 H), 9.20 (s, 1 H).

Example 85-176

1-(2-{4-[2-(1-azetidinyl)-1,3-thiazol-5-yl]phenoxy})-5-pyrimidinyl)-3-[5-phenyl-2-(trifluoromethyl)-4-pyridinyl]urea TCL: Rf 0.65 (Ethyl Acetate);
¹H-NMR (DMSO-d₆): δ 2.40-2.49 (m, 2 H), 4.03 (t, 4 H), 7.15 (d, 2 H), 7.50-7.60 (m, 8 H), 8.42 (s, 2 H), 8.65 (s, 2 H), 8.74 (s, 1 H), 9.71 (s, 1 H).

Example 85-177

1-(2-{4-[2-(1-azetidinyl)-1,3-thiazol-5-yl]phenoxy}-5-pyrimidinyl)-3-(2,3,4-trifluorophenyl)urea TCL: Rf 0.40 (Hexane:Ethyl Acetate=1:2);
¹H-NMR (DMSO-d₆): δ 2.37-2.50 (m, 2 H), 4.03 (t 4 H), 7.15 (dd, 2 H), 7.22-7.34 (m, 1 H), 7.50 (d, 2 H), 7.54 (s, 1 H), 7.73-7.90 (m, 1 H), 8.70 (s, 2 H), 8.89 (s, 1 H), 9.18 (s, 1 H).

Example 85-178

1-(2-{4-[2-(1-azetidinyl)-1,3-thiazol-5-yl]phenoxy}-5-pyrimidinyl)-3-(2,3,5,6-tetrafluorophenyl)urea TCL: Rf 0.40 (Hexane:Ethyl Acetate=1:2);
¹H-NMR (DMSO-d₆): δ 2.37-2.50 (m, 2 H), 4.03 (t, 4 H), 7.15 (d, 2 H), 7.50 (d, 2 H), 7.54 (s, 1 H), 7.70-7.90 (m, 1 H), 8.69 (s, 2 H), 8.87 (s, 1 H), 9.30 (s, 1 H).

Example 85-179

1-(2-{4-[2-(1-azetidinyl)-1,3-thiazol-5-yl]phenoxy}-5-pyrimidinyl)-3-[2-(1H-1,2,3-triazol-1-yl)-5-(trifluoromethyl)phenyl]urea TCL: Rf 0.52 (Ethyl Acetate);
¹H-NMR (DMSO-d₆): δ 2.37-2.51 (m, 2 H), 4.03 (t, 4 H), 7.15 (dd, 2 H), 7.50 (d, 2 H), 7.54 (s, 1 H), 7.61 (d, 1 H), 7.74 (d, 1 H), 8.10 (d, 1 H), 8.57 (s, 1 H), 8.65 (s, 2 H), 8.68-8.73 (m, 2 H), 9.64 (s, 1 H).

Example 85-180

1-(2-{4-[2-(1-azetidinyl)-1,3-thiazol-5-yl]phenoxy}-5-pyrimidinyl)-3-[2-(1H-pyrazol-1-yl)-5-(trifluoromethyl)phenyl]urea TCL: Rf 0.61 (Methylene Dichloride:Ethyl Acetate:Methanol=8:4:1);
¹H-NMR (DMSO-d₆): δ 2.42 (quin, 2 H), 4.03 (t, 4 H), 6.67 (t, 1 H), 7.16 (d, 2 H), 7.48-7.56 (m, 4 H), 7.75 (d, 1 H), 7.95 (d, 1 H), 8.41 (d, 1 H), 8.58 (d, 1 H), 8.68 (s, 2 H), 9.70 (s, 1 H), 9.95 (s, 1 H).

Example 85-181

1-(2-{4-[2-(1-azetidinyl)-1,3-thiazol-5-yl]phenoxy}-5-pyrimidinyl)-3-[2-methyl-5-(trifluoromethyl)phenyl]urea TCL: Rf 0.28 (Hexane:Ethyl Acetate=1:4);
¹H-NMR (DMSO-d₆): δ 2.32-2.49 (m, 5 H), 4.03 (t, 4 H), 7.16 (d, 2 H), 7.29 (d, 1 H), 7.41 (d, 1 H), 7.49-7.54 (m, 3 H), 8.27 (s, 1 H), 8.37 (s, 1 H), 8.72 (s, 2 H), 9.32 (s, 1 H).

Example 85-182

1-(2-{4-[2-(1-azetidinyl)-1,3-thiazol-5-yl]phenoxy}-5-pyrimidinyl)-3-[2-(trifluoromethyl)-4-pyridinyl]urea TCL: Rf 0.60 (Hexane:Ethyl Acetate=1:4);
¹H-NMR (DMSO-d₆): δ 2.37-2.49 (m, 2 H), 4.06 (t, 4 H), 7.16 (d, 2 H), 7.48-7.63 (m, 4 H), 8.02 (s, 1 H), 8.52 (d, 1 H), 8.71 (s, 2 H), 9.23 (s, 1 H), 9.82 (s, 1 H).

Example 85-183

1-(2-{4-[2-(propylamino)-1,3-thiazol-5-yl]phenoxy}-5-pyrimidinyl)-3-[2-(1H-pyrazol-1-yl)-5-(trifluoromethyl)phenyl]urea Purity (UPLC-MS/ELSD): 99% (Retention Time: 0.91 minutes);
MASS (ESI, Pos.): 581 (M+H)$^+$;
$^1$H-NMR (DMSO-d$_6$): δ 0.91 (t, 3 H), 1.51-1.63 (m, 2 H), 3.16-3.22 (m, 2 H), 6.66-6.68 (m, 1 H), 7.11-7.15 (m, 2 H), 7.41-7.45 (m, 3 H), 7.51 (dd, 1 H), 7.73-7.78 (m, 2 H), 7.95 (d, 1 H), 8.44 (d, 1 H), 8.58 (dd, 1 H), 8.67 (s, 2 H), 9.69 (s, 1 H), 9.94 (s, 1 H).

Example 85-184

1-(2-{4-[2-(propylamino)-1,3-thiazol-5-yl]phenoxy}-5-pyrimidinyl)-3-{5-(trifluoromethyl)-2-[3-(trifluoromethyl)-1H-pyrazol-1-yl]phenyl}urea Purity (UPLC-MS/ELSD): 97% (Retention Time: 0.97 minutes);
MASS (ESI, Pos.): 649 (M+H)$^+$;
$^1$H-NMR (DMSO-d$_6$): δ 0.91 (t, 3 H), 1.51-1.63 (m, 2 H), 3.16-3.22 (m, 2 H), 7.10-7.15 (m, 3 H), 7.41-7.46 (m, 3 H), 7.57 (dd, 1 H), 7.70 (d, 1 H), 7.76 (t, 1 H), 8.46-8.47 (m, 2 H), 8.57 (s, 1 H), 8.63 (s, 2 H), 9.45 (s, 1 H).

Example 85-185

1-[2-(1-methyl-1H-pyrazol-5-yl)-5-(trifluoromethyl)phenyl]-3-(2-{4-[2-(propylamino)-1,3-thiazol-5-yl]phenoxy}-5-pyrimidinyl)urea Purity (UPLC-MS/ELSD): 99% (Retention Time: 0.89 minutes);
MASS (ESI, Pos.): 595 (M+H)$^+$;
$^1$H-NMR (DMSO-d$_6$): δ 0.91 (t, 3 H), 1.51-1.63 (m, 2 H), 3.16-3.22 (m, 2 H), 3.65 (s, 3 H), 6.45 (d, 1 H), 7.10-7.15 (m, 2 H), 7.42-7.51 (m, 5 H), 7.62 (d, 1 H), 7.76 (t, 1 H), 8.08 (s, 1 H), 8.55 (s, 1 H), 8.65 (s, 2 H), 9.45 (s, 1 H).

Example 85-186

1-[2-(3-methyl-1H-pyrazol-1-yl)-5-(trifluoromethyl)phenyl]-3-(2-{4-[2-(propylamino)-1,3-thiazol-5-yl]phenoxy}-5-pyrimidinyl)urea Purity (UPLC-MS/ELSD): 96% (Retention Time: 0.94 minutes);
MASS (ESI, Pos.): 595 (M+H)$^+$;
$^1$H-NMR (DMSO-d$_6$): δ 0.91 (t, 3 H), 1.51-1.63 (m, 2 H), 2.36 (s, 3 H), 3.16-3.22 (m, 2 H), 6.45 (d, 1 H), 7.11-7.16 (m, 2 H), 7.42-7.50 (m, 4 H), 7.69 (d, 1 H), 7.76 (t, 1 H), 8.28 (d, 1 H), 8.56 (d, 1 H), 8.67 (s, 2 H), 9.80 (s, 1 H), 9.91 (s, 1 H).

Example 85-187

1-[2-(4-methyl-1H-pyrazol-1-yl)-5-(trifluoromethyl)phenyl]-3-(2-{4-[2-(propylamino)-1,3-thiazol-5-yl]phenoxy}-5-pyrimidinyl)urea Purity (UPLC-MS/ELSD): 100% (Retention Time: 0.96 minutes);
MASS (ESI, Pos.): 595 (M+H)$^+$;
$^1$H-NMR (DMSO-d$_6$): δ 0.91 (t, 3 H), 1.51-1.63 (m, 2 H), 2.14 (s, 3 H), 3.16-3.22 (m, 2 H), 7.11-7.16 (m, 2 H), 7.42-7.51 (m, 4 H), 7.70 (d, 1 H), 7.74-7.78 (m, 2 H), 8.18 (s, 1 H), 8.57 (d, 1 H), 8.68 (s, 2 H), 9.82 (s, 1 H), 9.95 (s, 1 H).

Example 85-188

1-[2-(4-methyl-1H-1,2,3-triazol-1-yl)-5-(trifluoromethyl)phenyl]-3-(2-{4-[2-(propylamino)-1,3-thiazol-5-yl]phenoxy}-5-pyrimidinyl)urea Purity (UPLC-MS/ELSD): 99% (Retention Time: 0.86 minutes);
MASS (ESI, Pos.): 596 (M+H)$^+$;
$^1$H-NMR (DMSO-d$_6$): δ 0.91 (t, 3 H), 1.51-1.63 (m, 2 H), 2.38 (d, 3 H), 3.16-3.22 (m, 2 H), 7.11-7.16 (m, 2 H), 7.42-7.46 (m, 3 H), 7.59 (dd, 1 H), 7.69 (d, 1 H), 7.76 (t, 1 H), 8.39 (d, 1 H), 8.64 (d, 1 H), 8.66 (s, 2 H), 8.75 (s, 1 H), 9.68 (s, 1 H).

Example 85-189

1-(2-{4-[2-(propylamino)-1,3-thiazol-5-yl]phenoxy})-5-pyrimidinyl)-3-[2-(1H-pyrazol-1-yl)-4-(trifluoromethyl)phenyl]urea

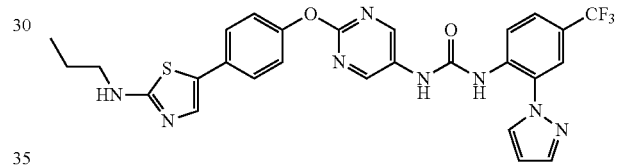

Purity (UPLC-MS/ELSD): 100% (Retention Time: 0.93 minutes);
MASS (ESI, Pos.): 581 (M+H)$^+$;
$^1$H-NMR (DMSO-d$_6$): δ 0.91 (t, 3 H), 1.51-1.63 (m, 2 H), 3.16-3.22 (m, 2 H), 6.65 (t, 1 H), 7.12-7.16 (m, 2 H), 7.41-7.46 (m, 3 H), 7.72-7.78 (m, 2 H), 7.82 (d, 1 H), 7.93 (d, 1 H), 8.40-8.43 (m, 2 H), 8.67 (s, 2 H), 9.55 (s, 1 H), 9.95 (s, 1 H).

Example 85-190

1-(2-{4-[2-(propylamino)-1,3-thiazol-5-yl]phenoxy}-5-pyrimidinyl)-3-[2-(3-pyridinyl)-4-(trifluoromethyl)phenyl]urea Purity (UPLC-MS/ELSD): 92% (Retention Time: 0.81 minutes);
MASS (ESI, Pos.): 592 (M+H)$^+$;
$^1$H-NMR (DMSO-d$_6$): δ 0.91 (t, 3 H), 1.51-1.63 (m, 2 H), 3.16-3.22 (m, 2 H), 7.11-7.15 (m, 2 H), 7.41-7.45 (m, 3 H), 7.53-7.57 (m, 2 H), 7.74-7.78 (m, 2 H), 7.88-7.92 (m, 1 H), 8.23 (s, 1 H), 8.27 (d, 1 H), 8.63-8.69 (m, 4 H), 9.27 (s, 1 H).

Example 85-191

1-[5-chloro-2-(1H-pyrazol-1-yl)phenyl]-3-(2-{4-[2-(propylamino)-1,3-thiazol-5-yl]phenoxy}-5-pyrimidinyl)urea Purity (UPLC-MS/ELSD): 99% (Retention Time: 0.88 minutes);
MASS (ESI, Pos.): 547 (M+H)$^+$;

¹H-NMR (DMSO-d₆): δ 0.91 (t, 3 H), 1.51-1.63 (m, 2 H), 3.16-3.22 (m, 2 H), 6.61-6.63 (m, 1 H), 7.11-7.16 (m, 2 H), 7.22 (dd, 1 H), 7.42-7.46 (m, 3 H), 7.51 (d, 1 H), 7.76 (t, 1 H), 7.89-7.90 (m, 1 H), 8.25-8.28 (m, 2 H), 8.66 (s, 2 H), 9.37 (s, 1 H), 9.88 (s, 1 H).

Example 85-192

1-[5-chloro-2-(3-pyridinyl)phenyl]-3-(2-{4-[2-(propylamino)-1,3-thiazol-5-yl]phenoxy}-5-pyrimidinyl)urea Purity (UPLC-MS/ELSD): 76% (Retention Time: 0.74 minutes);
MASS (ESI, Pos.): 558 (M+H)⁺;
¹H-NMR (DMSO-d₆): δ 0.91 (t, 3 H), 1.51-1.63 (m, 2 H), 3.16-3.22 (m, 2 H), 7.10-7.16 (m, 2 H), 7.22-7.28 (m, 2 H), 7.41-7.55 (m, 4 H), 7.74-7.85 (m, 2 H), 8.08 (d, 1 H), 8.23 (s, 1 H), 8.56-8.62 (m, 4 H), 9.18 (s, 1 H).

Example 85-193

1-(6-{4-[2-(propylamino)-1,3-thiazol-5-yl]phenoxy}-3-pyridinyl)-3-[2-(1H-pyrazol-1-yl)-5-(trifluoromethyl)phenyl]urea Purity (UPLC-MS/ELSD): 99% (Retention Time: 0.95 minutes);
MASS (ESI, Pos.): 580 (M+H)⁺;
¹H-NMR (DMSO-d₆): δ 0.91 (t, 3 H), 1.51-1.63 (m, 2 H), 3.15-3.22 (m, 2 H), 6.66-6.68 (m, 1 H), 6.98-7.06 (m, 3 H), 7.39-7.44 (m, 3 H), 7.50 (dd, 1 H), 7.71-7.76 (m, 2 H), 7.94 (d, 1 H), 7.99 (dd, 1 H), 8.15 (d, 1 H), 8.40 (d, 1 H), 8.60 (s, 1 H), 9.54 (s, 1 H), 9.80 (s, 1 H).

Example 85-194

1-(6-{4-[2-(propylamino)-1,3-thiazol-5-yl]phenoxy}-3-pyridinyl)-3-{5-(trifluoromethyl)-2-[3-(trifluoromethyl)-1H-pyrazol-1-yl]phenyl}urea Purity (UPLC-MS/ELSD): 99% (Retention Time: 1.02 minutes);
MASS (ESI, Pos.): 648 (M+H)⁺;
¹H-NMR (DMSO-d₆): δ 0.91 (t, 3 H), 1.51-1.63 (m, 2 H), 3.15-3.22 (m, 2 H), 6.98-7.05 (m, 3 H), 7.13 (d, 1 H), 7.39-7.43 (m, 3 H), 7.55 (dd, 1 H), 7.68 (d, 1 H), 7.74 (t, 1 H), 7.96 (dd, 1 H), 8.10 (d, 1 H), 8.43 (s, 1 H), 8.46-8.48 (m, 1 H), 8.52 (d, 1 H), 9.38 (s, 1 H).

Example 85-195

1-[2-(1-methyl-1H-pyrazol-5-yl)-5-(trifluoromethyl)phenyl]-3-(6-{4-[2-(propylamino)-1,3-thiazol-5-yl]phenoxy}-3-pyridinyl)urea Purity (UPLC-MS/ELSD): 99% (Retention Time: 0.93 minutes);
MASS (ESI, Pos.): 594 (M+H)⁺;
¹H-NMR (DMSO-d₆): δ 0.91 (t, 3 H), 1.51-1.63 (m, 2 H), 3.15-3.22 (m, 2 H), 3.65 (s, 3 H), 6.45 (d, 1 H), 6.98-7.06 (m, 3 H), 7.39-7.50 (m, 5 H), 7.62 (d, 1 H), 7.74 (t, 1 H), 7.96-8.01 (m, 2 H), 8.10 (d, 1 H), 8.59 (s, 1 H), 9.41 (s, 1 H).

Example 85-196

1-[2-(3-methyl-1H-pyrazol-1-yl)-5-(trifluoromethyl)phenyl]-3-(6-{4-[2-(propylamino)-1,3-thiazol-5-yl]phenoxy}-3-pyridinyl)urea Purity (UPLC-MS/ELSD): 100% (Retention Time: 0.99 minutes);
MASS (ESI, Pos.): 594 (M+H)⁺;
¹H-NMR (DMSO-d₆): δ 0.91 (t, 3 H), 1.51-1.63 (m, 2 H), 2.36 (s, 3 H), 3.16-3.22 (m, 2 H), 6.45 (d, 1 H), 6.99-7.06 (m, 3 H), 7.39-7.48 (m, 4 H), 7.68 (d, 1 H), 7.74 (t, 1 H), 7.97 (dd, 1 H), 8.16 (d, 1 H), 8.26 (d, 1 H), 8.58 (s, 1 H), 9.66 (s, 1 H), 9.76 (s, 1 H).

Example 85-197

1-[2-(4-methyl-1H-pyrazol-1-yl)-5-(trifluoromethyl)phenyl]-3-(6-{4-[2-(propylamino)-1,3-thiazol-5-yl]phenoxy}-3-pyridinyl)urea Purity (UPLC-MS/ELSD): 99% (Retention Time: 1.01 minutes);
MASS (ESI, Pos.): 594 (M+H)⁺;
¹H-NMR (DMSO-d₆): δ 0.91 (t, 3 H), 1.51-1.63 (m, 2 H), 2.14 (s, 3 H), 3.16-3.22 (m, 2 H), 6.98-7.06 (m, 3 H), 7.39-7.49 (m, 4 H), 7.68 (d, 1 H), 7.72-7.77 (m, 2 H), 7.99 (dd, 1 H), 8.15-8.17 (m, 2 H), 8.59 (s, 1 H), 9.67 (s, 1 H), 9.81 (s, 1 H).

Example 85-198

1-(6-{4-[2-(propylamino)-1,3-thiazol-5-yl]phenoxy}-3-pyridinyl)-3-[2-(1H-pyrazol-1-yl)-4-(trifluoromethyl)phenyl]urea Purity (UPLC-MS/ELSD): 98% (Retention Time: 0.97 minutes);
MASS (ESI, Pos.): 580 (M+H)⁺;
¹H-NMR (DMSO-d₆): δ 0.91 (t, 3 H), 1.51-1.63 (m, 2 H), 3.15-3.22 (m, 2 H), 6.65 (t, 1H), 6.99-7.07 (m, 3 H), 7.39-7.45 (m, 3 H), 7.72-7.75 (m, 2 H), 7.81 (d, 1 H), 7.92 (d, 1 H), 7.96 (dd, 1 H), 8.17 (d, 1 H), 8.41-8.44 (m, 2 H), 9.40 (s, 1 H), 9.81 (s, 1 H).

Example 85-199

1-(6-{4-[2-(propylamino)-1,3-thiazol-5-yl]phenoxy}-3-pyridinyl)-3-[2-(3-pyridinyl)-4-(trifluoromethyl)phenyl]urea Purity (UPLC-MS/ELSD): 96% (Retention Time: 0.87 minutes);
MASS (ESI, Pos.): 591 (M+H)⁺;
¹H-NMR (DMSO-d₆): δ 0.91 (t, 3 H), 1.51-1.63 (m, 2 H), 3.15-3.22 (m, 2 H), 6.97-7.06 (m, 3 H), 7.39-7.44 (m, 3 H), 7.53-7.58 (m, 2 H), 7.72-7.76 (m, 2 H), 7.88-7.96 (m, 2 H), 8.09-8.10 (m, 2 H), 8.29 (d, 1 H), 8.64-8.69 (m, 2 H), 9.19 (s, 1 H).

Example 85-200

1-[5-chloro-2-(1H-pyrazol-1-yl)phenyl]-3-(6-{4-[2-(propylamino)-1,3-thiazol-5-yl]phenoxy}-3-pyridinyl)urea Purity (UPLC-MS/ELSD): 97% (Retention Time: 0.93 minutes);

MASS (ESI, Pos.): 547 (M+H)+;

$^1$H-NMR (DMSO-d$_6$): δ 0.91 (t, 3 H), 1.51-1.63 (m, 2 H), 3.15-3.22 (m, 2 H), 6.61-6.62 (m, 1 H), 6.98-7.07 (m, 3 H), 7.20 (dd, 1 H), 7.39-7.43 (m, 3 H), 7.49 (d, 1 H), 7.74 (t, 1 H), 7.89 (d, 1 H), 7.96 (dd, 1 H), 8.15 (d, 1 H), 8.26-8.29 (m, 2 H), 9.21 (s, 1 H), 9.73 (s, 1 H).

Example 85-201

1-[5-chloro-2-(3-pyridinyl)phenyl]-3-(6-{4-[2-(propylamino)-1,3-thiazol-5-yl]phenoxy}-3-pyridinyl)urea Purity (UPLC-MS/ELSD): 98% (Retention Time: 0.81 minutes);

MASS (ESI, Pos.): 557 (M+H)+;

$^1$H-NMR (DMSO-d$_6$): δ 0.91 (t, 3 H), 1.51-1.63 (m, 2 H), 3.15-3.22 (m, 2 H), 6.97-7.06 (m, 3 H), 7.19-7.28 (m, 2 H), 7.38-7.43 (m, 3 H), 7.54 (dd, 1 H), 7.74 (t, 1 H), 7.81-7.85 (m, 1 H), 7.92-7.97 (m, 2 H), 8.08 (d, 1 H), 8.10 (d, 1 H), 8.59 (dd, 1 H), 8.64 (dd, 1 H), 9.11 (s, 1 H).

Example 85-202

1-(2-{4-[2-(propylamino)-1,3-thiazol-5-yl]phenoxy}-5-pyrimidinyl)-3-[2-(2H-1,2,3-triazol-2-yl)-5-(trifluoromethyl)phenyl]urea Purity (UPLC-MS/ELSD): 100% (Retention Time: 0.93 minutes);

MASS (ESI, Pos.): 582 (M+H)+;

$^1$H-NMR (DMSO-d$_6$): δ 0.91 (t, 3 H), 1.51-1.63 (m, 2 H), 3.16-3.22 (m, 2 H), 7.12-7.16 (m, 2 H), 7.41-7.46 (m, 3 H), 7.58 (dd, 1 H), 7.76 (t, 1 H), 8.06 (d, 1 H), 8.32 (s, 2 H), 8.65-8.69 (m, 3 H), 9.66 (s, 1 H), 10.0 (s, 1 H).

Example 85-203

1-[5-chloro-2-(1H-1,2,3-triazol-1-yl)phenyl]-3-(2-{4-[2-(propylamino)-1,3-thiazol-5-yl]phenoxy}-5-pyrimidinyl)urea Purity (UPLC-MS/ELSD): 100% (Retention Time: 0.80 minutes);

MASS (ESI, Pos.): 548 (M+H)+;

$^1$H-NMR (DMSO-d$_6$): δ 0.91 (t, 3 H), 1.51-1.63 (m, 2 H), 3.16-3.22 (m, 2 H), 7.11-7.15 (m, 2 H), 7.32 (dd, 1 H), 7.42-7.52 (m, 4 H), 7.76 (t, 1 H), 8.06 (d, 1 H), 8.27 (d, 1 H), 8.49 (s, 1 H), 8.59 (d, 1 H), 8.64 (s, 2 H), 9.57 (s, 1 H).

Example 85-204

1-[5-chloro-2-(2H-1,2,3-triazol-2-yl)phenyl]-3-(2-{4-[2-(propylamino)-1,3-thiazol-5-yl]phenoxy}-5-pyrimidinyl)urea Purity (UPLC-MS/ELSD): 100% (Retention Time: 0.90 minutes);

MASS (ESI, Pos.): 548 (M+H)+;

$^1$H-NMR (DMSO-d$_6$): δ 0.91 (t, 3 H), 1.51-1.63 (m, 2 H), 3.16-3.22 (m, 2 H), 7.12-7.16 (m, 2 H), 7.28 (dd, 1 H), 7.42-7.46 (m, 3 H), 7.74-7.81 (m, 2 H), 8.26 (s, 2 H), 8.32 (d, 1 H), 8.68 (s, 2 H), 9.35 (s, 1 H), 9.91 (s, 1 H).

Example 85-205

1-[2-fluoro-5-(trifluoromethyl)phenyl]-3-(2-{4-[2-(propylamino)-1,3-thiazol-5-yl]phenoxy}-5-pyrimidinyl)urea

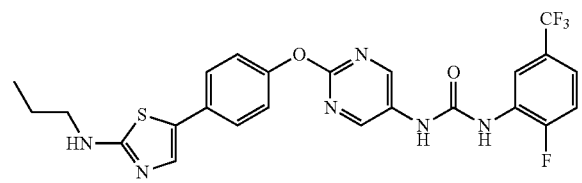 [SMILES: CCCNc1ncc(-c2ccc(Oc3ncc(NC(=O)Nc4cc(C(F)(F)F)ccc4F)cn3)cc2)s1]

Purity (UPLC-MS/ELSD): 100% (Retention Time: 0.89 minutes);

MASS (ESI, Pos.): 533 (M+H)+;

$^1$H-NMR (DMSO-d$_6$): δ 0.91 (t, 3 H), 1.51-1.63 (m, 2 H), 3.16-3.22 (m, 2 H), 7.12-7.16 (m, 2 H), 7.38-7.53 (m, 5 H), 7.76 (t, 1 H), 8.52 (dd, 1 H), 8.71 (s, 2 H), 9.09 (s, 1 H), 9.28 (s, 1 H).

Example 85-206

1-[2-methyl-5-(trifluoromethyl)phenyl]-3-(2-{4-[2-(propylamino)-1,3-thiazol-5-yl]phenoxy}-5-pyrimidinyl)urea TCL: Rf 0.48 (Ethyl Acetate);

$^1$H-NMR (DMSO-d$_6$): δ 0.91 (t, 3 H), 1.51-1.63 (m, 2 H), 2.32 (s, 3 H), 3.16-3.23 (m, 2 H), 7.12-7.16 (m, 2 H), 7.29 (d, 1 H), 7.40-7.46 (m, 4 H), 7.76 (t, 1 H), 8.26 (s, 1 H), 8.37 (s, 1 H), 8.72 (s, 2 H), 9.32 (s, 1 H).

Example 85-207

1-(2,5-dichlorophenyl)-3-(2-{4-[2-(propylamino)-1,3-thiazol-5-yl]phenoxy}-5-pyrimidinyl)urea Purity (UPLC-MS/ELSD): 100% (Retention Time: 0.89 minutes);

MASS (ESI, Pos.): 515 (M+H)+;

$^1$H-NMR (DMSO-d$_6$): δ 0.91 (t, 3 H), 1.51-1.63 (m, 2 H), 3.13-3.23 (m, 2 H), 7.10-7.18 (m, 2 H), 7.36-7.47 (m, 4 H), 7.63 (d, 1 H), 7.71-7.81 (m, 1 H), 8.14 (d, 1 H), 8.59 (s, 1 H), 8.70 (s, 2 H), 9.58 (s, 1 H).

Example 85-208

1-(2,4-dichlorophenyl)-3-(2-{4-[2-(propylamino)-1,3-thiazol-5-yl]phenoxy}-5-pyrimidinyl)urea Purity (UPLC-MS/ELSD): 99% (Retention Time: 0.90 minutes);

MASS (ESI, Pos.): 515 (M+H)+;

¹H-NMR (DMSO-d₆): δ 0.91 (t, 3 H), 1.51-1.63 (m, 2 H), 3.16-3.23 (m, 2 H), 7.11-7.16 (m, 2 H), 7.36-7.47 (m, 4 H), 7.63 (d, 1 H), 7.76 (t, 1 H), 8.13 (d, 1 H), 8.57 (s, 1 H), 8.70 (s, 2 H), 9.57 (s, 1 H).

Example 85-209

1-(2,5-difluorophenyl)-3-(2-{4-[2-(propylamino)-1,3-thiazol-5-yl]phenoxy}-5-pyrimidinyl)urea Purity (UPLC-MS/ELSD): 98% (Retention Time: 0.81 minutes);
MASS (ESI, Pos.): 483 (M+H)⁺;
¹H-NMR (DMSO-d₆): δ 0.91 (t, 3 H), 1.51-1.63 (m, 2 H), 3.16-3.22 (m, 2 H), 6.80-6.89 (m, 1 H), 7.12-7.16 (m, 2 H), 7.26-7.34 (m, 1 H), 7.39-7.46 (m, 3 H), 7.76 (t, 1 H), 7.93-8.00 (m, 1 H), 8.70 (s, 2 H), 8.96 (s, 1 H), 9.26 (s, 1 H).

Example 85-210

1-[3-(difluoromethyl)phenyl]-3-(2-{4-[2-(propylamino)-1,3-thiazol-5-yl]phenoxy}-5-pyrimidinyl)urea Purity (UPLC-MS/ELSD): 100% (Retention Time: 0.77 minutes);
MASS (ESI, Pos.): 497 (M+H)⁺;
¹H-NMR (DMSO-d₆): δ 0.91 (t, 3 H), 1.51-1.63 (m, 2 H), 3.16-3.23 (m, 2 H), 6.81-7.18 (m, 4 H), 7.39-7.53 (m, 5 H), 7.74-7.76 (m, 2 H), 8.70 (s, 2 H), 8.91 (s, 1 H), 9.17 (s, 1 H).

Example 85-211

1-[2-chloro-5-(trifluoromethyl)phenyl]-3-(6-{4-[2-(propylamino)-1,3-thiazol-5-yl]phenoxy}-3-pyridinyl)urea Purity (UPLC-MS/ELSD): 100% (Retention Time: 0.98 minutes);
MASS (ESI, Pos.): 548 (M+H)⁺;
¹H-NMR (DMSO-d₆): δ 0.91 (t, 3 H), 1.51-1.63 (m, 2 H), 3.16-3.22 (m, 2 H), 7.01-7.08 (m, 3 H), 7.36-7.44 (m, 4 H), 7.70-7.76 (m, 2 H), 8.04 (dd, 1 H), 8.17 (d, 1 H), 8.60 (d, 1 H), 8.66 (s, 1 H), 9.63 (s, 1 H).

Example 85-212

1-[2-fluoro-5-(trifluoromethyl)phenyl]-3-(6-{4-[2-(propylamino)-1,3-thiazol-5-yl]phenoxy}-3-pyridinyl)urea Purity (UPLC-MS/ELSD): 99% (Retention Time: 0.94 minutes);
MASS (ESI, Pos.): 532 (M+H)⁺;
¹H-NMR (DMSO-d₆): δ 0.91 (t, 3 H), 1.51-1.63 (m, 2 H), 3.16-3.22 (m, 2 H), 7.01-7.07 (m, 3 H), 7.39-7.52 (m, 5 H), 7.74 (t, 1 H), 8.03 (dd, 1 H), 8.16 (d, 1 H), 8.56 (dd, 1 H), 8.95 (d, 1 H), 9.23 (s, 1 H).

Example 85-213

1-[2-methyl-5-(trifluoromethyl)phenyl]-3-(6-{4-[2-(propylamino)-1,3-thiazol-5-yl]phenoxy}-3-pyridinyl)urea Purity (UPLC-MS/ELSD): 98% (Retention Time: 0.95 minutes);
MASS (ESI, Pos.): 528 (M+H)⁺;
¹H-NMR (DMSO-d₆): δ 0.91 (t, 3 H), 1.51-1.63 (m, 2 H), 2.31 (s, 3 H), 3.15-3.22 (m, 2 H), 7.00-7.07 (m, 3 H), 7.26 (d, 1 H), 7.39-7.44 (m, 4 H), 7.74 (t, 1 H), 8.04 (dd, 1 H), 8.16 (d, 1 H), 8.23 (s, 1 H), 8.31 (s, 1 H), 9.26 (s, 1 H).

Example 85-214

1-(2,5-dichlorophenyl)-3-(6-{4-[2-(propylamino)-1,3-thiazol-5-yl]phenoxy}-3-pyridinyl)urea Purity (UPLC-MS/ELSD): 100% (Retention Time: 0.96 minutes);
MASS (ESI, Pos.): 514 (M+H)⁺;
¹H-NMR (DMSO-d₆): δ 0.91 (t, 3 H), 1.51-1.63 (m, 2 H), 3.15-3.22 (m, 2 H), 7.01-7.11 (m, 4 H), 7.39-7.48 (m, 4 H), 7.74 (t, 1 H), 8.01 (dd, 1 H), 8.17 (d, 1 H), 8.29 (d, 1 H), 8.51 (s, 1 H), 9.59 (s, 1 H).

Example 85-215

1-(2,4-dichlorophenyl)-3-(6-{4-[2-(propylamino)-1,3-thiazol-5-yl]phenoxy}-3-pyridinyl)urea Purity (UPLC-MS/ELSD): 100% (Retention Time: 0.93 minutes);
MASS (ESI, Pos.): 514 (M+H)⁺;
¹H-NMR (DMSO-d₆): δ 0.91 (t, 3 H), 1.51-1.63 (m, 2 H), 3.15-3.22 (m, 2 H), 7.00-7.07 (m, 3 H), 7.36-7.44 (m, 4 H), 7.62 (d, 1 H), 7.74 (t, 1 H), 8.00 (dd, 1 H), 8.17-8.18 (m, 2 H), 8.44 (s, 1 H), 9.51 (s, 1 H).

Example 85-216

1-(2,5-difluorophenyl)-3-(6-{4-[2-(propylamino)-1,3-thiazol-5-yl]phenoxy}-3-pyridinyl)urea Purity (UPLC-MS/ELSD): 99% (Retention Time: 0.88 minutes);
MASS (ESI, Pos.): 482 (M+H)⁺;
¹H-NMR (DMSO-d₆): δ 0.91 (t, 3 H), 1.51-1.63 (m, 2 H), 3.15-3.22 (m, 2 H), 6.78-6.86 (m, 1 H), 7.01-7.07 (m, 3 H), 7.24-7.33 (m, 1 H), 7.39-7.44 (m, 3 H), 7.74 (t, 1 H), 7.96-8.03 (m, 2 H), 8.16 (d, 1 H), 8.82 (s, 1 H), 9.20 (s, 1 H).

Example 85-217

1-[3-(difluoromethyl)phenyl]-3-(6-{4-[2-(propylamino)-1,3-thiazol-5-yl]phenoxy}-3-pyridinyl)urea Purity (UPLC-MS/ELSD): 100% (Retention Time: 0.82 minutes);
MASS (ESI, Pos.): 496 (M+H)⁺;
¹H-NMR (DMSO-d₆): δ 0.91 (t, 3 H), 1.51-1.63 (m, 2 H), 3.15-3.22 (m, 2 H), 6.81-7.18 (m, 5 H), 7.39-7.51 (m, 5 H), 7.72-7.77 (m, 2 H), 7.90 (dd, 1 H), 8.19 (dd, 1 H), 8.81 (s, 1 H), 8.99 (s, 1 H).

Example 85-218

1-[2-chloro-4-(trifluoromethyl)phenyl]-3-(6-{4-[2-(propylamino)-1,3-thiazol-5-yl]phenoxy}-3-pyridinyl)urea Purity (UPLC-MS/ELSD): 100% (Retention Time: 1.00 minutes);
MASS (ESI, Pos.): 548 (M+H)⁺;

¹H-NMR (DMSO-d₆): δ 0.91 (t, 3 H), 1.51-1.63 (m, 2 H), 3.15-3.22 (m, 2 H), 7.02-7.09 (m, 3 H), 7.39-7.44 (m, 3 H), 7.68 (dd, 1 H), 7.74 (t, 1 H), 7.87 (d, 1 H), 8.02 (dd, 1 H), 8.19 (d, 1 H), 8.44 (d, 1 H), 8.67 (s, 1 H), 9.68 (s, 1 H).

Example 85-219

1-(6-{4-[2-(propylamino)-1,3-thiazol-5-yl]phenoxy}-3-pyridinyl)-3-[2-(2H-1,2,3-triazol-2-yl)-5-(trifluoromethyl)phenyl]urea Purity (UPLC-MS/ELSD): 100% (Retention Time: 0.98 minutes);
MASS (ESI, Pos.): 581 (M+H)⁺;
¹H-NMR (DMSO-d₆): δ 0.91 (t, 3 H), 1.51-1.63 (m, 2 H), 3.15-3.22 (m, 2 H), 7.00-7.07 (m, 3 H), 7.39-7.44 (m, 3 H), 7.56 (dd, 1 H), 7.74 (t, 1 H), 7.99-8.06 (m, 2 H), 8.16 (d, 1 H), 8.32 (s, 2 H), 8.67 (s, 1 H), 9.54 (s, 1 H), 9.87 (s, 1 H).

Example 85-220

1-[5-chloro-2-(1H-1,2,3-triazol-1-yl)phenyl]-3-(6-{4-[2-(propylamino)-1,3-thiazol-5-yl]phenoxy}-3-pyridinyl)urea Purity (UPLC-MS/ELSD): 99% (Retention Time: 0.86 minutes);
MASS (ESI, Pos.): 547 (M+H)⁺;
¹H-NMR (DMSO-d₆): δ 0.90 (t, 3 H), 1.50-1.62 (m, 2 H), 3.15-3.21 (m, 2 H), 6.97-7.05 (m, 3 H), 7.29 (dd, 1 H), 7.38-7.49 (m, 4 H), 7.73 (t, 1 H), 7.94 (dd, 1 H), 8.05 (d, 1 H), 8.10 (d, 1 H), 8.28 (d, 1 H), 8.34 (s, 1 H), 8.58 (d, 1 H), 9.47 (s, 1 H).

Example 85-221

1-[5-chloro-2-(2H-1,2,3-triazol-2-yl)phenyl]-3-(6-{4-[2-(propylamino)-1,3-thiazol-5-yl]phenoxy}-3-pyridinyl)urea Purity (UPLC-MS/ELSD): 100% (Retention Time: 0.93 minutes);
MASS (ESI, Pos.): 547 (M+H)⁺;
¹H-NMR (DMSO-d₆): δ 0.91 (t, 3 H), 1.51-1.63 (m, 2 H), 3.15-3.22 (m, 2 H), 6.99-7.10 (m, 3 H), 7.27 (dd, 1 H), 7.39-7.45 (m, 3 H), 7.72-7.79 (m, 2 H), 7.98 (dd, 1 H), 8.15 (d, 1 H), 8.25 (s, 1 H), 8.33 (d, 1 H), 9.24 (s, 1 H), 9.77 (s, 1 H).

Example 85-222

1-(3,5-difluorophenyl)-3-(2-{4-[2-(propylamino)-1,3-thiazol-5-yl]phenoxy}-5-pyrimidinyl)urea Purity (UPLC-MS/ELSD): 100% (Retention Time: 0.80 minutes);
MASS (ESI, Pos.): 483 (M+H)⁺;
¹H-NMR (DMSO-d₆): δ 0.91 (t, 3 H), 1.51-1.63 (m, 2 H), 3.16-3.22 (m, 2 H), 6.77-6.86 (m, 1 H), 7.13-7.20 (m, 4 H), 7.42-7.46 (m, 3 H), 7.76 (t, 1 H), 8.69 (s, 2 H), 9.01 (s, 1 H), 9.35 (s, 1 H).

Example 85-223

1-{2-[3-(difluoromethyl)-1H-pyrazol-1-yl]-5-(trifluoromethyl)phenyl}-3-(2-{4-[2-(propylamino)-1,3-thiazol-5-yl]phenoxy}-5-pyrimidinyl)urea TCL: Rf 0.79 (Hexane:Ethyl Acetate=1:2);
¹H-NMR (DMSO-d₆): δ 0.91 (t, 3 H), 1.52-1.62 (m, 2 H), 3.16-3.22 (m, 2 H), 6.93 (d, 1 H), 6.99 (dd, 1 H), 7.13 (d, 2 H), 7.43 (d, 2 H), 7.43 (s, 1 H), 7.50 (dd, 1 H), 7.71-7.78 (m, 2 H), 8.44 (d, 1 H), 8.54 (d, 1 H), 8.66 (s, 2 H), 8.94 (s, 1 H), 9.65 (s, 1 H).

Example 85-224

1-[2-(4-{2-[3-(2-hydroxy-2-propanyl)-2-oxo-1-pyrrolidinyl]-1,3-thiazol-5-yl}phenoxy)-5-pyrimidinyl]-3-2-(methylsulfonyl)-5-(trifluoromethyl)phenyl urea

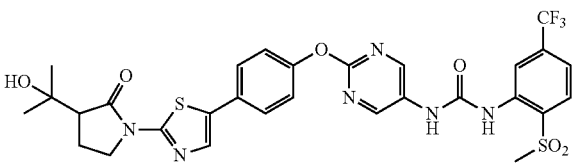 [SMILES: CC(C)(O)C1CCN(c2ncc(-c3ccc(Oc4ncc(NC(=O)Nc5cc(C(F)(F)F)ccc5S(C)(=O)=O)cn4)cc3)s2)C1=O]

TCL: Rf 0.30 (Methanol: Chloroform=1:19);
¹H-NMR (DMSO-d₆): δ 1.27 (d, 6 H), 2.20-2.28 (m, 2 H), 2.28 (t, 1 H), 3.84-4.07 (m, 2 H), 4.65 (s, 1 H), 7.20-7.27 (m, 2 H), 7.61-7.70 (m, 3 H), 7.90 (s, 1 H), 8.06 (d, 1 H), 8.61-8.63 (m, 1 H), 8.73 (s, 2 H), 8.96 (s, 1 H), 10.3 (s, 1 H).

Example 85-225

N,N-dimethyl-2-{[(2-{4-[2-(propylamino)-1,3-thiazol-5-yl]phenoxy}-5-pyrimidinyl)carbamoyl]amino}-4-(trifluoromethyl)benzenesulfonamide

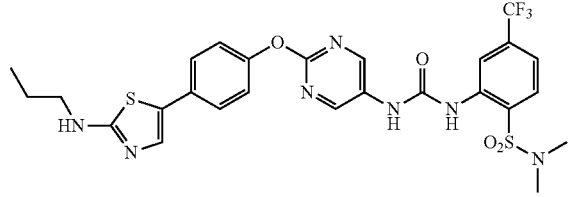 [SMILES: CCCNc1ncc(-c2ccc(Oc3ncc(NC(=O)Nc4cc(C(F)(F)F)ccc4S(=O)(=O)N(C)C)cn3)cc2)s1]

TCL: Rf 0.79 (Ethyl Acetate);
¹H-NMR (DMSO-d₆): δ 0.90 (t, 3 H), 1.51-1.65 (m, 2 H), 2.75 (s, 6 H), 3.15-3.24 (m, 2 H), 7.12-7.18 (m, 2 H), 7.41-7.50 (m, 3 H), 7.56-7.64 (m, 1 H), 7.77 (t, 1 H), 7.94 (d, 1 H), 8.60 (s, 1 H), 8.71 (s, 2 H), 8.98 (s, 1 H), 10.3 (s, 1 H).

Example 85-226

1-[2-(methylsulfonyl)-5-(trifluoromethyl)phenyl]-3-(2-{4-[2-(propylamino)-1,3-thiazol-5-yl]phenoxy}-5-pyrimidinyl)urea TCL: Rf 0.23 (Hexane:Ethyl Acetate=1:2);
¹H-NMR (DMSO-d₆): δ 0.91 (t, 3 H), 1.51-1.63 (m, 2 H), 3.16-3.23 (m, 2 H), 3.38 (s, 3 H), 7.11-7.18 (m, 2 H), 7.41-

7.48 (m, 3 H), 7.64 (dd, 1 H), 7.77 (t, 1 H), 8.07 (d, 1 H), 8.63 (d, 1 H), 8.73 (s, 2 H), 8.96 (s, 1 H), 10.3 (s, 1 H).

PHARMACOLOGICAL EXPERIMENT EXAMPLES

Pharmacological Experiment Example 1

Measurement of TrkA Enzyme-Inhibiting Activity (In Vitro Test)

TrkA-inhibiting activity was measured according to the following method using LanthaScreen™ kinase assay reagents (Invitrogen; Fluorescein-Poly GT, LanthaScreen™ Tb-PY20 and TR-FRET Dilution Buffer), TrkA (Invitrogen), ATP (Sigma-Aldrich), a kinase reaction buffer (50 mM HEPES buffer (Sigma-Aldrich) (pH 7.5) containing 0.01% Brij35 (Sigma-Aldrich), 10 mM $MgCl_2$ (Sigma-Aldrich) and 1 mM EGTA (Sigma-Aldrich)) and 0.5 M EDTA (pH 8.0) (Invitrogen).

The present compound was dissolved in dimethylsulfoxide (hereinafter abbreviated as DMSO) to prepare a 10 mM solution. The test compound at 10 mM was distributed into a 96-well plate and serially diluted with DMSO with the geometrical ratio of 3. The serial dilutions (DMSO solutions) were diluted with the kinase reaction buffer to 20-fold to prepare solutions of the present compound with 5-times concentrations (DMSO concentration: 5%). TrkA was diluted with the kinase reaction buffer to prepare a solution at 38.5 ng/mL (enzyme solution). Adenosine triphosphate (hereinafter abbreviated as ATP) was preliminarily diluted in distilled water to prepare a 10 mM solution which was then divided into containers and stored at −20° C. The 10 mM ATP solution and Fluorescein-Poly GT were diluted in the kinase reaction buffer to prepare a solution containing 375 mM of ATP and 500 nM of Fluorescein-Poly GT (ATP-substrate solution). EDTA (0.5 M; pH 8.0) and LanthaScreen™ Tb-PY20 were diluted in the TR-FRET Dilution Buffer to prepare a solution containing 20 mM of EDTA and 4 nM of LanthaScreen™ Tb-PY20 (detection buffer).

The solutions of the present compound (5 μL/well) and the enzyme solution (10 μL/well) were added to a 96-half well assay plate and the plate was shaken at room temperature for 10 minutes on a plate shaker (IKA™ MTS2/4 digital microplate, IKA Japan K.K.). As a control and a blank, the kinase reaction buffer containing 5% DMSO (5 μL/well) was added in place of the solution of the present compound. As a blank, the kinase reaction buffer (10 μL/well) was added in the place of the enzyme solution. The ATP-substrate solution (10 μL/well) was then added to the plate to initiate kinase reaction and the plate was shaken in the dark at room temperature for 1 hour on the plate shaker (final concentration of TrkA: 15.4 ng/mL, final concentration of the substrate: 200 nM and final concentration of ATP: 150 μM). Kinase reaction was terminated by adding the detection buffer (25 μL/well) to the plate and the plate was shaken in the dark at room temperature for 30 minutes on the plate shaker. On an Analyst GT (Molecular Devices Japan, K.K.) the wells were irradiated with excitation light at 340 nm and the fluorescence intensities at 520 nm and 495 nm were measured. The fluorescence intensity at 520 nm for each well was divided by the fluorescence intensity at 495 nm to calculate the time resolved fluorescence resonance energy transfer (TR-FRET) ratio.

The inhibition rate (%) of the present compound was calculated according to the following Equation 1:

Inhibition rate (%)=$\{1-(A_X-A_B)/(A_C-A_B)\}\times 100$    Equation 1 wherein $A_X$: the TR-FRET ratio when the present compound is added;
$A_B$: the TR-FRET of the blank; and
$A_C$: the TR-FRET of the control.

The value for 50% inhibition by the present compound ($IC_{50}$ value) was calculated from the inhibition curve based on the inhibition rate of the present compound at respective concentrations.

As a result, it was found that the present compounds had $IC_{50}$ values of 0.5 μM or lower and had TrkA enzyme-inhibiting activity. $IC_{50}$ values of some of the present compounds are shown in the following Table 1.

TABLE 1

| Example | TrkA inhibitory activity ($IC_{50}$; μM) |
|---|---|
| 9 | 0.16 |
| 23 | 0.09 |
| 34 | 0.18 |
| 48 | 0.12 |
| 50 | 0.04 |
| 54 | 0.04 |
| 57 | 0.03 |
| 59 | 0.19 |
| 65-1 | 0.08 |
| 66-19 | 0.02 |
| 66-27 | 0.13 |
| 66-28 | 0.08 |
| 66-72 | 0.05 |
| 71 | 0.03 |
| 72-1 | 0.05 |
| 72-3 | 0.06 |
| 72-7 | 0.03 |
| 80-2 | 0.07 |
| 84-41 | 0.09 |
| 85-117 | 0.02 |

Pharmacological Experiment Example 2

Enzyme Inhibition Activity Tests for Kinases Other than Trk (Selectivity Tests)

A test substance (present compound or comparative compound) was dissolved in dimethylsulfoxide and further diluted with dimethylsulfoxide to prepare a solution having a concentration of 100 times the test concentration of 3 μM. The solution was further diluted to 25-fold with an assay buffer (20 mM HEPES, 0.01% Triton X-100, 2 mM DTT, pH 7.5) to obtain a test substance solution. In a similar manner a positive control substance solution was prepared with a positive control substance.

A 4-times concentration solution (5 μL) of the test substance prepared with the assay buffer, 5 μL of a 4-times concentration solution of substrate/ATP/metal (Mg) and 10 μL of a 2-times concentration solution of kinase were mixed in a well of a polypropylene 384-well plate and allowed to react at room temperature for 1 hour. The reaction was terminated by adding 60 μL of a Termination Buffer (QuickScout Screening Assist MSA; Carna Biosciences). The substrate peptide and the phosphorylated peptide in the reaction solution were separated and quantified. The kinase reaction was assessed from the product ratio (P/(P+S)) calculated from the height (S) of the peak of the substrate peptide and the height (P) of the peak of the phosphorylated peptide. Other kinases used in the kinase selectivity experiments were, for example, Abl, c-Met, b-Raf, c-Kit and KDR. The following Table 2 indicates substrates, substrate concentrations, ATP concentrations and positive control substances used in respective kinase enzyme inhibition activity tests.

TABLE 2

| Kinase | Substrate Name | (nM) | ATP (μM) | Positive control |
|---|---|---|---|---|
| Abl | ABLtide | 1000 | 25 | Stautosporine |
| c-Met | Srctide | 1000 | 25 | Stautosporine |
| b-Raf | MAP2K1 | 1 | 1000 | ZM336372 |
| c-Kit | Srctide | 1000 | 400 | Stautosporine |
| KDR | CSKtide | 1000 | 75 | Stautosporine |

The inhibition rate was calculated from the average signal intensity of the test wells containing respective test substances provided that the average signal intensity of control wells each containing all reaction components was 0% inhibition and the average signal intensity of background wells (without addition of the enzyme) was 100% inhibition. As a result, the present compounds at a concentration of 3 μM had the inhibition rates of kinases as shown in the following Table 3.

TABLE 3

| | Inhibition Rate (%) | | | | |
|---|---|---|---|---|---|
| Example | Abl | c-Met | b-Raf | c-Kit | KDR |
| 23 | 25 | 6.5 | 23 | 31 | 15 |
| 54 | 8.9 | 0 | 17 | 7.2 | 2.4 |
| 57 | 0 | 4.9 | 18 | 9.1 | 0 |
| 84-3 | 5.6 | 11 | 36 | 28 | 5.2 |
| 85-117 | 0 | 0 | 13 | 19 | 0 |

From this result, it is demonstrated that the present compounds show low inhibition of kinases other than TrkA, e.g., Abl, c-Met, b-Raf, c-Kit and KDR, while exhibit strong inhibition of TrkA. In other words, the present compounds have TrkA inhibition as strong as $IC_{50}$ of 0.5 μM or less according to the result from Pharmacological Example 1, while the present compounds inhibit kinases other than TrkA only at 0% to about 30% even at the concentration of 3 μM according to the result from Pharmacological Example 2. Thus it is demonstrated that the present compounds have high selectivity towards TrkA inhibition and have excellent kinase selectivity.

Pharmacological Experiment Example 3

Measurement of TrkA Kinase-Inhibiting Activity Using Human TrkA Expressing Cells TrkA kinase-inhibiting activity in cell systems was measured using CHO-K1 cells expressing human TrkA and NFAT-bla (CellSenser™ TrkA-NFAT-bla CHO-K1 cells, Invitrogen).

On the day before the assay, CellSenser™ TrkA-NFAT-bla CHO-K1 cells were suspended in an assay medium (Opti-MEM1 Reduced Serum Medium (Invitrogen) containing 0.5% dialysed fetal bovine serum (Invitrogen), 0.1 mM nonessential amino acids (Invitrogen), 1 mM sodium pyruvate (Invitrogen) and antibiotics (100 U/mL penicillin and 100 μg/mL streptomycin (Invitrogen)) and plated at a density of $2.4 \times 10^4$ cells/40 μL/well in a 96-well clear bottom plate (Corning, Catalogue No.: 3882). In some wells were added only the assay medium at 40 μL/well (Cell-free). On the day of the assay, 10 mM of the present compound (DMSO solution) was distributed in a 96-well plate (Costar, Catalogue No.: 3363) and serially diluted with DMSO with the geometrical ratio of 3. The serial dilutions were diluted with the assay medium to 100-fold to prepare a solution of the present compound with a 10-times concentration (DMSO concentration: 1%). To the plate where cells were plated was added the present compound at 5 μL/well and the plate was incubated in a $CO_2$ incubator with 5% $CO_2$, 95% Air at 37° C. for 30 minutes. For a control and a blank, the assay medium containing 1% DMSO was added at 5 μL/well in place of the solution of the present compound. Subsequently the assay medium containing NGF (Mouse 2.5s, Natural, Invitrogen) was added to the plate at 5 L/well (final concentration of NGF: 50 ng/ml) and the plate was incubated in a $CO_2$ incubator with 5% $CO_2$, 95% Air at 37° C. for 5 hours. For a group of blanks, the assay medium was added in place of NGF at 5 μL/well. A reporter assay detection reagent (10 μL/well) was added to the plate and the plate was then incubated in the dark at room temperature for 120 minutes. The reporter assay detection reagent was prepared from LiveBLAzer™-FRET B/G Loading Kit (Invitrogen). On an Analyst GT (Molecular Devices Japan, K.K.) the wells were irradiated with excitation light at 405 nm and the fluorescence intensities at 460 nm and 530 nm were measured. The time resolved fluorescence resonance energy transfer (TR-FRET) ratio of each well was calculated according to the following Equation 2.

$$\text{TR-FRET Ratio} = (A_{460X} - A_{460F})/(A_{530X} - A_{530F}) \quad \text{Equation 2}$$

wherein $A_{460X}$: the fluorescence intensity at 460 nm of the present compound, control or blank;

$A_{460F}$: the fluorescence intensity at 460 nm of the Cell-free;

$A_{530X}$: the fluorescence intensity at 530 nm of the present compound, control or blank; and $A_{530F}$: the fluorescence intensity at 530 nm of the Cell-free.

The TR-FRET inhibition rate (%) of the present compound was calculated according to the following Equation 3:

$$\text{Inhibition rate (\%)} = \{1 - (A_X - A_B)/(A_C - A_B)\} \times 100 \quad \text{Equation 3}$$

wherein $A_X$: the TR-FRET ratio when the present compound is added;

$A_B$: the TR-FRET of the blank; and $A_C$: the TR-FRET of the control.

The $IC_{50}$ value of the present compound was calculated from the inhibition curve based on the inhibition rate of the present compound at respective concentrations.

As a result, it was found that the present compounds had $IC_{50}$ values of 0.5 μM or lower and had TrkA enzyme-inhibiting activity. $IC_{50}$ values for some of the present compounds are shown in the following Table 4.

TABLE 4

| Example | TrkA inhibitory activity ($IC_{50}$; μM) |
|---|---|
| 9 | 0.093 |
| 23 | 0.004 |
| 34 | 0.006 |
| 48 | 0.010 |
| 50 | 0.012 |
| 54 | 0.004 |
| 57 | 0.003 |
| 59 | 0.070 |
| 65-1 | 0.002 |
| 66-19 | 0.004 |
| 66-27 | 0.010 |
| 66-28 | 0.014 |

TABLE 4-continued

| Example | TrkA inhibitory activity (IC$_{50}$; μM) |
|---|---|
| 66-72 | 0.032 |
| 71 | 0.002 |
| 72-1 | 0.011 |
| 72-3 | 0.018 |
| 72-7 | 0.033 |
| 85-117 | 0.002 |
| 85-184 | 0.002 |
| 85-209 | 0.004 |
| 85-225 | 0.004 |
| 85-226 | 0.001 |

Pharmacological Experiment Example 4

Suppression of Rat NGF-induced Vascular Hyper Permeability (In Vivo Tests)

TrkA-inhibiting activity of the present compound was evaluated in vivo. The present compound dissolved in a medium was orally administered (adminstered volume: 5 mL/kg) to male CD(SD)IGS rats (7- to 9-week old, Charles River laboratories Japan, Inc.) shaved on the back. A medium was orally administered (adminstered volume: 5 mL/kg) to the control and normal groups. After 6 or 12 hours of administration, 3 μg/mL of a NGF (Mouse 2.5s, Natural, Invitrogen) solution prepared in 0.1% BSA (Sigma-Aldrich)-containing saline was intracutaneously administered (dose; 50 μL/site) at 3 sites on the back of animals under halothane anesthesia. For the normal group, 0.1% BSA-containing saline was intracutaneously administered (dose; 50 μL/site) at 3 sites on the back. Immediately after intracutaneous administration, 1% Evans Blue (Tokyo Chemical Industry Co., Ltd.) was administered intravenously from tail (adminstered volume: 3 mL/kg). After 10 minutes of administration, the animals were sacrificed by bleeding due to incision of the abdominal aorta. The sites of intracutaneous administration on the back (3 sites) were excised and the skin samples were respectively transferred to the wells in a 48-well plate (Asahi Glass Co., Ltd.). Formamide (0.8 mL/well) was added to the plate and the plate was sealed and incubated overnight at 60° C. The formamide extraction solution (200 μL) was transferred to a 96-well plate and the absorbance (wavelength: 620 nm) of Evans Blue extracted in formamide was measured on an absorbance microplate reader (SpectraMAX 190, Molecular Devices Japan, K.K.). Standard samples of Evans Blue dissolved in formamide (0, 0.78, 1.56, 3.13, 6.25, 12.5, 25 and 50 μg/mL) were measured at the same time for the absorbance (wavelength: 620 nm) to generate a calibration curve. Based on the calibration curve and the absorbances of samples, the concentrations of Evans Blue in the sample was calculated. The concentrations of Evans Blue for three skin samples collected from one aminal were averaged to obtain the vale for the animal. The rate of suppression for rat NGF-induced vascular hyper permeability of the present compound was calculated according to the following Equation 4:

$$\text{Suppression rate (\%)} = \{1 - (A_X - A_N)/(A_C - A_N)\} \times 100 \quad \text{Equation 4}$$

wherein $A_X$: the concentration of Evans Blue of the test compound (an average value of 3 samples from one animal);
$A_N$: the concentration of Evans Blue of the normal group (an average value of 3 samples from one animal);
$A_C$: the concentration of Evans Blue of the control group (an average value of 3 samples from one animal).

As a result, the present compound (3 mg/kg; 6 hours after administration) had the rate of suppression for rat NGF-induced vascular hyper permeability of about 70%.

The rates of suppression for rat NGF-induced vascular hyper permeability of some of the present compounds (1 mg/kg; 12 hours after administration), for example, are shown in the following Table 5. It is demonstrated that the present compounds have strong in vivo activity based on Trk-inhibiting activity and have persistent activity.

On the other hand, the compound of Example 42 disclosed in Patent Document 3 had the rate of suppression for rat NGF-induced vascular hyper permeability of 21% (1 mg/kg; 12 hours after administration) and it is found that the compound has significantly low in vivo activity based on Trk-inhibiting activity.

TABLE 5

| Example | Rates of Suppression for Vascular Hyper Permeability (%) (1 mg/kg; 12 hours after administration) |
|---|---|
| 23 | 78 |
| 34 | 75 |
| 48 | 71 |
| 54 | 88 |
| 57 | 78 |
| 84-3 | 94 |
| 85-117 | 74 |
| 85-184 | 96 |
| 85-209 | 81 |
| 85-225 | 94 |
| 85-226 | 100 |

FORMULATION EXAMPLES

Formulation Example 1

The following components were mixed and compressed to tablets according to a conventional method to give 10,000 tablets containing 10 mg of the active ingredient per tablet.

| | |
|---|---|
| 1-(2-{4-[2-(2-oxo-1-pyrrolidinyl)-1,3-thiazol-5-yl]phenoxy}-5-pyrimidinyl)-3-[2-phenyl-5-(trifluoromethyl)-3-pyridinyl]urea | 100 g |
| Calcium carboxymethylcellulose (disintegrating agent) | 20 g |
| Magnesium stearate (lubricant) | 10 g |
| Microcrystalline cellulose | 870 g |

Formulation Example 2

The following components were mixed according to a conventional method, filtered through a dust filter, distributed to ampoules at 5 ml and thermally sterilized in an autoclave to obtain 10,000 ampoules containing 20 mg of the active ingredient per ampoule.

| | |
|---|---|
| 1-(2-{4-[2-(2-oxo-1-pyrrolidinyl)-1,3-thiazol-5-yl]phenoxy}-5-pyrimidinyl)-3-[2-phenyl-5-(trifluoromethyl)-3-pyridinyl]urea | 200 g |
| Mannitol | 20 g |
| Distilled water | 50 L |

INDUSTRIAL APPLICABILITY

The present compound has Trk-inhibiting activity and thus is useful for prophylaxis and/or therapy of diseases to which Trk is involved, for example, pain, pruritus, lower urinary tract dysfunction, asthma, allergic rhinitis, inflammatory bowel disease and Chagas disease.

The invention claimed is:

1. A compound represented by the general formula (I):

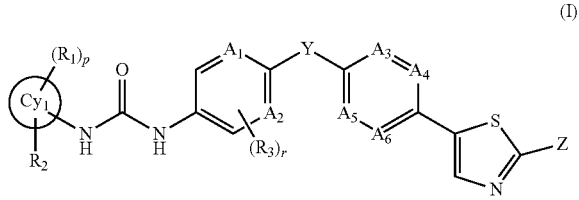

wherein:

a ring $Cy_1$ represents a C3-10 monocyclic carbocycle or bicyclic carbocycle or a 4- to 10-membered monocyclic heterocycle or bicyclic heterocycle;

$R_1$ represents:
(1) a halogen;
(2) a C1-6 alkyl group optionally substituted with a halogen or an oxo group;
(3) a C3-6 cycloalkyl group optionally substituted with a halogen or a C1-3 alkyl group;
(4) a C1-6 alkyl group having an oxygen atom substituting for a carbon atom and optionally substituted with a halogen or an oxo group; or
(5) a C3-6 cycloalkyl group having an oxygen atom substituting for a carbon atom and optionally substituted with a halogen or a C1-3 alkyl group;

$R_2$ represents:
(1) a C1-6 alkyl group, a C2-6 alkenyl group or a C2-6 alkynyl group optionally substituted with a substituent selected from the group consisting of:
  (i) a halogen;
  (ii) a hydroxy group;
  (iii) —NH(C1-3 alkyl);
  (iv) —N(C1-3 alkyl)$_2$;
  (v) an amino group;
  (vi) a cyano group;
  (vii) a nitro group;
  (viii) a C1-4 alkylsulfonyl group,
  (ix) a sulfonamide group;
  (x) a C1-4 alkylsulfonamide group;
  (xi) an oxo group;
  (xii) a carboxyl group;
  (xiii) —C(O)(O—C1-4 alkyl);
  (xiv) a phosphonooxy group;
  (xv) —OP(O)(O—C1-4 alkyl)$_2$;
  (xvi) a carbamoyl group;
  (xvii) a C1-4 alkylamide group; and
  (xviii) a C1-4 alkylcarbamate group;
(2) a hydrogen atom;
(3) a hydroxy group;
(4) a carboxyl group;
(5) —C(O)(O—C1-4 alkyl);
(6) a phosphonooxy group;
(7) —OP(O)(O—C1-4 alkyl)$_2$;
(8) an amino group;
(9) a cyano group;
(10) a nitro group;
(11) a C1-4 alkylsulfonyl group;
(12) a sulfonamide group;
(13) a C1-4 alkylsulfonamide group;
(14) an oxo group;
(15) a carbamoyl group;
(16) a C1-4 alkylamide group;
(17) a C1-4 alkylcarbamate group; or
(18)

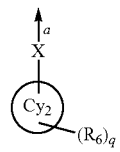

wherein an arrow a represents binding to the ring $Cy_1$;

X represents a bond, an oxygen atom, C=O or NH;

a ring $Cy_2$ represents a C3-10 monocyclic carbocycle or bicyclic carbocycle or a 4- to 10-membered monocyclic heterocycle or bicyclic heterocycle;

$R_6$ represents:
(1) a C1-6 alkyl group, a C2-6 alkenyl group, a C2-6 alkynyl group or a C3-6 cycloalkyl group optionally substituted with a substituent selected from the group consisting of:
  (i) a halogen;
  (ii) a hydroxy group;
  (iii) an oxo group;
  (iv) —NH(C1-3 alkyl);
  (v) —N(C1-3 alkyl)$_2$;
  (vi) a C1-6 alkoxy group;
  (vii) an amino group;
  (viii) a cyano group;
  (ix) a nitro group;
  (x) a C1-4 alkylsulfonyl group;
  (xi) a sulfonamide group;
  (xii) a C1-4 alkylsulfonamide group;
  (xiii) a carboxyl group;
  (xiv) —C(O)(O—C1-4 alkyl);
  (xv) a phosphonooxy group;
  (xvi) —OP(O)(O—C1-4 alkyl)$_2$;
  (xvii) a carbamoyl group;
  (xviii) a C1-4 alkylamide group; and
  (xix) a C1-4 alkylcarbamate group;
(2) a halogen;
(3) a C1-4 alkoxy group;
(4) a phosphonooxy group;
(5) —OP(O)(O—C1-4 alkyl)$_2$;
(6) a sulfonamide group;
(7) an oxo group;
(8) —NH(C1-3 alkyl);
(9) —N(C1-3 alkyl)$_2$;
(10) a carboxyl group;
(11) —C(O)(O—C1-4 alkyl);
(12) a carbamoyl group;
(13) a C1-4 alkylamide group;
(14) a hydroxy group;
(15) an amino group;
(16) a cyano group;
(17) a nitro group;
(18) a C1-4 alkylsulfonyl group;
(19) a C1-4 alkylsulfonamide group; or
(20) a C1-4 alkylcarbamate group;

$A_1$ and $A_2$ respectively and independently represent =$CR_3$—, =CH— or =N—;

$A_3$, $A_4$, $A_5$ and $A_6$ respectively and independently represent =$CR_4$— or =N—;

R$_3$ represents:

(1) a halogen; or (2) a C1-3 alkyl group or C1-3 alkoxy group optionally substituted with a halogen;

R$_4$ represents (1) a halogen;

(2) a C1-3 alkyl group or C1-3 alkoxy group optionally substituted with a halogen; or (3) a hydrogen atom;

Y represents an oxygen atom, an optionally oxidized sulfur atom, a methylene group or C=O;

Z represents:

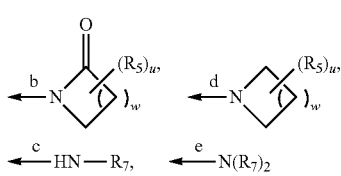

or a group:

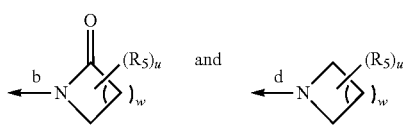

having an oxygen atom substituting for a carbon atom forming the ring;

R$_5$ represents a halogen, a hydroxy group or a C1-4 alkyl group optionally substituted with a hydroxy group;

R$_7$ respectively and independently represents:

(1) a C1-6 alkyl group, a C3-6 cycloalkyl group, a C1-6 alkyl group having an oxygen atom substituting for a carbon atom or a C3-6 cycloalkyl group having an oxygen atom substituting for a carbon atom, all of which may be optionally substituted with:

(i) a halogen;

(ii) a C3-6 cycloalkyl group;

(iii) a hydroxy group;

(iv) an oxo group; and (v) a 4- to 6-membered monocyclic heterocycle; or (2) a hydrogen atom;

arrows b, c, d and e represent binding to the thiazole ring;

p represents an integer of 0 to 5;

q represents an integer of 0 to 7;

r represents an integer of 0 to 2;

w represents an integer of 1 to 5; and u represents an integer of 0 to 2;

provided that when p, q, r and u respectively represent an integer of 2 or more, R$_1$, R$_3$, R$_5$ and R$_6$ groups may be respectively and independently the same or different; a salt thereof, an N-oxide thereof, or a solvate thereof.

2. The compound according to claim 1, wherein the general formula (I) is:

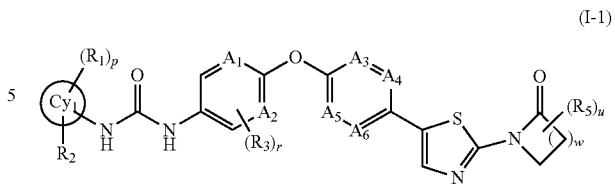

(I-1)

wherein all symbols represent the same meanings as those described in claim 1.

3. The compound according to claim 2, wherein the general formula (I-1) is:

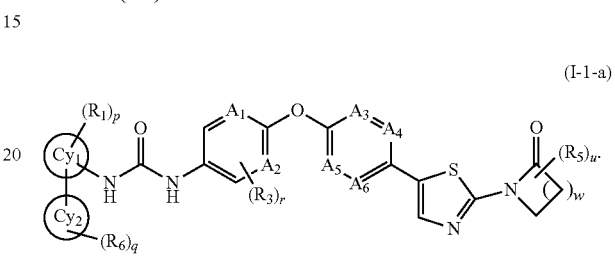

(I-1-a)

4. The compound according to claim 2, wherein the ring Cy$_1$ is a benzene ring or a 5- to 6-membered monocyclic aromatic heterocycle.

5. The compound according to claim 1, wherein one of A$_1$ and A$_2$ is =N— and the other is =CH— or both are =N— and A$_3$, A$_4$, A$_5$ and A$_6$ are =CH—.

6. The compound according to claim 1, wherein the general formula (I) is:

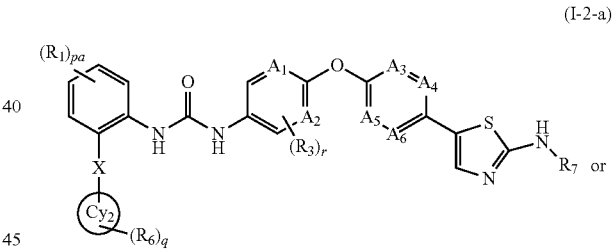

(I-2-a)

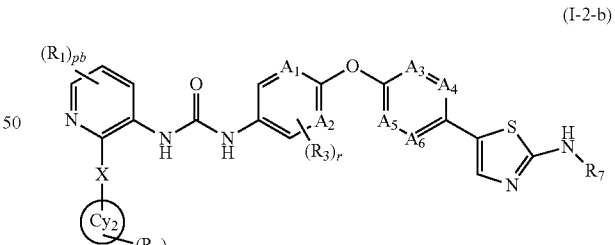

(I-2-b)

wherein pa represents an integer of 0 to 4; pb represents an integer of 0 to 3; and other symbols represent the same meanings as those described in claim 1, provided that when pa and pb respectively represent an integer of 2 or more, R$_1$ groups may be the same or different.

7. The compound according to claim 6, wherein one of A$_1$ and A$_2$ is =N—and the other is =CH— or both are =N— and A$_3$, A$_4$, A$_5$ and A$_6$ are =CH—.

8. The compound according to claim 1, wherein the general formula (I) is:

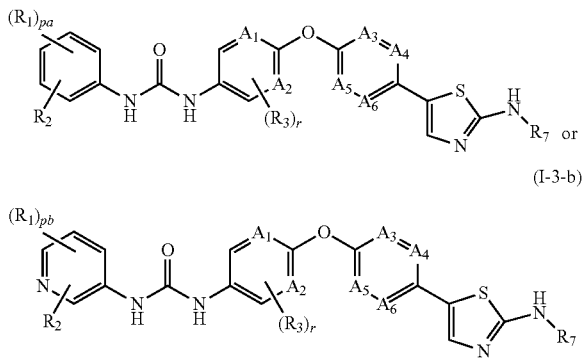

wherein all symbols represent the same meanings as those described in claim 1 and claim 6.

9. The compound according to claim 8, wherein one of $A_1$ and $A_2$ is =N— and the other is =CH— or both are =N— and $A_3$, $A_4$, $A_5$ and $A_6$ are =CH—.

10. A pharmaceutical composition comprising the compound represented by the general formula (I) according to claim 1, a salt thereof, an N-oxide thereof, or a solvate thereof as an active ingredient.

11. The pharmaceutical composition according to claim 10, which is an agent for treating pain, pruritus, asthma, allergic rhinitis or inflammatory bowel disease.

12. The pharmaceutical composition according to claim 11, wherein the pain is pain of osteoarthritis, cancer pain, chronic low back pain, low back pain of osteoporosis, pain of bone fracture, pain of rheumatoid arthritis, neuropathic pain, postherpetic pain, pain of diabetic neuropathy, fibromyalgia, pain of pancreatitis, pain of interstitial cystitis, pain of endometriosis, pain of irritable bowel syndrome, migraine or pain of pulpitis.

13. A medicament which is a combination of the compound represented by the general formula (I) according to claim 1, a salt thereof, an N-oxide thereof, or a solvate thereof and at least one selected from acetaminophen, a nonsteroid antiinflammatory drug, an opioid, an antidepressant, an antiepileptic agent, an N-methyl-D-aspartate antagonist, a muscle relaxant, an antiarrhythmic agent, a steroid and a bisphosphonate.

14. A method for treating pain, pruritus, asthma, allergic rhinitis or inflammatory bowel disease, comprising administering, to a patient, an effective amount of the compound represented by the general formula (I) according to claim 1, a salt thereof, an N-oxide thereof, or a solvate thereof.

15. The compound represented by the general formula (I) according to claim 1, a salt thereof, an N-oxide thereof, or a solvate thereof for treating pain, pruritus, asthma, allergic rhinitis inflammatory bowel disease.

* * * * *